(12) United States Patent
Boyce et al.

(10) Patent No.: US 8,921,309 B2
(45) Date of Patent: Dec. 30, 2014

(54) LIPOPEPTIDE COMPOUNDS AND THEIR USE

(75) Inventors: Rustum S. Boyce, Scarsdale, NY (US);
Joseph Cherian, Singapore (SG);
Cleofe Calanasan, Singapore (SG);
Muhammad Sofian Asi Sihombing,
Singapore (SG)

(73) Assignee: Uniquest Pty Limited, Brisbane, Queensland (AU)

( * ) Notice: Subject to any disclaimer, the term of this patent is extended or adjusted under 35 U.S.C. 154(b) by 523 days.

(21) Appl. No.: 13/128,661

(22) PCT Filed: Nov. 24, 2009

(86) PCT No.: PCT/SG2009/000444
§ 371 (c)(1),
(2), (4) Date: May 11, 2011

(87) PCT Pub. No.: WO2010/062264
PCT Pub. Date: Jun. 3, 2010

(65) Prior Publication Data
US 2011/0224129 A1  Sep. 15, 2011

Related U.S. Application Data

(60) Provisional application No. 61/117,589, filed on Nov. 25, 2008.

(30) Foreign Application Priority Data

Nov. 25, 2008  (GB) .................................. 0821540.2

(51) Int. Cl.
| | | |
|---|---|---|
| C07K 7/56 | (2006.01) | |
| C07K 7/54 | (2006.01) | |
| C07K 7/52 | (2006.01) | |
| C07K 7/50 | (2006.01) | |
| A61K 38/12 | (2006.01) | |
| A61K 38/04 | (2006.01) | |
| A61K 38/00 | (2006.01) | |
| A01N 37/18 | (2006.01) | |

(52) U.S. Cl.
CPC .. *C07K 7/56* (2013.01); *A61K 38/00* (2013.01)
USPC ......................................... 514/2.9

(58) Field of Classification Search
None
See application file for complete search history.

(56) References Cited

U.S. PATENT DOCUMENTS

| | | | |
|---|---|---|---|
| 5,629,288 | A | 5/1997 | Lattrell et al. |
| 6,194,383 | B1 | 2/2001 | Hammann et al. |
| 6,624,143 | B1 | 9/2003 | Vértesy et al. |
| 7,026,352 | B1 | 4/2006 | Mizui et al. |
| 2007/0219124 | A1 | 9/2007 | Labischinski et al. |

FOREIGN PATENT DOCUMENTS

| | | | |
|---|---|---|---|
| AU | 696566 | * | 9/1998 |
| AU | 696566 B | | 9/1998 |
| WO | WO 99/43700 | | 9/1999 |
| WO | WO 03/057724 | | 7/2003 |
| WO | WO 2005/000878 | | 1/2005 |
| WO | WO2005000878 | * | 1/2005 |

OTHER PUBLICATIONS

Vippagunta. Crystalline Solids. Advanced Drug Delivery Reviews 48 (2001), 3-26.*
International Search Report and Written Opinion mailed Jan. 13, 2010 for PCT/SG2009/000444.
GB Search Report mailed Mar. 25, 2009 in GB 0821540.2.
Search Report issued in EP 09829415.0 on Feb. 2, 2012.
International Preliminary Report on Patentability for PCT/SG2009/000444 mailed Jun. 9, 2011.

* cited by examiner

*Primary Examiner* — Maury Audet
(74) *Attorney, Agent, or Firm* — Swanson & Bratschun, L.L.C.

(57) ABSTRACT

The present invention pertains generally to the field of therapeutic compounds, and more specifically to certain lipopeptide compounds comprising a cyclic peptide bearing a lipid side chain (for convenience, collectively referred to herein as "LP compounds"), which, inter alia, are antimicrobial, particularly antibacterial. The present invention also pertains to pharmaceutical compositions comprising such compounds, and the use of such compounds and compositions, both in vitro and in vivo, to provide an antimicrobial function, particularly an antibacterial function, and in the treatment of diseases and conditions that are mediated by microbes, particularly bacteria, that are ameliorated by the antimicrobial function, particularly an antibacterial function, including bacterial diseases, optionally in combination with another agent, for example, another antibacterial agent.

12 Claims, No Drawings

LIPOPEPTIDE COMPOUNDS AND THEIR USE

RELATED APPLICATIONS

This application is a 35 U.S.C. §371 national phase application of PCT/SG2009/000444, filed Nov. 24, 2009 (WO 2010/062264), entitled "Lipopeptide Compounds and Their Use." PCT/SG2009/000444 claims priority to U.S. Provisional Application Ser. No. 61/117,589, filed Nov. 25, 2008 and Great Britain Application Serial No. 0821540.2, filed Nov. 25, 2008. Each of these applications is incorporated herein by reference in its entirety.

TECHNICAL FIELD

The present invention pertains generally to the field of therapeutic compounds, and more specifically to certain lipopeptide compounds comprising a cyclic peptide bearing a lipid side chain (for convenience, collectively referred to herein as "LP compounds"), which, inter alia, are antimicrobial, particularly antibacterial.

The present invention also pertains to pharmaceutical compositions comprising such compounds, and the use of such compounds and compositions, both in vitro and in vivo, to provide an antimicrobial function, particularly an antibacterial function, and in the treatment of diseases and conditions that are mediated by microbes, particularly bacteria, that are ameliorated by the antimicrobial function, particularly an antibacterial function, including bacterial diseases, optionally in combination with another agent, for example, another antibacterial agent.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers, or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Lipopeptides

Secondary metabolites from microorganisms are successfully employed for the treatment of infectious diseases. Secondary metabolites are low molecular weight compounds whose production takes place in "biosynthetic oneway streets" which branch off from the primary metabolism, and whose function for the particular producer is unclear. The main area of use of these secondary metabolites is the therapy of infectious diseases. However, owing to the wide use, there is frequently development of resistance so that there is a continuous need for novel antibiotics and active substances with novel mechanisms of action (Neu H. C., Science 257, 1992, pages 1064-1073). A therapeutically adequate effect on penicillin- or methicillin-resistant strains (MRSA strains) which have developed further antibiotic resistances is often possessed only by glycopeptides such as vancomycin or teicoplanin. However, strains also resistant to these antibiotics are increasingly appearing (FEMS Microbiol. Lett. 98 (1992) 5 109 to 116).

Antibiotics from the class of the lipopeptides, which are characterized by a linear or cyclic peptide portion or a combination of both, with naturally and/or non-naturally derivatized and/or non-derivatized amino acids, with which a saturated or unsaturated acyl residue is connected, have been found in the past as effective against fungi and Gram-positive bacteria. One example of such a lipopeptide is Friulimicin B, shown below.

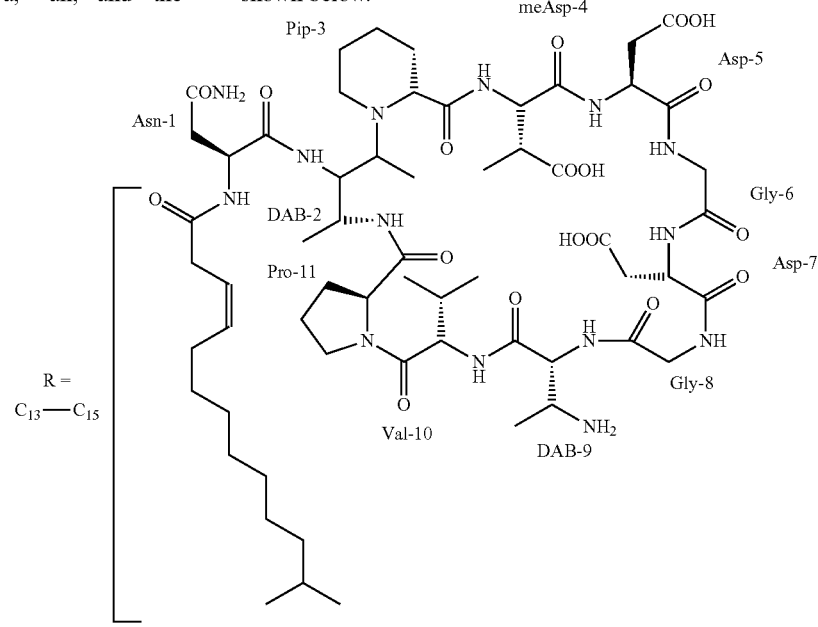

For the majority of these compounds, however, toxic properties are also known.

European Patent Application No. 0 629 636 proposes lipopeptides which have homologous amino acid sequences but different fatty acid residues (lipid portion) and which are synthesized by *Actinoplanes* sp. during the fermentation and released into the culture medium, as well as a process for isolating the lipopeptides from the culture medium, their purification and the use of the lipopeptides as pharmacological active substances, in particular against Gram-positive bacteria. However, these lipopeptides exhibit toxic properties, in particular hemolysis.

There remains a need to provide pharmacologically active substances that can be used in the treatment of bacterial infection, particularly resistant strains (e.g. MRSA), whilst avoiding the toxic effects discussed above.

SUMMARY OF THE INVENTION

One aspect of the invention pertains to certain lipopeptide compounds related to friulimicin but with modified acyl side chains, as described herein. For convenience, these compounds are collectively referred to herein as "LP compounds".

Another aspect of the invention pertains to a composition (e.g., a pharmaceutical composition) comprising a LP compound, as described herein, and a pharmaceutically acceptable carrier or diluent.

Another aspect of the invention pertains to method of preparing a composition (e.g., a pharmaceutical composition) comprising the step of admixing a LP compounds, as described herein, and a pharmaceutically acceptable carrier or diluent.

Another aspect of the present invention pertains to a method of killing microbes in a host (e.g. a subject/patient), in vitro or in vivo, comprising contacting the host with an effective amount of a LP compound, as described herein. Thus, the present invention is concerned with providing an antimicrobial action (e.g. an antibacterial and/or antifungal action).

Another aspect of the present invention pertains to a method of inhibiting (e.g. reducing or preventing) growth or reproduction of bacteria, killing bacteria, or a combination of both these, in vitro or in vivo, comprising contacting a host (e.g. a subject/patient) with an effective amount of a LP compound, as described herein.

In one embodiment, the method further comprises contacting the host with one or more other antibacterial agents.

Another aspect of the present invention pertains to a method of killing bacteria in a host (e.g. a subject/patient), in vitro or in vivo, comprising contacting the host with an effective amount of a LP compound, as described herein.

In one embodiment, the method further comprises contacting the host with one or more other antibacterial agents.

Another aspect of the present invention pertains to a bacteriocidal method using an effective amount of a LP compound.

Another aspect of the present invention pertains to a method of reducing or preventing the growth or reproduction of bacteria in a host (e.g. a subject/patient), in vitro or in vivo, comprising contacting the host with an effective amount of a LP compound, as described herein.

In one embodiment, the method further comprises contacting the host with one or more other antibacterial agents.

Another aspect of the present invention pertains to a bacteriostatic method using an effective amount of a LP compound.

Another aspect of the present invention pertains to a method of treatment comprising administering to a subject in need of treatment a therapeutically-effective amount of a LP compound, as described herein, preferably in the form of a pharmaceutical composition.

In one embodiment, the method further comprises administering to the subject one or more other antibacterial agents.

Another aspect of the present invention pertains to a LP compound as described herein for use in a method of treatment of the human or animal body by therapy.

In one embodiment, the method of treatment comprises treatment with both (i) a LP compound as described herein and (ii) one or more other antibacterial agents.

Another aspect of the present invention pertains to use of a LP compound, as described herein, in the manufacture of a medicament for use in treatment.

In one embodiment, the treatment comprises treatment with both (i) a medicament comprising a LP compound as described herein and (ii) one or more other antibacterial agents.

In one embodiment, the treatment is treatment of a disease or condition that is mediated or caused by bacteria.

In one embodiment, the treatment is treatment of a disease or condition that is ameliorated by the inhibition of bacteria growth or reproduction and/or bacteria death.

In one embodiment, the treatment is treatment of a bacterial infection.

In one embodiment, the treatment is treatment of a bacterial disease.

Another aspect of the present invention pertains to a kit comprising (a) a LP compound, as described herein, preferably provided as a pharmaceutical composition and in a suitable container and/or with suitable packaging; and (b) instructions for use, for example, written instructions on how to administer the compound.

In one embodiment, the kit further comprises one or more other antibacterial agents.

Another aspect of the present invention pertains to a LP compound obtainable by a method of synthesis as described herein, or a method comprising a method of synthesis as described herein.

Another aspect of the present invention pertains to a LP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

Another aspect of the present invention pertains to a method of synthesis of a LP compound, as described herein.

Another aspect of the present invention pertains to a method of forming a lipopeptide having an acyl side chain (e.g. a LP compound, as described herein), wherein the method comprises the step of reacting an ester precursor of the acyl side chain with a lipopeptide in the presence of calcium chloride.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain lipopeptide compounds related structurally to friulimicin but containing modified acyl side chains (for convenience, collectively referred to herein as "LP compounds").

In one embodiment, the compounds are selected from compounds of the following formula, and pharmaceutically acceptable salts, hydrates, and solvates thereof:

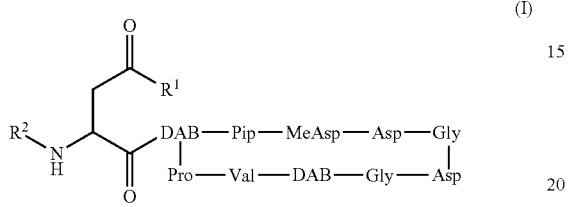

(I)

wherein:
—$R^1$ is independently —OH or —$NH_2$
and wherein:
—$R^2$ is independently —$R^A$ or —$R^B$
  wherein:
    —$R^A$ is independently $R^{A4}$—$R^{A3}$-$L^{A2}$-$R^{A2}$-$L^{A1}$-$R^{A1}$—C(O)—
      wherein:
        each of —$R^{A1}$—, —$R^{A2}$—, and —$R^{A3}$— is independently phenylene and is optionally substituted
        and wherein:
        each of -$L^{A1}$- and -$L^{A2}$- is independently -$L^S$- or -$L^{AA}$-
          wherein:
            each -$L^S$-, if present, is independently a single bond
            and wherein:
            each -$L^{AA}$-, if present, is independently saturated aliphatic $C_{1-4}$alkylene, and is optionally substituted
        and wherein:
        —$R^{A4}$ is independently —$R^{A4X}$, —$R^{A4A}$ or —$R^{A4O}$
          wherein:
            —$R^{A4X}$, if present, is independently halo
            and wherein:
            —$R^{A4A}$, if present, is independently saturated or unsaturated aliphatic or alicyclic $C_{1-10}$alkyl, and is optionally substituted
            and wherein:
            —$R^{A4O}$, if present, is independently saturated or unsaturated aliphatic or alicyclic $C_{1-10}$alkoxy, and is optionally substituted
    and wherein:
    —$R^B$ is independently $R^{B4}$—$R^{B3}$-$L^{B2}$-$R^{B2}$-$L^{B1}$-$R^{B1}$—C(O)—
      wherein:
        —$R^{B1}$— is independently —$R^{BP}$— or —$R^{BN}$—,
        and wherein:
        each of —$R^{B2}$—, and —$R^{B3}$— is independently —$R^{BS}$—, —$R^{BP}$—, —$R^{BN}$— or —$R^{BH}$—,
        and wherein:
        either
          (A) at least one of —$R^{B1}$—, —$R^{B2}$—, and —$R^{B3}$— is independently —$R^{BN}$—;
          or
          (B) at least one of —$R^{B2}$— and —$R^{B3}$— is independently —$R^{BH}$—
        wherein:
          each —$R^{BP}$—, if present, is independently phenylene, and is optionally substituted
          and wherein:
          each —$R^{BN}$—, if present, is independently naphthylene, and is optionally substituted
          and wherein:
          each —$R^{BH}$—, if present, is independently aromatic or saturated or unsaturated non-aromatic $C_{4-14}$ heterocyclylene, and is optionally substituted
          and wherein:
          each —$R^{BS}$—, if present, is independently a single bond
        and wherein:
        each of -$L^{B1}$- and -$L^{B2}$- is independently -$L^S$-, -$L^{BB}$- or -$L^{BO}$-
          wherein:
            each -$L^S$-, if present, is independently a single bond
            and wherein:
            each -$L^{BB}$-, if present, is independently saturated aliphatic $C_{1-4}$alkylene, and is optionally substituted
            and wherein:
            each -$L^{BO}$-, if present, is independently saturated aliphatic $C_{1-4}$alkoxylene, and is optionally substituted
        and wherein:
        —$R^{B4}$ is independently —H, —$R^{B4A}$, —$R^{B4AA}$ or —$R^{B4O}$
          wherein:
            —$R^{B4A}$, if present, is independently saturated or unsaturated aliphatic or alicyclic $C_{1-10}$alkyl, and is optionally substituted
            and wherein:
            —$R^{B4AA}$, if present, is independently $C_{6-10}$aryl-$C_{1-6}$alkyl, and is optionally substituted
            and wherein:
            —$R^{B4O}$, if present, is independently —$R^{B4O1}$ or $R^{B4O2}$
              wherein:
                —$R^{B4O1}$, if present, is independently saturated or unsaturated aliphatic or alicyclic $C_{1-10}$alkoxy, and is optionally substituted
                and wherein:
                —$R^{B4O2}$, if present, is independently $C_{6-10}$aryloxy, and is optionally substituted.

For the avoidance of doubt, the indices such as "$C_{4-7}$" in terms such as "$C_{4-14}$ heterocyclylene" refer to the number of ring atoms, whether carbon atoms or heteroatoms. For example, cyclohexylene, piperidinylene, pyridinylene and piperazinylene are example of a $C_6$cyclylene group.

For the avoidance of doubt, it is not intended that the groups —$R^1$ and —$R^2$ are linked, other than via the acyl chain as shown in the above formula.

For the avoidance of doubt, where two or more neighbouring groups are each a single bond, they form only one single bond.

The Group —$R^1$

In one embodiment, —$R^1$ is independently —OH or —$NH_2$.
In one embodiment, —$R^1$ is independently —OH.
In one embodiment, —$R^1$ is independently —$NH_2$.

The Group —$R^2$

In one embodiment, —$R^2$ is independently —$R^A$ or —$R^B$.
In one embodiment, —$R^2$ is independently —$R^A$.
In one embodiment, —$R^2$ is independently —$R^B$.

The Group —$R^A$

In one embodiment, —$R^A$ is independently $R^{A4}$—$R^{A3}$-$L^{A2}$-$R^{A2}$-$L^{A1}$-$R^{A1}$—C(O)—.

The Groups —$R^{A1}$—, —$R^{A2}$—, and —$R^{A3}$—

In one embodiment, each of —$R^{A1}$—, —$R^{A2}$—, and —$R^{A3}$— is independently phenylene and is optionally substituted.

In one embodiment, each of —$R^{A1}$—, —$R^{A2}$—, and —$R^{A3}$— is independently

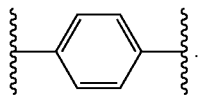

In one embodiment, —$R^{A1}$— is independently phenylene and is optionally substituted.

In one embodiment, —$R^{A2}$— is independently phenylene and is optionally substituted.

In one embodiment, —$R^{A3}$— is independently phenylene and is optionally substituted.

In one embodiment, —$R^{A1}$— is independently

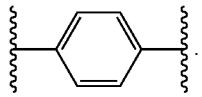

In one embodiment, —$R^{A2}$— is independently

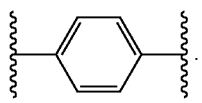

In one embodiment, —$R^{A3}$— is independently

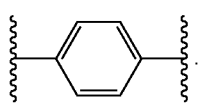

The Groups -$L^{A1}$- and -$L^{A2}$-

In one embodiment, each of -$L^{A1}$- and -$L^{A2}$- is independently -$L^S$- or -$L^{AA}$-.

In one embodiment, each of -$L^{A1}$- and -$L^{A2}$- is independently -$L^S$-.

In one embodiment, each of -$L^{A1}$- and -$L^{A2}$- is independently -$L^{AA}$-.

In one embodiment, -$L^{A1}$- is independently -$L^S$-.
In one embodiment, -$L^{A1}$- is independently -$L^{AA}$-.
In one embodiment, -$L^{A2}$- is independently -$L^S$-.
In one embodiment, -$L^{A2}$- is independently -$L^{AA}$-.

The Group -$L^S$-

In one embodiment, each -$L^S$-, if present, is independently a single bond.

The Group -$L^{AA}$-

In one embodiment, each -$L^{AA}$-, if present, is independently saturated aliphatic $C_{1-4}$alkylene, and is optionally substituted.

In one embodiment, each -$L^{AA}$-, if present, is independently saturated linear $C_{1-4}$alkylene, and is optionally substituted.

In one embodiment, each -$L^{AA}$-, if present, is independently —$CH_2$— or —$CH_2$—$CH_2$—.

In one embodiment, each -$L^{AA}$-, if present, is independently —$CH_2$—.

In one embodiment, each -$L^{AA}$-, if present, is independently —$CH_2$—$CH_2$—.

The Group —$R^{A4}$

In one embodiment, —$R^{A4}$ is independently —$R^{A4X}$, —$R^{A4A}$ or —$R^{A4O}$.

In one embodiment, —$R^{A4}$ is independently —$R^{A4X}$.
In one embodiment, —$R^{A4}$ is independently —$R^{A4A}$.
In one embodiment, —$R^{A4}$ is independently —$R^{A4O}$.

The Group —$R^{A4X}$

In one embodiment, —$R^{A4X}$, if present, is independently halo.

In one embodiment, —$R^{A4X}$, if present, is independently —F, —Cl, —Br or —I.

In one embodiment, —$R^{A4X}$, if present, is independently —F, —Cl or —Br.

In one embodiment, —$R^{A4X}$, if present, is independently —F or —Cl.

In one embodiment, —$R^{A4X}$, if present, is independently —F.

In one embodiment, —$R^{A4X}$, if present, is independently —Cl.

In one embodiment, —$R^{A4X}$, if present, is independently —Br.

In one embodiment, —$R^{A4X}$, if present, is independently —I.

The Group —$R^{A4A}$

In one embodiment, —$R^{A4A}$, if present, is independently saturated or unsaturated aliphatic or alicyclic $C_{1-10}$alkyl, and is optionally substituted.

In one embodiment, —$R^{A4A}$, if present, is independently saturated or unsaturated aliphatic or alicyclic $C_{1-6}$alkyl, and is optionally substituted.

In one embodiment, —$R^{A4A}$, if present, is independently saturated or unsaturated aliphatic $C_{1-5}$alkyl, and is optionally substituted.

In one embodiment, —$R^{A4A}$, if present, is independently saturated or unsaturated aliphatic $C_{1-4}$alkyl, and is optionally substituted.

In one embodiment, —$R^{A4A}$, if present, is independently saturated or unsaturated linear $C_{1-4}$alkyl, and is optionally substituted.

In one embodiment, —$R^{A4A}$, if present, is independently saturated linear $C_{1-4}$alkyl, and is optionally substituted.

In one embodiment, —$R^{A4A}$, if present, is independently saturated $C_{1-2}$alkyl, and is optionally substituted.

In one embodiment, —$R^{A4A}$, if present, is independently —$CH_3$ or —$CH_2$—$CH_2$—$CH_2$—$CH_3$.

In one embodiment, —$R^{A4A}$, if present, is independently —$CH_3$.

In one embodiment, —$R^{A4A}$, if present, is independently —$CH_2$—$CH_2$—$CH_2$—$CH_3$.

The Group —$R^{A4O}$

In one embodiment, —$R^{A4O}$, if present, is independently saturated or unsaturated aliphatic or alicyclic $C_{1-10}$alkoxy, and is optionally substituted.

In one embodiment, —$R^{A4O}$, if present, is independently saturated or unsaturated aliphatic $C_{1-10}$alkoxy, and is optionally substituted.

In one embodiment, —$R^{A4O}$, if present, is independently saturated or unsaturated aliphatic $C_{1-7}$alkoxy, and is optionally substituted.

In one embodiment, —$R^{A4O}$, if present, is independently saturated aliphatic $C_{1-7}$alkoxy, and is optionally substituted.

In one embodiment, $-R^{44O}$, if present, is independently saturated aliphatic $C_{1-3}$alkoxy, and is optionally substituted.

In one embodiment, $-R^{44O}$, if present, is independently saturated aliphatic $C_{5-7}$alkoxy, and is optionally substituted.

In one embodiment, $-R^{44O}$, if present, is independently $-O-CH_3$, $-O-CH_2-CH_2-CH_3$, $-O-CH_2-CH_2-CH_2-CH_2-CH_3$, $-O-CH_2-CH_2-CH_2-CH_2-CH_2-CH_3$, or $-O-CH_2-CH_2-CH_2-CH_2-CH_2-CH_2-CH_3$.

In one embodiment, $-R^{44O}$, if present, is independently $-O-CH_3$.

In one embodiment, $-R^{44O}$, if present, is independently $-O-CH_2-CH_2-CH_3$.

In one embodiment, $-R^{44O}$, if present, is independently $-O-CH_2-CH_2-CH_2-CH_2-CH_3$.

In one embodiment, $-R^{44O}$, if present, is independently $-O-CH_2-CH_2-CH_2-CH_2-CH_2-CH_3$.

In one embodiment, $-R^{44O}$, if present, is independently $-O-CH_2-CH_2-CH_2-CH_2-CH_2-CH_2-CH_3$.

The Group $-R^B$

In one embodiment, $-R^B$ is independently $R^{B4}-R^{B3}-L^{B2}-R^{B2}-L^{B1}-R^{B1}-C(O)-$.

The Groups $-R^{B1}-$, $R^{B2}-$, and $-R^{B3}-$

In one embodiment, $-R^{B1}-$ is independently $-R^{BP}-$ or $-R^{BN}-$ and each of $-R^{B2}-$ and $-R^{B3}-$ is independently $-R^{BS}-$, $-R^{BP}-$, $-R^{BN}-$ or $-R^{BH}-$, wherein either (A) at least one of $-R^{B1}-$, $R^{B2}-$, and $-R^{B3}-$ is independently $-R^{BN}-$; or (B) at least one of $-R^{B2}-$ and $-R^{B3}-$ is independently $-R^{BH}-$ In one embodiment, $-R^{B1}-$ is independently $-R^{BP}-$ or $-R^{BN}-$, and each of $-R^{B2}-$ and $-R^{B3}-$ is independently $-R^{BS}-$, $-R^{BP}-$, $-R^{BN}-$ or $-R^{BH}-$, wherein at least one of $-R^{B1}-$, $-R^{B2}-$, and $-R^{B3}-$ is independently $-R^{BN}-$.

In one embodiment, $-R^{B1}-$ is independently $-R^{BP}-$ or $-R^{BN}-$, and each of $-R^{B2}-$ and $-R^{B3}-$ is independently $-R^{BS}$, $-R^{BN}-$ or $-R^{BH}-$, wherein at least one of $-R^{B2}-$, and $-R^{B3}-$ is independently $-R^{BH}-$.

In one embodiment, $-R^{B1}-$ is independently $-R^{BP}-$ or $-R^{BN}-$, wherein at least one of $-R^{B2}-$, and $-R^{B3}-$ is independently $-R^{BH}-$ and wherein at least one of $-R^{B2}-$, and $-R^{B3}-$ is independently $-R^{BP}-$.

In one embodiment, $-R^{B1}-$ is independently $-R^{BP}-$, and each of $-R^{B2}-$ and $-R^{B3}-$ is independently $-R^{BP}-$, $-R^{BN}-$ or $-R^{BH}-$, wherein at least one of $-R^{B2}-$, and $-R^{B3}-$ is independently $-R^{BN}-$.

In one embodiment, $-R^{B1}-$ is independently $-R^{BP}-$, and each of $-R^{B2}-$ and $-R^{B3}-$ is independently $-R^{BP}-$, $-R^{BN}-$ or $-R^{BP}-$, wherein at least one of $-R^{B2}-$, and $-R^{B3}-$ is independently $-R^{BH}-$.

In one embodiment, $-R^{B1}-$ is independently $-R^{BP}-$, and at least one of $-R^{B2}-$, and $-R^{B3}-$ is independently $-R^{BN}-$ and the other is independently $-R^{BP}-$.

In one embodiment, $-R^{B1}-$ is independently $-R^{BP}-$, and at least one of $-R^{B2}-$, and $-R^{B3}-$ is independently $-R^{BN}-$ and the other is independently $-R^{BP}-$.

In one embodiment, $-R^{B1}-$ is independently $-R^{BN}-$, and each of $-R^{B2}-$ and $-R^{B3}-$ is independently $-R^{BS}-$, $-R^{BP}-$ or $-R^{BN}-$.

In one embodiment, $-R^{B1}-$ is independently $-R^{BN}-$, and each of $-R^{B2}-$ and $-R^{B3}-$ is independently $-R^{BP}-$ or $-R^{BN}-$.

In one embodiment, $-R^{B1}-$ is independently $-R^{BN}-$, and each of $-R^{B2}-$ and $-R^{B3}-$ is independently $-R^{BP}-$.

In one embodiment, $-R^{BS}-$ is independently $-R^{BN}-$, and each of $-R^{B2}-$ and $-R^{B3}-$ is independently $-R^{BS}-$.

In one embodiment, one of $-R^{B1}-$, $-R^{B2}-$, and $-R^{B3}-$ is independently $-R^{BN}-$ and the other two are independently $-R^{BS}-$ or $-R^{BP}-$.

In one embodiment, one of $-R^{B1}-$, $R^{B2}-$, and $-R^{B3}-$ is independently $-R^{BN}-$ and the other two are independently $-R^{BS}-$.

In one embodiment, one of $-R^{B1}-$ $R^{B2}-$, and $-R^{B3}-$ is independently $-R^{BN}-$ and the other two are independently $-R^{BP}-$.

In one embodiment, $-R^{B1}-$ is independently $-R^{BP}-$.
In one embodiment, $-R^{B1}-$ is independently $-R^{BN}-$.
In one embodiment, $-R^{B2}-$ is independently $-R^{BS}-$.
In one embodiment, $-R^{B2}-$ is independently $-R^{BP}-$.
In one embodiment, $-R^{B2}-$ is independently $-R^{BN}-$.
In one embodiment, $-R^{B2}-$ is independently $-R^{BH}-$.
In one embodiment, $-R^{B3}-$ is independently $-R^{BS}-$.
In one embodiment, $-R^{B3}-$ is independently $-R^{BP}-$.
In one embodiment, $-R^{B3}-$ is independently $-R^{BN}-$.
In one embodiment, $-R^{B3}-$ is independently $-R^{BH}-$.
In one embodiment, $-R^{B1}-$ is independently $-R^{BP}-$, is independently $-R^{BH}-$ and $-R^{B3}-$ is independently $-R^{BP}-$.

In one embodiment, (A) $-R^{B1}-$ is independently $-R^{BP}-$, $-R^{B2}-$ is independently $-R^{BH}-$ and $-R^{B3}-$ is independently $-R^{BP}-$, or (B) one of $-R^{B1}-$, $-R^{B2}-$, and $-R^{B3}-$ is independently $-R^{BN}-$ and the other two are independently $-R^{BP}-$.

The Group $-R^{BS}-$

In one embodiment, each $-R^{BS}-$, if present, is independently a single bond.

The Group $-R^{BP}-$

In one embodiment, each $-R^{BP}-$, if present, is independently phenylene, and is optionally substituted.

In one embodiment, each $-R^{BP}-$, if present, is independently

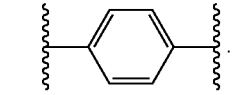

The Group $-R^{BN}-$

In one embodiment, each $-R^{BN}-$, if present, is independently naphthylene, and is optionally substituted.

In one embodiment, each $-R^{BN}-$, if present, is independently

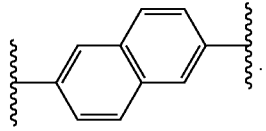 [SMILES: *c1ccc2cc(*)ccc2c1]

The Group $-R^{BH}-$

In one embodiment, each $-R^{BH}-$, if present, is independently aromatic or saturated or unsaturated non-aromatic $C_{4-14}$ heterocyclylene, and is optionally substituted.

In one embodiment, each $-R^{BH}-$, if present, is independently aromatic or saturated or unsaturated non-aromatic $C_{4-10}$ heterocyclylene, and is optionally substituted.

In one embodiment, each $-R^{BH}-$, if present, is independently aromatic or saturated or unsaturated non-aromatic $C_{4-6}$ heterocyclylene, and is optionally substituted.

In one embodiment, each —R$^{BH}$—, if present, is independently aromatic or saturated or unsaturated non-aromatic C$_{5-6}$ heterocyclylene, and is optionally substituted.

In one embodiment, each —R$^{BH}$—, if present, is independently aromatic or unsaturated non-aromatic C$_5$ heterocyclylene, and is optionally substituted.

In one embodiment, each —R$^{BH}$—, if present, is independently aromatic or saturated or unsaturated non-aromatic C$_{4-10}$ heterocyclylene, wherein at least one ring atom is N, and is optionally substituted.

In one embodiment, each —R$^{BH}$—, if present, is independently aromatic or saturated or unsaturated non-aromatic C$_{4-10}$ heterocyclylene, wherein at least one ring atom is O, and is optionally substituted.

In one embodiment, each —R$^{BH}$—, if present, is independently aromatic or saturated or unsaturated non-aromatic C$_{4-10}$ heterocyclylene, wherein at least one ring atom is S, and is optionally substituted.

In one embodiment, each —R$^{BH}$—, if present, is independently aromatic or unsaturated non-aromatic C$_{5-6}$ heterocyclylene containing at least one of N, O or S as a ring atom, and is optionally substituted.

In one embodiment, each —R$^{BH}$—, if present, is independently aromatic or unsaturated non-aromatic C$_{5-6}$ heterocyclylene containing at least one N as a ring atom, and is optionally substituted.

In one embodiment, each —R$^{BH}$—, if present, is independently aromatic or unsaturated non-aromatic C$_{5-6}$ heterocyclylene containing at least one N and one O as ring atoms, and is optionally substituted.

In one embodiment, each —R$^{BH}$—, if present, is independently isoxazolylene, oxazolylene, thiazolylene, pyrazolylene, imidazolylene, pyrrolyl, indazolyl, triazolyl, tetrazolyl, oxadiazolylene, pyridinylene or piperazinylene, pyrimidinyl, Pyrazinyl, thiadiazolyl oxadiazolylene, pyridinylene or piperazinylene, and is optionally substituted.

In one embodiment, each —R$^{BH}$—, if present, is independently isoxazolylene, oxazolylene, thiazolylene, pyrazolylene, imidazolylene, oxadiazolylene or pyridinylene, and is optionally substituted.

In one embodiment, each —R$^{BH}$, if present, is independently isoxazolylene, and is optionally substituted.

In one embodiment, each —R$^{BH}$, if present, is independently

The Groups -L$^{B1}$- and -L$^{B2}$-

In one embodiment, each of -L$^{B1}$- and -L$^{B2}$- is independently -L$^S$-, -L$^{BB}$- or -L$^{BO}$-.

In one embodiment, each of -L$^{B1}$- and -L$^{B2}$- is independently -L$^S$-.

In one embodiment, each of -L$^{B1}$- and -L$^{B2}$- is independently -L$^{BB}$-.

In one embodiment, each of -L$^{B1}$- and -L$^{B2}$- is independently -L$^{BO}$-.

In one embodiment, -L$^{B1}$- is independently -L$^S$-.
In one embodiment, -L$^{B1}$- is independently -L$^{BB}$-.
In one embodiment, -L$^{B1}$- is independently -L$^{BO}$-.
In one embodiment, -L$^{B2}$- is independently -L$^S$-.
In one embodiment, -L$^{B2}$- is independently -L$^{BB}$-.
In one embodiment, -L$^{B2}$- is independently -L$^{BO}$-.

The Group -L$^S$-

In one embodiment, each -L$^S$-, if present, is independently a single bond.

The Group -L$^{BB}$-

In one embodiment, each -L$^{BB}$-, if present, is independently saturated aliphatic C$_{1-4}$alkylene, and is optionally substituted.

In one embodiment, each -L$^{BB}$-, if present, is independently saturated aliphatic C$_{1-2}$alkylene, and is optionally substituted.

In one embodiment, each -L$^{BB}$-, if present, is independently —CH$_2$—CH$_2$—.

The Group -L$^{BO}$-

In one embodiment, each -L$^{BO}$-, if present, is independently saturated aliphatic C$_{1-4}$alkoxylene, and is optionally substituted.

In one embodiment, each -L$^{BO}$-, if present, is independently saturated aliphatic C$_{1-2}$alkoxylene, and is optionally substituted.

In one embodiment, each -L$^{BO}$-, if present, is independently —CH$_2$—O—.

The Group —R$^{B4}$—

In one embodiment, —R$^{B4}$ is independently —H, —R$^{B4A}$, —R$^{B4AA}$ or —R$^{B4O}$.

In one embodiment, —R$^{B4}$ is independently —H.
In one embodiment, —R$^{B4}$ is independently —R$^{B4A}$.
In one embodiment, —R$^{B4}$ is independently —R$^{B4AA}$.
In one embodiment, —R$^{B4}$ is independently —R$^{B4O}$.

The Group —R$^{B4A}$

In one embodiment, —R$^{B4A}$, if present, is independently saturated or unsaturated aliphatic or alicyclic C$_{1-10}$alkyl, and is optionally substituted.

In one embodiment, —$R^{B4A}$, if present, is independently saturated or unsaturated aliphatic or alicyclic $C_{1-8}$alkyl, and is optionally substituted.

In one embodiment, —$R^{B4A}$, if present, is independently saturated or unsaturated aliphatic or alicyclic $C_{2-8}$alkyl, and is optionally substituted.

In one embodiment, —$R^{B4A}$, if present, is independently saturated or unsaturated aliphatic or alicyclic $C_{3-8}$alkyl, and is optionally substituted.

In one embodiment, —$R^{B4A}$, if present, is independently saturated aliphatic $C_{3-8}$alkyl, and is optionally substituted.

In one embodiment, —$R^{B4A}$, if present, is independently saturated linear $C_{3-8}$alkyl, and is optionally substituted.

In one embodiment, —$R^{B4A}$, if present, is independently saturated alicyclic $C_{3-8}$alkyl, and is optionally substituted.

In one embodiment, —$R^{B4A}$, if present, is independently cyclohexyl, and is optionally substituted.

The Group —$R^{B4AA}$

In one embodiment, —$R^{B4AA}$, if present, is independently $C_{6-10}$aryl-$C_{1-6}$alkyl, and is optionally substituted.

In one embodiment, —$R^{B4AA}$, if present, is independently $C_6$aryl-$C_{1-6}$alkyl, and is optionally substituted.

In one embodiment, —$R^{B4AA}$, if present, is independently $C_6$aryl-$C_{1-2}$alkyl, and is optionally substituted.

In one embodiment, —$R^{B4AA}$, if present, is independently

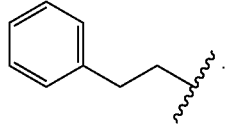

The Group —$R^{B4O}$

In one embodiment, —$R^{B4O}$, if present, is independently —$R^{B4O1}$ or $R^{B4O2}$.

In one embodiment, —$R^{B4O}$, if present, is independently —$R^{B4O1}$.

In one embodiment, —$R^{B4O}$, if present, is independently —$R^{B4O2}$.

The Group —$R^{B4O1}$

In one embodiment, —$R^{B4O1}$, if present, is independently saturated or unsaturated aliphatic or alicyclic $C_{1-10}$alkoxy, and is optionally substituted.

In one embodiment, —$R^{B4O1}$, if present, is independently saturated or unsaturated aliphatic $C_{1-10}$alkoxy, and is optionally substituted.

In one embodiment, —$R^{B4O1}$, if present, is independently saturated or unsaturated aliphatic $C_{3-8}$alkoxy, and is optionally substituted.

In one embodiment, —$R^{B4O1}$, if present, is independently saturated or unsaturated aliphatic $C_{4-7}$alkoxy, and is optionally substituted.

In one embodiment, —$R^{B4O1}$, if present, is independently saturated or unsaturated aliphatic $C_{5-7}$alkoxy, and is optionally substituted.

In one embodiment, —$R^{B4O1}$, if present, is independently saturated or unsaturated aliphatic $C_6$alkoxy, and is optionally substituted.

In one embodiment, —$R^{B4O1}$, if present, is independently —O—$(CH_2)_3$—$CH_3$, —O—$(CH_2)_4$—$CH_3$, —O—$(CH_2)_5$—$CH_3$ or —O—$(CH_2)_6$—$CH_3$.

In one embodiment, —$R^{B4O1}$, if present, is independently —O—$(CH_2)_3$—$CH_3$.

In one embodiment, —$R^{B4O1}$, if present, is independently —O—$(CH_2)_4$—$CH_3$.

In one embodiment, —$R^{B4O1}$, if present, is independently —O—$(CH_2)_5$—$CH_3$.

In one embodiment, —$R^{B4O1}$, if present, is independently —O—$(CH_2)_6$—$CH_3$.

The Group —$R^{B4O2}$

In one embodiment, —$R^{B4O2}$, if present, is independently $C_{6-10}$aryloxy, and is optionally substituted.

In one embodiment, —$R^{B4O2}$, if present, is independently $C_6$aryloxy, and is optionally substituted.

In one embodiment, —$R^{B4O2}$, if present, is independently

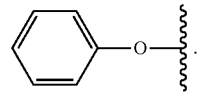

Optional Substituents on -$L^{AA}$-, -$L^{BB}$- and -$L^{BO}$-

In one embodiment, -$L^{AA}$-, if present, is independently unsubstituted.

In one embodiment, -$L^{AA}$-, if present, is independently optionally substituted with one or more substituents, —$R^{S1}$.

In one embodiment, -$L^{BB}$-, if present, is independently unsubstituted.

In one embodiment, -$L^{BB}$-, if present, is independently optionally substituted with one or more substituents, —$R^{S1}$.

In one embodiment, -$L^{BO}$, if present, is independently unsubstituted.

In one embodiment, -$L^{BO}$, if present, is independently optionally substituted with one or more substituents, —$R^{S1}$.

In one embodiment, each $R^{S1}$, if present, is independently selected from:
—$R^{SS1}$,
—F, —Cl, —Br, —I,
—$CF_3$, —$OCF_3$, —$SCF_3$,
—OH, -$L^{SS1}$-OH, —O-$L^{SS1}$-OH, —NH-$L^{SS1}$-OH, —$NR^{SS1}$-$L^{SS1}$-OH,
—$OR^{SS1}$,
—$NH_2$, —$NHR^{SS1}$, —$NR^{SS1}_2$; and
-$L^{SS1}$-$NH_2$, -$L^{SS1}$-$NHR^{SS1}$, -$L^{SS1}$-$NR^{SS1}_2$ In one embodiment, each $R^{S1}$, if present, is independently selected from:
—F, —Cl, —Br, —I, or
—OH, -$L^{SS1}$-OH,
—$OR^{SS1}$,
—$NH_2$; and
-$L^{SS1}$-$NH_2$ In one embodiment, each $R^{S1}$, if present; is independently selected from —$R^{SS1}$.

Optional Substituents on —$R^{A4A}$, —$R^{B4A}$, $R^{A4O}$, —$R^{B4O1}$, —$R^{B4O2}$ and —$R^{B4AA}$ In one embodiment, —$R^{A4A}$, if present, is independently unsubstituted.

In one embodiment, —$R^{A4A}$, if present, is independently optionally substituted with one or more substituents, —$R^{S2}$.

In one embodiment, —$R^{B4A}$, if present, is independently unsubstituted.

In one embodiment, —$R^{B4A}$, if present, is independently optionally substituted with one or more substituents, —$R^{S2}$.

In one embodiment, —$R^{A4O}$, if present, is independently unsubstituted.

In one embodiment, —$R^{A4O}$, if present, is independently optionally substituted with one or more substituents, —$R^{S2}$.

In one embodiment, —$R^{B4O1}$, if present, is independently unsubstituted.

In one embodiment, —$R^{B4O1}$, if present, is independently optionally substituted with one or more substituents, —$R^{S2}$.

In one embodiment, —R$^{B4O2}$, if present, is independently unsubstituted.

In one embodiment, —R$^{B4O2}$, if present, is independently optionally substituted with one or more substituents, —R$^{S2}$.

In one embodiment, —R$^{B4AA}$, if present, is independently unsubstituted.

In one embodiment, —R$^{B4AA}$, if present, is independently optionally substituted with one or more substituents, —R$^{S2}$.

In one embodiment, each —R$^{S2}$, if present, is independently selected from:
- —R$^{JA1}$,
- —F, —Cl, —Br, —I,
- —CF$_3$, —OCF$_3$, —SCF$_3$,
- —OH, -L$^{JA}$-OH, —O-L$^{JA}$-OH, —NH-L$^{JA}$-OH, —NR$^{JA1}$-L$^{JA}$-OH,
- —OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
- —SH, —SR$^{JA1}$,
- —CN,
- —NH$_2$, —NHR$^{JA1}$, —NR$^{JA1}$$_2$, —NR$^{JA2}$R$^{JA3}$,
- -L$^{JA}$-NH$_2$, -L$^{JA}$-NHR$^{JA1}$, -L$^{JA}$-NR$^{JA1}$$_2$, -L$^{JA}$-NR$^{JA2}$R$^{JA3}$,
- —O-L$^{JA}$-NH$_2$, —O-L$^{JA}$-NHR$^{JA1}$, —O-L$^{JA}$-NR$^{JA1}$$_2$, —O-L$^{JA}$-NR$^{JA2}$R$^{JA3}$,
- —NH-L$^{JA}$-NH$_2$, —NR$^{JA1}$-L$^{JA}$-NH$_2$, —NH-L$^{JA}$-NHR$^{JA1}$, —NR$^{JA1}$-L$^{JA}$-NHR$^{JA1}$,
- —NH-L$^{JA}$-NR$^{JA1}$$_2$, —NR$^{JA1}$-L$^{JA}$-NR$^{JA1}$$_2$,
- —NH-L$^{JA}$-NR$^{JA2}$R$^{JA3}$, —NR$^{JA1}$-L$^{JA}$-NR$^{JA2}$R$^{JA3}$,
- —OC(=O)R$^{JA1}$,
- —C(=O)OH, —C(=O)OR$^{JA1}$,
- —C(=O)R$^{JA1}$,
- —C(=O)NH$_2$, —C(=O)NHR$^{JA1}$, —C(=O)NR$^{JA1}$$_2$, —C(=O)NR$^{JA2}$R$^{JA3}$,
- —NHC(=O)R$^{JA1}$, —NR$^{JA1}$C(=O)R$^{JA1}$,
- —NHC(=O)OR$^{JA1}$, —NR$^{JA1}$C(=O)OR$^{JA1}$,
- —OC(=O)NH$_2$, —OC(=O)NHR$^{JA1}$, —OC(=O)NR$^{JA1}$$_2$, —OC(=O)NR$^{JA2}$R$^{JA3}$,
- —NHC(=O)NH$_2$, —NHC(=O)NHR$^{JA1}$,
- —NHC(=O)NR$^{JA1}$$_2$, —NHC(=O)NR$^{JA2}$R$^{JA3}$,
- —NR$^{JA1}$C(=O)NH$_2$, —NR$^{JA1}$C(=O)NHR$^{JA1}$,
- —NR$^{JA1}$C(=O)NR$^{JA1}$$_2$, —NR$^{JA1}$C(=O)NR$^{JA2}$R$^{JA3}$,
- —NHS(=O)$_2$R$^{JA1}$, —NR$^{JA1}$S(=O)$_2$R$^{JA1}$,
- —S(=O)$_2$NH$_2$, —S(=O)$_2$NHR$^{JA1}$, —S(=O)$_2$NR$^{JA1}$$_2$, —S(=O)$_2$NR$^{JA2}$R$^{JA3}$,
- —S(=O)R$^{JA1}$, —S(=O)$_2$R$^{JA1}$, —OS(=O)$_2$R$^{JA1}$,
- —S(=O)$_2$OH, —S(=O)$_2$OR$^{JA1}$; and
- =O;

In one embodiment, each —R$^{S2}$, if present, is independently selected from:
- —R$^{JA1}$,
- —F, —Cl, —Br,
- —CF$_3$, —OCF$_3$,
- —OH, -L$^{JA}$-OH, —O-L$^{JA}$-OH,
- —OR$^{JA1}$, -L$^{JA}$-OR$^{JA1}$, —O-L$^{JA}$-OR$^{JA1}$,
- —CN,
- —NH$_2$, —NHR$^{JA1}$, —NR$^{JA1}$$_2$, —NR$^{JA2}$R$^{JA3}$,
- -L$^{JA}$-NH$_2$, -L$^{JA}$-NHR$^{JA1}$, -L$^{JA}$-NR$^{JA1}$$_2$, -L$^{JA}$-NR$^{JA2}$R$^{JA3}$,
- —C(=O)OH, —C(=O)OR$^{JA1}$,
- —C(=O)R$^{JA1}$,
- —C(=O)NH$_2$, —C(=O)NHR$^{JA1}$, —C(=O)NR$^{JA1}$$_2$, —C(=O)NR$^{JA2}$R$^{JA3}$,
- —NHC(=O)R$^{JA1}$, —NR$^{JA1}$C(=O)R$^{JA1}$,
- —NHC(=O)NH$_2$, —NHC(=O)NHR$^{JA1}$,
- —NHC(=O)NR$^{JA1}$$_2$, —NHC(=O)NR$^{JA2}$R$^{JA3}$,
- —NR$^{JA1}$C(=O)NH$_2$, —NR$^{JA1}$C(=O)NHR$^{JA1}$,
- —NR$^{JA1}$C(=O)NR$^{JA1}$$_2$, —NR$^{JA1}$C(=O)NR$^{JA2}$R$^{JA3}$,
- —NHS(=O)$_2$R$^{JA1}$, —NR$^{JA1}$S(=O)$_2$R$^{JA1}$,
- —S(=O)$_2$NH$_2$, —S(=O)$_2$NHR$^{JA1}$, —S(=O)$_2$NR$^{JA1}$$_2$, —S(=O)$_2$NR$^{JA2}$R$^{JA3}$,
- —S(=O)R$^{JA1}$, —S(=O)$_2$R$^{JA1}$, —OS(=O)$_2$R$^{JA1}$,
- —S(=O)$_2$OH, —S(=O)$_2$OR$^{JA1}$; and
- =O.

In one embodiment, each —R$^{S2}$, if present, is independently selected from:
- —R$^{JA1}$,
- —F, —Cl, —Br,
- —CF$_3$, —OCF$_3$, —SCF$_3$,
- —OH, -L$^{JA}$-OH, —O-L$^{JA}$-OH, —NH-L$^{JA}$-OH, —NR$^{JA1}$-L$^{JA}$-OH,
- —OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
- —SH, —SR$^{JA1}$,
- —CN,
- —NH$_2$, —NHR$^{JA1}$, —NR$^{JA1}$$_2$,
- -L$^{JA}$-NH$_2$, -L$^{JA}$-NHR$^{JA1}$, -L$^{JA}$-NR$^{JA1}$$_2$,
- —OC(O)R$^{JA1}$,
- —C(O)OH, —C(O)OR$^{JA1}$,
- —C(O)R$^{JA1}$,
- —C(O)NH$_2$, —C(O)NHR$^{JA1}$, —C(O)N(R$^{JA1}$)$_2$,
- —NHC(O)R$^{JA1}$, —NR$^{JA1}$C(O)R$^{JA1}$; and
- =O.

In one embodiment, each —R$^{S2}$, if present, is independently selected from:
- —R$^{SS1}$,
- —F, —Cl, —Br,
- —CF$_3$, —OCF$_3$, —SCF$_3$,
- —OH, -L$^{SS1}$-OH, —O-L$^{SS1}$-OH, —NH-L$^{SS1}$-OH, —NR$^{SS1}$-L$^{SS1}$-OH,
- —NH$_2$, —NHR$^{SS1}$, —NR$^{SS1}$$_2$,
- -L$^{SS1}$-NH$_2$, -L$^{SS1}$-NHR$^{SS1}$, -L$^{SS1}$-NR$^{SS1}$$_2$; and
- =O.

Optional Substituents on —R$^{A1}$—, R$^{A2}$—, —R$^{A3}$—, —R$^{BP}$— and R$^{BN}$—

In one embodiment, —R$^{A1}$—, if present, is independently unsubstituted.

In one embodiment, —R$^{A1}$— if present, is independently optionally substituted with one or more substituents, —R$^{S3}$.

In one embodiment, —R$^{A2}$—, if present, is independently unsubstituted.

In one embodiment, —R$^{A2}$—, if present, is independently optionally substituted with one or more substituents, —R$^{S3}$.

In one embodiment, —R$^{A3}$—, if present, is independently unsubstituted.

In one embodiment, —R$^{A3}$—, if present, is independently optionally substituted with one or more substituents, —R$^{S3}$.

In one embodiment, —R$^{BP}$—, if present, is independently unsubstituted.

In one embodiment, —R$^{BP}$—, if present, is independently optionally substituted with one or more substituents, —R$^{S3}$.

In one embodiment, —R$^{BN}$—, if present, is independently unsubstituted.

In one embodiment, —R$^{BP}$—, if present, is independently optionally substituted with one or more substituents, —R$^{S3}$.

In one embodiment, each R$^{S3}$, if present, is independently selected from:
- —R$^{JA1}$,
- —F, —Cl, —Br,
- —CF$_3$, —OCF$_3$, —SCF$_3$,
- —OH, -L$^{JA}$-OH, —O-L$^{JA}$-OH, —NH-L$^{JA}$-OH, —NR$^{JA1}$-L$^{JA}$-OH,
- —OR$^{JA1}$, -L$^{JA}$-OR$^{JA1}$, —O-L$^{JA}$-OR$^{JA1}$, —NH-L$^{JA}$-OR$^{JA1}$, —NR$_{JA1}$-L$^{JA}$-OR$^{JA1}$,
- —SH, —SR$^{JA1}$,
- —CN, —$NH_2$, —$NHR^{JA1}$, —$NR^{JA1}_2$,
-$L^{JA}$-$NH_2$, -$L^{JA}$-$NHR^{JA1}$, -$L^{JA}$-$NR^{JA1}_2$,
—$OC(O)R^{JA1}$,
—$C(O)OH$, —$C(O)OR^{JA1}$,
—$C(O)R^{JA1}$,
—$C(O)NH_2$, —$C(O)NHR^{JA1}$, —$C(O)N(R^{JA1})_2$; and
—$NHC(O)R^{JA1}$, —$NR^{JA1}C(O)R^{JA1}$.

In one embodiment, each $R^{S3}$, if present, is independently selected from:
—$R^{SS1}$,
—F, —Cl, —Br, —I; and
—OH Optional Substituents on —$R^{BH}$ In one embodiment, —$R^{BH}$—, if present, is independently unsubstituted.

In one embodiment, —$R^{BH}$—, if present, is optionally substituted with one or more substituents, —$R^{S4}$.

In one embodiment, each $R^{S4}$, if present, is independently selected from:
—$R^{JA1}$
—F, —Cl, —Br,
—$CF_3$, —$OCF_3$, —$SCF_3$,
—OH, -$L^{JA}$-OH, —O-$L^{JA}$-OH, —NH-$L^{JA}$-OH, —$NR^{JA1}$-$L^{JA}$-OH,
—$OR^{JA1}$, -$L^{JA}$-$OR^{JA1}$, —O-$L^{JA}$-$OR^{JA1}$, —NH-$L^{JA}$-$OR^{JA1}$,
—SH, —$SR^{JA1}$,
—CN,
—$NH_2$, —$NHR^{JA1}$, —$NR^{JA1}_2$,
-$L^{JA}$-$NH_2$, -$L^{JA}$-$NHR^{JA1}$, -$L^{JA}$-$NR^{JA1}_2$,
—$OC(O)R^{JA1}$,
—$C(O)OH$, —$C(O)OR^{JA1}$,
—$C(O)R^{JA1}$,
—$C(O)NH_2$, —$C(O)NHR^{JA1}$, —$C(O)N(R^{JA1})_2$; and
—$NHC(O)R^{JA1}$, —$NR^{JA1}C(O)R^{JA1}$.

In one embodiment, each $R^{S4}$, if present, is independently selected from:
—$R^{SS1}$,
—F, —Cl, —Br, —I; and
—OH Elements of the Optional Substituents —$R^{S2}$, —$R^{S3}$ and —$R^{S4}$ In one embodiment:
each -$L^{JA}$-, if present, is independently saturated aliphatic $C_{1-5}$alkylene;
each —$NR^{JA2}R^{JA3}$, if present, is independently $C_{4-7}$ heterocyclyl, and is optionally substituted, for example, with one or more groups selected from —$R^{J44}$, —$CF_3$, —F, —OH, —$OR^{J44}$, —$NH_2$, —$NHR^{J44}$, —$NR^{J44}_2$, and =O; wherein each —$R^{J44}$ is independently saturated aliphatic $C_{1-4}$alkyl;
each —$R^{JA1}$ is independently:
—$R^{JB1}$, —$R^{JB2}$, —$R^{JB3}$, —$R^{JB4}$, —$R^{JB5}$, —$R^{JB6}$, —$R^{JB7}$, —$R^{JB8}$,
-$L^{JB}$-$R^{JB4}$, -$L^{JB}$-$R^{JB5}$, -$L^{JB}$-$R^{JB6}$, -$L^{JB}$-$R^{JB7}$, or -$L^{JB}$-$R^{JB8}$;
each —$R^{JB1}$ is independently saturated aliphatic $C_{1-6}$alkyl;
each —$R^{JB2}$ is independently aliphatic $C_{2-6}$alkenyl;
each —$R^{JB3}$ is independently aliphatic $C_{2-6}$alkynyl;
each —$R^{JB4}$ is independently saturated $C_{3-6}$cycloalkyl;
each —$R^{JB5}$ is independently $C_{3-6}$cycloalkenyl;
each —$R^{JB6}$ is independently non-aromatic $C_{4-7}$ heterocyclyl;
each —$R^{JB7}$ is independently $C_{6-10}$-carboaryl;
each —$R^{JB8}$ is independently $C_{5-10}$heteroaryl;
each -$L^{JB}$- is independently saturated aliphatic $C_{1-3}$alkylene;

wherein:
each —$R^{JB4}$, —$R^{JB5}$, —$R^{JB6}$, —$R^{JB7}$, and —$R^{JB8}$ is optionally substituted, for example, with one or more substituents —$R^{JC1}$ and/or one or more substituents —$R^{JC2}$,
each —$R^{JB1}$, —$R^{JB2}$, —$R^{JB3}$, and -$L^{JB}$- is optionally substituted, for example, with one or more substituents —$R^{JB2}$, and wherein:
each —$R^{JC1}$ is independently saturated aliphatic $C_{1-4}$alkyl, phenyl, or benzyl;
each —$R^{JC2}$ is independently:
—F, —Cl, —Br,
—$CF_3$, —$OCF_3$,
—OH,
—CN,
—$NO_2$,
—$NH_2$,
—C(=O)OH,
—C(=O)$NH_2$.

In one embodiment, each -$L^{JA}$-, if present, is independently —$(CH_2)_{n2}$—, wherein n2 is independently 1 to 4.

In one embodiment, each -$L^{JA}$-, if present, is independently —$CH_2$— or —$CH_2CH_2$—.

In one embodiment, each —$NR^{JA2}R^{JA3}$, if present, is independently azetidino, pyrrolidine, imidazolidino, pyrazolidino, piperidino, piperazino, morpholino, azepino, or diazepino, and is optionally substituted, for example, with one or more groups selected from —$R^{J44}$, —$CF_3$, —F, —OH, —$OR^{J44}$, —$NH_2$, —$NHR^{J44}$, —$NR^{J44}_2$, and =O.

In one embodiment, each —$R^{JA1}$, if present, is independently:
—$R^{JB1}$, —$R^{JB4}$, —$R^{JB6}$, —$R^{JB7}$, —$R^{JB8}$,
-$L^{JB}$-$R^{JB4}$, -$L^{JB}$-$R^{JB6}$, -$L^{JB}$-$R^{JB7}$, or -$L^{JB}$-$R^{JB8}$.

In one embodiment, each —$R^{JA1}$, if present, is independently:
—$R^{JB1}$, —$R^{JB6}$, —$R^{JB7}$, —$R^{JB8}$,
-$L^{JB}$-$R^{JB6}$, -$L^{JB}$-$R^{JB7}$, -$L^{JB}$-$R^{JB6}$, or -$L^{JB}$-$R^{JB8}$.

In one embodiment, each —$R^{JA1}$, if present, is independently:
—$R^{JB1}$, —$R^{JB6}$, —$R^{JB7}$, or -$L^{JB}$-$R^{JB7}$.

In one embodiment, each —$R^{JB6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{JB6}$, if present, is independently pyrrolidinyl, piperidinyl, piperazinyl, morpholinyl, tetrahydrofuranyl, or tetrahydropyranyl, and is optionally substituted.

In one embodiment, each —$R^{JB7}$, if present, is independently phenyl, and is optionally substituted.

In one embodiment, each —$R^{JB8}$, if present, is independently $C_{5-6}$ heteroaryl, and is optionally substituted.

In one embodiment, each —$R^{JB8}$, if present, is independently $C_{9-10}$ heteroaryl, and is optionally substituted.

In one embodiment, each —$R^{JB8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyridazinyl, benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each —R$^{JB8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each -L$^{JB}$-, if present, is independently —CH$_2$— or —CH$_2$CH$_2$—.

In one embodiment, each -L$^{JB}$-, if present, is independently —CH$_2$—.

In one embodiment, each —R$^{SS1}$, if present, is independently saturated aliphatic C$_{1-6}$alkyl.

In one embodiment, each —R$^{SS1}$, if present, is independently saturated aliphatic C$_{1-3}$alkyl.

In one embodiment, each —R$^{SS1}$, if present, is independently -Me.

In one embodiment, each -L$^{SS1}$-, if present, is independently —(CH$_2$)$_n$—, wherein n is independently 1 to 4.

In one embodiment, each -L$^{SS1}$-, if present, is independently —CH$_2$— or —CH$_2$CH$_2$—.

EMBODIMENTS

In one embodiment, —R$^2$ is independently:

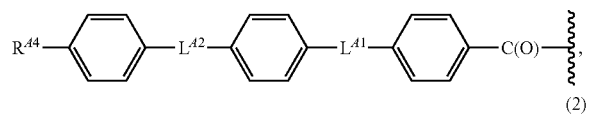
(1)

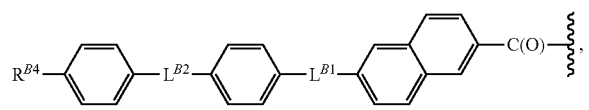
(2)

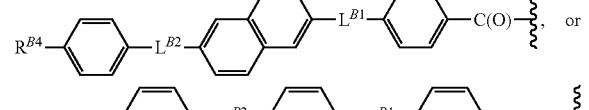

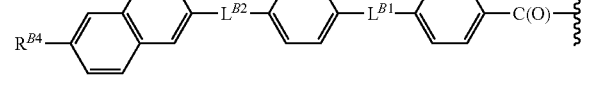
or wherein each of -L$^{B1}$- and -L$^{B2}$- is independently a single bond, —CH$_2$—CH$_2$— or —CH$_2$—O—,

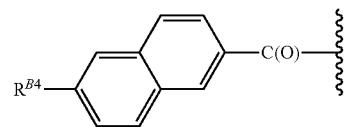
(3)

wherein R$^{B4}$— is independently —R$^{B4A}$, —R$^{B4AA}$ or —R$^{B4O}$, or

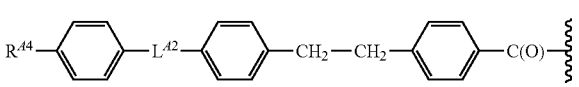
(4)

Preferred definitions in respect of each of (1) to (4) are set out below.

In one embodiment, —R$^2$ is independently:

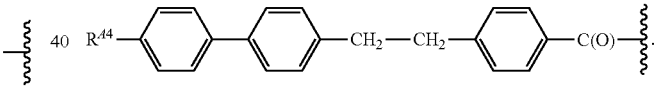

wherein each of -L$^{A1}$- and -L$^{A2}$- is independently a single bond or —CH$_2$—CH$_2$—.

In one embodiment, —R$^2$ is independently:

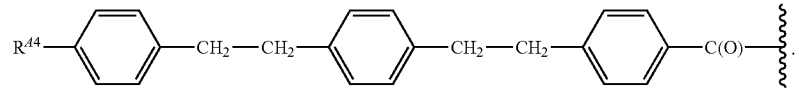

wherein -L$^{A2}$- is independently a single bond or —CH$_2$—CH$_2$—.

In one embodiment, —R$^2$ is independently:

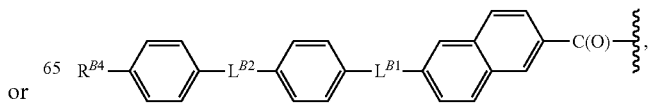

In one embodiment, —R$^2$ is independently:

In one embodiment, —R$^2$ is independently:

In one embodiment, —R$^2$ is independently:

-continued

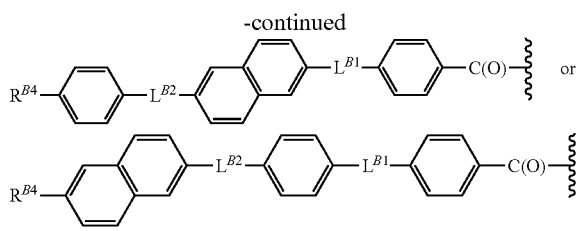

wherein each of -$L^{B1}$- and -$L^{B2}$- is independently a single bond, —CH$_2$—CH$_2$— or —CH$_2$—O—.

In one embodiment, —R$^2$ is independently:

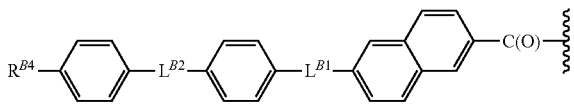

wherein each of -$L^{B1}$- and -$L^{B2}$- is independently a single bond, —CH$_2$—CH$_2$— or —CH$_2$—O—.

In one embodiment, —R$^2$ is independently:

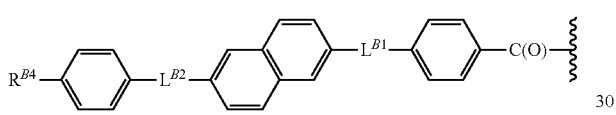

wherein each of -$L^{B1}$- and -$L^{B2}$- is independently a single bond, —CH$_2$—CH$_2$— or —CH$_2$—O—.

In one embodiment, —R$^2$ is independently:

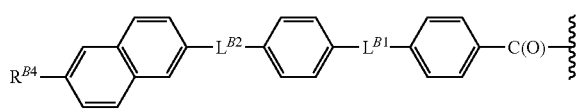

wherein each of -$L^{B1}$- and -$L^{B2}$- is independently a single bond, —CH$_2$—CH$_2$— or —CH$_2$—O—.

In one embodiment, —R$^2$ is independently:

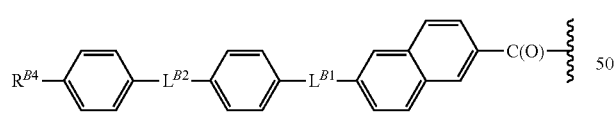

wherein -$L^{B1}$- is independently a single bond or —CH$_2$—O—, and wherein -$L^{B2}$- is independently a single bond or —CH$_2$—CH$_2$—.

In one embodiment, —R$^2$ is independently:

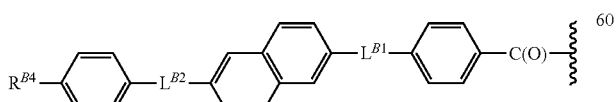

wherein each of -$L^{B1}$- and -$L^{B2}$- is independently a single bond or —CH$_2$—CH$_2$—.

In one embodiment, —R$^2$ is independently:

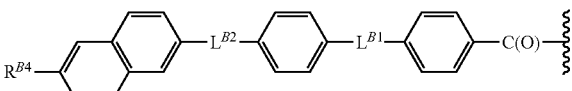

wherein each of -$L^{B1}$- and -$L^{B2}$- is independently a single bond or —CH$_2$—CH$_2$—.

In one embodiment, if any one of —R$^{B1}$—, and —R$^{B3}$— is —R$^{BN}$—, then —R$^{B4}$ is —H.

In one embodiment, if —R$^{B2}$— is —R$^{BN}$—, then —R$^{B4}$ is —H.

In one embodiment, —R$^2$ is independently:

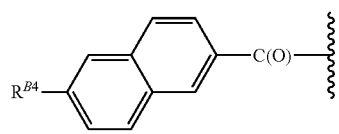

wherein R$^{B4}$— is independently —R$^{B4A}$, —R$^{B4AA}$ or —R$^{B4O}$.

In one embodiment, —R$^2$ is independently:

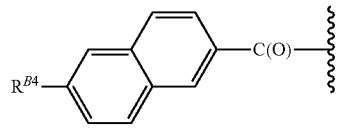

wherein R$^{B4}$— is independent —R$^{B4O}$.

In one embodiment, —R$^2$ is independently:

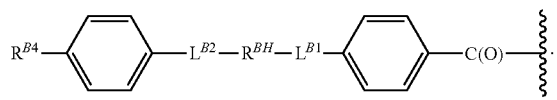

In one embodiment, —R$^2$ is independently:

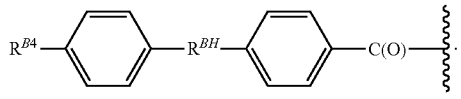

In one embodiment, —R$^2$ is independently:

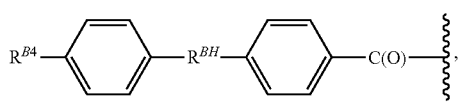

wherein —R$^{BH}$— is independently aromatic or saturated or unsaturated non-aromatic C$_{5-6}$ heterocyclylene, and is optionally substituted.

In one embodiment, —R² is independently:

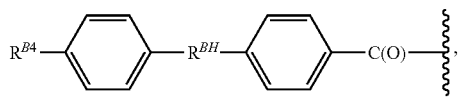

wherein —R^{BH}— is independently aromatic or saturated or unsaturated non-aromatic $C_{5-6}$ heterocyclylene, and is optionally substituted, and wherein —R^{B4} is independently —R^{B4A}, —R^{B4AA} or —R^{B4O}.

In one embodiment, —R² is independently:

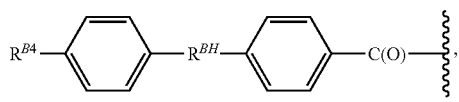

wherein —R^{BH}— is independently aromatic or saturated or unsaturated non-aromatic $C_{5-6}$ heterocyclylene, and is optionally substituted, and wherein —R^{B4} is independently —R^{B4A} or —R^{B4O}.

In one embodiment, if any one of —R^{B1}—, —R^{B2}— and —R^{B3}— is —R^{BH}—, then —R^{B4} is —R^{B4A}, —R^{B4AA} or —R^{B4O}.

In one embodiment, if —R^{B2}— is —R^{BH}—, then —R^{B4} is —R^{B4A}, —R^{B4AA} or —R^{B4O}.

In one embodiment, —R² is independently selected from:

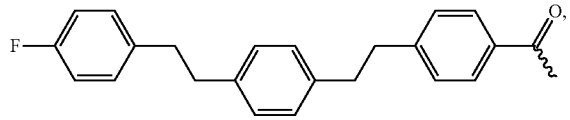

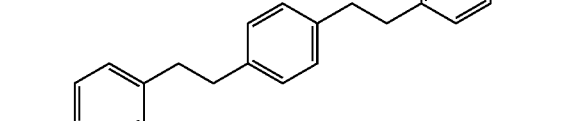

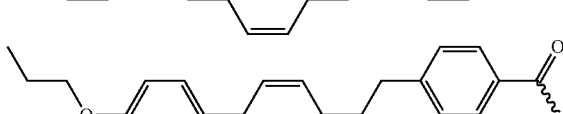

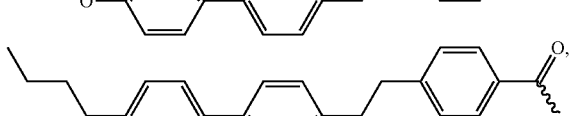

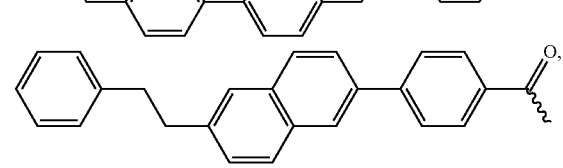

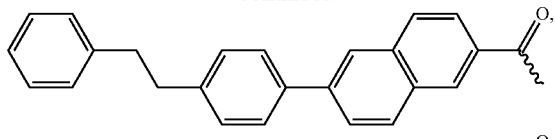

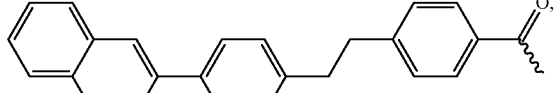

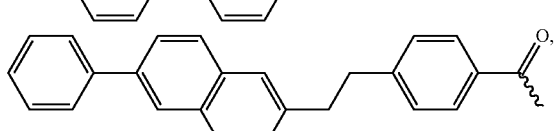

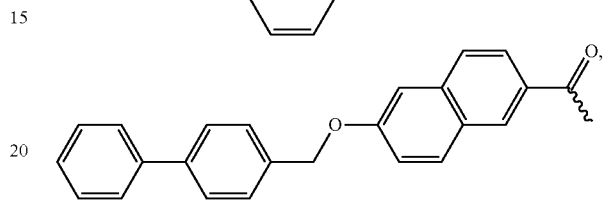

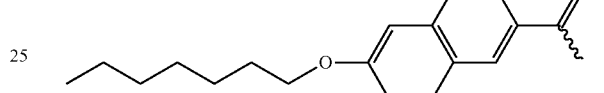

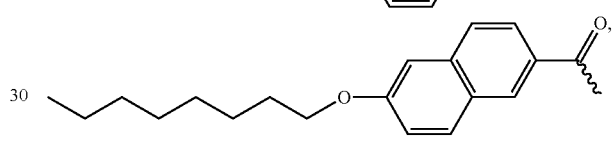

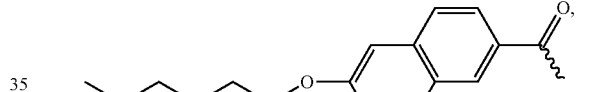

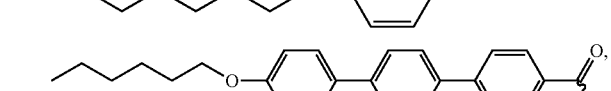

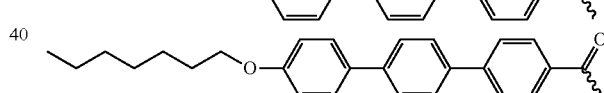

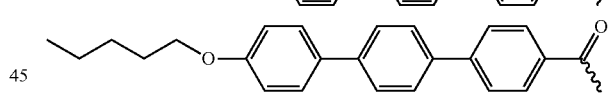

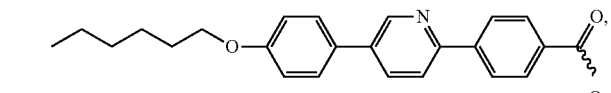

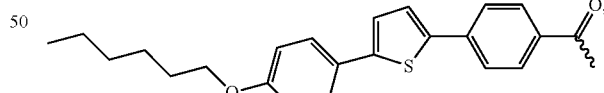

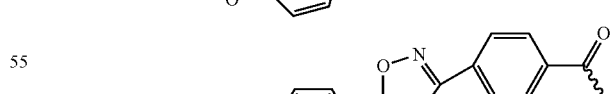

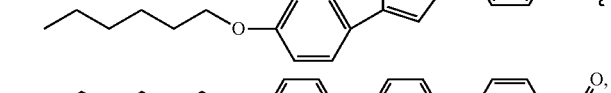

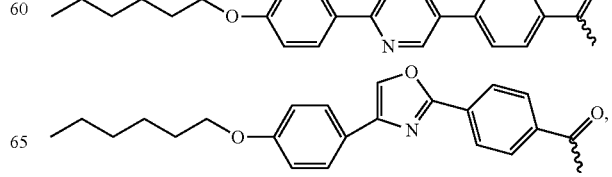

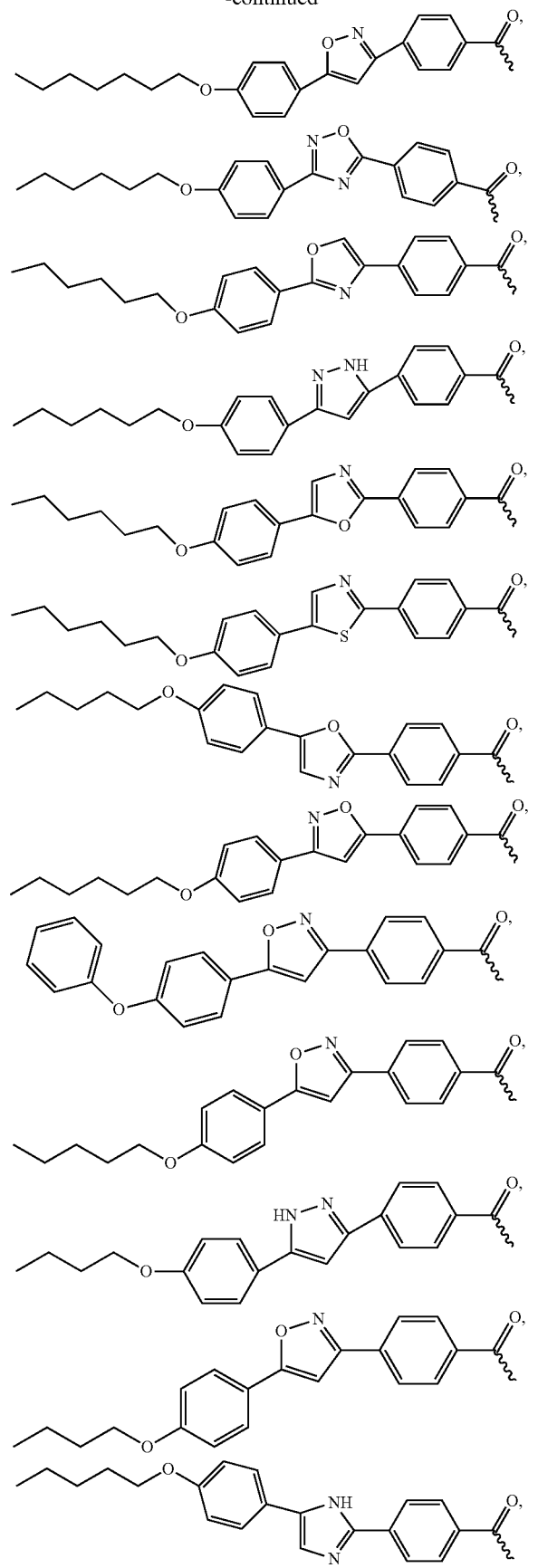
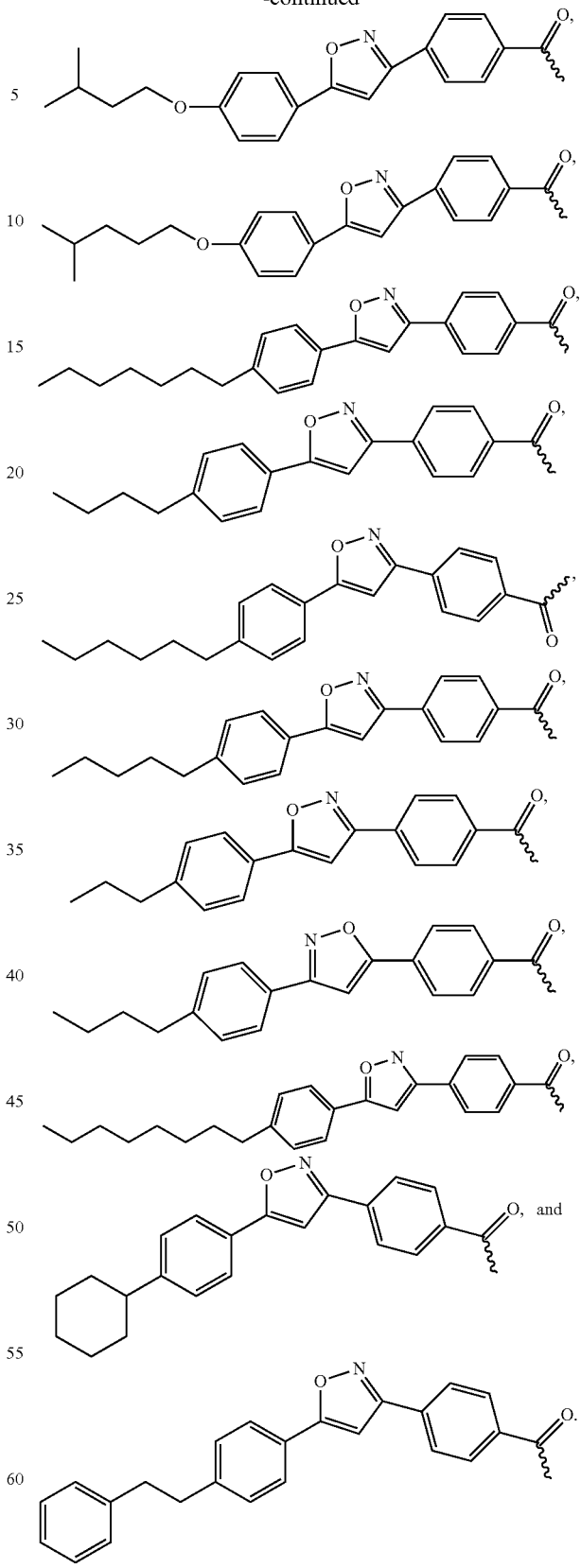
In one embodiment, the LP compound, as described herein, is a salt.

In one embodiment, the LP compound, as described herein, is a sodium or calcium salt.

In one embodiment, the LP compound, as described herein, is a $Ca_2Cl_2$ salt.

FURTHER EMBODIMENTS

Further embodiments of the present invention are as follows:

1. A compound selected from compounds of the following formula, and pharmaceutically acceptable salts, hydrates, and solvates thereof:

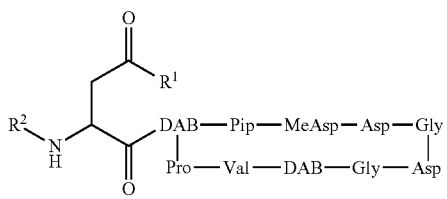
(I)

wherein:
—$R^1$ is independently —OH or —$NH_2$
and wherein:
—$R^2$ is independently —$R^A$ or —$R^B$
  wherein:
    —$R^A$ is independently $R^{A4}$—$R^{A3}$-$L^{A2}$-$R^{A2}$-$L^{A1}$-$R^{A1}$—C(O)—
    wherein:
      each of —$R^{A1}$—, —$R^{A2}$—, and —$R^{A3}$— is independently phenylene and is optionally substituted
    and wherein:
      each of -$L^{A1}$- and -$L^{A2}$- is independently -$L^S$- or -$L^{AA}$-
      wherein:
        each -$L^S$-, if present, is independently a single bond
      and wherein:
        each -$L^{AA}$-, if present, is independently saturated aliphatic $C_{1-4}$alkylene, and is optionally substituted
    and wherein:
      —$R^{A4}$ is independently —$R^{A4X}$, —$R^{A4A}$ or —$R^{A4O}$
      wherein:
        —$R^{A4X}$, if present, is independently halo and wherein:
        —$R^{A4A}$, if present, is independently saturated or unsaturated aliphatic or alicyclic $C_{1-10}$alkyl, and is optionally substituted
      and wherein:
        —$R^{A4O}$, if present, is independently saturated or unsaturated aliphatic or alicyclic $C_{1-10}$alkoxy, and is optionally substituted
  and wherein:
    —$R^B$ is independently $R^{B4}$—$R^{B3}$-$L^{B2}$-$R^{B2}$-$L^{B1}$-$R^{B1}$—C(O)—
    wherein:
      —$R^{B1}$— is independently —$R^{BP}$— or —$R^{BN}$—,
    and wherein:
      each of —$R^{B2}$—, and —$R^{B3}$— is independently —$R^{BS}$, —$R^{BP}$—, —$R^{BN}$— or
    and wherein:
    either
      (A) at least one of —$R^{B1}$—, —$R^{B2}$—, and —$R^{B3}$— is independently —$R^{BN}$—;
    or
      (B) at least one of —$R^{B2}$— and —$R^{B3}$— is independently —$R^{BH}$—
    wherein:
      each —$R^{BP}$—, if present, is independently phenylene, and is optionally substituted
    and wherein:
      each —$R^{BN}$—, if present, is independently naphthylene, and is optionally substituted
    and wherein:
      each —$R^{BH}$—, if present, is independently aromatic or saturated or unsaturated non-aromatic $C_{4-14}$ heterocyclylene, and is optionally substituted
    and wherein:
      each —$R^{BS}$—, if present, is independently a single bond
    and wherein:
      each of -$L^{B1}$- and -$L^{B2}$- is independently -$L^S$-, -$L^{BB}$ or -$L^{BO}$-
      wherein:
        each -$L^S$-, if present, is independently a single bond
      and wherein:
        each -$L^{BB}$-, if present, is independently saturated aliphatic $C_{1-4}$alkylene, and is optionally substituted
      and wherein:
        each -$L^{BO}$-, if present, is independently saturated aliphatic $C_{1-4}$alkoxylene, and is optionally substituted
    and wherein:
      —$R^{B4}$ is independently —H, —$R^{B4A}$, —$R^{B4AA}$ or —$R^{B4O}$
      wherein:
        —$R^{B4A}$, if present, is independently saturated or unsaturated aliphatic or alicyclic $C_{1-10}$alkyl, and is optionally substituted
      and wherein:
        —$R^{B4AA}$, if present, is independently $C_{6-10}$aryl-$C_{1-6}$alkyl, and is optionally substituted
      and wherein:
        —$R^{B4O}$, if present, is independently —$R^{B4O1}$ or $R^{B4O2}$
        wherein:
          —$R^{B4O1}$, if present, is independently saturated or unsaturated aliphatic or alicyclic $C_{1-10}$alkoxy, and is optionally substituted
        and wherein:
          —$R^{B4O2}$, if present, is independently $C_{6-10}$aryloxy, and is optionally substituted.

2. A compound according to paragraph 1, wherein —$R^1$ is independently —OH.

3. A compound according to paragraph 1, wherein —$R^1$ is independently —$NH_2$.

4. A compound according to any one of paragraphs 1 to 3, wherein —$R^2$ is independently. —$R^A$.

5. A compound according to any one of paragraphs 1 to 3, wherein —$R^2$ is independently —$R^B$.

6. A compound according to any one of paragraphs 1 to 5, wherein each of —$R^{A1}$—, —$R^{A2}$—, and —$R^{A3}$— is independently

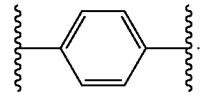

7. A compound according to any one of paragraphs 1 to 5, wherein —$R^{41}$— is independently phenylene and is optionally substituted.

8. A compound according to any one of paragraphs 1 to 5, wherein —$R^{42}$— is independently phenylene and is optionally substituted.

9. A compound according to any one of paragraphs 1 to 5, wherein —$R^{43}$— is independently phenylene and is optionally substituted.

10. A compound according to any one of paragraphs 1 to 5, wherein —$R^{41}$— is independently

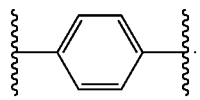 [SMILES: *c1ccc(*)cc1]

11. A compound according to any one of paragraphs 1 to 5, wherein —$R^{42}$— is independently

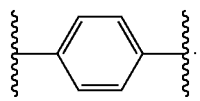

12. A compound according to any one of paragraphs 1 to 5, wherein —$R^{43}$— is independently

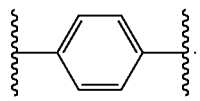

13. A compound according to any one of paragraphs 1 to 12, wherein each of -$L^{41}$- and -$L^{42}$- is independently -$L^S$-.

14. A compound according to any one of paragraphs 1 to 12, wherein each of -$L^{41}$- and -$L^{42}$- is independently -$L^{AA}$-.

15. A compound according to any one of paragraphs 1 to 12, wherein -$L^{41}$- is independently -$L^S$-.

16. A compound according to any one of paragraphs 1 to 12, wherein -$L^{41}$- is independently -$L^{AA}$-.

17. A compound according to any one of paragraphs 1 to 12, wherein -$L^{42}$- is independently -$L^S$-.

18. A compound according to any one of paragraphs 1 to 12, wherein -$L^{42}$- is independently -$L^{AA}$-.

19. A compound according to any one of paragraphs 1 to 18, wherein each -$L^{AA}$-, if present, is independently saturated linear $C_{1-4}$alkylene, and is optionally substituted.

20. A compound according to any one of paragraphs 1 to 18, wherein each -$L^{AA}$-, if present, is independently —$CH_2$— or —$CH_2$—$CH_2$—.

21. A compound according to any one of paragraphs 1 to 18, wherein each -$L^{AA}$-, if present, is independently —$CH_2$—.

22. A compound according to any one of paragraphs 1 to 18, wherein each -$L^{AA}$-, if present, is independently —$CH_2$—$CH_2$—.

23. A compound according to any one of paragraphs 1 to 22, wherein —$R^{44}$ is independently —$R^{44X}$.

24. A compound according to any one of paragraphs 1 to 22, wherein —$R^{44}$ is independently —$R^{44A}$.

25. A compound according to any one of paragraphs 1 to 22, wherein —$R^{44}$ is independently —$R^{44O}$.

26. A compound according to any one of paragraphs 1 to 25, wherein —$R^{44X}$, if present, is independently —F, —Cl, —Br or —I.

27. A compound according to any one of paragraphs 1 to 25, wherein —$R^{44X}$, if present, is independently —F, —Cl or —Br.

28. A compound according to any one of paragraphs 1 to 25, wherein —$R^{44X}$, if present, is independently —F or —Cl.

29. A compound according to any one of paragraphs 1 to 25, wherein —$R^{44X}$, if present, is independently —F.

30. A compound according to any one of paragraphs 1 to 25, wherein —$R^{44X}$, if present, is independently —Cl.

31. A compound according to any one of paragraphs 1 to 25, wherein —$R^{44X}$, if present, is independently —Br.

32. A compound according to any one of paragraphs 1 to 25, wherein —$R^{44X}$, if present, is independently —I.

33. A compound according to any one of paragraphs 1 to 32, wherein —$R^{44A}$, if present, is independently saturated or unsaturated aliphatic or alicyclic $C_{1-6}$alkyl, and is optionally substituted.

34. A compound according to any one of paragraphs 1 to 32, wherein —$R^{44A}$, if present, is independently saturated or unsaturated aliphatic $C_{1-6}$alkyl, and is optionally substituted.

35. A compound according to any one of paragraphs 1 to 32, wherein —$R^{44A}$, if present, is independently saturated or unsaturated aliphatic $C_{1-4}$alkyl, and is optionally substituted.

36. A compound according to any one of paragraphs 1 to 32, wherein —$R^{44A}$, if present, is independently saturated or unsaturated linear $C_{1-4}$alkyl, and is optionally substituted.

37. A compound according to any one of paragraphs 1 to 32, wherein —$R^{44A}$, if present, is independently saturated linear $C_{1-4}$alkyl, and is optionally substituted.

38. A compound according to any one of paragraphs 1 to 32, wherein —$R^{44A}$, if present, is independently saturated $C_{1-2}$alkyl, and is optionally substituted.

39. A compound according to any one of paragraphs 1 to 32, wherein —$R^{44A}$, if present, is independently —$CH_3$ or —$CH_2$—$CH_2$—$CH_2$—$CH_3$.

40. A compound according to any one of paragraphs 1 to 32, wherein —$R^{44A}$, if present, is independently —$CH_3$.

41. A compound according to any one of paragraphs 1 to 32, wherein —$R^{44A}$, if present, is independently —$CH_2$—$CH_2$—$CH_2$—$CH_3$.

42. A compound according to any one of paragraphs 1 to 41, wherein —$R^{44O}$, if present, is independently saturated or unsaturated aliphatic $C_{1-10}$alkoxy, and is optionally substituted.

43. A compound according to any one of paragraphs 1 to 41, wherein —$R^{44O}$, if present, is independently saturated or unsaturated aliphatic $C_{1-7}$alkoxy, and is optionally substituted.

44. A compound according to any one of paragraphs 1 to 41, wherein —$R^{44O}$, if present, is independently saturated aliphatic $C_{1-7}$alkoxy, and is optionally substituted.

45. A compound according to any one of paragraphs 1 to 41, wherein —$R^{44O}$, if present, is independently saturated aliphatic $C_{1-3}$alkoxy, and is optionally substituted.

46. A compound according to any one of paragraphs 1 to 41, wherein —$R^{44O}$, if present, is independently saturated aliphatic $C_{5-7}$alkoxy, and is optionally substituted.

47. A compound according to any one of paragraphs 1 to 41, wherein —$R^{44O}$, if present, is independently —O—$CH_3$, —O—$CH_2$—$CH_2$—$CH_3$, —O—$CH_2$—$CH_2$—$CH_2$—$CH_3$, —O—$CH_2$—$CH_2$—$CH_2$—$CH_2$—$CH_2$—$CH_3$, or —O—$CH_2$—$CH_2$—$CH_2$—$CH_2$—$CH_2$—$CH_2$—$CH_3$.

48. A compound according to any one of paragraphs 1 to 41, wherein —$R^{44O}$, if present, is independently —O—$CH_3$.

49. A compound according to any one of paragraphs 1 to 41, wherein —$R^{44O}$, if present, is independently —O—$CH_2$—$CH_2$—$CH_3$.

50. A compound according to any one of paragraphs 1 to 41, wherein —$R^{44O}$, if present, is independently —O—$CH_2$—$CH_2$—$CH_2$—$CH_2$—$CH_3$.

51. A compound according to any one of paragraphs 1 to 41, wherein —$R^{44O}$, if present, is independently —O—$CH_2$—$CH_2$—$CH_2$—$CH_2$—$CH_2$—$CH_3$.

52. A compound according to any one of paragraphs 1 to 41, wherein —$R^{44O}$, if present, is independently —O—$CH_2$—$CH_2$—$CH_2$—$CH_2$—$CH_2$—$CH_3$.

53. A compound according to any one of paragraphs 1 to 52, wherein —$R^{B1}$— is independently —$R^{BP}$— or —$R^{BN}$—, and each of —$R^{B2}$— and —$R^{B3}$— is independently —$R^{BS}$—, —$R^{BP}$—, —$R^{BN}$— or —$R^{BH}$—, wherein at least one of —$R^{B1}$—, —$R^{B2}$—, and —$R^{B3}$— is independently —$R^{BN}$—.

54. A compound according to any one of paragraphs 1 to 52, wherein —$R^{B1}$— is independently —$R^{BP}$— or —$R^{BN}$—, and each of —$R^{B2}$— and —$R^{B3}$— is independently —$R^{BS}$—, —$R^{BP}$—, —$R^{BN}$— or —$R^{BN}$—, wherein at least one of —$R^{B2}$—, and —$R^{B3}$— is independently —$R^{BH}$—.

55. A compound according to any one of paragraphs 1 to 52, wherein —$R^{B1}$— is independently —$R^{BP}$— or —$R^{BN}$—, wherein at least one of —$R^{B2}$—, and —$R^{B1}$— is independently —$R^{BH}$— and wherein at least one of —$R^{B2}$—, and —$R^{B3}$— is independently —$R^{BP}$—.

56. A compound according to any one of paragraphs 1 to 52, wherein —$R^{B1}$— is independently —$R^{BP}$—, and each of —$R^{B2}$— and —$R^{B3}$— is independently —$R^{BP}$—, —$R^{BN}$— or —$R^{BH}$—, wherein at least one of —$R^{B2}$—, and —$R^{B3}$— is independently —$R^{BN}$—.

57. A compound according to any one of paragraphs 1 to 52, wherein —$R^{B1}$— is independently —$R^{BP}$—, and each of —$R^{B2}$— and —$R^{B3}$— is independently —$R^{BP}$—, —$R^{BN}$— or —$R^{BH}$—, wherein at least one of —$R^{B2}$—, and —$R^{B3}$— is independently —$R^{BH}$—.

58. A compound according to any one of paragraphs 1 to 52, wherein —$R^{B1}$— is independently —$R^{BP}$—, and at least one of —$R^{B2}$—, and —$R^{B3}$— is independently —$R^{BN}$— and the other is independently —$R^{BP}$—.

59. A compound according to any one of paragraphs 1 to 52, wherein —$R^{B1}$— is independently —$R^{BP}$—, and at least one of —$R^{B2}$—, and —$R^{B3}$— is independently —$R^{BH}$— and the other is independently —$R^{BP}$—.

60. A compound according to any one of paragraphs 1 to 52, wherein —$R^{B1}$— is independently —$R^{BN}$—, and each of —$R^{B2}$— and —$R^{B3}$— is independently —$R^{BS}$—, —$R^{BP}$— or —$R^{BN}$—.

61. A compound according to any one of paragraphs 1 to 52, wherein —$R^{B1}$— is independently —$R^{BN}$—, and each of —$R^{B2}$— and —$R^{B3}$— is independently —$R^{BP}$— or —$R^{BN}$—.

62. A compound according to any one of paragraphs 1 to 52, wherein —$R^{B1}$— is independently —$R^{BN}$—, and each of —$R^{B2}$— and —$R^{B3}$— is independently —$R^{BP}$—.

63. A compound according to any one of paragraphs 1 to 52, wherein —$R^{B1}$— is independently —$R^{BN}$—, and each of —$R^{B2}$— and —$R^{B3}$— is independently —$R^{BS}$—.

64. A compound according to any one of paragraphs 1 to 52, wherein one of —$R^{B1}$—, —$R^{B2}$—, and —$R^{B3}$— is independently —$R^{BN}$— and the other two are independently —$R^{BS}$— or —$R^{BP}$—.

65. A compound according to any one of paragraphs 1 to 52, wherein one of —$R^{B1}$—, —$R^{B2}$—, and —$R^{B3}$— is independently —$R^{BN}$— and the other two are independently —$R^{BS}$—.

66. A compound according to any one of paragraphs 1 to 52, wherein one of —$R^{B1}$—, —$R^{B2}$—, and —$R^{B3}$— is independently —$R^{BN}$— and the other two are independently —$R^{BP}$—.

67. A compound according to any one of paragraphs 1 to 52, wherein, —$R^{B1}$— is independently —$R^{BP}$—.

68. A compound according to any one of paragraphs 1 to 52, wherein —$R^{B1}$— is independently —$R^{BN}$—.

69. A compound according to any one of paragraphs 1 to 52, wherein —$R^{B2}$— is independently —$R^{BS}$—.

70. A compound according to any one of paragraphs 1 to 52, wherein —$R^{B2}$— is independently —$R^{BP}$—.

71. A compound according to any one of paragraphs 1 to 52, wherein —$R^{B2}$— is independently —$R^{BN}$—.

72. A compound according to any one of paragraphs 1 to 52, wherein, —$R^{B2}$— is independently —$R^{BH}$—.

73. A compound according to any one of paragraphs 1 to 52, wherein —$R^{B3}$— is independently —$R^{BS}$—.

74. A compound according to any one of paragraphs 1 to 52, wherein —$R^{B3}$— is independently —$R^{BP}$—.

75. A compound according to any one of paragraphs 1 to 52, wherein —$R^{B3}$— is independently —$R^{BN}$—.

76. A compound according to any one of paragraphs 1 to 52, wherein —$R^{B3}$— is independently —$R^{BH}$—.

77. A compound according to any one of paragraphs 1 to 52, wherein —$R^{B1}$— is independently —$R^{BP}$—, —$R^{B2}$— is independently —$R^{BH}$— and —$R^{B3}$— is independently —$R^{BP}$—.

78. A compound according to any one of paragraphs 1 to 52, wherein (A) —$R^{B1}$— is independently —$R^{BP}$—, —$R^{B2}$— is independently —$R^{BH}$— and —$R^{B3}$— is independently —$R^{BP}$—, or (B) one of —$R^{B1}$—, —$R^{B2}$—, and —$R^{B3}$— is independently —$R^{BN}$— and the other two are independently —$R^{BP}$—.

79. A compound according to any one of paragraphs 1 to 78, wherein each —$R^{BP}$—, if present, is independently

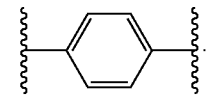

80. A compound according to any one of paragraphs 1 to 79, wherein each —$R^{BN}$—, if present, is independently

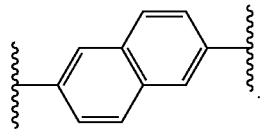 [SMILES: *c1ccc2cc(*)ccc2c1]

81. A compound according to any one of paragraphs 1 to 80, wherein each —$R^{BH}$—, if present, is independently aromatic or saturated or unsaturated non-aromatic $C_{4-10}$heterocyclylene, and is optionally substituted.

82. A compound according to any one of paragraphs 1 to 80, wherein each —$R^{BH}$—, if present, is independently aromatic or saturated or unsaturated non-aromatic $C_{4-6}$heterocyclylene, and is optionally substituted.

83. A compound according to any one of paragraphs 1 to 80, wherein, each —$R^{BH}$—, if present, is independently aromatic or saturated or unsaturated non-aromatic $C_{5-6}$heterocyclylene, and is optionally substituted.

84. A compound according to any one of paragraphs 1 to 80, wherein each —$R^{BH}$—, if present, is independently aromatic or unsaturated non-aromatic $C_5$ heterocyclylene, and is optionally substituted.

85. A compound according to any one of paragraphs 1 to 80, wherein each —$R^{BH}$—, if present, is independently aromatic or saturated or unsaturated non-aromatic $C_{4-10}$heterocyclylene, wherein at least one ring atom is N, and is optionally substituted.

86. A compound according to any one of paragraphs 1 to 80, wherein each —$R^{BH}$—, if present, is independently aromatic or saturated or unsaturated non-aromatic $C_{4-10}$heterocyclylene, wherein at least one ring atom is O, and is optionally substituted.

87. A compound according to any one of paragraphs 1 to 80, wherein each —$R^{BH}$—, if present, is independently aromatic or saturated or unsaturated non-aromatic $C_{4-10}$heterocyclylene, wherein at least one ring atom is S, and is optionally substituted.

88. A compound according to any one of paragraphs 1 to 80, wherein each —$R^{BH}$—, if present, is independently aromatic or unsaturated non-aromatic $C_{5-6}$ heterocyclylene containing at least one of N, O or S as a ring atom, and is optionally substituted.

89. A compound according to any one of paragraphs 1 to 80, wherein each —$R^{BH}$—, if present, is independently aromatic or unsaturated non-aromatic $C_{5-6}$ heterocyclylene containing at least one N as a ring atom, and is optionally substituted.

90. A compound according to any one of paragraphs 1 to 80, wherein each —$R^{BH}$—, if present, is independently aromatic or unsaturated non-aromatic $C_{5-6}$ heterocyclylene containing at least one N and one O as ring atoms, and is optionally substituted.

91. A compound according to any one of paragraphs 1 to 80, wherein each —$R^{BH}$—, if present, is independently isoxazolylene, oxazolylene, thiazolylene, pyrazolylene, imidazolylene, pyrrolyl, indazolyl, triazolyl, tetrazolyl, oxadiazolylene, pyridinylene or piperazinylene, pyrimidinyl, Pyrazinyl, thiadiazolyl oxadiazolylene, pyridinylene or piperazinylene, and is optionally substituted.

92. A compound according to any one of paragraphs 1 to 80, wherein each —$R^{BH}$—, if present, is independently isoxazolylene, oxazolylene, thiazolylene, pyrazolylene, imidazolylene, oxadiazolylene or pyridinylene, and is optionally substituted.

93. A compound according to any one of paragraphs 1 to 80, wherein each —$R^{BH}$, if present, is independently isoxazolylene, and is optionally substituted.

94. A compound according to any one of paragraphs 1 to 80, wherein each —$R^{BH}$, if present, is independently

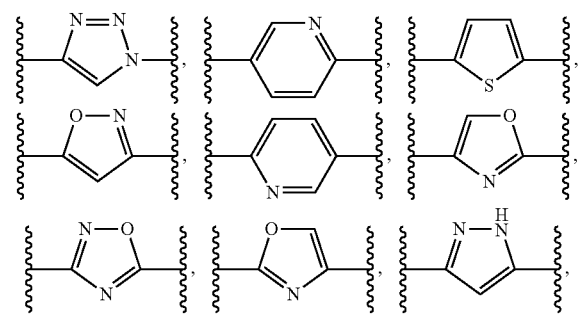

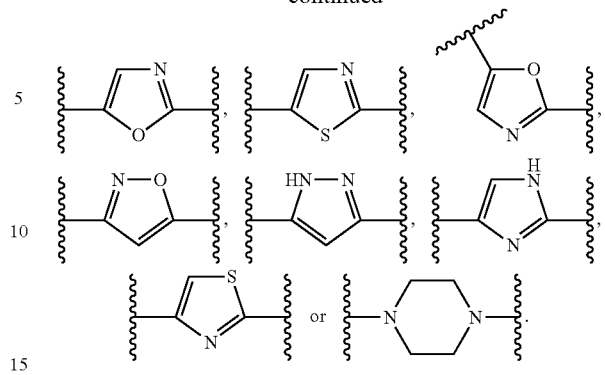

-continued

95. A compound according to any one of paragraphs 1 to 94, wherein each of -$L^{B1}$- and -$L^{B2}$- is independently -$L^S$-.
96. A compound according to any one of paragraphs 1 to 94, wherein each of -$L^{B1}$- and -$L^{B2}$- is independently -$L^{BB}$-.
97. A compound according to any one of paragraphs 1 to 94, wherein each of -$L^{B1}$- and -$L^{B2}$- is independently -$L^{BO}$-.
98. A compound according to any one of paragraphs 1 to 94, wherein -$L^{B1}$- is independently -$L^S$-.
99. A compound according to any one of paragraphs 1 to 94, wherein -$L^{B1}$- is independently -$L^{BB}$-.
100. A compound according to any one of paragraphs 1 to 94, wherein -$L^{B1}$- is independently -$L^{BO}$-.
101. A compound according to any one of paragraphs 1 to 94, wherein -$L^{B2}$- is independently -$L^S$-.
102. A compound according to any one of paragraphs 1 to 94, wherein -$L^{B2}$- is independently -$L^{BB}$-.
103. A compound according to any one of paragraphs 1 to 94, wherein -$L^{B2}$- is independently -$L^{BO}$-.
104. A compound according to any one of paragraphs 1 to 103, wherein each -$L^{BB}$-, if present, is independently saturated aliphatic $C_{1-2}$alkylene, and is optionally substituted.
105. A compound according to any one of paragraphs 1 to 103, wherein each -$L^{BB}$-, if present, is independently —$CH_2$—$CH_2$—.
106. A compound according to any one of paragraphs 1 to 105, wherein each -$L^{BO}$-, if present, is independently saturated aliphatic $C_{1-2}$alkoxylene, and is optionally substituted.
107. A compound according to any one of paragraphs 1 to 105, wherein each -$L^{BO}$-, if present, is independently —$CH_2$—O—.
108. A compound according to any one of paragraphs 1 to 107, wherein —$R^{B4}$ is independently —H.
109. A compound according to any one of paragraphs 1 to 107, wherein —$R^{B4}$ is independently —$R^{B4A}$.
110. A compound according to any one of paragraphs 1 to 107, wherein —$R^{B4}$ is independently —$R^{B4AA}$.
111. A compound according to any one of paragraphs 1 to 107, wherein —$R^{B4}$ is independently —$R^{B4O}$.
112. A compound according to any one of paragraphs 1 to 111, wherein —$R^{B4A}$, if present, is independently saturated or unsaturated aliphatic or alicyclic $C_{1-8}$alkyl, and is optionally substituted.
113. A compound according to any one of paragraphs 1 to 111, wherein —$R^{B4A}$, if present, is independently saturated or unsaturated aliphatic or alicyclic $C_{2-8}$alkyl, and is optionally substituted.
114. A compound according to any one of paragraphs 1 to 111, wherein —$R^{B4A}$, if present, is independently saturated or unsaturated aliphatic or alicyclic $C_{3-8}$alkyl, and is optionally substituted.

115. A compound according to any one of paragraphs 1 to 111, wherein —R$^{B4A}$, if present, is independently saturated aliphatic C$_{3-8}$alkyl, and is optionally substituted.

116. A compound according to any one of paragraphs 1 to 111, wherein —R$^{B4A}$, if present, is independently saturated linear C$_{3-8}$alkyl, and is optionally substituted.

117. A compound according to any one of paragraphs 1 to 111, wherein —R$^{B4A}$, if present, is independently saturated alicyclic C$_{3-8}$alkyl, and is optionally substituted.

118. A compound according to any one of paragraphs 1 to 111, wherein —R$^{B4A}$, if present, is independently cyclohexyl, and is optionally substituted.

119. A compound according to any one of paragraphs 1 to 118, wherein —R$^{B4AA}$, if present, is independently C$_6$aryl-C$_{1-6}$alkyl, and is optionally substituted.

120. A compound according to any one of paragraphs 1 to 118, wherein —R$^{B4AA}$, if present, is independently C$_6$aryl-C$_{1-2}$alkyl, and is optionally substituted.

121. A compound according to any one of paragraphs 1 to 118, wherein —R$^{B4AA}$, if present, is independently

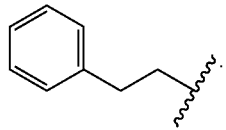 [SMILES: *CCc1ccccc1]

122. A compound according to any one of paragraphs 1 to 121, wherein —R$^{B4O}$, if present, is independently —R$^{B4O1}$.

123. A compound according to any one of paragraphs 1 to 121, wherein —R$^{B4O}$, if present, is independently —R$^{B4O2}$.

124. A compound according to any one of paragraphs 1 to 123, wherein —R$^{B4O1}$, if present, is independently saturated or unsaturated aliphatic C$_{1-10}$alkoxy, and is optionally substituted.

125. A compound according to any one of paragraphs 1 to 123, wherein —R$^{B4O1}$, if present, is independently saturated or unsaturated aliphatic C$_{3-8}$alkoxy, and is optionally substituted.

126. A compound according to any one of paragraphs 1 to 123, wherein —R$^{B4O1}$, if present, is independently saturated or unsaturated aliphatic C$_{4-7}$alkoxy, and is optionally substituted.

127. A compound according to any one of paragraphs 1 to 123, wherein —R$^{B4O1}$, if present, is independently saturated or unsaturated aliphatic C$_{5-7}$alkoxy, and is optionally substituted.

128. A compound according to any one of paragraphs 1 to 123, wherein —R$^{B4O1}$, if present, is independently saturated or unsaturated aliphatic C$_6$alkoxy, and is optionally substituted.

129. A compound according to any one of paragraphs 1 to 123, wherein —R$^{B4O1}$, if present, is independently —O—(CH$_2$)$_3$—CH$_3$, —O—(CH$_2$)$_4$—CH$_3$, —O—(CH$_2$)$_5$—CH$_3$ or —O—(CH$_2$)$_6$—CH$_3$.

130. A compound according to any one of paragraphs 1 to 123, wherein —R$^{B4O1}$, if present, is independently —O—(CH$_2$)$_3$—CH$_3$.

131. A compound according to any one of paragraphs 1 to 123, wherein —R$^{B4O1}$, if present, is independently —O—(CH$_2$)$_4$—CH$_3$.

132. A compound according to any one of paragraphs 1 to 123, wherein —R$^{B4O1}$, if present, is independently —O—(CH$_2$)$_5$—CH$_3$.

133. A compound according to any one of paragraphs 1 to 123, wherein —R$^{B4O1}$, if present, is independently —O—(CH$_2$)$_6$—CH$_3$.

134. A compound according to any one of paragraphs 1 to 133, wherein —R$^{B4O2}$, if present, is independently C$_6$aryloxy, and is optionally substituted.

135. A compound according to any one of paragraphs 1 to 133, wherein —R$^{B4O2}$, if present, is independently

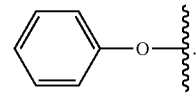 [SMILES: *Oc1ccccc1]

135. A compound according to any one of paragraphs 1 to 135, wherein each of -L$^{AA}$-, if present, -L$^{BB}$-, if present, and -L$^{BO}$-, if present, is independently optionally substituted with one or more substituents, —R$^{S1}$, wherein each R$^{S1}$, if present, is independently selected from:
—R$^{SS1}$,
—F, —Cl, —Br, —I,
—CF$_3$, —OCF$_3$, —SCF$_3$,
—OH, -L$^{SS1}$-OH, —O-L$^{SS1}$-OH, —NH-L$^{SS1}$-OH, —NR$^{SS1}$-L$^{SS1}$-OH,
—NH$_2$, —NHR$^{SS1}$, —NR$^{SS1}_2$; and
-L$^{SS1}$-NH$_2$, -L$^{SS1}$-NHR$^{SS1}$, -L$^{SS1}$-NR$^{SS1}_2$;

each of —R$^{A4A}$, if present, —R$^{B4A}$, if present, —R$^{A4O}$, if present, —R$^{B4O1}$, if present, —R$^{B4O2}$, if present, and —R$^{B4AA}$, if present, is independently optionally substituted with one or more substituents, —R$^{S2}$, wherein each R$^{S2}$, if present, is independently selected from:
—R$^{JA1}$,
—F, —Cl, —Br, —I,
—CF$_3$, —OCF$_3$, —SCF$_3$,
—R$^{JA1}$,
—F, —Cl, —Br, —I,
—CF$_3$, —OCF$_3$, —SCF$_3$,
—OH, -L$^{JA}$-OH, —O-L$^{JA}$-OH, —NH-L$^{JA}$-OH, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—SH, —SR$^{JA1}$,
—CN,
—NH$_2$, —NHR$^{JA1}$, —NR$^{JA1}_2$, —NR$^{JA2}$R$^{JA3}$,
-L$^{JA}$-NH$_2$, -L$^{JA}$-NHR$^{JA1}$, -L$^{JA}$-NR$^{JA1}_2$, -L$^{JA}$-NR$^{JA2}$R$^{JA3}$,
—O-L$^{JA}$-NH$_2$, —O-L$^{JA}$-NHR$^{JA1}$, —O-L$^{JA}$-NR$^{JA1}_2$, —O-L$^{JA}$-NR$^{JA2}$R$^{JA3}$,
—NH-L$^{JA}$-NH$_2$, —NR$^{JA1}$-L$^{JA}$-NH$_2$, —NH-L$^{JA}$-NHR$^{JA1}$, —NR$^{JA1}$-L$^{JA}$-NHR$^{JA1}$,
—NH-L$^{JA}$-NR$^{JA1}_2$, —NR$^{JA1}$-L$^{JA}$-NR$^{JA1}_2$,
—NH-L$^{JA}$-NR$^{JA2}$R$^{JA3}$, —NR$^{JA1}$-L$^{JA}$-NR$^{JA2}$R$^{JA3}$,
—OC(=O)R$^{JA1}$,
—C(=O)OH, —C(=O)OR$^{JA1}$,
—C(=O)R$^{JA1}$,
—C(=O)NH$_2$, —C(=O)NHR$^{JA1}$, —C(=O)NR$^{JA1}_2$, —C(=O)NR$^{JA2}$R$^{JA3}$,
—NHC(=O)R$^{JA1}$, —NR$^{JA1}$C(=O)R$^{JA1}$,
—NHC(=O)OR$^{JA1}$, —NR$^{JA1}$C(=O)OR$^{JA1}$,
—OC(=O)NH$_2$, —OC(=O)NHR$^{JA1}$, —OC(=O)NR$^{JA1}_2$, —OC(=O)NR$^{JA2}$R$^{JA3}$,
—NHC(=O)NH$_2$, —NHC(=O)NHR$^{JA1}$,
—NHC(=O)NR$^{JA1}_2$, —NHC(=O)NR$^{JA2}$R$^{JA3}$,
—NR$^{JA1}$C(=O)NH$_2$, —NR$^{JA1}$C(=O)NHR$^{JA1}$,
—NR$^{JA1}$C(=O)NR$^{JA1}_2$, —NR$^{JA1}$C(=O)NR$^{JA2}$R$^{JA3}$,
—NHS(=O)$_2$R$^{JA1}$, —NR$^{JA1}$S(=O)$_2$R$^{JA1}$, —S(=O)$_2$NH$_2$, —S(=O)$_2$NHR$^{JA1}$, —S(=O)$_2$NR$^{JA1}$$_2$,
—S(=O)$_2$NR$^{JA2}$R$^{JA3}$,
—S(=O)R$^{JA1}$, —S(=O)$_2$R$^{JA1}$, —OS(=O)$_2$R$^{JA1}$,
—S(=O)$_2$OH, —S(=O)$_2$OR$^{JA1}$; and
=O;

each of, —R$^{A1}$—, if present, —R$^{A2}$—, if present, —R$^{A3}$—, if present, —R$^{BP}$—, if present, and —R$^{BN}$—, if present, is independently optionally substituted with one or more substituents, —R$^{S3}$, wherein each R$^{S3}$, if present, is independently selected from:
—R$^{JA1}$,
—F, —Cl, —Br,
—CF$_3$, —OCF$_3$, —SCF$_3$,
—OH, -L$^{JA}$-OH, —O-L$^{JA}$-OH, —NH-L$^{JA}$-OH, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—SH, —SR$^{JA1}$,
—CN,
—NH$_2$, —NHR$^{JA1}$, —NR$^{JA1}$$_2$,
-L$^{JA}$-NH$_2$, -L$^{JA}$-NHR$^{JA1}$, -L$^{JA}$-NR$^{JA1}$$_2$,
—OC(O)R$^{JA1}$,
—C(O)OH, —C(O)OR$^{JA1}$,
—C(O)R$^{JA1}$,
—C(O)NH$_2$, —C(O)NHR$^{JA1}$, —C(O)N(R$^{JA1}$)$_2$; and
—NHC(O)R$^{JA1}$, —NR$^{JA1}$C(O)R$^{JA1}$;

and —R$^{BH}$—, if present, is independently is optionally substituted with one or more substituents, —R$^{S4}$, wherein each R$^{S4}$, if present, is independently selected from:
—R$^{JA1}$,
—F, —Cl, —Br,
—CF$_3$, —OCF$_3$, —SCF$_3$,
—OH, -L$^{JA}$-OH, —O-L$^{JA}$-OH, —NH-L$^{JA}$-OH, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—SH, —SR$^{JA1}$,
—CN,
—NH$_2$, —NHR$^{JA1}$, —NR$^{JA1}$$_2$,
-L$^{JA}$-NH$_2$, -L$^{JA}$-NHR$^{JA1}$, -L$^{JA}$-NR$^{JA1}$$_2$,
—OC(O)R$^{JA1}$,
—C(O)OH, —C(O)OR$^{JA1}$,
—C(O)R$^{JA1}$,
—C(O)NH$_2$, —C(O)NHR$^{JA1}$, —C(O)N(R$^{JA1}$)$_2$; and
—NHC(O)R$^{JA1}$, —NR$^{JA1}$C(O)R$^{JA1}$;

wherein:
each —R$^{SS1}$, if present, is independently saturated aliphatic C$_{1-6}$alkyl;
each -L$^{SS1}$-, if present, is independently —(CH$_2$)$_n$—, wherein n is independently 1 to 4;
each -L$^{JA}$-, if present, is independently saturated aliphatic C$_{1-5}$alkylene;
each —NR$^{JA2}$R$^{JA3}$, if present, is independently C$_{4-7}$ heterocyclyl, and is optionally substituted, for example, with one or more groups selected from —R$^{J44}$, —CF$_3$, —F, —OH, —OR$^{J44}$, —NH$_2$, —NHR$^{J44}$, —NR$^{J44}$$_2$, and =O; wherein each —R$^{J44}$ is independently saturated aliphatic C$_{1-4}$alkyl;
each —R$^{JA1}$ is independently:
—R$^{JB1}$, —R$^{JB2}$, —R$^{JB3}$, —R$^{JB4}$, —R$^{JB5}$, —R$^{JB6}$, —R$^{JB7}$, —R$^{JB8}$,
-L$^{JB}$-R$^{JB4}$, -L$^{JB}$-R$^{JB5}$, -L$^{JB}$-R$^{JB6}$, -L$^{JB}$-R$^{JB7}$, or -L$^{JB}$-R$^{JB8}$;
each —R$^{JB1}$ is independently saturated aliphatic C$_{1-6}$alkyl;
each —R$^{JB2}$ is independently aliphatic C$_{2-6}$alkenyl;
each —R$^{JB3}$ is independently aliphatic C$_{2-6}$alkynyl;
each —R$^{JB4}$ is independently saturated C$_{3-6}$cycloalkyl;
each —R$^{JB5}$ is independently C$_{3-6}$cycloalkenyl;
each —R$^{JB6}$ is independently non-aromatic C$_{4-7}$ heterocyclyl;
each —R$^{JB7}$ is independently C$_{6-10}$-carboaryl;
each —R$^{JB8}$ is independently C$_{5-10}$heteroaryl;
each -L$^{JB}$- is independently saturated aliphatic C$_{1-3}$alkylene;

wherein:
each —R$^{JB4}$, —R$^{JB5}$, —R$^{JB6}$, —R$^{JB7}$, and —R$^{JB8}$ is optionally substituted, for example, with one or more substituents —R$^{JC1}$ and/or one or more substituents —R$^{JC2}$,
each —R$^{JB1}$, —R$^{JB2}$, —R$^{JB3}$, and -L$^{JB}$- is optionally substituted, for example, with one or more substituents —R$^{JB2}$, and wherein:
each —R$^{JC1}$ is independently saturated aliphatic C$_{1-4}$alkyl, phenyl, or benzyl;
each —R$^{JC2}$ is independently:
—F, —Cl, —Br,
—CF$_3$, —OCF$_3$,
—OH,
—CN,
—NO$_2$,
—NH$_2$,
—C(=O)OH,
—C(=O)NH$_2$.

136. A compound according to paragraph 135, wherein each R$^{S1}$, if present, is independently selected from:
—F, —Cl, —Br, —I, or
—OH, -L$^{SS1}$-OH,
—OR$^{SS1}$,
—NH$_2$; and
-L$^{SS1}$-NH$_2$ 137. A compound according to paragraph 135, wherein each R$^{S1}$, if present, is independently selected from: —R$^{SS1}$.

138. A compound according to any one of paragraphs 135 to 137, wherein each —R$^{S2}$, if present, is independently selected from:
—R$^{JA1}$,
—F, —Cl, —Br,
—CF$_3$, —OCF$_3$,
—OH, -L$^{JA}$-OH, —O-L$^{JA}$-OH,
—OR$^{JA1}$, -L$^{JA}$-OR$^{JA1}$, —O-L$^{JA}$-OR$^{JA1}$,
—CN,
—NH$_2$, —NHR$^{JA1}$, —NR$^{JA1}$$_2$, —NR$^{JA2}$R$^{JA3}$,
-L$^{JA}$-NH$_2$, -L$^{JA}$-NHR$^{JA1}$, -L$^{JA}$-NR$^{JA1}$$_2$, -L$^{JA}$-NR$^{JA2}$R$^{JA3}$,
—C(=O)OH, —C(=O)OR$^{JA1}$,
—C(=O)R$^{JA1}$,
—C(=O)NH$_2$, —C(=O)NHR$^{JA1}$, —C(=O)NR$^{JA1}$$_2$, —C(=O)NR$^{JA2}$R$^{JA3}$,
—NHC(=O)R$^{JA1}$, —NR$^{JA1}$C(=O)R$^{JA1}$,
—NHC(=O)NH$_2$, —NHC(=O)NHR$^{JA1}$,
—NHC(=O)NR$^{JA1}$$_2$, —NHC(=O)NR$^{JA2}$R$^{JA3}$,
—NR$^{JA1}$C(=O)NH$_2$, —NR$^{JA1}$C(=O)NHR$^{JA1}$,
—NR$^{JA1}$C(=O)NR$^{JA1}$$_2$, —NR$^{JA1}$C(=O)NR$^{JA2}$R$^{JA3}$,
—NHS(=O)$_2$R$^{JA1}$, —NR$^{JA1}$S(=O)$_2$R$^{JA1}$,
—S(=O)$_2$NH$_2$, —S(=O)$_2$NHR$^{JA1}$, —S(=O)$_2$NR$^{JA1}$$_2$,
—S(=O)$_2$NR$^{JA2}$R$^{JA3}$,
—S(=O)R$^{JA1}$, —S(=O)$_2$R$^{JA1}$, —OS(=O)$_2$R$^{JA1}$,
—S(=O)$_2$OH, —S(=O)$_2$OR$^{JA1}$; and
=O.

139. A compound according to any one of paragraphs 135 to 137, wherein each —R$^{S2}$, if present, is independently selected from:
—R$^{JA1}$,
—F, —Cl, —Br, —CF$_3$, —OCF$_3$, —SCF$_3$,
—OH, -L$^{JA}$-OH, —O-L$^{JA}$-OH, —NH-L$^{JA}$, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—SH, —SR$^{JA1}$,
—CN,
—NH$_2$, —NHR$^{JA1}$, —NR$^{JA1}$$_2$,
-L$^{JA}$-NH$_2$, -L$^{JA}$-NHR$^{JA1}$-L$^{JA}$-NR$^{JA1}$$_2$,
—OC(O)R$^{JA1}$,
—C(O)OH, —C(O)OR$^{JA1}$,
—C(O)R$^{JA1}$,
—C(O)NH$_2$, —C(O)NHR$^{JA1}$, —C(O)N(R$^{JA1}$)$_2$,
—NHC(O)R$^{JA1}$, —NR$^{JA1}$C(O)R$^{JA1}$; and
═O.

140. A compound according to any one of paragraphs 135 to 137, wherein each —R$^{S2}$, if present, is independently selected from:
—R$^{SS1}$,
—F, —Cl, —Br,
—CF$_3$, —OCF$_3$, —SCF$_3$,
—OH, -L$^{SS1}$-OH, —O-L$^{SS1}$-OH, —NH-L$^{SS1}$-OH, —NR$^{SS1}$-L$^{SS1}$-OH,
—NH$_2$, —NHR$^{SS1}$, —NR$^{SS1}$$_2$,
-L$^{SS1}$-NH$_2$, -L$^{SS1}$-NHR$^{SS1}$, -L$^{SS1}$-NR$^{SS1}$$_2$; and
═O.

141. A compound according to any one of paragraphs 135 to 140, wherein each R$^{S3}$, if present, is independently selected from:
—R$^{SS1}$,
—F, —Cl, —Br, —I; and
—OH.

142. A compound according to any one of paragraphs 135 to 140, wherein each R$^{S4}$, if present, is independently selected from:
—R$^{SS1}$,
—F, —Cl, —Br, —I; and
—OH.

143. A compound according to any one of paragraphs 135 to 142, wherein each -L$^{JA}$-, if present, is independently —(CH$_2$)$_{n2}$—, wherein n2 is independently 1 to 4.

144. A compound according to any one of paragraphs 135 to 142, wherein each -L$^{JA}$-, if present, is independently —CH$_2$— or —CH$_2$CH$_2$—.

145. A compound according to any one of paragraphs 135 to 144, wherein each —NR$^{JA2}$R$^{JA3}$, if present, is independently azetidino, pyrrolidino, imidazolidino, pyrazolidino, piperidino, piperazino, morpholino, azepino, or diazepino, and is optionally substituted, for example, with one or more groups selected from —R$^{J44}$, —CF$_3$, —F, —OH, —OR$^{J44}$, —NH$_2$, —NHR$^{J44}$, —NR$^{J44}$$_2$, and ═O.

146. A compound according to any one of paragraphs 135 to 145, wherein each if present, is independently:
—R$^{JB1}$, —R$^{JB4}$, —R$^{JB6}$, —R$^{JB7}$, —R$^{JB8}$,
-L$^{JB}$-R$^{JB4}$, -L$^{JB}$-R$^{JB6}$, -L$^{JB}$-R$^{JB7}$, or -L$^{JB}$-R$^{JB8}$.

147. A compound according to any one of paragraphs 135 to 145, wherein each —R$^{JA1}$, if present, is independently:
—R$^{JB1}$, —R$^{JB6}$, —R$^{JB7}$, —R$^{JB8}$,
-L$^{JB}$-R$^{JB6}$, -L$^{JB}$-R$^{JB7}$, -L$^{JB}$-R$^{JB6}$, or -L$^{JB}$-R$^{JB8}$.

148. A compound according to any one of paragraphs 135 to 145, wherein each —R$^{JA1}$, if present, is independently:
—R$^{JB1}$, —R$^{JB6}$, —R$^{JB7}$, or -L$^{JB}$-R$^{JB7}$.

149. A compound according to any one of paragraphs 135 to 148, wherein each —R$^{JB6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

150. A compound according to any one of paragraphs 135 to 148, wherein each —R$^{JB6}$, if present, is independently pyrrolidinyl, piperidinyl, piperazinyl, morpholinyl, tetrahydrofuranyl, or tetrahydropyranyl, and is optionally substituted.

151. A compound according to any one of paragraphs 135 to 150, wherein each —R$^{JB7}$, if present, is independently phenyl, and is optionally substituted.

152. A compound according to any one of paragraphs 135 to 151, wherein each —R$^{JB8}$, if present, is independently C$_{5-6}$ heteroaryl, and is optionally substituted.

153. A compound according to any one of paragraphs 135 to 151, wherein each —R$^{JB8}$, if present, is independently C$_{9-10}$ heteroaryl, and is optionally substituted.

154. A compound according to any one of paragraphs 135 to 151, wherein each —R$^{JB8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyridazinyl, benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

155. A compound according to any one of paragraphs 135 to 151, wherein each —R$^{JB8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

156. A compound according to any one of paragraphs 135 to 155, wherein each -L$^{JB}$-, if present, is independently —CH$_2$— or —CH$_2$CH$_2$—.

157. A compound according to any one of paragraphs 135 to 155, wherein each -L$^{JB}$-, if present, is independently —CH$_2$—.

158. A compound according to any one of paragraphs 135 to 157, wherein each —R$^{SS1}$, if present, is independently saturated aliphatic C$_{1-6}$alkyl.

159. A compound according to any one of paragraphs 135 to 157, wherein each —R$^{SS1}$, if present, is independently saturated aliphatic C$_{1-3}$alkyl.

160. A compound according to any one of paragraphs 135 to 157, wherein each —R$^{SS1}$, if present, is independently -Me.

161. A compound according to any one of paragraphs 135 to 160, wherein each -L$^{SS1}$-, if present, is independently —(CH$_2$)$_n$—, wherein n is independently 1 to 4.

162. A compound according to any one of paragraphs 135 to 160, wherein each L$^{SS1}$-, if present, is independently —CH$_2$— or —CH$_2$CH$_2$—.

163. A compound according to any one of paragraphs 1 to 162, wherein —R$^2$ is independently:

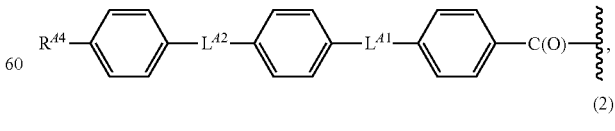
(1)

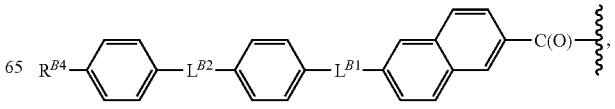
(2)

-continued

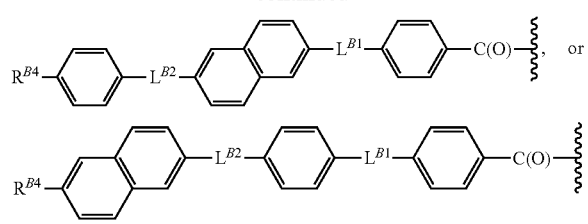

wherein each of -L$^{B1}$- and -L$^{B2}$- is independently a single bond, —CH$_2$—CH$_2$— or —CH$_2$—O—, (3)

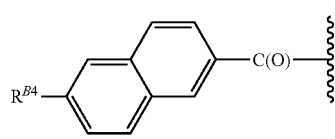

wherein R$^{B4}$- is independently —R$^{B4A}$, —R$^{B4AA}$ or —R$^{B4O}$, or (4)

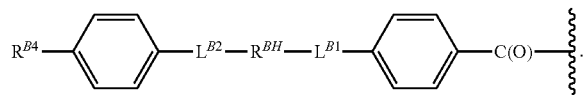

164. A compound according to any one of paragraphs 1 to 162, wherein —R$^2$ is independently:

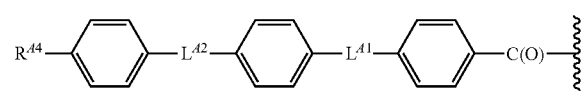

wherein each of -L$^{A1}$- and -L$^{A2}$- is independently a single bond or —CH$_2$—CH$_2$—.

165. A compound according to any one of paragraphs 1 to 162, wherein —R$^2$ is independently:

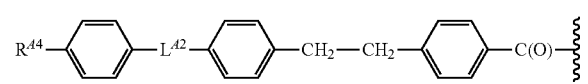

wherein -L$^{A2}$- is independently a single bond or —CH$_2$—CH$_2$—.

166. A compound according to any one of paragraphs 1 to 162, wherein —R$^2$ is independently:

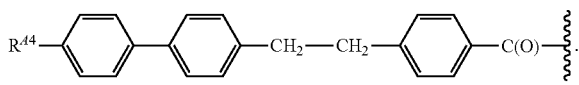

167. A compound according to any one of paragraphs 1 to 162, wherein —R$^2$ is independently:

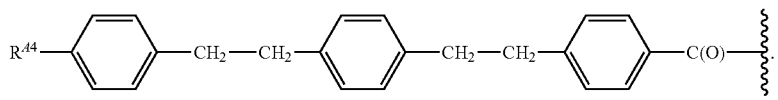

168. A compound according to any one of paragraphs 1 to 162, wherein —R$^2$ is independently:

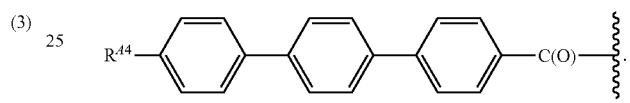

169. A compound according to any one of paragraphs 1 to 162, wherein —R$^2$ is independently:

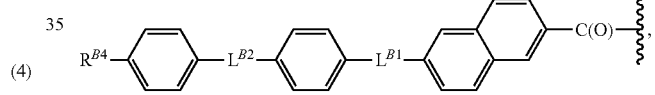

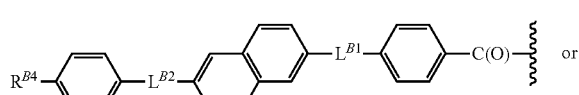

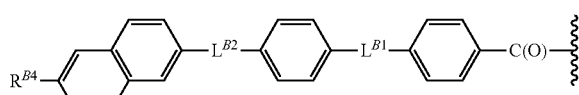

wherein each of -L$^{B1}$- and -L$^{B2}$- is independently a single bond, —CH$_2$—CH$_2$— or —CH$_2$—O—.

170. A compound according to any one of paragraphs 1 to 162, wherein —R$^2$ is independently:

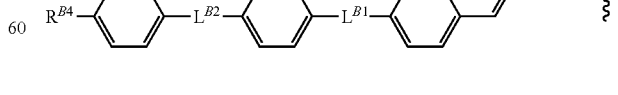

wherein each of -L$^{B1}$- and -L$^{B2}$- is independently a single bond, —CH$_2$—CH$_2$— or —CH$_2$—O—.

171. A compound according to any one of paragraphs 1 to 162, wherein —R$^2$ is independently:

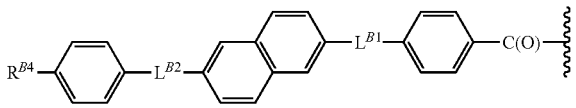

172. A compound according to any one of paragraphs 1 to 162, wherein each of -$L^{B1}$- and -$L^{B2}$- is independently a single bond, —$CH_2$—$CH_2$— or —$CH_2$—O—.

173. A compound according to any one of paragraphs 1 to 162, wherein —$R^2$ is independently:

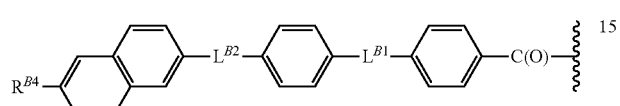

wherein each of -$L^{B1}$- and -$L^{B2}$- is independently a single bond, —$CH_2$—$CH_2$— or —$CH_2$—O—.

174. A compound according to any one of paragraphs 1 to 162, wherein —$R^2$ is independently:

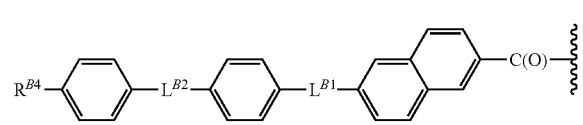

wherein -$L^{B1}$- is independently a single bond or —$CH_2$—O—, and wherein -$L^{B2}$- is independently a single bond or —$CH_2$—$CH_2$—.

175. A compound according to any one of paragraphs 1 to 162, wherein —$R^2$ is independently:

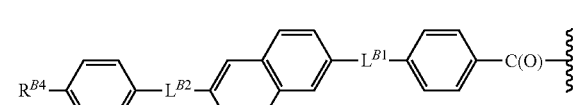

wherein each of -$L^{B1}$- and -$L^{B2}$- is independently a single bond or —$CH_2$—$CH_2$—.

176. A compound according to any one of paragraphs 1 to 162, wherein —$R^2$ is independently:

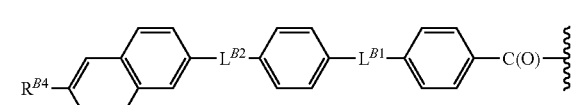

wherein each of -$L^{B1}$- and -$L^{B2}$- is independently a single bond or —$CH_2$—$CH_2$—.

177. A compound according to any one of paragraphs 1 to 162, wherein if any one of —$R^{B1}$—, —$R^{B2}$— and —$R^{B3}$— is —$R^{BN}$—, then —$R^{B4}$ is —H.

178. A compound according to any one of paragraphs 1 to 162, wherein if —$R^{B2}$— is —$R^{BN}$—, then —$R^{B4}$ is —H.

179. A compound according to any one of paragraphs 1 to 162, wherein —$R^2$ is independently:

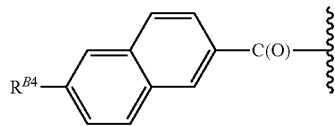

wherein $R^{B4}$— is independently —$R^{B4A}$, —$R^{B4AA}$ or —$R^{B4O}$.

180. A compound according to any one of paragraphs 1 to 162, wherein —$R^2$ is independently:

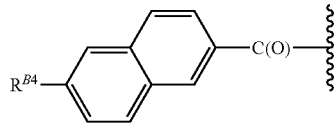

wherein $R^{B4}$— is independently —$R^{B4O}$.

181. A compound according to any one of paragraphs 1 to 162, wherein —$R^2$ is independently:

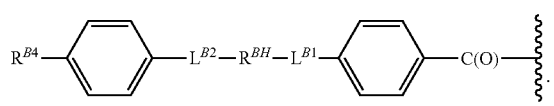

182. A compound according to any one of paragraphs 1 to 162, wherein —$R^2$ is independently:

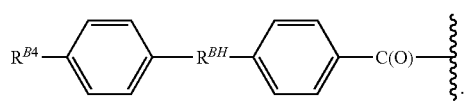

183. A compound according to any one of paragraphs 1 to 162, wherein —$R^2$ is independently:

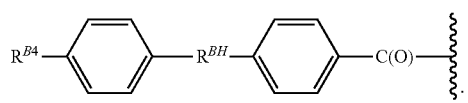

wherein —$R^{BH}$— is independently aromatic or saturated or unsaturated non-aromatic $C_{5-6}$ heterocyclylene, and is optionally substituted.

184. A compound according to any one of paragraphs 1 to 162, wherein —$R^2$ is independently:

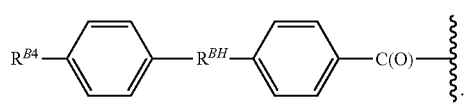

wherein —$R^{BH}$— is independently aromatic or saturated or unsaturated non-aromatic $C_{5-6}$ heterocyclylene, and is optionally substituted, and wherein —$R^{B4}$ is independently —$R^{B4A}$, —$R^{B4AA}$ or —$R^{B4O}$.

185. A compound according to any one of paragraphs 1 to 162, wherein —$R^2$ is independently:

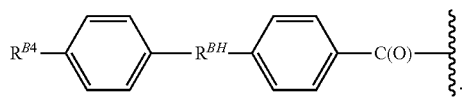

wherein —$R^{BH}$— is independently aromatic or saturated or unsaturated non-aromatic $C_{5-6}$ heterocyclylene, and is optionally substituted, and wherein —$R^{B4}$ is independently —$R^{B4A}$ or —$R^{B4O}$.

186. A compound according to any one of paragraphs 1 to 162, wherein if any one of —$R^{B1}$—, —$R^{B2}$— and —$R^{B3}$, is —$R^{BH}$—, then —$R^{B4}$ is —$R^{B4A}$, —$R^{B4AA}$ or —$R^{B4O}$.

187. A compound according to any one of paragraphs 1 to 162, wherein if —$R^{B2}$— is —$R^{BH}$—, then —$R^{B4}$ is —$R^{B4A}$, —$R^{B4AA}$ or —$R^{B4O}$.

188. A compound according to any one of paragraphs 1 to 162, wherein —$R^2$ is independently selected from:

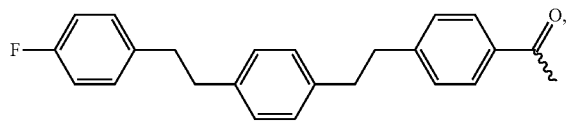
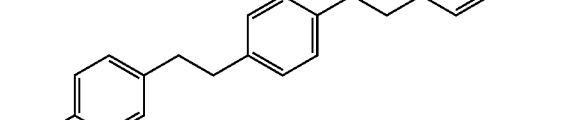
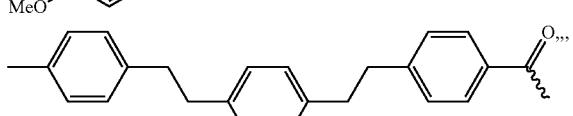
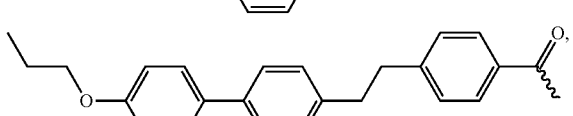
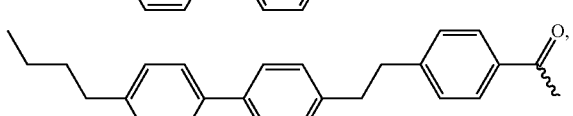
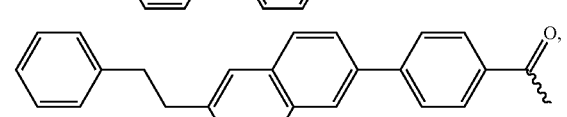
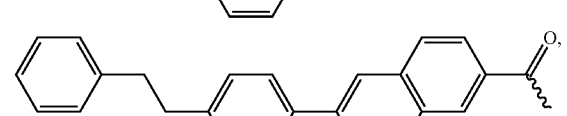
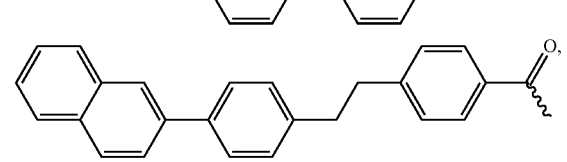
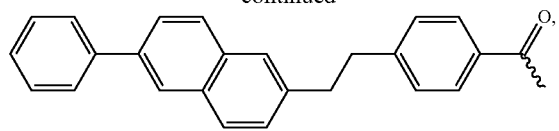
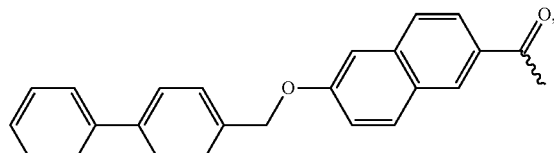
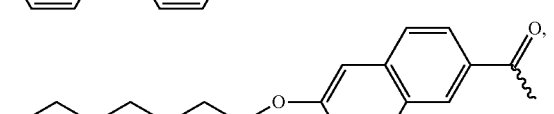
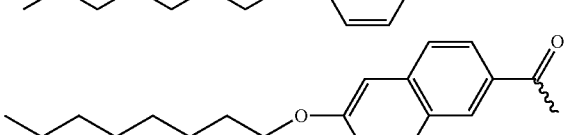
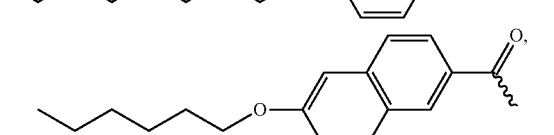
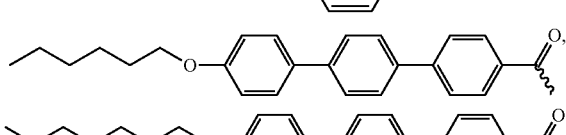
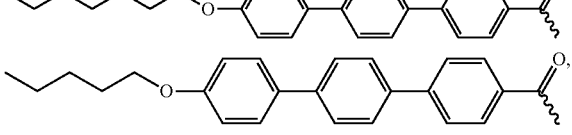
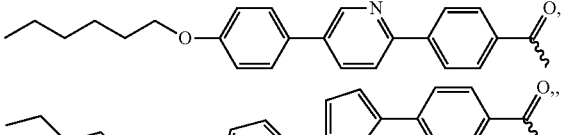
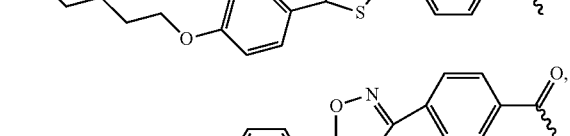
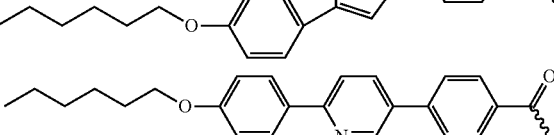
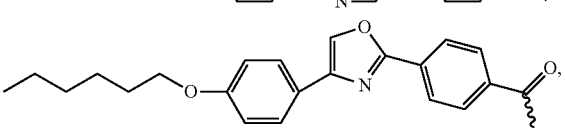
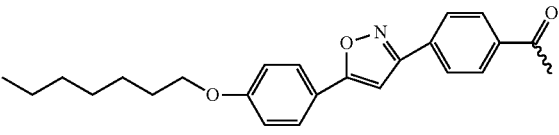
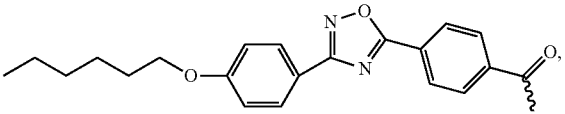

47
-continued
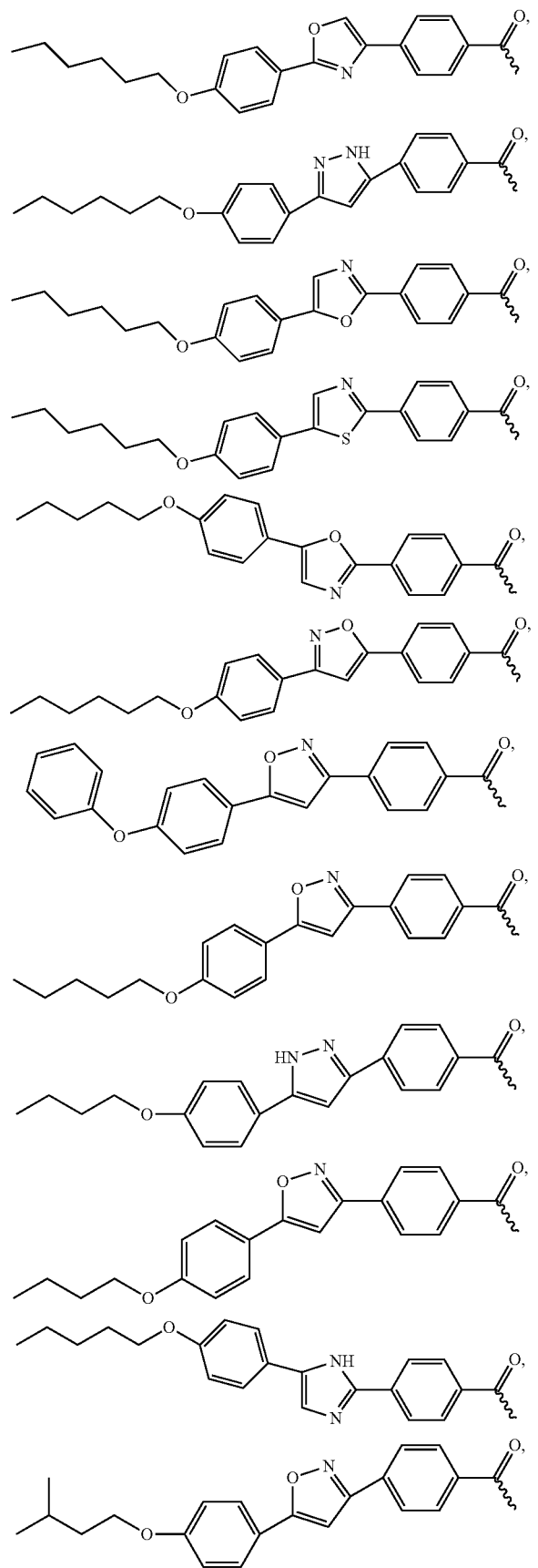
48
-continued
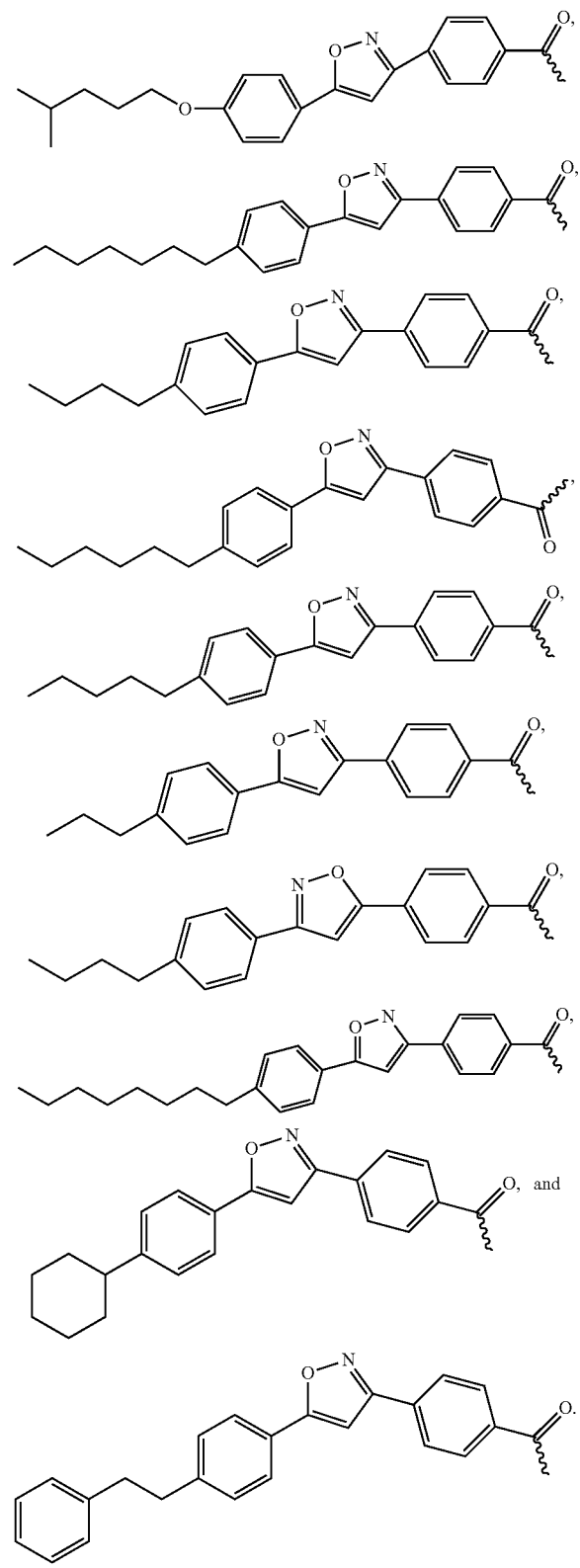
189. A compound according to any one of paragraphs 1 to 188, wherein the compound is a salt.
190. A compound according to any one of paragraphs 1 to 188, wherein the compound is a sodium or calcium salt.

191. A compound according to any one of paragraphs 1 to 188, wherein the compound is a $Ca_2Cl_2$ salt.
192. A pharmaceutical composition comprising a compound according to any one of paragraphs 1 to 191, and a pharmaceutically acceptable carrier, diluent, or excipient.
193. A method of preparing a pharmaceutical composition comprising the step of admixing a compound according to any one of paragraphs 1 to 191, and a pharmaceutically acceptable carrier, diluent, or excipient.
194. A compound according to any one of paragraphs 1 to 191, for use in a method of treatment of the human or animal body by therapy.
195. A compound according to any one of paragraphs 1 to 191, for use in the treatment of diseases and conditions that are ameliorated by the inhibition of microbe growth or reproduction and/or microbe death.
196. A compound according to any one of paragraphs 1 to 191, for use in the treatment of diseases and conditions that are ameliorated by the inhibition of bacteria growth or reproduction and/or bacteria death.
197. A compound according to any one of paragraphs 1 to 191, for use in the treatment of a bacterial infection or bacterial disease.
198. A compound according to any one of paragraphs 1 to 191, for use in the treatment of sequelae associated with diseases and conditions that are ameliorated by the inhibition of bacteria growth or reproduction and/or bacteria death.
199. A compound according to any one of paragraphs 1 to 191, for use in a method of (a) inhibiting bacteria growth or reproduction; (b) killing bacteria; or (c) a combination of both of these.
200. Use of a compound according to any one of paragraphs 1 to 191, in the manufacture of a medicament for use in treatment of a disease or condition that is ameliorated by the inhibition of microbe growth or reproduction and/or microbe death.
201. Use of a compound according to any one of paragraphs 1 to 191, in the manufacture of a medicament for use in treatment of a disease or condition that is ameliorated by the inhibition of bacteria growth or reproduction and/or bacteria death.
202. Use of a compound according to any one of paragraphs 1 to 191, in the manufacture of a medicament for use in treatment of a bacterial infection or bacterial disease.
203. A method of treatment comprising administering to a patient in need of treatment a therapeutically effective amount of a compound according to any one of paragraphs 1 to 191.
204. A method of treatment of a bacterial infection or bacterial disease comprising administering to a patient in need of treatment a therapeutically effective amount of a compound according to any one of paragraphs 1 to 191.
205. A method of inhibiting bacteria growth or reproduction, killing bacteria, or a combination of both of these, the method comprising contacting the bacteria with a compound according to any one of paragraphs 1 to 191.
206. A method according to paragraph 205, performed in vitro or in vivo.

Combinations

Each and every compatible combination of the optional features and embodiments described above is explicitly disclosed herein, as if each and every combination was individually and explicitly recited.

Specific Embodiments

In one embodiment, the compounds are selected from compounds of the following formulae and pharmaceutically acceptable salts, hydrates, and solvates thereof, wherein the lipopeptide to which the side chain is attached is:

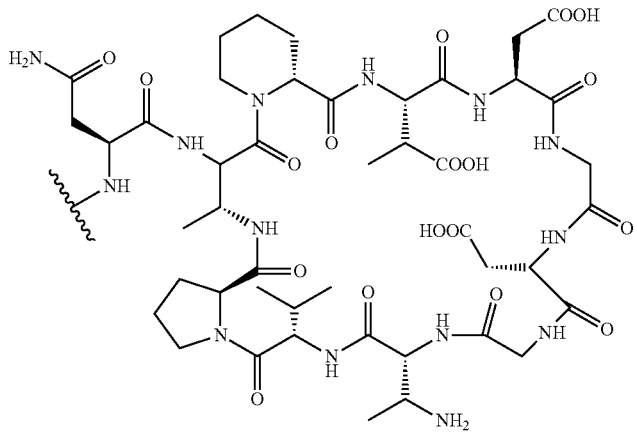

-continued
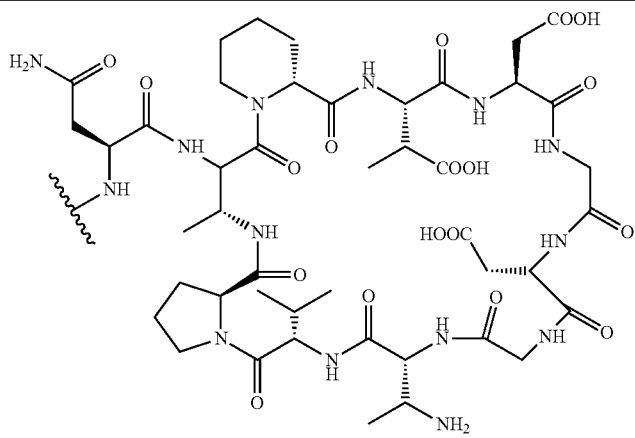
| Compound | Side Chain Structure |
|---|---|
| LP-002 | 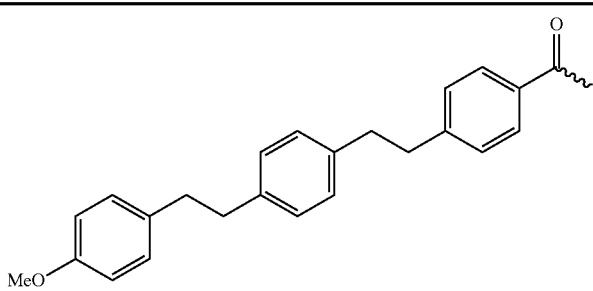 |
| LP-003 | 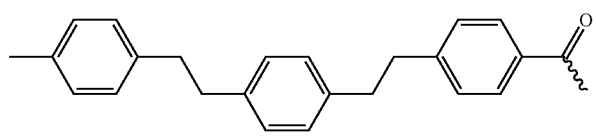 |
| LP-006 | 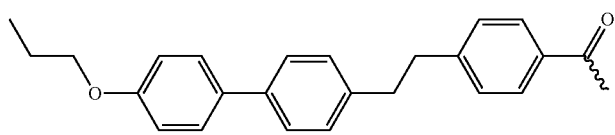 |
| LP-007 | 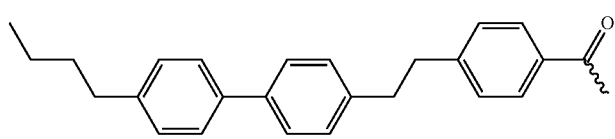 |
| LP-008 | 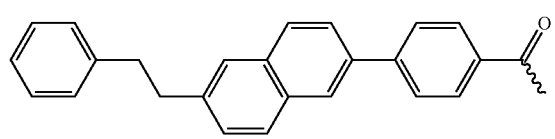 |
| LP-009 | 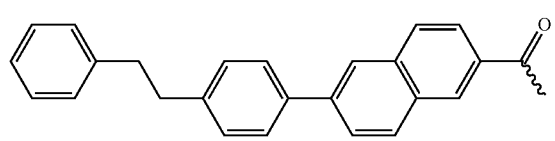 |
| LP-010 | 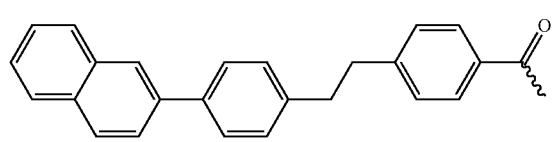 |

-continued
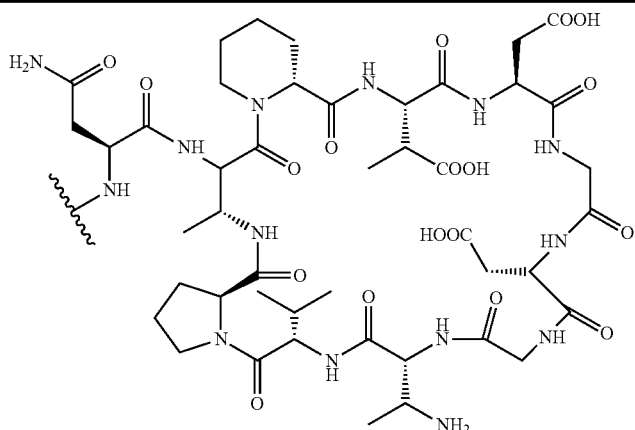
| Compound | Side Chain Structure |
|---|---|
| LP-011 | 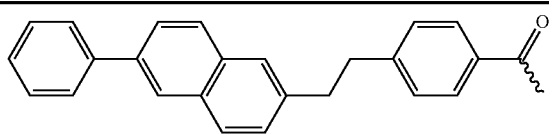 |
| LP-012 | 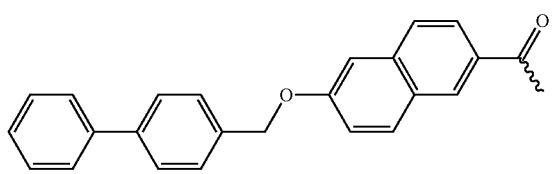 |
| LP-013 | 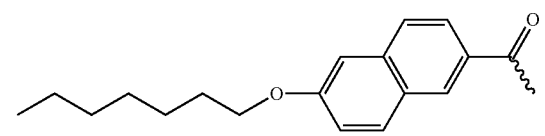 |
| LP-014 | 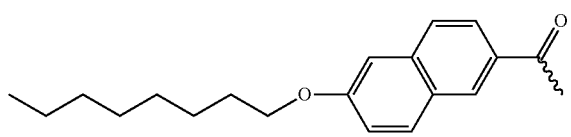 |
| LP-015 | 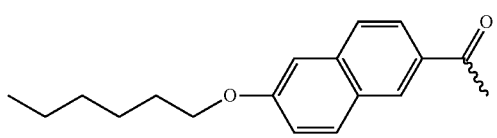 |
| LP-016 | 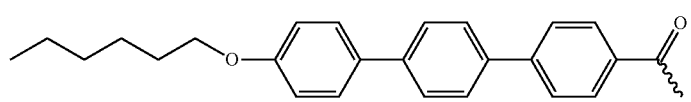 |
| LP-017 | 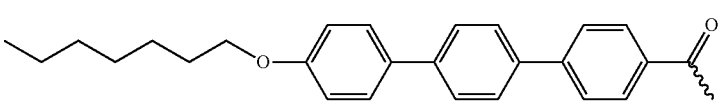 |
| LP-018 | 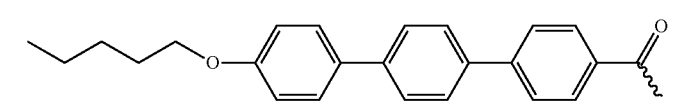 |
| LP-020 | 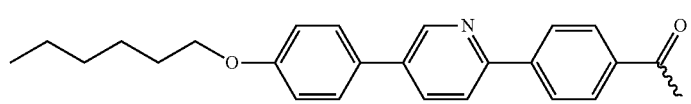 |

-continued
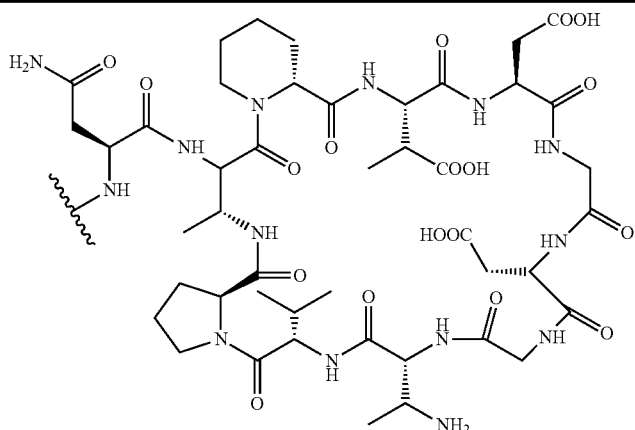
| Compound | Side Chain Structure |
|---|---|
| LP-021 | 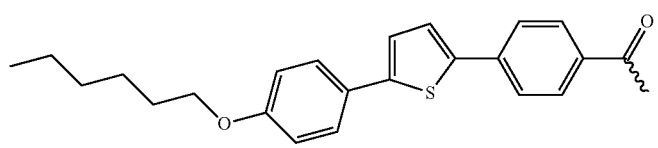 |
| LP-022 | 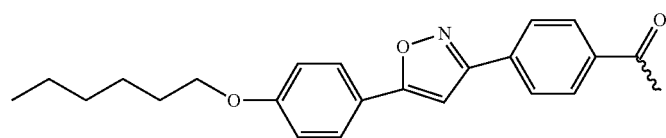 |
| LP-023 | 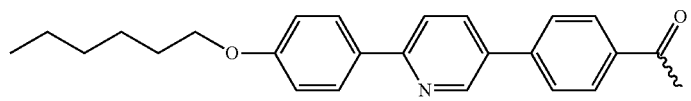 |
| LP-024 | 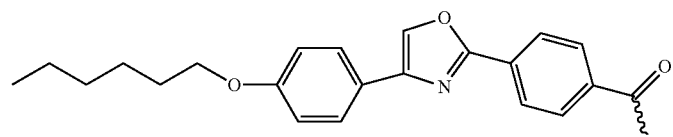 |
| LP-025 | 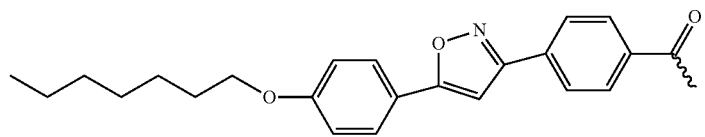 |
| LP-026 | 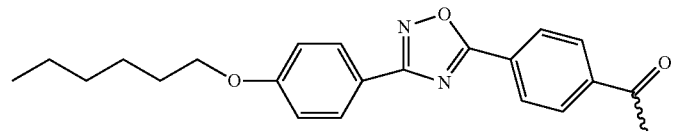 |
| LP-027 | 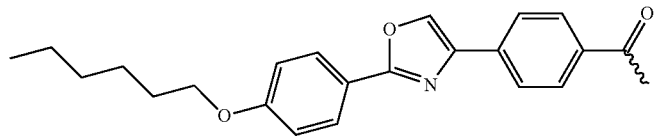 |
| LP-028 | 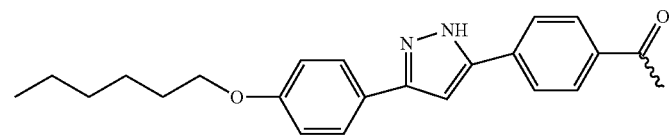 |

-continued
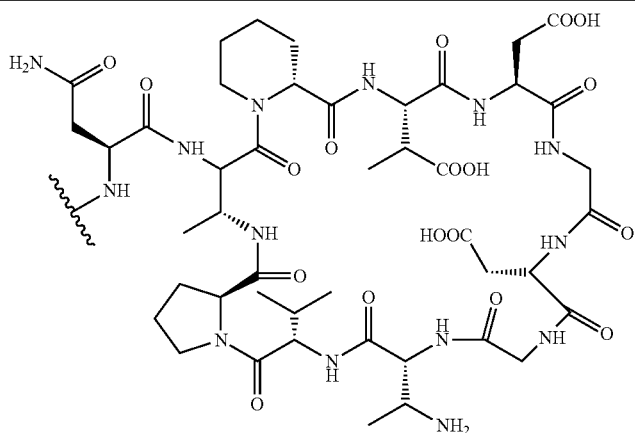
| Compound | Side Chain Structure |
|---|---|
| LP-029 | 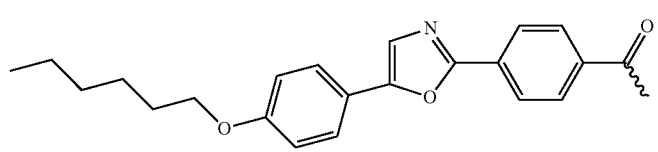 |
| LP-030 | 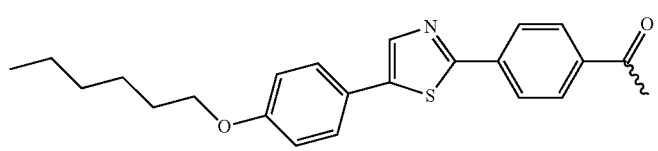 |
| LP-031 | 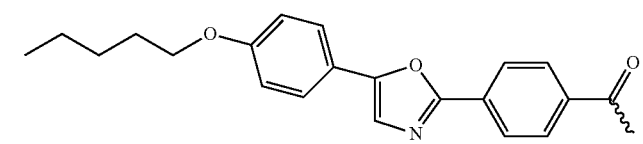 |
| LP-032 | 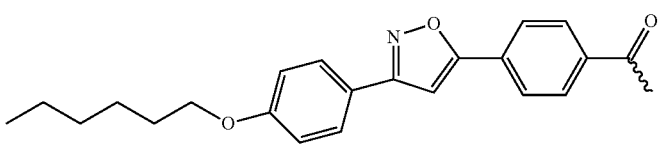 |
| LP-033 | 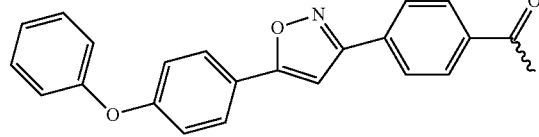 |
| LP-034 | 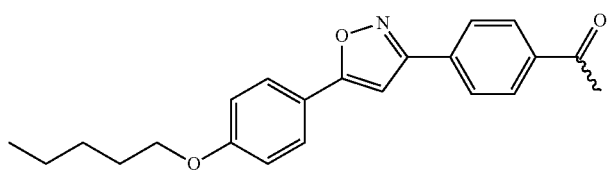 |
| LP-035 | 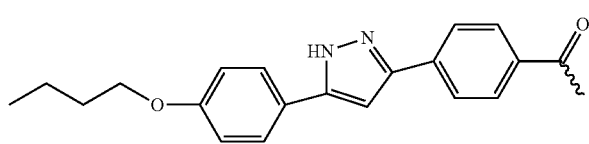 |

-continued
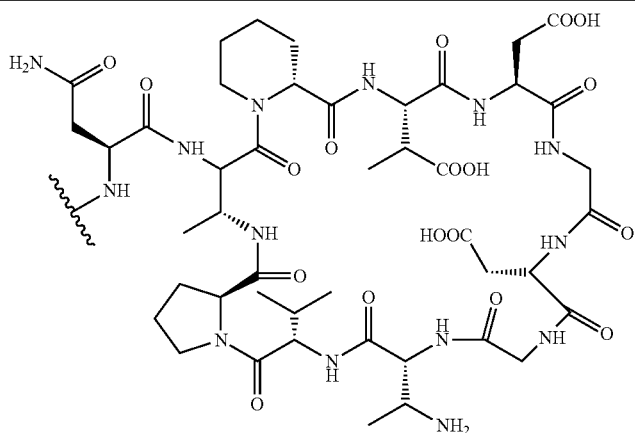
| Compound | Side Chain Structure |
|---|---|
| LP-036 | 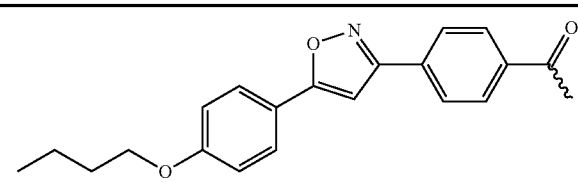 |
| LP-037 | 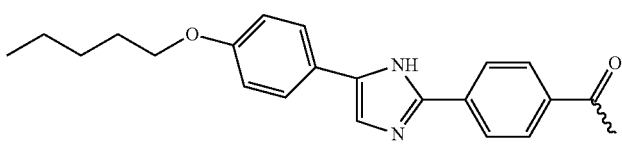 |
| LP-038 | 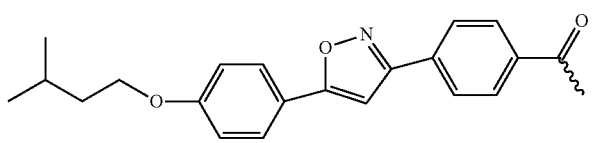 |
| LP-039 | 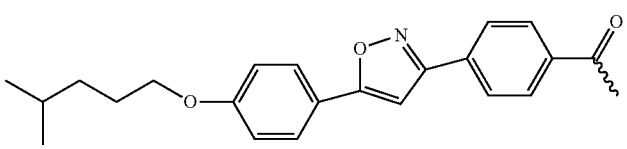 |
| LP-040 | 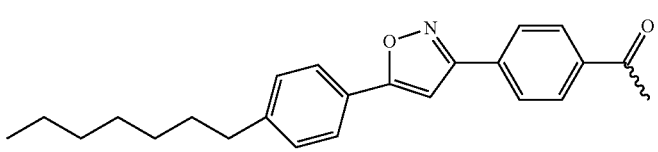 |
| LP-041 | 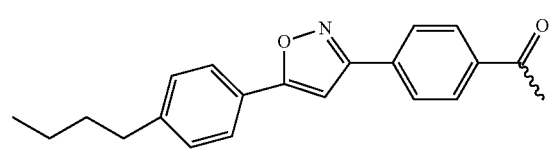 |
| LP-042 | 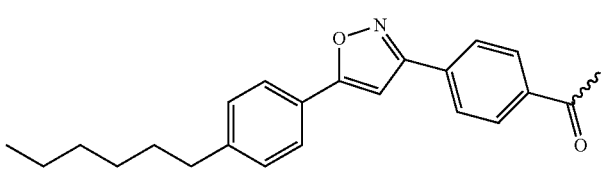 |

-continued
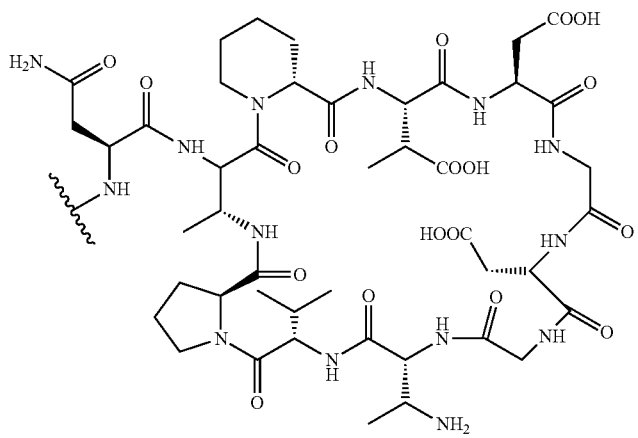
| Compound | Side Chain Structure |
|---|---|
| LP-043 | 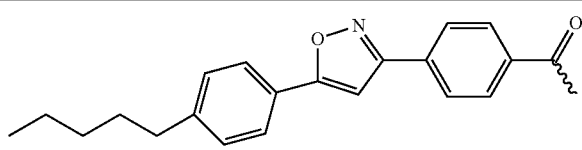 |
| LP-044 | 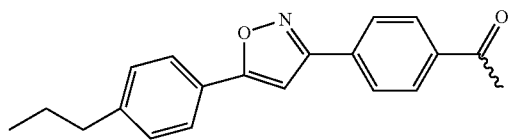 |
| LP-045 | 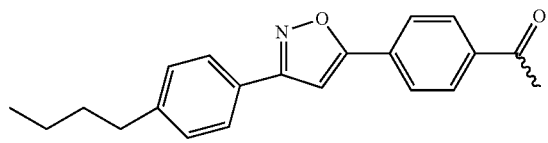 |
| LP-046 | 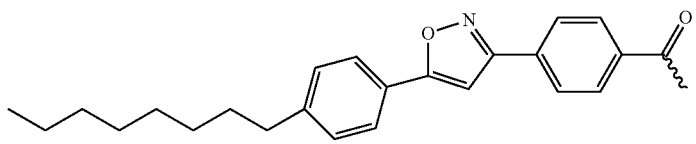 |
| LP-047 | 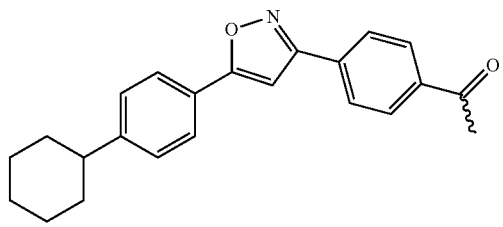 |
| LP-048 | 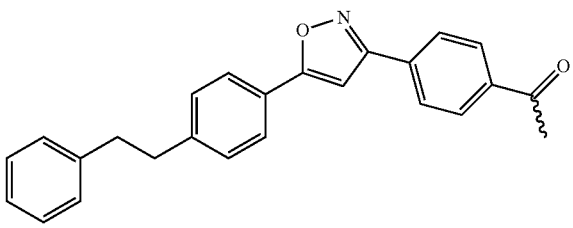 |

In embodiments, the compound is selected from LP-008, LP-009, LP-010, LP-011, LP-012, LP-013, LP-014, LP-015, LP-020, LP-021, LP-022, LP-023, LP-024, LP-025, LP-026, LP-027, LP-028, LP-029, LP-030, LP-031, LP-032, LP-034, LP-035, LP-036, LP-037, LP-040, LP-041, LP-042, LP-043, LP-044, LP-045, LP-046, LP-047 and LP-048.

In embodiments, the compound is selected from LP-013, LP-014, LP-020, LP-022, LP-023, LP-024, LP-025, LP-027, LP-028, LP-029, LP-031, LP-034, LP-041, LP-042, LP-043, LP-044, LP-045, LP-047 and LP-048.

In embodiments, the compound is selected from LP-020, LP-021, LP-022, LP-023, LP-024, LP-025, LP-026, LP-027, LP-028, LP-029, LP-030, LP-031, LP-032, LP-034, LP-035, LP-036 and LP-037.

In embodiments, the compound is selected from LP-040, LP-041, LP-042, LP-043, LP-044, LP-045, LP-046, LP-047 and LP-048.

In embodiments, the compound is selected from LP-008, LP-009, LP-010, LP-011, LP-012, LP-013, LP-014 and LP-015.

LP compounds, as described herein, exhibit antibacterial activity, for example against the test strains described herein. Suitably the LP compounds, as described herein, exhibit low levels of hemolysis, for example as demonstrated in the hemolysis assays reported herein.

LP compounds, as described herein, preferably exhibit improved performance as compared to known lipopeptide compounds in terms of one or more of toxicity, pharmacokinetics (including one or more of adsorption, distribution, metabolism and excretion), pharmacodynamics, bioavailability, solubility and pharmacological activity. In particular, LP compounds, as described herein, preferably exhibit low haemolytic activity.

Substantially Purified Forms

One aspect of the present invention pertains to LP compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r- forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

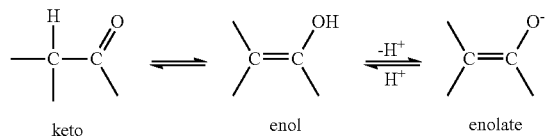

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

As discussed herein, a sodium or calcium salt (e.g. a $Ca_2Cl_2$ salt) is preferred, particularly a calcium salt.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH₃, —OAc).

For example, an aldehyde or ketone group may be protected as an acetal (R—CH(OR)₂) or ketal (R₂C(OR)₂), respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$ haloalkyl ester (e.g., a $C_{1-7}$-trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH₂NHC(=O)CH₃).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Methods for the chemical synthesis of LP compounds of the present invention are described herein. These and/or other well known methods may be modified and/or adapted in known ways in order to facilitate the synthesis of additional compounds within the scope of the present invention.

The synthesis of LP compounds, as described herein, involves deacylation of known Fmoc protected friulimicin B to yield the cyclic core peptide, preparing an activated ester which is the side chain precursor and then coupling the activated ester and cyclic core peptide.

Lipopeptide Precursor

Isolation of the lipopeptide precursor is achieved by deacylation, using deacylase, of a precursor lipopeptide, illustrated below by Fmoc-Friulimicin B:

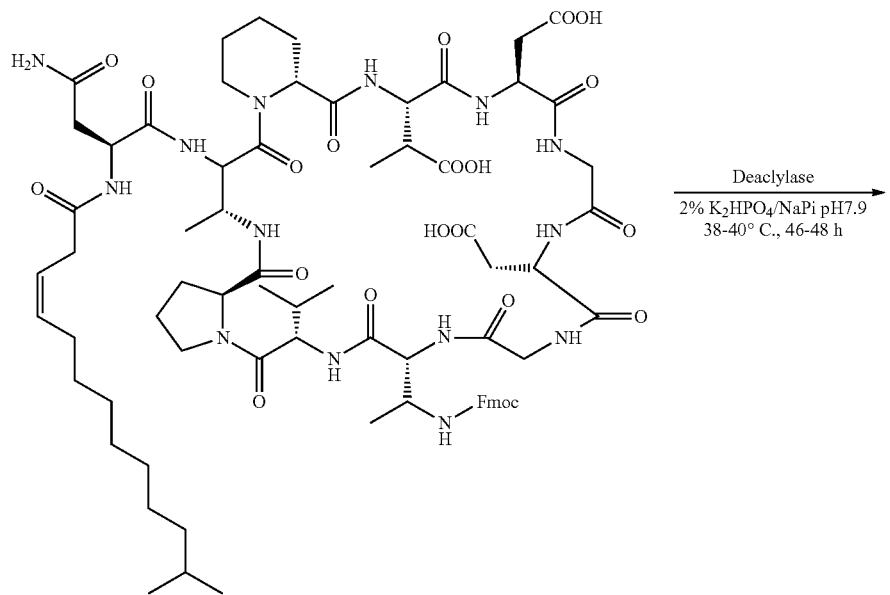

GM538

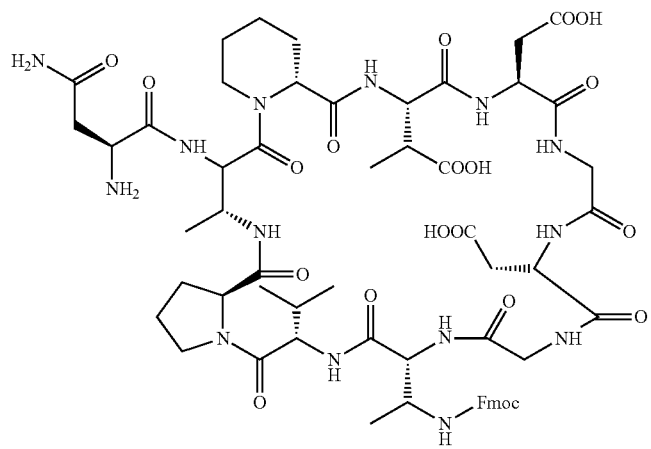

GM539

Side Chain Precursor

The following scheme shows the general method for synthesising the side chain precursors of LP compounds comprising a side chain of the form phenyl-heterocycle-phenyl-C(O)—.

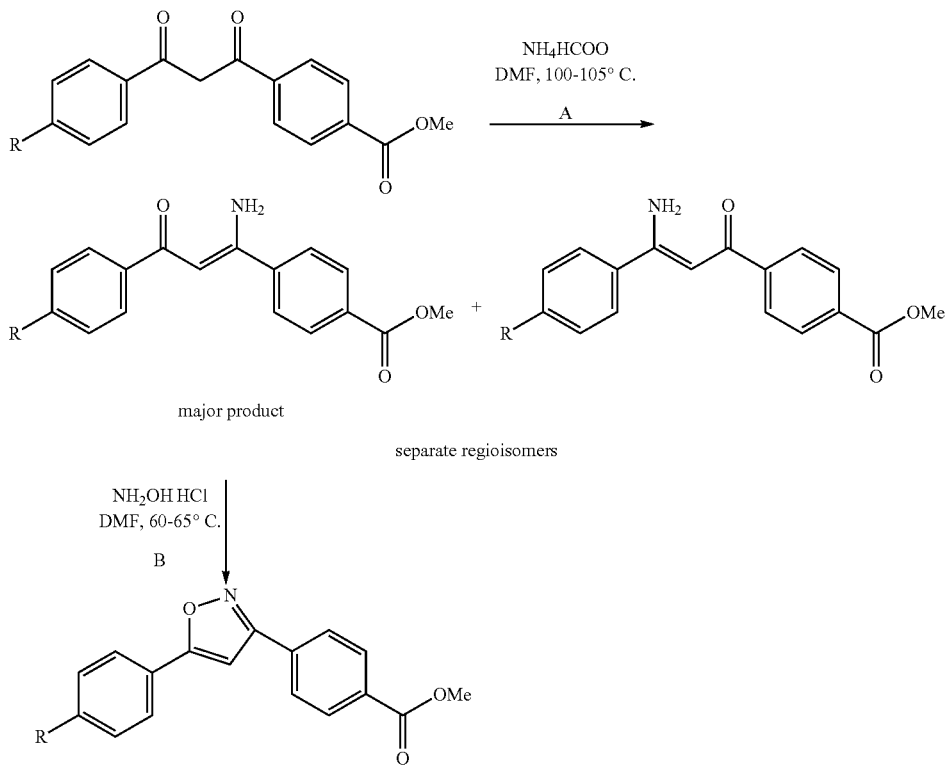

The scheme shows formation of the isoxazole product, but other heterocycles can be incorporated instead (for example, the regiosomeric isoxazole analogue can be obtained by using the minor regioisomer product).

Coupling of Side Chain Precursor with Lipopeptide Precursor

The side chain precursors are converted to activated esters (pentafluorophenyl esters or HOBt esters) by reaction with pentafluorophenol or HOBt in the presence of dicyclohexylcarbodiimide (DCC).

The activated esters are then coupled with the lipopeptide using one of the following coupling methods:

Method A: lipopeptide stirred with pentafluorophenol ester in the presence of DIPEA, followed by Fmoc deprotection with piperidine and purification by preparative HPLC.

Method B: $Et_3N$ added to lipopeptide and $CaCl_2$ at 0° C., followed by addition of pentafluorophenol ester and subsequent deprotection with piperidine and purification by preparative HPLC.

Method C: as per Method A except that HOBt ester used instead of pentafluorophenol ester.

Method D: as per Method B except that HOBt ester used instead of pentafluorophenol ester.

Method E: $Et_3N$ added to lipopeptide and $CaCl_2$ at 0° C., followed by addition of pentafluorophenol ester, warming to room temperature and purification by preparative RP-HPLC; product fractions being dissolved in DMF, to which TBAF hydrate is added, followed by addition of piperidine and subsequent purification by preparative RP-HPLC.

Method F: $CaCl_2$ was added to lipopeptide and pentafluorophenol ester at room temperature, followed by $Et_3N$ addition at 0° C. and then stirring. Warming to room temperature and addition of piperidine followed by purification by preparative RP-HPLC.

Coupling Method

Another aspect of the present invention pertains to a method of forming a lipopeptide having an acyl side chain (e.g. a LP compound, as described herein), wherein the method comprises the step of reacting an ester precursor of the acyl side chain with a cyclic peptide in the presence of calcium chloride.

In one embodiment, the ester is a pentafluorophenyl ester or a HOBt ester.

Compositions

One aspect of the present invention pertains to a composition (e.g., a pharmaceutical composition) comprising a LP compound, as described herein, and a pharmaceutically acceptable carrier, diluent, or excipient.

Another aspect of the present invention pertains to a method of preparing a composition (e.g., a pharmaceutical composition) comprising admixing a LP compound, as described herein, and a pharmaceutically acceptable carrier, diluent, or excipient.

Uses

The compounds described herein are useful, for example, in the treatment of diseases and conditions that are ameliorated by the inhibition of microbe growth or reproduction and/or microbe death.

The compounds described herein are useful, for example, in the treatment of diseases and conditions that are ameliorated by the inhibition of bacteria growth or reproduction and/or bacteria death.

The compounds described herein are useful, for example, in the treatment of infectious diseases and conditions.

The compounds described herein are useful, for example, in the treatment of sequelae associated with diseases and conditions that are ameliorated by the inhibition of bacteria growth or reproduction and/or bacteria death.

The compounds according to the invention have pharmacological activity, in particular as antibiotic for Grampositive bacteria. Preferably the LP compounds, as described herein, have activity against MRSA and/or glycopeptide-resistant strains. A therapeutically adequate effect on penicillin- or methicillin-resistant strains (MRSA strains) which have developed further antibiotic resistances is often possessed only by glycopeptides such as vancomycin or teicoplanin. However, strains also resistant to these antibiotics are increasingly appearing (FEMS Microbiol. Lett. 98 (1992) δ 109 to 116). Preferably LP compounds, as described herein, have activity against these problem organisms.

Use in Methods of Killing Bacteria or Inhibiting Bacteria Growth or Reproduction The LP compounds described herein are for use in a method of (a) inhibiting bacteria growth or reproduction; (b) killing bacteria; or (c) a combination of both of these.

Thus, the LP compounds as described herein have a bacteriocidal and/or bacteriostatic activity.

Suitable assays for determining antibacterial activity (e.g. bacteriostatic or bacteriocidal activity) are described herein and/or are known in the art.

Suitably, inhibiting bacteria growth or reproduction is preventing or stopping bacteria growth or reproduction.

One aspect of the present invention pertains to a method of inhibiting bacteria growth or reproduction, killing bacteria, or a combination of both of these.

The method can be performed in vitro or in vivo. In one embodiment, the method is performed in vitro. In one embodiment, the method is performed in vivo.

In one embodiment, the bacteria is in a host (e.g. a human or animal) and the method includes contacting the host with an effective amount of a LP compound, as described herein.

Suitably the method comprises contacting the bacteria with an effective amount of a LP compound, as described herein.

One aspect of the present invention pertains to a method of inhibiting bacteria growth or reproduction (e.g., inhibiting binary fission of bacteria cells), comprising contacting the bacteria with an effective amount of a LP compound, as described herein.

In one embodiment, the method is a method of inhibiting bacteria growth or reproduction in vitro or in vivo, comprising contacting the bacteria with an effective amount of a LP compound, as described herein.

One aspect of the present invention pertains to a method of inhibiting bacteria growth or reproduction (e.g., inhibiting binary fission of bacteria cells) in a host, comprising contacting the host with an effective amount of a LP compound, as described herein.

In one embodiment, the method further comprises contacting the host with one or more other antibacterial agents.

One aspect of the present invention pertains to a method of killing bacteria, comprising contacting the bacteria with an effective amount of a LP compound, as described herein.

In one embodiment, the method is a method of killing bacteria in vitro or in vivo, comprising contacting the bacteria with an effective amount of a LP compound, as described herein.

One aspect of the present invention pertains to a method of killing bacteria in a host, comprising contacting the host with an effective amount of a LP compound, as described herein.

In one embodiment, the method further comprises contacting the host with one or more other antibacterial agents.

In one embodiment, the LP compound is provided in the form of a pharmaceutically acceptable composition.

Any type of bacteria may be treated, including but not limited to those described herein.

One of ordinary skill in the art is readily able to determine whether or not a candidate compound possesses bacteriocidal and/or bacteriostatic activity. For example, assays which may conveniently be used to assess the activity offered by a particular compound are described herein.

For example, a sample of bacteria cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient having a bacterial infection or disease of the same type.

Use in Methods of Therapy

Another aspect of the present invention pertains to a LP compound, as described herein, for use in a method of treatment of the human or animal body by therapy.

In one embodiment, the method of treatment comprises treatment with both (i) a LP compound, as described herein, and (ii) one or more other antibacterial agents.

Use in the Manufacture of Medicaments

Another aspect of the present invention pertains to use of a LP compound, as described herein, in the manufacture of a medicament for use in treatment.

In one embodiment, the medicament comprises the LP compound.

In one embodiment, the treatment comprises treatment with both (i) a medicament comprising a LP compound, as described herein, and (ii) one or more other antibacterial agents.

Methods of Treatment

Another aspect of the present invention pertains to a method of treatment comprising administering to a patient in need of treatment a therapeutically effective amount of a LP compound, as described herein, preferably in the form of a pharmaceutical composition.

In one embodiment, the method further comprises administering to the subject one or more other antibacterial agents.

Conditions Treated—Bacterial Infections and Bacterial Diseases

The LP compounds of the present invention can be used to treat any bacterial infection or disease. In particular, the LP compounds of the present invention can be used to reduce or prevent growth or reproduction of an infecting bacterium and/or kill an infecting bacterium.

By "infecting bacterium" is meant a bacterium that has established infection in the host, and which may be associated with a disease or undesirable symptom as a result. Generally, infecting bacteria of interest are pathogenic bacteria, and may include a culture of multiple bacteria which together act to cause the pathology. Treatment may require elimination of a single, or multiple types of bacteria.

By "pathogenic bacteria" is meant bacteria that causes, or is capable of causing disease. Pathogenic bacteria propagate on or in tissues and may obtain nutrients and other essential materials from their hosts. As used herein, the term "pathogenicity", "pathogenic" and the like refers to a capability of causing disease and/or degree of capacity to cause disease to its host. The term is applied to parasitic micro-organisms in relation to their hosts.

Pathogenic bacteria are a major cause of human death and disease and cause infections such as tetanus, typhoid fever, diphtheria, syphilis, cholera, foodborne illness, leprosy and tuberculosis. Bacterial diseases are also important in agriculture, with bacteria causing leaf spot, fire blight and wilts in plants, as well as Johne's disease, mastitis, *salmonella* and anthrax in farm animals.

By "drug-resistant bacteria" or "antibiotic-resistant bacteria" is meant a bacterial strain that is resistant to growth inhibition or killing by an antibiotic. Multi-drug resistant bacteria are resistant to two or more antibiotics classes. Drug resistance can encompass, for example, ineffective killing of the infecting bacteria such that at least an infectious dose remains in the subject and the infection continues, resulting in continued symptoms of the associated infectious disease or later evidence of such symptoms. Drug resistance can also encompass inhibiting growth of the drug-resistant bacteria until such time therapy is discontinued, after which the bacteria begin to replicate and further the infectious disease.

By "inhibition of bacterial growth or reproduction" in the context of infection of an incapacitated bacterial cell according to the invention is meant that, following infection of the bacteria, the bacterial host cell's normal transcriptional and/or translational mechanisms are compromised such that the infected bacteria does not undergo substantial cell division (replication by binary fission) and is caused to enter a state of bacteriostasis. The stasis causes pathogenic effects to also regress.

By "infectious disease" or "infectious disorder" is meant a disease arising from the presence of a microbial agent, particularly a bacteria, in a host. The microbial agent may be an infectious bacteria or an infectious fungi, which gives rise to a bacterial infectious disease or a fungal infectious disease, respectively.

Types of Disease/Disorder

LP compounds as described herein can be used to treat diseases or conditions arising from infection of a host with one or more species of bacteria.

In one embodiment (e.g., of use in methods of therapy, of use in the manufacture of medicaments, of methods of treatment), treatment is treatment of any one of the diseases, disorders or conditions described herein.

The activity of the LP compounds as described herein may be a bacteriocidal or bacteriostatic activity, or both.

The anti-bacterial effect may arise through one or more mechanisms. The compounds of the present invention may be used in the treatment of the bacterial diseases described herein, independent of the mechanism.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of bacterial infection, reducing the incidence of bacterial infection, alleviating the symptoms of bacterial infection, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, other antibacterial compounds.

For example, it may be beneficial to combine treatment with a compound as described herein with one or more other (e.g., 1, 2, 3, 4) agents or therapies that regulates bacteria growth or reproduction and/or bacteria survival. In this way, several characteristic features of bacterial infection may be treated.

One aspect of the present invention pertains to a LP compound as described herein, in combination with one or more additional therapeutic agents.

The agents (i.e., the compound described here, plus one or more other agents) may be formulated together in a single dosage form, or alternatively, the individual agents may be formulated separately and presented together in the form of a kit, optionally with instructions for their use.

Other Uses

The LP compounds described herein may also be used as cell culture additives to inhibit bacteria growth or reproduction.

The LP compounds described herein may also be used as part of an in vitro assay, for example, in order to determine whether a candidate host is likely to benefit from treatment with the compound in question.

The LP compounds described herein may also be used as a standard, for example, in an assay, in order to identify other antibacterial compounds, etc.

Kits

One aspect of the invention pertains to a kit comprising (a) a LP compound as described herein, or a composition comprising a LP compound as described herein, e.g., preferably provided in a suitable container and/or with suitable packaging; and (b) instructions for use, e.g., written instructions on how to administer the compound or composition.

In one embodiment, the kit further comprises one or more other antibacterial agents.

The written instructions may also include a list of indications for which the active ingredient is a suitable treatment.

Routes of Administration

The LP compound or pharmaceutical composition comprising the LP compound may be administered to a subject by any convenient route of administration, whether systemically/peripherally or topically (i.e., at the site of desired action). Oral administration is an example.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird (e.g. a chicken)), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

In another embodiment, the subject/patient is not a human.

Formulations

While it is possible for the LP compound to be administered alone, it is preferable to present it as a pharmaceutical formulation (e.g., composition, preparation, medicament) comprising at least one LP compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one LP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

EXAMPLES

The following examples are provided solely to illustrate the present invention and are not intended to limit the scope of the invention, as described herein.

Chemical Synthesis

With reference to the general scheme given above, the following compounds were synthesised.

(A) Production and Isolation of Lipopeptide (1) Production of Lipopeptide Precursor GM538 was made from friulimicin B.

Protection of Dab-9 Amino Group of Friulimicin-B with Fmoc-Cl:

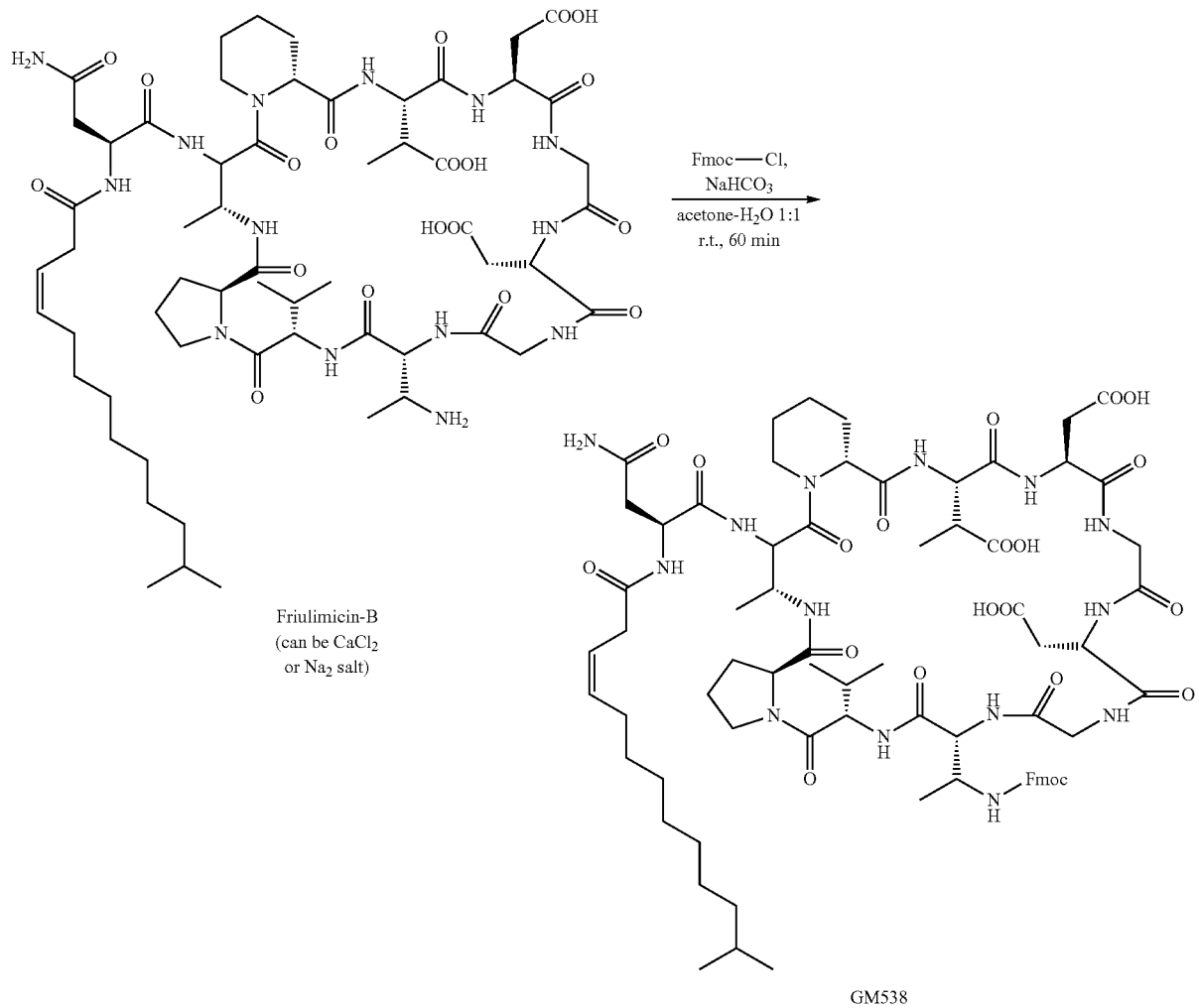

To a 500-mL round bottom flask containing Friulimicin-B Na₂ (MW1347; 0.744 mmol) was added NaHCO₃ (MW84; 3.72 mmol), Milli-Q water (91.7 mL) and acetone (63.5 mL). A solution of Fmoc-Cl (MW258.7; 1.12 mmol) in acetone (23.4 mL) was then added. The resultant reaction mixture was stirred at room temperature for 1 hour and progress of the reaction was monitored by HPLC. The solvents were removed under reduced pressure to give a white residue, which was purified by preparative RP-HPLC (Waters Nova-pak® 40×100 mm column, acetonitrile-water with 0.1% formic acid as solvent) to give the Fmoc-Friulimicin-B (GM538) as a white solid (MW1525; 840 mg, 74%).

(2) Deacylation of Lipopeptide Precursor

Deacylation can be effected using purified enzyme deacylation or whole cell biotransformation.

(a) Deacylation Using Purified Enzyme

The fermentation conditions described apply to *Streptomyces lividans* (TK23) which contains the AAC-fragment from *Actinoplanes utahensis* (NRRL 12052) cloned into pUWL201PW expression vector.

Tryptic soy broth (TSB) was the nutrient solution utilised for both seed culture and deacylase production culture. TSB (tryptone 17 g/L, soytone 3 g/L, glucose 2.5 g/L, NaCl 5 g/L and K₂HPO₄ 2.5 g/L) was supplemented with thiostrepton (25 μg/ml) to ensure the stabilisation of the expression vector.

Fermentation

Seed culture was inoculated with approximately six agar plugs from a 7-10 day old culture, grown on ISP2 agar (yeast extract 4 g/L, malt extract 10 g/L, glucose 4 g/L, agar 20 g/L), supplemented with 25 μg/L of thiostrepton. The fermentation was carried out in 250 ml Erlenmeyer flasks each containing 50 ml of TSB, also supplemented with 25 μg/L of thiostrepton. All flasks were incubated at 28° C., for 24 hours on a rotary shaker (50 mm orbit) set at 200 rpm. The production fermentation was carried out in 250 ml Erlenmeyer flasks each containing 50 ml of TSB supplemented with 25 μg/L of thiostrepton. Each flask was inoculated with 1 ml of seed culture (2%) and was incubated at 28° C., for 72-96 hours on a rotary shaker (50 mm orbit) set at 200 rpm.

Enzyme Purification

Enzyme (deacylase) purification was achieved through (NH₄)₂SO₄ precipitation. The harvested broth was filtered through filter paper under vacuum and transferred to 4° C. The filtrate was stirred and (NH₄)₂SO₄ was added slowly at a rate of 194.4 g per 800 ml of filtrate to achieve a final concentration of 40% (NH₄)₂SO₄. This mixture was slowly stirred over night at 4° C. and precipitated by centrifugation preferably at 12,000 g for 15 minutes at 4° C. The resulting precipitate was placed in a dialysis bag with 10 ml of 2% K₂HPO₄/NaPi (pH 7.9). The solution was dialyzed overnight against a solution of 2% K₂HPO₄/NaPi (pH 7.9). The dialyzed solution was stored at 4° C.

Deacylation

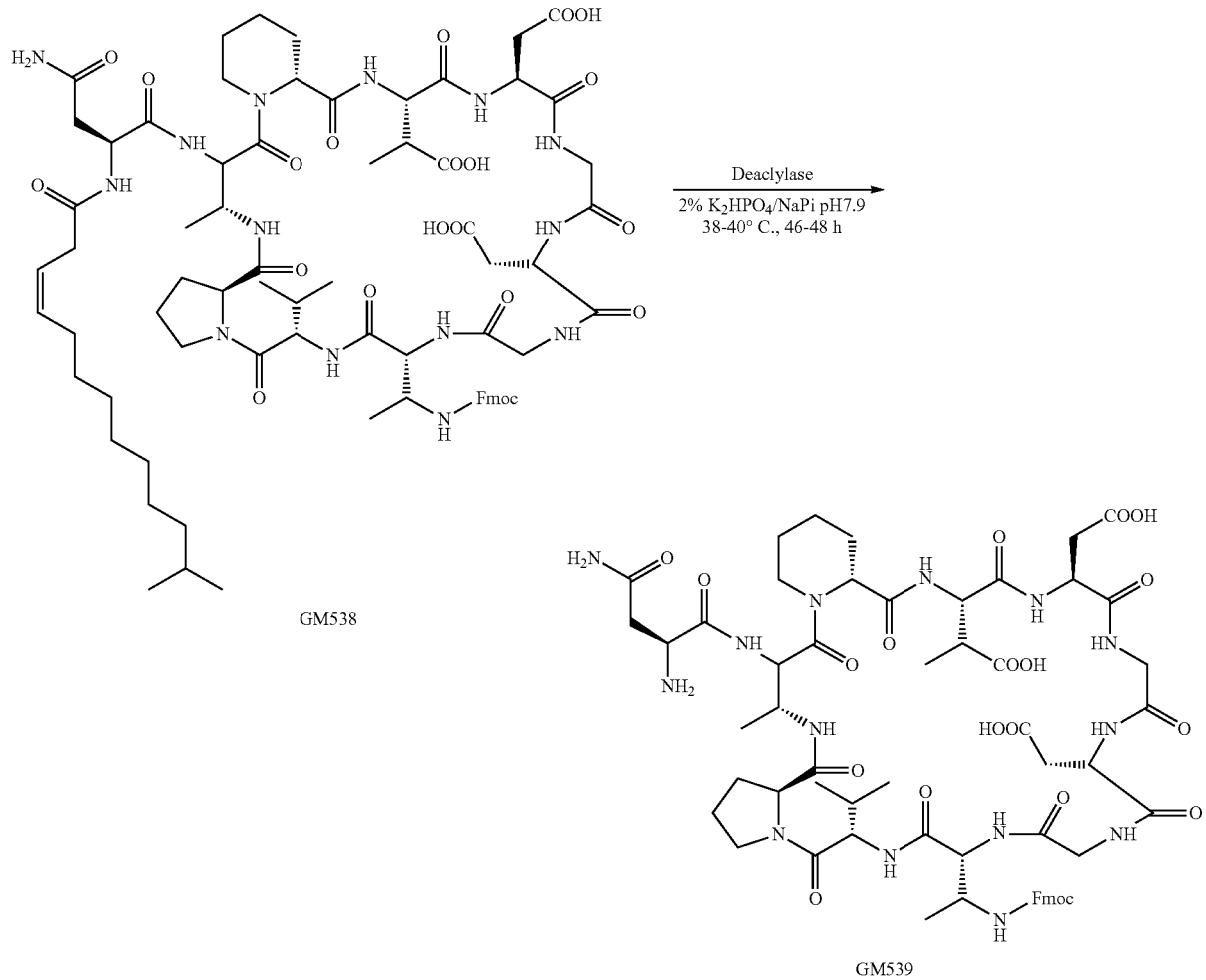

To a 250-mL round bottom flask containing Fmoc-Friulimicin-B (GM538, MW1525, 0.55 mmol) was added 2% $K_2HPO_4$/NaPi pH7.9 solution (20 mL). The solution was stirred gently and warmed to 28-30° C. before the deacylase (15 mL) was added. The reaction mixture was stirred gently at 28-30° C. for 48-72 hours and then concentrated under reduced pressure. The progress of reaction was monitored by HPLC. The concentrated residue was purified by preparative RP-HPLC (Waters Novapak® 40×100 mm column, acetonitrile-water with 0.1% formic acid as solvent) and freeze-dried to give the deacylated product GM539 as white solid (MW1317; ave. isolated yield 40%).

(b) Whole Cell Biotransformation

Fermentation

Seed culture was inoculated with approximately six agar plugs from a 7-10 day old culture, grown on ISP2 agar (yeast extract 4 g/L, malt extract 10 g/L, glucose 4 g/L, agar 20 g/L), supplemented with 25 µg/L of thiostrepton. The fermentation was carried out in 250 ml Erlenmeyer flasks each containing 50 ml of TSB, also supplemented with 25 µg/L of thiostrepton. All flasks were incubated at 28° C., for 24 hours on a rotary shaker (50 mm orbit) set at 200 rpm. The production fermentation was carried out in 250 ml Erlenmeyer flasks each containing 50 ml of TSB supplemented with 25 µg/L of thiostrepton. Each flask was inoculated with 1 ml of seed culture (2%) and was incubated at 28° C., for 72-96 hours on a rotary shaker (50 mm orbit) set at 200 rpm.

Deacylation

After 24 hours the flasks were removed from the shaker and inoculated with up to 100 mg of GM538 (dissolved in 2% $K_2HPO_4$/NaPi (pH 7.9). The biotransformation was typically complete within three days, and the material was harvested by centrifugation. The cells can be washed in RO water and reused successfully for at least 3 cycles of biotransformation, although by the third round the length of time required to obtain full conversion (50 mg of GM538) lengthens to over four days. All subsequent biotransformation cycles were undertaken in a non-nutritional buffer solution (TRIS-HCl).

The whole cell biotransformation methodology was found to provide a more efficient conversion to deacylated product, with higher yields.

(B) Synthesis of (Precursor) Side Chains (1) Side Chains Comprising a Heterocycle Unless stated otherwise, the following scheme was used to synthesis the side chain precursors of compounds comprising a side chain of the form phenyl-heterocycle-phenyl-C(O)—.

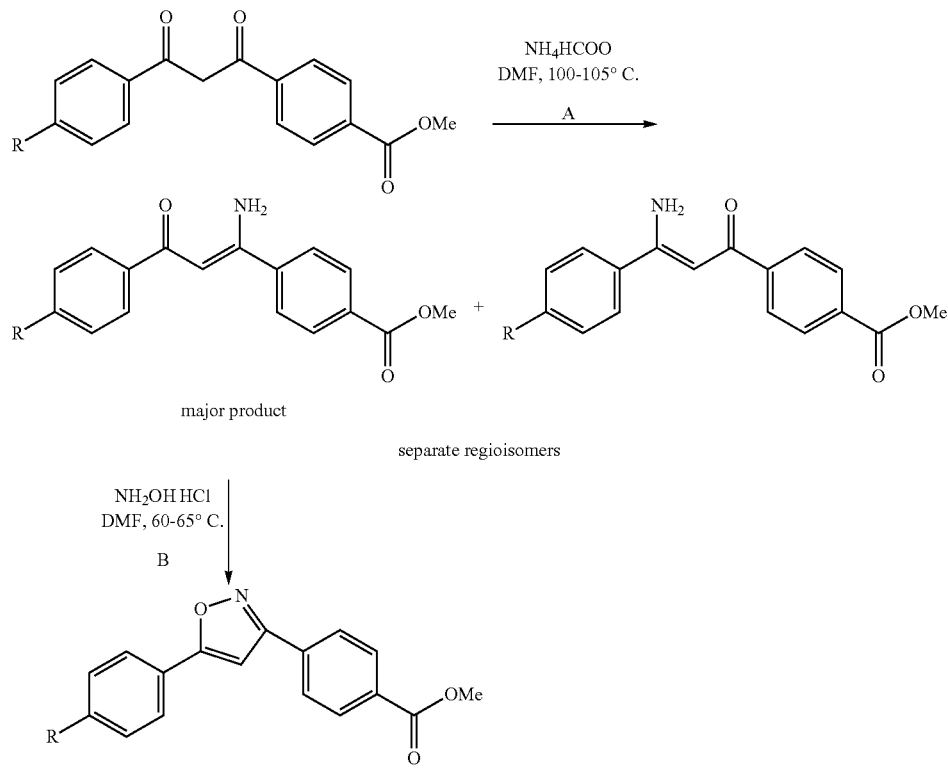

Scheme for preparation of Isoxazole-containing Carboxylic Acids

Synthesis of β-Keto Enamine from the Diaryl-β-Diketone

The β-aryldiketone (0.53 mmol) and ammonium formate (2.65 mmol, 5 eq) were dissolved in 2 mL DMF and the reaction mixture was heated to 100-105° C. C until the disappearance of starting material as monitored by analytical hplc. The resulting mixture was partitioned between water and ethyl acetate then the organic layer washed with saturated aqueous sodium chloride. The ethyl acetate layer was dried with anhydrous sodium sulfate and the solvent removed under reduced pressure. The solid, semi-solid or oily mixture obtained was purified by either recrystallization with ethyl acetate-heptane (1:5) or silica gel chromatography (Combiflash®) with gradient elution using EA-hexane as solvent or preparative RP-HPLC (X-Terra® PrepRP$_{18}$ 19×50 mm column with gradient elution (acetonitrile-water with 0.1% formic acid as solvent).

Synthesis of 3,5-Diarylisoxazole from the β-Keto Enamine

The β-keto enamine (0.107 mmol), DMF (1 mL), and hydroxylamine hydrochloride (5.45 mmol) were combined in a reaction vessel, and the mixture was stirred at 60-65° C. until the disappearance of starting material as monitored by analytical hplc. The mixture was partitioned between water and dichloromethane (DCM). The organic layer was evaporated under reduced pressure and then purified by silica gel chromatography (Combiflash®) with gradient elution using DCM-hexane as solvent.

(a) Side Chains of the Form Alkyl-Phenyl-Heterocycle-Phenyl-C(O)—

LP-041 Precursor

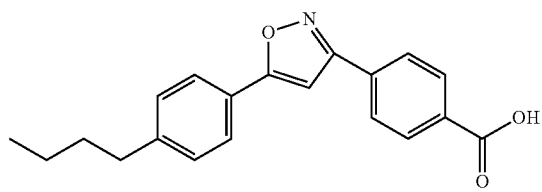 [SMILES: CCCCc1ccc(-c2cc(-c3ccc(C(=O)O)cc3)no2)cc1]

Methyl 4-{3-Oxo-3-[4-(butyl)phenyl]propanoyl}-benzoate

HPLC retention time, $R_T$ 5.80 min

Methyl 4-{1-Amino-3-[4-(butylphenyl)-3-oxo-1-propenyl}benzoate

Purified by silica gel chromatography (Combiflash®) with gradient elution using EA-hexane as solvent; HPLC retention time $R_T$, 4.55 min; 95% hplc purity; 26% isolated yield as major regioisomer product; $^1$H NMR (500 MHz, CDCl$_3$-d, δ) 0.94 (3H, t, J 7.4 Hz), 1.35-1.39 (2H, m), 1.61-1.64 (2H, m), 2.67 (2H, t, J 7.8 Hz), 3.94 (3H, s), 6.16 (1H, s), 7.24 (2H, d, J 8.1 Hz), 7.71 (2H, dd, J 1.8, 6.6 Hz), 7.88 (2H, dd, J 1.7, 6.6 Hz), 8.12 (2H, d, J 8.4 Hz).

Methyl 4-{5-[4-(butyl)phenyl]-3-isoxazolyl}benzoate

>95% hplc purity, 51% yield; $^1$H NMR (500 MHz, CDCl$_3$-d, δ) 0.96 (3H, t, J 7.4 Hz), 1.37-1.41 (2H, m), 1.62-1.67 (2H, m), 2.68 (2H, t, J 7.8 Hz), 3.96 (3H, s), 6.83 (1H, s), 7.32 (2H, d, J 8.2 Hz), 7.77 (2H, dd, J 1.6, 6.5 Hz), 7.96 (2H, dd, J 1.8, 6.7 Hz), 8.16 (2H, d, J 8.2 Hz).

4-{5-[4-(butyl)phenyl]-3-isoxazolyl}benzoic acid

HPLC retention time $R_T$, 4.55 min, >95% hplc purity; quantitative yield.

LP-040 Precursor

Using the same methodology as described above in respect of LP-041, and with a heptyl substituted β-aryldiketone starting material in place of the butyl substituted starting material, the heptyl substituted analogue was synthesised.

LP-045 Precursor

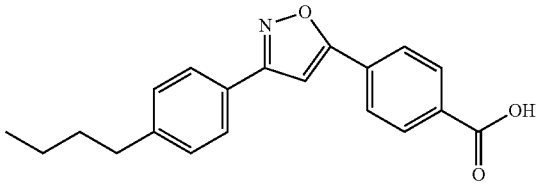 [SMILES: CCCCc1ccc(-c2cc(-c3ccc(C(=O)O)cc3)on2)cc1]

Methyl 4-{3-Amino-3-[4-(butylphenyl)-1-oxo-2-propenyl}benzoate

Purified by silica gel chromatography (Combiflash®) with gradient elution using EA-hexane as solvent; HPLC retention time $R_T$, 4.55 min; 95% hplc purity; 16% isolated yield as minor regioisomer product; $^1$H NMR (500 MHz, CDCl$_3$-d, δ) 0.94 (3H, t, J 7.4 Hz), 1.35-1.42 (2H, m), 1.63-1.67 (2H, m), 2.67 (2H, t, J 7.8 Hz), 3.95 (3H, s), 6.16 (1H, s), 7.32 (2H, d, J 8.7 Hz), 7.57 (2H, d, J 8.2 Hz), 7.99 (2H, d, J 8.4 Hz), 8.10 (2H, d, J 8.4 Hz).

Methyl 4-{4-[4-(butyl)phenyl]-3-isoxazolyl}benzoate

HPLC retention time $R_T$, 5.53 min >95% hplc purity, 83% yield; $^1$H NMR (500 MHz, CDCl$_3$-d, δ) 0.96 (3H, t, J 7.4 Hz), 1.37-1.43 (2H, m), 1.65-1.68 (2H, m), 2.68 (2H, t, J 7.7 Hz), 3.97 (3H, s), 6.83 (1H, s), 7.31 (2H, d, J 8.1 Hz), 7.78 (2H, d, J 8.2 Hz), 7.91 (2H, dd, J 1.8, 6.9 Hz), 8.16 (2H, dd, J 1.8, 6.8 Hz).

4-{4-[4-(butyl)phenyl]-3-isoxazolyl}benzoic acid

HPLC retention time $R_T$, 4.47 min, >95% hplc purity; quantitative yield; $^1$H NMR (500 MHz, DMSO-d$_6$, δ) 0.91 (3H, t, J 7.3 Hz), 1.30-1.34 (2H, m), 1.57-1.60 (2H, m), 2.65 (2H, t, J 7.4 Hz), 7.37 (2H, d, J 8.2 Hz), 7.72 (1H, s), 7.83 (2H, dd, J 8.2 Hz), 8.02 (2H, d, J 8.5 Hz), 8.10 (2H, dd, J 1.9, 6.7 Hz).

LP-044 Precursor

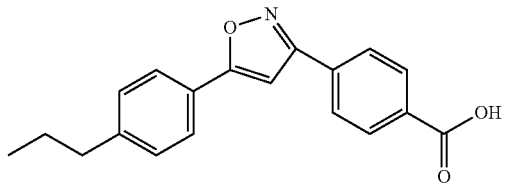 [SMILES: CCCc1ccc(-c2cc(-c3ccc(C(=O)O)cc3)no2)cc1]

Methyl 4-{3-Oxo-3-[4-(propyl)phenyl]propanoyl}-benzoate $^1$H NMR (500 MHz, CDCl$_3$-d, δ) 0.99 (3H, t, J 7.2 Hz), 1.68-1.75 (2H, m), 2.70 (2H, t, J 7.5 Hz), 4.02 (3H, s), 6.90 (1H, s), 7.34 (2H, d, J 8.0 Hz), 7.95 (2H, d, J 8.0 Hz), 8.06 (2H, d, J 8.1 Hz), 8.17 (2H, d, J 8.2 Hz).

Methyl 4-{1-Amino-3-[4-(propylphenyl)-3-oxo-1-propenyl}benzoate

Purified by silica gel chromatography (Combiflash®) with gradient elution using EA-hexane as solvent; HPLC retention time $R_T$, 4.05 min; 95% hplc purity; 47% yield; $^1$H NMR (500 MHz, CDCl$_3$-d, δ) 0.98 (3H, t, J 7.3 Hz), 1.65-1.72 (2H, m), 2.65 (2H, t, J 7.8 Hz), 3.98 (3H, s), 6.16 (1H, s), 7.26 (2H, d, J 8.1 Hz), 7.71 (2H, dd, J 1.8, 6.7 Hz), 7.88 (2H, dd, J 1.6, 6.6 Hz), 8.11 (2H, d, J 8.4 Hz).

Methyl 4-{5-[4-(propyl)phenyl]-3-isoxazolyl}benzoate

>95% hplc purity, 76% yield; $^1$H NMR (500 MHz, CDCl$_3$-d, δ) 0.98 (3H, t, J 7.3 Hz), 1.66-1.74 (2H, m), 2.65 (2H, t, J 7.8 Hz), 3.97 (3H, s), 6.83 (1H, s), 7.32 (2H, d, J 8.3 Hz), 7.77 (2H, d, J 8.2 Hz), 7.96 (2H, dd, J 1.8, 6.7 Hz), 8.16 (2H, dd, J 1.8, 6.7 Hz).

4-{5-[4-(propyl)phenyl]-3-isoxazolyl}benzoic acid

HPLC retention time $R_T$, 4.1 min, >95% hplc purity; quantitative yield; $^1$H NMR (500 MHz, DMSO-d$_6$, δ) 0.91 (3H, t, J 7.4 Hz), 1.59-1.65 (2H, m), 2.63 (2H, t, J 7.4 Hz), 7.39 (2H, d, J 8.3 Hz), 7.60 (1H, s), 7.83 (2H, dd, J 1.7, 6.6 Hz), 7.99 (2H, d, J 8.4 Hz), 8.07 (2H, dd, J 1.7, 6.7 Hz).

LP-043 Precursor

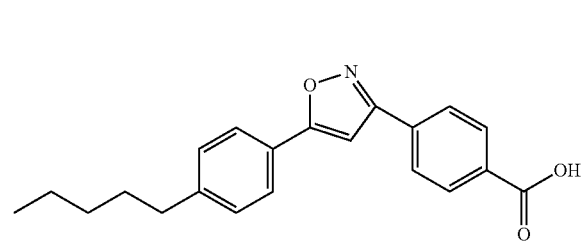 [SMILES: CCCCCc1ccc(-c2cc(-c3ccc(C(=O)O)cc3)no2)cc1]

Methyl 4-{3-Oxo-3-[4-(pentyl)phenyl]propanoyl}-benzoate $^1$H NMR (500 MHz, CDCl$_3$-d, δ) 0.91 (3H, t, J 6.8 Hz), 1.32-1.38 (4H, m), 1.63-1.69 (2H, m), 2.69 (2H, t, J 7.9 Hz), 4.00 (3H, s), 5.3 (0.29H, s, keto CH$_2$) 6.7 (1H, s, enol), 7.31 (2H, d, J 8.2 Hz), 7.93 (2H, d, J 8.2 Hz), 8.03 (2H, dd, J 1.8, 6.9 Hz), 8.15 (2H, dd, J 1.7, 6.8 Hz), (exists as its keto-enol tautomer).

Methyl 4-{1-Amino-3-[4-(pentylphenyl)-3-oxo-1-propenyl}benzoate

Purified by silica gel chromatography (Combiflash®) with gradient elution using EA-hexane as solvent; HPLC retention time $R_T$, 4.95 min; >95% hplc purity; 55% yield; $^1$H NMR (500 MHz, CDCl$_3$-d, δ) 0.90 (3H, t, 6.9 Hz), 1.31-1.36 (4H, m), 1.63-1.68 (2H, m), 2.69 (2H, t, J 7 Hz), 3.99 (3H, s), 6.16 (1H, s), 7.25 (2H, d, J 8.3 Hz), 7.7 (2H, dd, J 1.8, 6.7 Hz), 7.87 (2H, dd, J 1.7, 6.6 Hz), 8.13 (2H, dd, J 1.8, 6.6 Hz).

Methyl 4-{5-[4-(pentyl)phenyl]-3-isoxazolyl}benzoate

>95% hplc purity, 74% yield; $^1$H NMR (500 MHz, CDCl$_3$-d, δ) 0.90 (3H, t, 7.1 Hz), 1.34-1.39 (4H, m), 1.64-1.68 (2H, m), 2.68 (2H, t, J 7.9 Hz), 3.99 (3H, s), 6.83 (1H, s), 7.32 (2H, d, J 8.2 Hz), 7.77 (2H, dd, J 1.7, 6.6 Hz), 7.96 (2H, d, J 8.3 Hz), 8.16 (2H, dd, J 1.8, 6.7 Hz).

4-{5-[4-(pentyl)phenyl]-3-isoxazolyl}benzoic acid

HPLC retention time $R_T$, 4.96 min, >95% hplc purity; quantitative yield; $^1$H NMR (500 MHz, DMSO-d$_6$, δ) 0.86 (3H, t, 6.9 Hz), 1.27-1.33 (4H, m), 1.59-1.62 (2H, m), 2.64 (2H, t, J 7.5 Hz), 7.39 (2H, d, J 8.2 Hz), 7.61 (1H, s), 7.83 (2H, d, J 8.2 Hz), 8.0 (2H, d, J 8.4 Hz), 8.07 (2H, d, J 8.4 Hz).

LP-042 Precursor

Methyl 4-[3-oxo-3-(4-hexylphenyl)propanoyl]benzoate (MP198-261)

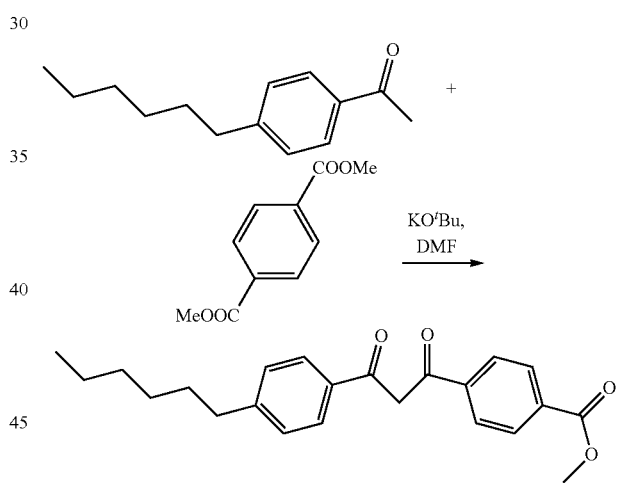

Starting from 4-hexylphenylacetophenone, 0.82 g (2.24 mmol, 46%) of the product was isolated. $^1$H NMR (CDCl$_3$, 500 MHz): δ=8.15 (d, 2H, J=6.7 Hz), 8.04 (d, 2H, J=6.7 Hz), 7.92 (d, 2H, J=6.7 Hz), 7.33 (d, 2H, J=6.7 Hz), 6.88 (s, 1H), 3.97 (s, 3H), 2.70 (t, 2H, J=7.6 Hz), 1.65 (m, 1H), 1.33 (m, 2H), 0.90 (t, 3H, J=7.3 Hz). HPLC: 6.543 min.

Methyl 4-[5-(4-hexylphenyl)isoxazol-3-yl]benzoate (MP198-263)

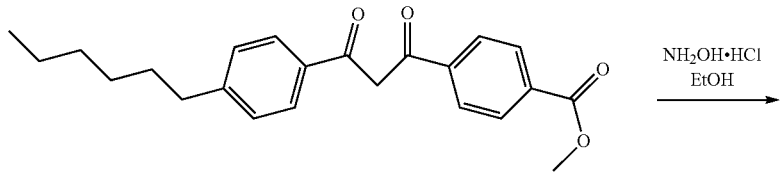

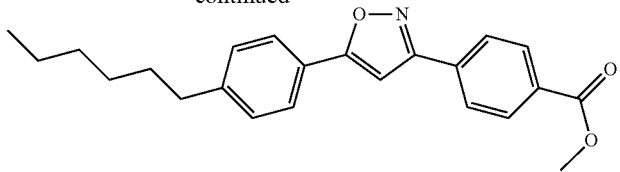

Starting from methyl 4-[3-oxo-3-(4-hexylphenyl)propanoyl]benzoate, 268 mg (0.74 mmol, 68%) of the product was isolated. ¹H NMR (CDCl₃, 500 MHz): δ=8.17 (d, 2H, J=6.6 Hz), 7.95 (d, 2H, J=6.6 Hz), 7.77 (d, 2H, J=6.6 Hz), 7.32 (d, 2H, J=6.6 Hz), 6.79 (s, 1H), 3.96 (s, 3H), 2.68 (t, 2H, J=7.7 Hz), 1.66 (m, 1H), 1.33 (m, 2H), 0.90 (t, 3H, J=7.3 Hz). HPLC: 6.299 min.

4-[5-(4-Hexylphenyl)isoxazol-3-yl]benzoic acid (MP206-165)

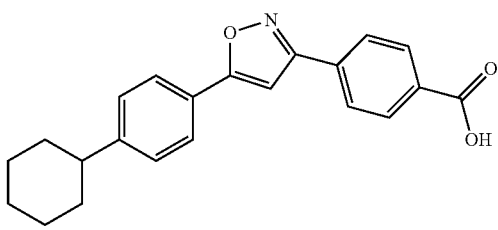 [SMILES: O=C(O)c1ccc(-c2cc(-c3ccc(C4CCCCC4)cc3)on2)cc1]

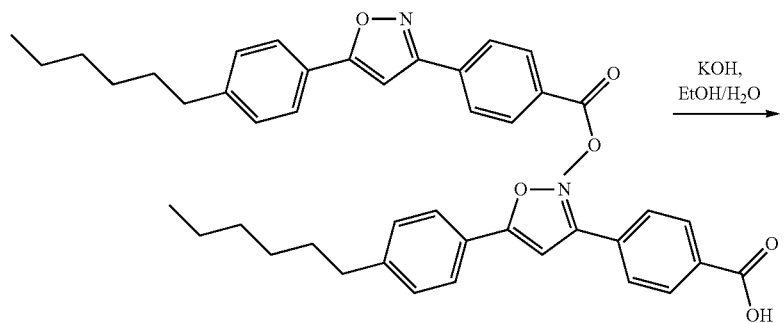

Starting from methyl 4-[5-(4-hexylphenyl)isoxazol-3-yl] benzoate, 107 mg (0.31 mmol, 94%) of the product was isolated. HPLC: 5.388 min.

1-H-Benzotriazole 4-[5-(4-hexylphenyl)isoxazol-3-yl] benzoate (MP206-174)

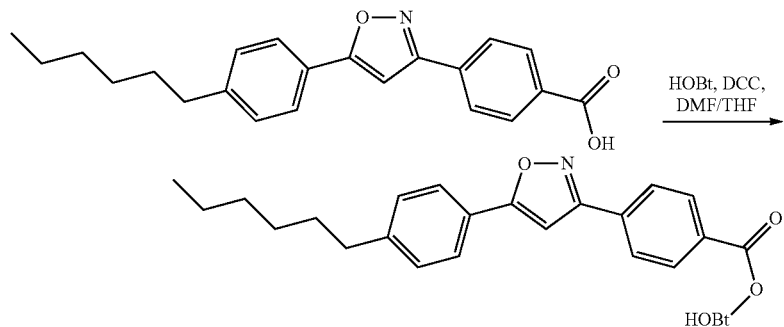

28 mg (0.08 mmol) 4-[5-(4-Hexylphenyl)isoxazol-3-yl] benzoic acid was dissolved in 5 mL THF and 13 mg (1.2 eq) HOBt and 18 mg (1.1 eq) DCC were added. After stirring over night the mixture was filtered through cotton wool and the solvent was evaporated in vacuo. The crude material was directly used for the coupling. HPLC: 6.634 min.

LP-047 Precursor

Using the methodology described above, the following compound was synthesised.

Methyl 4-[3-oxo-3-(4-cyclohexylphenyl)-propanoyl]-benzoate

HPLC retention time $R_T$ 6.29 min

Methyl 4-{1-Amino-3-[4-(cyclohexylphenyl)-3-oxo-1-propenyl}benzoate

HPLC retention time $R_T$, 4.96 min, 51.2% yield

Methyl 4-{5-[4-cyclohexylphenyl]-3-isoxazolyl}benzoate

HPLC retention time $R_T$, 6.03 min, 79% yield

87

4-{5-[4-(cyclohexylphenyl]-3-isoxazolyl}benzoic acid

HPLC retention time $R_T$, 4.98 min, M" 346.14

LP-046 Precursor

Using the methodology described above, the following compound was synthesised.

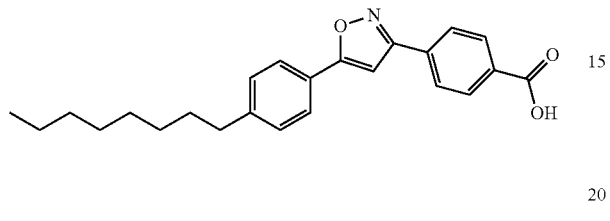

Methyl 4-[3-Oxo-3-(4-octylphenyl)-propanoyl]-benzoate

HPLC retention time $R_T$ 5.43 min, 29% yield

Methyl 4-{1-Amino-3-[4-(octylphenyl)-3-oxo-1-propenyl}benzoate

HPLC retention time $R_T$, 6.21 min, 61% yield

Methyl 4-{5-[4-octylphenyl]-3-isoxazolyl}benzoate

HPLC retention time $R_T$, 5.75, 80% yield

4-{5-[4-(octylphenyl]-3-isoxazolyl}benzoic acid

HPLC retention time $R_T$ 7.19 min

88

(b) Side Chains of the Form Phenyl-Alkyl-Phenyl-Heterocycle-Phenyl-C(O)—

LP-048 Precursor

4-[5-(4-Phenethyl-phenyl)-isoxazol-3-yl]-benzoic acid

Following same sequence of reaction, 4-[5-(4-Phenethyl-phenyl)-isoxazol-3-yl]-benzoic acid was made from 1-(4-Phenethyl-phenyl)-ethanone and dimethyl terephthalate. HPLC Rt: 4.42 min.

(c) Side Chains of the Form Alkoxy-Phenyl-Heterocycle-Phenyl-C(O)—

(i) With the Heterocycle being Isoxazole

Unless stated otherwise, the following methodology was used to synthesise the side isoxazole-containing side chains.

Preparation of Isoxazole-containing Carboxylic Acids

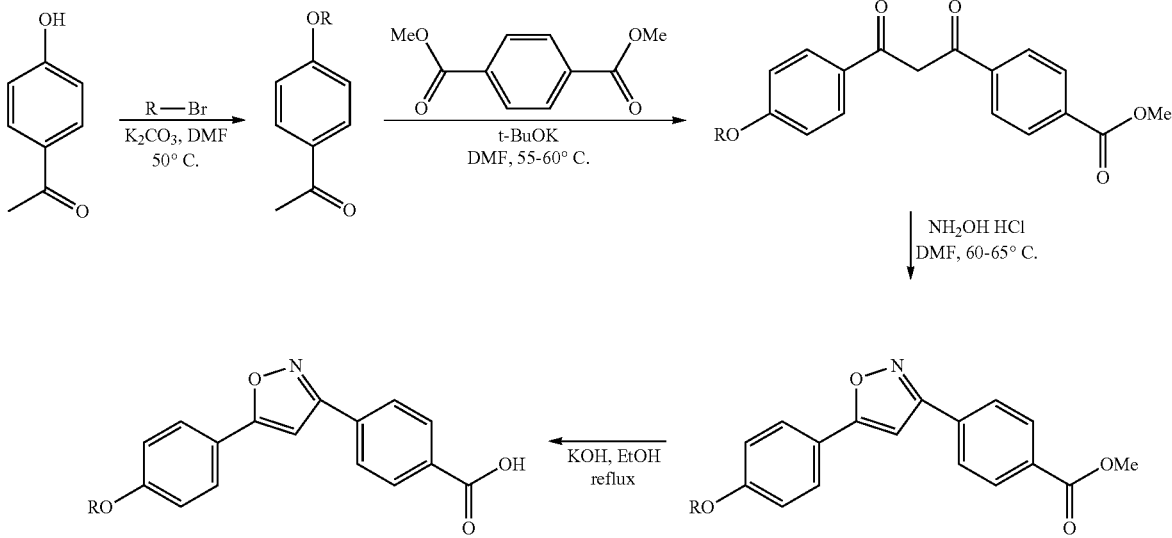

4-Alkoxyacetophenone

4-Hydroxyacetophenone (1 g, 7.34 mmol), DMF (10 mL), alkyl halide (8.1 mmol), and potassium carbonate (8.81 mmol) were combined in a 50-mL round bottom flask. The mixture was stirred at 50° C. for 17 h, and then water (25 mL) and n-hexane (2×25 ml) were added to the reaction mixture at room temperature. The organic layer was separated and washed with 1M aqueous sodium hydroxide solution (25 mL), and then with 1M aqueous hydrochloric acid solution water (25 mL). The organic layer was dried with anhydrous sodium sulfate and dried under reduced pressure (average yield: 90%).

Diaryl-β-Diketone

The acetophenone (5.61 mmol) was added to a solution of dimethyl terepthalate (8.98 mmol) in DMF (45 mL). To this solution was added potassium t-butoxide (8.42 mmol) at room temperature then the mixture was stirred around 55-60° C. for 2-3 days. The mixture was diluted with methanol (110 mL) at 0° C. and then quenched and crystallized by the slow addition of aqueous hydrochloric acid solution (10 mL, 1:1 conc HCl and water). The mixture was filtered and washed with water. The wet solid was dried under vacuum to give the product. (average yield: 52%)

LP-039 Precursor

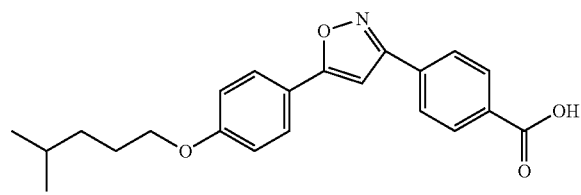 [SMILES: CC(C)CCCOc1ccc(-c2cc(-c3ccc(C(=O)O)cc3)no2)cc1]

4'-(4-methylpentyloxy)acetophenone $^1$H NMR (500 MHz, CDCl$_3$-d, δ) 0.94 (6H, d, J 4 Hz), 1.35-1.38 (1H, m), 1.58-1.62 (2H, m), 1.80-1.83 (2H, m), 2.55 (3H, s), 4.01 (2H, t, J 6.6 Hz), 6.93 (2H, d, J 6.9 Hz), 7.94 (2H, d, J 7.0 Hz).

Methyl 4-{3-Oxo-3-[4-(4-methylpentyloxy)phenyl]propanoyl}-benzoate

HPLC retention time, R$_T$ 6.19 min

Methyl 4-{5-[4-(4-methylpentyloxy)phenyl]-3-isoxazolyl}benzoate

HPLC retention time R$_T$, 5.92 min, 90% pure (by $^1$H NMR), 19% yield; $^1$H NMR (500 MHz, CDCl$_3$-d, δ) 0.94 (3H, d, J 6.6 Hz), 1.35-1.39 (2H, m), 1.63-1.64 (1H, m), 1.82-1.85 (2H, m), 4.01 (3H, s), 4.06 (2H, t, J 6.6 Hz), 6.75 (1H, s), 7.01 (2H, d, J 8.8 Hz), 7.81 (2H, d, J 8.9 Hz), 7.94 (2H, dd, J 1.9, 6.7 Hz), 8.16 (2H, d, J 8.2 Hz).

4-{5-[4-(4-methylpentyloxy)phenyl]-3-isoxazolyl}benzoic

90% pure (by $^1$H NMR), quantitative yield; $^1$H NMR (500 MHz, DMSO-d$_6$, δ) 0.88 (6H, d, J 6.6 Hz), 1.28-1.33 (2H, m), 1.54-1.62 (1H, m), 1.70-1.75 (2H, m), 4.03 (2H, t, J 6.5 Hz), 7.11 (2H, d, J 8.8 Hz), 7.53 (1H, s), 7.87 (2H, d, J 8.8 Hz), 8.04 (2H, d, J 8.3 Hz), 8.11 (2H, d, J 8.3 Hz).

LP-022 Precursor

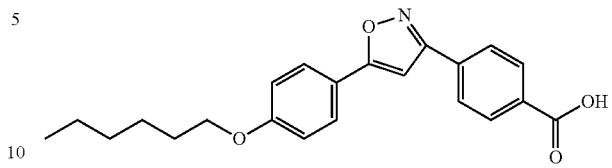

4'-Hexyloxyacetophenone $^1$H NMR (500 MHz, CDCl$_3$-d, δ) 0.93 (3H, t, J 6.9 Hz), 1.34-1.38 (4H, m), 1.46-1.48 (2H, m), 1.80-1.84 (2H, m), 2.56 (3H, s), 4.03 (2H, t, J 6.6 Hz), 6.93 (2H, dd, J 1.9, 7.1 Hz), 7.94 (2H, dd, J 2.0, 7.0 Hz).

Methyl 4-{3-Oxo-3-[4-(hexyloxy)phenyl]propanoyl}-benzoate

HPLC retention time R$_T$, 6.37 min; $^1$H NMR (500 MHz, CDCl$_3$-d, δ) 0.92 (3H, t, J 6.5 Hz), 1.35-1.40 (4H, m), 1.46-1.51 (2H, m), 1.80-1.86 (2H, m), 3.97 (3H, s), 4.05 (2H, t, J 6.6 Hz), 4.61 (0.05H, s, keto CH$_2$) 6.84 (0.98H, s, enol), 6.99 (2H, d, J 8.8 Hz), 7.99 (2H, d, J 8.8 Hz), 8.03 (2H, d, J 8.3 Hz), 8.15 (2H, d, J 8.3 Hz) 16.89 (0.75H, s, enol OH), (exists as its keto-enol tautomer).

Methyl 4-{1-Amino-3-[4-(hexyloxyphenyl)-3-oxo-1-propenyl}benzoate

Recrystallized from EA-heptane (1:5), >95% hplc purity, 54% yield; $^1$H NMR (500 MHz, CDCl$_3$-d, δ) 0.93 (3H, t, 6.6 Hz), 1.35-1.37 (4H, m), 1.48-1.59 (2H, m), 1.80-1.83 (2H, m), 3.97 (3H, s), 4.01 (2H, t, J 6.6 Hz), 6.14 (1H, bs), 6.94 (2H, dd, J 6.9, 2.0 Hz), 7.71 (2H, dd, J 6.6, 1.8 Hz), 7.94 (2H, dd, J 6.9, 2.0 Hz), 8.14 (2H, dd, J 6.6, 1.8 Hz).

Methyl 4-{5-[4-(Hexyloxy)phenyl]-3-isoxazolyl}benzoate

HPLC retention time R$_T$, 6.02 min, >95% hplc purity, 82% yield; $^1$H NMR (500 MHz, CDCl$_3$-d, δ) 0.94 (3H, t, J 6.6 Hz), 1.36-1.39 (4H, m), 1.48-1.58 (2H, m), 1.81-1.84 (2H, m), 3.96 (3H, s), 4.02 (2H, t, J 6.6 Hz), 6.56 (1H, s), 7.0 (2H, dd, J 8.8, 2.0 Hz), 7.77 (2H, dd, J 8.8, 2.0 Hz), 7.94 (2H, dd, J 8.4, 2.0 Hz), 8.15 (2H, dd, J 8.4, 2.0 Hz).

4-{5-[4-(Hexyloxy)phenyl]-3-isoxazolyl}benzoic acid

HPLC retention time R$_T$ 5.02 min, >95% hplc purity, quantitative yield; $^1$H NMR (500 MHz, DMSO-d$_6$, δ) 0.88 (3H, t, J 7.0 Hz), 1.30-1.43 (4H, m), 1.41-1.42 (2H, m), 1.70-1.74 (2H, m), 4.05 (2H, t, J 6.5 Hz), 7.11 (2H, d, J 8.8 Hz), 7.51 (1H, s), 7.84 (2H, d, J 8.8 Hz), 8.0 (2H, d, J 8.3 Hz), 8.07 (2H, d, J 8.3 Hz).

LP-025 Precursor

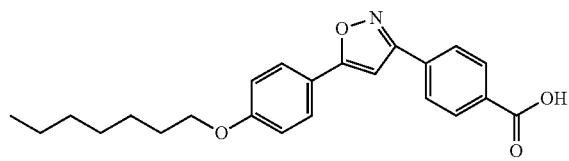 [SMILES: CCCCCCCOc1ccc(-c2cc(-c3ccc(C(=O)O)cc3)no2)cc1]

4′-Heptyloxyacetophenone

¹H NMR (500 MHz, CDCl₃-d, δ) 0.91 (3H, t, J 7.0 Hz), 1.31-1.37 (6H, m), 1.46-1.48 (2H, m), 1.80-1.83 (2H, m), 2.56 (3H, s), 4.03 (2H, t, J 6.6 Hz), 6.93 (2H, dd, J 2.1, 6.9 Hz), 7.93 (2H, dd, J 2.1, 6.9 Hz).

Methyl 4-{3-Oxo-3-[4-(heptyloxy)phenyl]propanoyl}-benzoate

HPLC retention time, $R_T$ 6.73 min

Methyl 4-{1-Amino-3-[4-(heptyloxyphenyl)-3-oxo-1-propenyl}benzoate

Recrystallized from EA-heptane (1:5), HPLC retention time $R_T$, 5.49 min, 92% hplc purity, 62% yield; ¹H NMR (500 MHz, CDCl₃-d, δ) 0.91 (3H, t, 6.7 Hz), 1.32-1.39 (6H, m), 1.46-1.49 (2H, m), 1.79-1.83 (2H, m), 3.97 (3H, s), 4.02 (2H, t, J 6.6 Hz), 6.14 (1H, bs), 6.94 (2H, dd, J 6.9, 2.0 Hz), 7.71 (2H, dd, J 6.6, 1.9 Hz), 7.94 (2H, dd, J 6.8, 2.0 Hz), 8.14 (2H, dd, J 6.6, 2.0 Hz).

Methyl 4-{5-[4-(Heptyloxy)phenyl]-3-isoxazolyl}benzoate

HPLC retention time $R_T$, 6.37 min, >95% hplc purity, 82% yield; ¹H NMR (500 MHz, CDCl₃-d, δ) 0.91 (3H, t, J 7.0 Hz), 1.31-1.39 (6H, m), 1.44-1.51 (2H, m), 1.80-1.88 (2H, m), 3.96 (3H, s), 4.03 (2H, t, J 6.6 Hz), 6.75 (1H, s), 7.0 (2H, dd, J 6.8, 2.0 Hz), 7.78 (2H, dd, J 6.8, 2.0 Hz), 7.95 (2H, dd, J 6.7, 1.8 Hz), 8.16 (2H, dd, J 8.3, 1.7 Hz).

4-{5-[4-(Heptyloxy)phenyl]-3-isoxazolyl}benzoic acid

HPLC retention time $R_T$, 5.49 min, quantitative yield; ¹H NMR (500 MHz, DMSO-d₆, δ) 0.87 (3H, t, J 7.0 Hz), 1.23-1.35 (6H, m), 1.39-1.45 (2H, m), 1.70-1.76 (2H, m), 4.05 (2H, t, J 6.5 Hz), 7.10 (2H, d, J 8.8 Hz), 7.47 (1H, s), 7.83 (2H, d, J 8.8 Hz), 8.0 (2H, b), 8.16 (2H, b).

LP-038 Precursor

1-[4-(3-Methylbutoxy)phenyl]ethanone

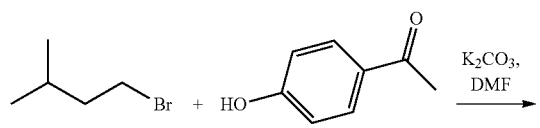

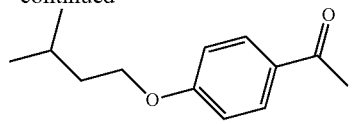

Starting from 1-bromo-3-methylbutane, 1.47 g (7.13 mmol, 97%) of the title compound was isolated and directly used for the next step. ¹H NMR (CDCl₃, 500 MHz): δ=7.95 (d, 2H, J=6.9 Hz), 6.94 (d, 2H, J=6.9 Hz), 4.05 (t, 2H, J=8.5 Hz), 2.56 (s, 3H). 1.86 (m, 1H), 1.71 (m, 2H), 0.99 (m, 6H).

Methyl 4-[3-oxo-3-(4-(3-methylbutoxy)propoxyphenyl)propanoyl]benzoate

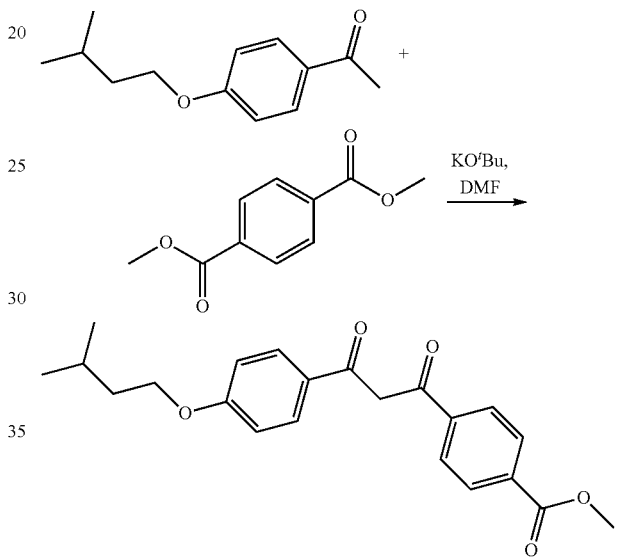

Starting from 1-[4-(3-methylbutoxy)phenyl]ethanone, 0.86 g (2.33 mmol, 48%) of the title compound was isolated. ¹H NMR (CDCl₃, 500 MHz): δ=8.08 (m, 4H), 7.29 (d, 2H, J=6.4 Hz), 7.00 (d, 2H, J=3.0 Hz), 6.85 (s, 1H), 4.10 (m, 2H), 3.98 (s, 3H), 1.87 (m, 1H), 1.73 (m, 2H), 1.00 (m, 6H). HPLC: 5.826 min.

Methyl 4-[5-(4-(3-methylbutoxy)phenyl)isoxazol-3-yl]benzoate

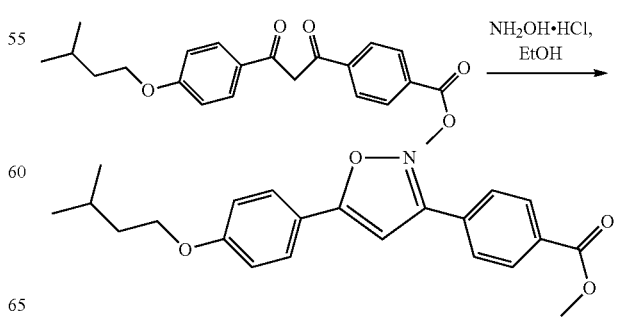

Starting from methyl 4-[3-oxo-3-(4-(3-ethylbutoxy)pro-poxyphenyl)propanoyl]benzoate, 637 mg (1.74 mmol, 75%) of the product was isolated. HPLC: 5.561 min.

4-[5-(4-(3-Methylbutoxy)phenyl)isoxazol-3-yl]benzoic acid

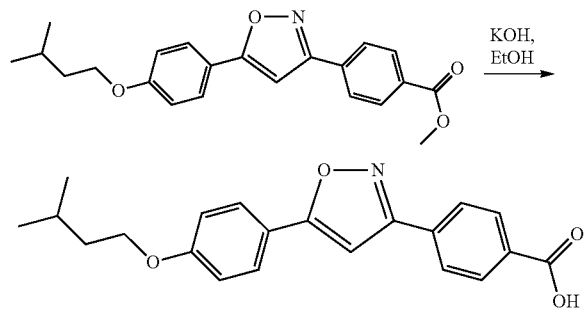

Starting from methyl 4-[5-(4-(3-methylbutoxy)phenyl) isoxazol-3-yl]benzoate, 213 mg (0.60 mmol, 88%) of the title compound was isolated. HPLC: 4.539 min.

1-H-Benzoltriazole 4-[5-(4-(3-methylbutoxy)phenyl) isoxazol-3-yl]benzoate

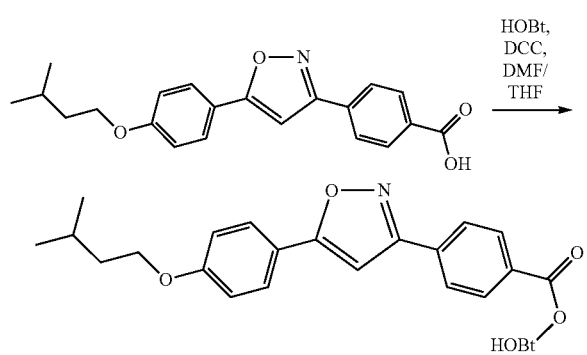

Starting from 4-[5-(4-(3-methylbutoxy)phenyl)isoxazol-3-yl]benzoic acid, 40 mg (0.085 mmol, 50%) of the title compound was isolated. HPLC: 5.878 min.

LP-036 Precursor

Methyl 4-[3-(4-butyloxyphenyl)-3-oxopropanoyl]benzoate

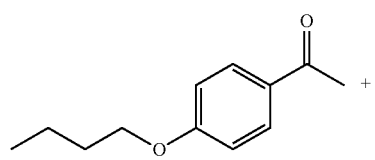

-continued

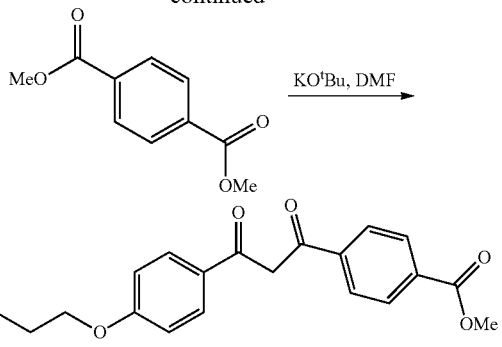

Starting from 4-pentyloxyacetophenone, 0.58 g (32%) of the product was isolated. $^1$H NMR (CDCl$_3$, 500 MHz): δ=8.15 (d, 2H, J=8.4 Hz), 8.03 (d, 2H, J=8.4 Hz), 8.00 (d, 2H, J=8.0 Hz), 6.96 (d, 2H, J=8.4. Hz), 6.84 (s, 1H), 4.07 (t, 2H, J=7.6 Hz), 3.96 (s, 3H), 1.83 (m, 2H), 1.52 (m, 2H), 1.03 (t, 3H, J=7.4 Hz). HPLC: 5.518 min.

Methyl 4-{5-[4-(butyloxy)phenyl]isoxazol-3-yl}benzoate

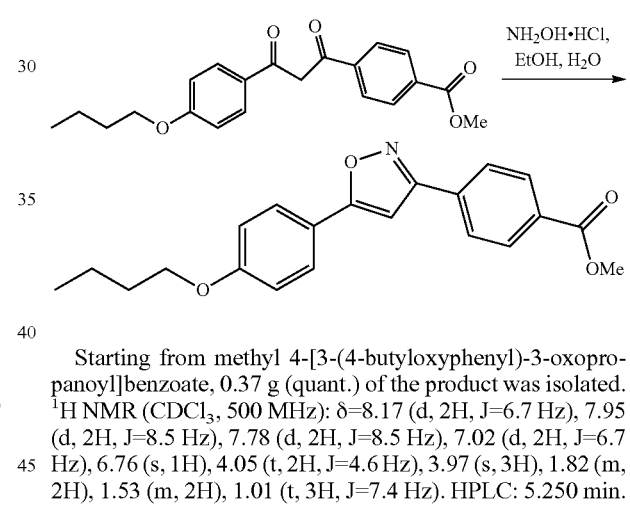

Starting from methyl 4-[3-(4-butyloxyphenyl)-3-oxopropanoyl]benzoate, 0.37 g (quant.) of the product was isolated. $^1$H NMR (CDCl$_3$, 500 MHz): δ=8.17 (d, 2H, J=6.7 Hz), 7.95 (d, 2H, J=8.5 Hz), 7.78 (d, 2H, J=8.5 Hz), 7.02 (d, 2H, J=6.7 Hz), 6.76 (s, 1H), 4.05 (t, 2H, J=4.6 Hz), 3.97 (s, 3H), 1.82 (m, 2H), 1.53 (m, 2H), 1.01 (t, 3H, J=7.4 Hz). HPLC: 5.250 min.

4-{5-[4-(butyloxy)phenyl]isoxazol-3-yl}benzoic acid

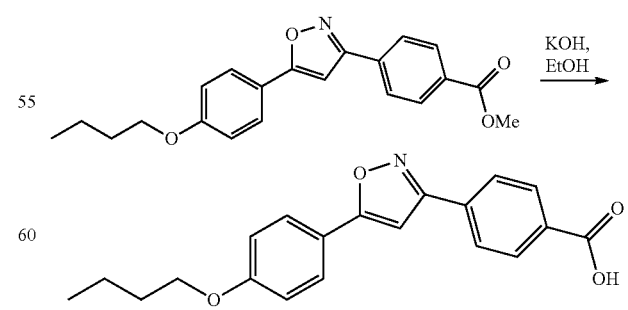

Starting from methyl 4-{5-[4-(butyloxy)phenyl]isoxazol-3-yl}benzoate, 0.34 g (97%) of the product was isolated. HPLC: 4.221 min.

95

1H-benzotriazole 4-{5-[4-(butyloxy)phenyl]isoxazol-3-yl}benzoate

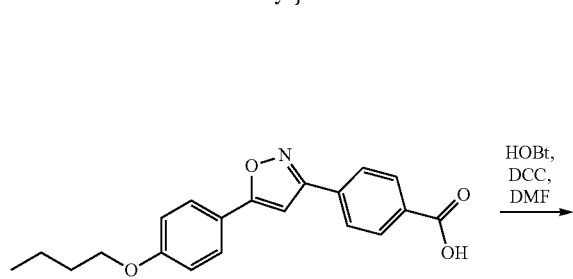

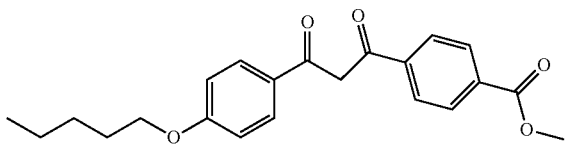

Starting from 4-pentyloxyphenylacetophenone, 0.48 g (1.54 mmol, 12%) of the product was isolated. HPLC: 4.905 min.

4-{5-[4-(Pentyloxy)phenyl]isoxazol-3-yl}benzoic acid

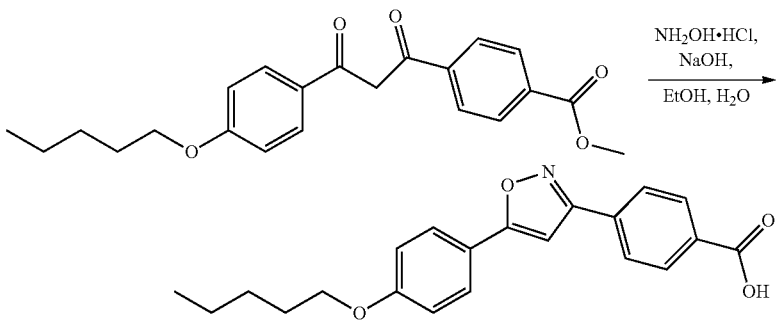

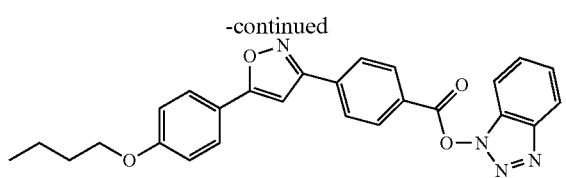

Starting from 4-{5-[4-(butyloxy)phenyl]isoxazol-3-yl}benzoic acid, 53 mg (117 mmol, 67%) of the product was isolated. HPLC: 5.608 min.

LP-034 Precursor

Methyl 4-[3-(4-pentyloxyphenyl)-3-oxopropanoyl]benzoate

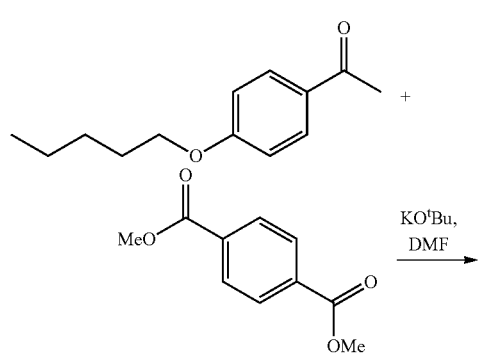

To 92 mg (0.26 mmol) methyl 4-[3-(4-pentyloxyphenyl)-3-oxopropanoyl]benzoate in 10 mL ethanol was added 146 mg (3.63 mmol) sodium hydroxide and 500 mg (7.25 mmol) hydroxylamine hydrochloride in 2 mL water. The solution was refluxed for 7 h. After cooling to room temperature, 1 M hydrochloric acid was added and the precipitate formed was filtered off and washed with water. Upon drying, the product was obtained as a white solid (22 mg, 0.06 mmol, 23%). $^1$H NMR (D$_6$-acetone, 500 MHz): δ=8.18 (d, 2H, J=8.6 Hz), 8.06 (d, 2H, J=8.5 Hz), 7.89 (d, 2H, J=8.6 Hz), 7.30 (s, 1H), 7.11 (d, 2H, J=8.6 Hz), 4.08 (t, 2H, J=7.3 Hz), 1.82 (m, 2H), 1.47 (m, 4H), 0.93 (t, 3H, J=7.3 Hz). HPLC: 4.641 min.

1H-benzotriazole 4-{5-[4-(pentyloxy)phenyl]isoxazol-3-yl}benzoate

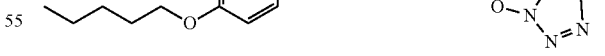

Starting from 4-{5-[4-(pentyloxy)phenyl]isoxazol-3-yl}benzoic acid, 30 mg of a crude mixture was obtained that was directly used for the next step. HPLC: 5.946 min.

LP-032 Precursor 4-(5-octylisoxazol-3-yl)benzoic acid

Adopting the same method as for LP-033 discussed below, using the alkyne (I) and oxime (II)

97

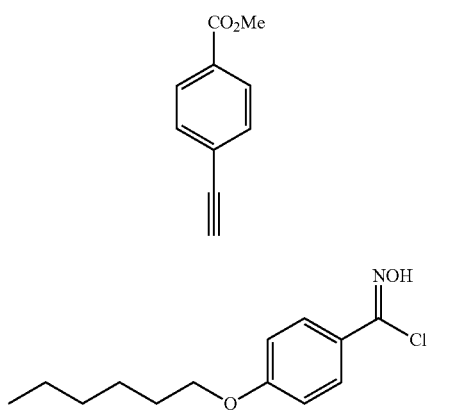

the following compound was synthesized:

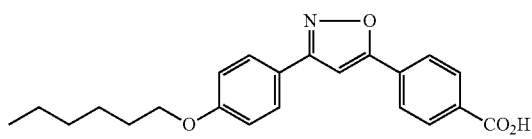 [SMILES: CCCCCCOc1ccc(-c2cc(-c3ccc(C(=O)O)cc3)on2)cc1]

(ii) With the Heterocycle being Oxazole

LP-031 Precursor 1-(4-(pentyloxy)phenyl)ethanone

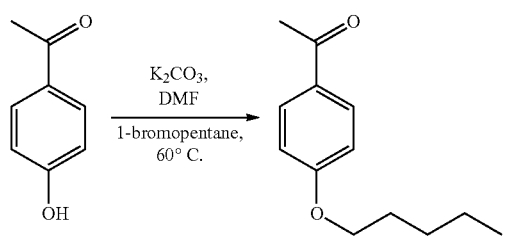

To a solution of the 4-hydroxyacetophenone (1.0 g, 7.3 mmol) in 5 mL DMF under Ar was added $K_2CO_3$ (1.0 g, 7.3 mmol) and 1-bromopentane (1.1 mL, 8.7 mmol) and heated at 60° C. overnight. The reaction mixture was cooled to room temperature, poured into water (100 mL) and extracted with EtOAc. The organic layer was washed with brine, dried and evaporated to afford a residue which upon purification by combiflash, eluting with 5% EtOAc in Hexane afforded 1.3 g product (86%). $^1$H NMR (500 MHz, CDCl$_3$): δ 0.98 (t, 3H, J=7.0 Hz), 1.41-1.49 (m, 4H), 1.83-1.86 (m, 2H), 2.59 (s, 3H), 4.09 (t, 2H, J=6.5 Hz), 6.98 (d, 2H, J=7.0 Hz), 7.98 (d, 2H, J=7.0 Hz).

98

2-bromo-1-(4-(pentyloxy)phenyl)ethanone

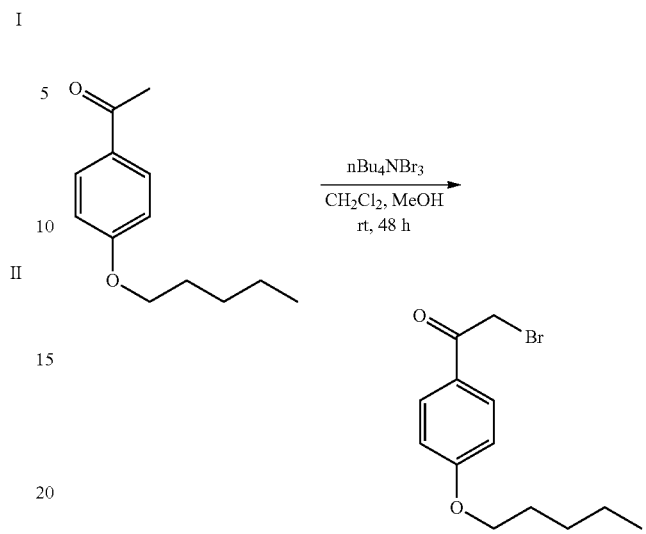

4-Pentyloxyacetophenone (1.3 g, 6.3 mmol) was dissolved in anhydrous $CH_2Cl_2$ (20 mL) and anhydrous MeOH (10 mL) under Ar. Tetrabutylammoniumtribromide (3.3 g, 6.9 mmol) was added and the reaction mixture stirred at room temperature for 48 h. Solvent was removed under vacuum and the thick residue passed through a short plug of silica gel eluting with 10% EtOAc in hexane to afford 1.6 g product (91%). $^1$H NMR (500 MHz, CDCl$_3$): δ 0.96 (t, 3H, J=7.1 Hz), 1.41-1.49 (m, 4H), 1.82-1.87 (m, 2H), 4.04 (t, 2H, J=6.5 Hz), 4.41 (s, 2H), 6.98 (d, 2H, J=7.2 Hz), 7.98 (d, 2H, J=7.2 Hz).

2-(azidomethyl)-2-(4-(pentyloxy)phenyl)-1,3-dioxolane

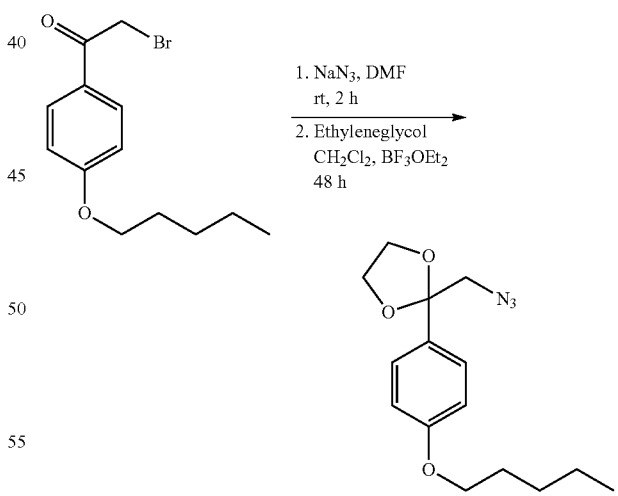

To a solution of the bromide (1.6 g, 5.6 mmol) in DMF (10 mL) was added sodium azide (445 mg, 5.8 mmol) and stirred at room temperature. After 2 h, the mixture was poured into water and extracted with EtOAc. The organic layer was washed with water, brine, dried and evaporated to afford the product as yellow syrup which was redissolved in anhydrous $CH_2Cl_2$ (60 mL) containing ethyleneglycol (7.5 mL, 150.0 mmol) and BF$_3$.OEt$_2$ (7.5 mL, 59.0 mmol) and stirred under argon for 48 h. The solution was washed with sat. aq.

NaHCO₃, the organic layer was dried and evaporated to afford crude product which was passed through a short plug of silica eluting with 5% EtOAc in hexane to afford product (1.1 g, 68%). ¹H NMR (500 MHz, CDCl₃): δ 0.96 (t, 3H, J=7.0 Hz), 1.40-1.46 (m, 4H), 1.79-1.82 (m, 2H), 3.44 (s, 2H), 3.91 (t, 2H, J=3.5 Hz), 3.96 (t, 2H, J=6.5 Hz), 4.18 (t, 2H, J=3.5 Hz), 6.90 (d, 2H, J=7.0 Hz), 7.42 (d, 2H, J=7.0 Hz).

(2-(4-(pentyloxy)phenyl)-1,3-dioxolan-2-yl)methanamine

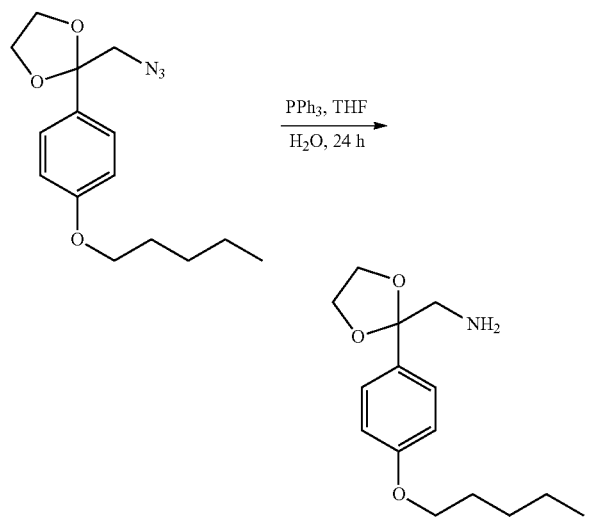

To a solution of the keto-protected azide (1.1 g, 3.8 mmol) in anhydrous THF (5 mL) was added Ph₃P (1.5 g, 5.6 mmol) under argon and stirred at room temperature for 24 h. The solution was concentrated to 2 mL and 200 μL water added. After stirring 5 h, the solvent was evaporated and the residue purified by combiflash, eluting with 80-100% EtOAc to afford 0.8 g (80%) product. ¹H NMR (500 MHz, CDCl₃): δ 0.97 (t, 3H, J=7.0 Hz), 1.27-1.41 (m, 4H), 1.79-1.83 (m, 2H), 2.92 (s, 2H), 3.85 (t, 2H, J=3.5 Hz), 3.97 (t, 2H, J=6.5 Hz), 4.06 (t, 2H, J=3.5 Hz), 6. (d, 2H, J=70 Hz), 7.37 (d, 2H, J=7. Hz). Mass: m/z 266 (M+1).

2-(4-carbomethoxybenzoyl)amino-1-(4-(pentyloxy)phenyl)ethanone

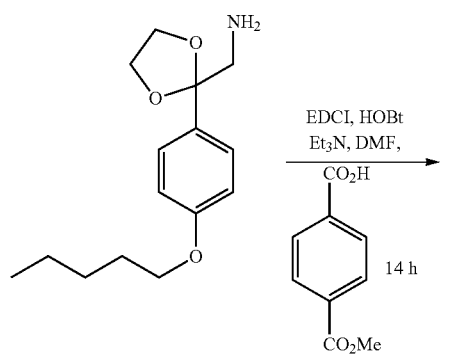

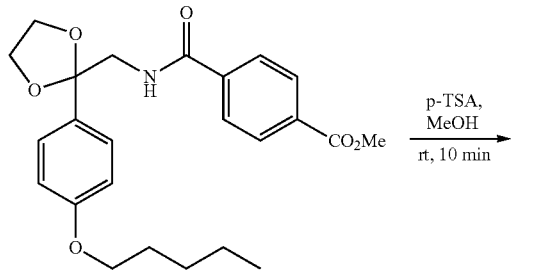

To a solution of the amine (800 mg, 2.8 mmol) in DMF (10 mL) under argon was added EDCl (820 mg, 4.2 mmol), HOBt (650 mg, 4.2 mmol), DIPEA (800 μL, 5.6 mmol) and terephthalic acid monomethyl ester (735 mg, 4.2 mmol). After stirring at room temperature or 24 h, the mixture was poured into water and extracted with EtOAc. Organic layer was washed with water, brine and dried. The residue was redissolved in 20 mL MeOH containing 2 mL CH₂Cl₂ and 20 mg p-TSA monohydrate. After stirring 30 min at room temperature, the solution was evaporated and the residue diluted with EtOAc. The organic layer was washed with sat. aq. NaHCO₃, brine and dried. Evaporation of the organic layer afforded product which was pure enough for next step (crude wt. 800 mg, 61%). ¹H NMR (500 MHz, CDCl₃): δ 0.97 (t, 3H, J=7.0 Hz), 1.40-1.56 (m, 4H), 1.84-1.87 (m, 2H), 3.98 (s, 3H), 4.08 (t, 2H, J=6.5 Hz), 4.93 (s, 2H), 7.01 (d, 2H, J=7.0 Hz), 7.97 (d, 2H, J=7.0 Hz), 8.02 (d, 2H, J=7.0 Hz), 8.17 (d, 2H, J=7.0 Hz). Mass: m/z 384 (M+1).

4-(5-(4-(pentyloxy)phenyl)oxazol-2-yl)benzoic acid

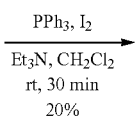

-continued

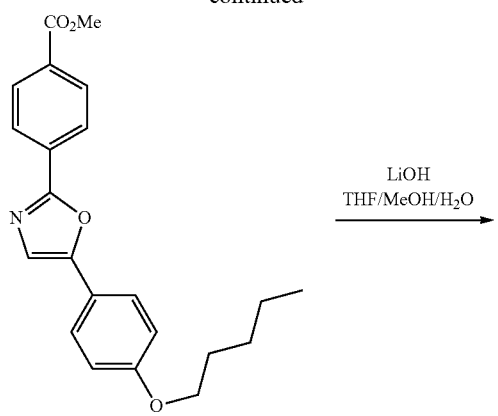

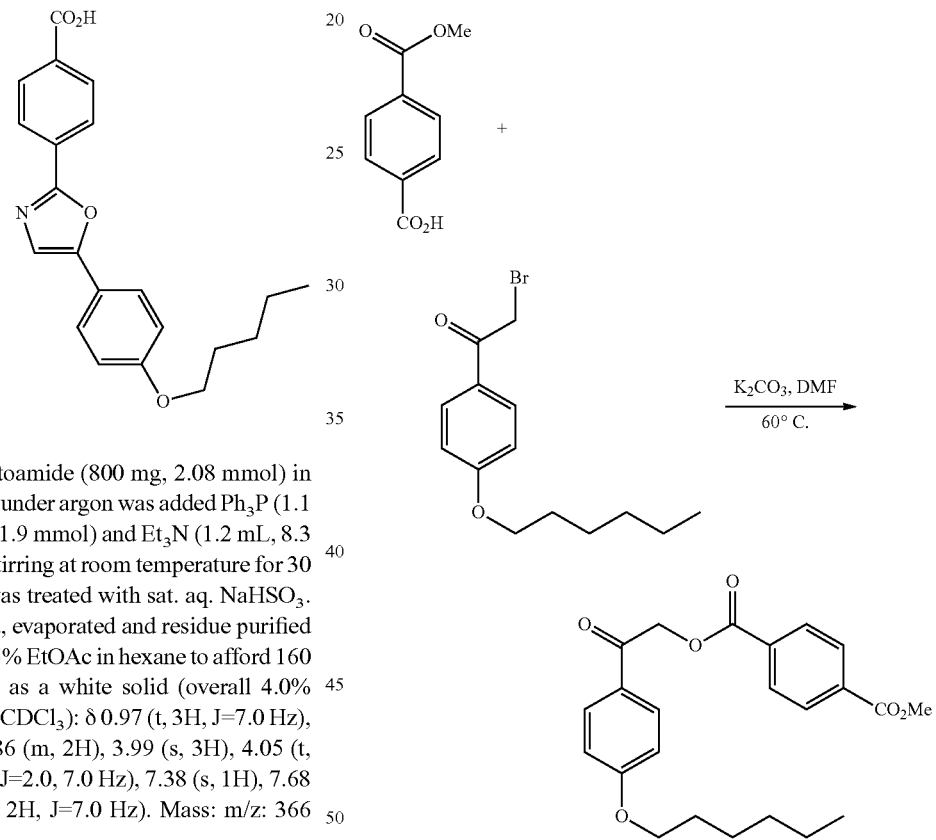

HPLC retention time: 4.839.

LP-024 Precursor 1-(4-(hexyloxy)phenyl)-2-hydroxyethanone
4-carbomethoxybenozic acid ester To a solution of the β-ketoamide (800 mg, 2.08 mmol) in anhydrous CH$_2$Cl$_2$ (30 mL) under argon was added Ph$_3$P (1.1 g, 4.1 mmol), iodine (1.0 g, 1.9 mmol) and Et$_3$N (1.2 mL, 8.3 mmol) successively. After stirring at room temperature for 30 min, the reaction mixture was treated with sat. aq. NaHSO$_3$. The organic layer was dried, evaporated and residue purified by combiflash eluting with 5% EtOAc in hexane to afford 160 mg (20%) of pure product as a white solid (overall 4.0% yield). $^1$H NMR (500 MHz, CDCl$_3$): δ 0.97 (t, 3H, J=7.0 Hz), 1.42-1.53 (m, 4H), 1.83-1.86 (m, 2H), 3.99 (s, 3H), 4.05 (t, 2H, J=6.5 Hz), 7.0 (dd, 2H, J=2.0, 7.0 Hz), 7.38 (s, 1H), 7.68 (d, 2H, J=7.0 Hz), 8.19 (d, 2H, J=7.0 Hz). Mass: m/z: 366 (M+1).

To a solution of the oxazole (160 mg, 0.4 mmol) in THF-MeOH—H$_2$O (6 mL, 4:2:1) was added LiOH (16 mg) and stirred overnight at room temperature. The mixture was evaporated to dryness and diluted with 1 N HCl (2 mL). Solid formed was filtered, washed with water, Et$_2$O and dried to afford 100 mg (60%) of the carboxylic acid. Mass: m/z 352 (M+1); HPLC retention time: 4.404

LP-029 Precursor

In a similar fashion, 4-(5-(4-(hexyloxy)phenyl)oxazol-2-yl)benzoic acid derivative was synthesized from 4-hydroxyacetophenone with an overall yield 4.0%.

To a solution of terephthalic acid monomethyl ester (1.0 g, 5.6 mmol) and 4-hexyloxy-2'-bromoacetophenone (synthesized by following (2.0 g, 6.7 mmol) in DMF (10 mL) was added K$_2$CO$_3$ (0.77 g, 5.6 mmol) and heated at 60° C. After 10 h, the reaction mixture was cooled to room temperature and poured into water. The product was extracted using EtOAc, washed with brine, dried and concentrated. The crude residue was purified by combiflash to afford 1.0 g (45%) product. $^1$H NMR (500 MHz, CDCl$_3$): δ 0.94 (t, 3H, J=7.0 Hz), 1.36-1.39 (m, 4H), 1.48-1.58 (m, 2H), 1.81-1.85 (m, 2H), 3.99 (s, 3H), 4.07 (t, 2H, J=6.5 Hz), 5.58 (s, 2H), 6.99 (d, 2H, J=9.0 Hz), 7.92 (d, 2H, J=9.0 Hz), 8.16 (d, 2H, J=9.0), 8.122 (d, 2H, J=9.0 Hz).

103

4-(4-(4-(hexyloxy)phenyl)oxazol-2-yl)benzoic acid

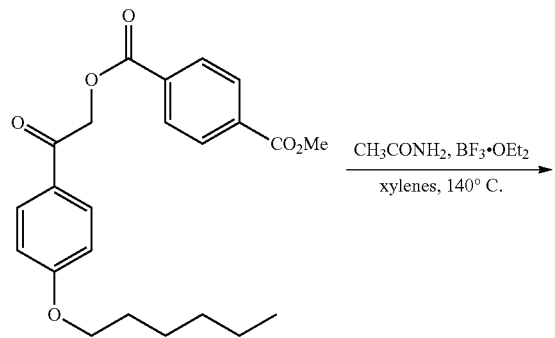

To a suspension of the β-ketoester (0.3 g, 0.7 mmol) and acetamide (0.225 g, 3.75 mmol) in xylenes (2 mL) was added BF$_3$.OEt$_2$ (10 uL) and the mixture was heated to 140° C. After 3 h, another 20 μL BF$_3$.OEt$_2$ was added and heating continued overnight. After cooling to room temperature, the mixture was diluted with EtOAc and washed with water. The organic layer was dried, evaporated and the residue purified by combiflash to afford the desired oxazole (40 mg, 20% yield wrt 40 mg recovered starting material). $^1$H NMR (500 MHz, CDCl$_3$): δ 0.94 (t, 3H, J=7.0 Hz), 1.37-1.39 (m, 4H), 1.42-1.50 (m, 2H), 1.81-1.84 (m, 2H), 3.99 (s, 3H), 4.03 (t, 2H, J=6.5 Hz), 6.99 (d, 2H, J=6.7 Hz), 7.77 (d, 2H, J=6.7 Hz), 7.94 (s, 1H), 8.17 (d, 2H, J=6.7 Hz), 8.24 (d, 2H, J=6.7 Hz).

The oxazole thus obtained (40 mg) was hydrolyzed to the corresponding acid as described previously to afford 30 mg (79% yield) of acid (12% overall yield). HPLC retention time: 5.130.

104

LP-027 Precursor

2-[4-(Methoxycarbonyl)phenyl]-2-oxoethyl 4-hexyloxybenzoate

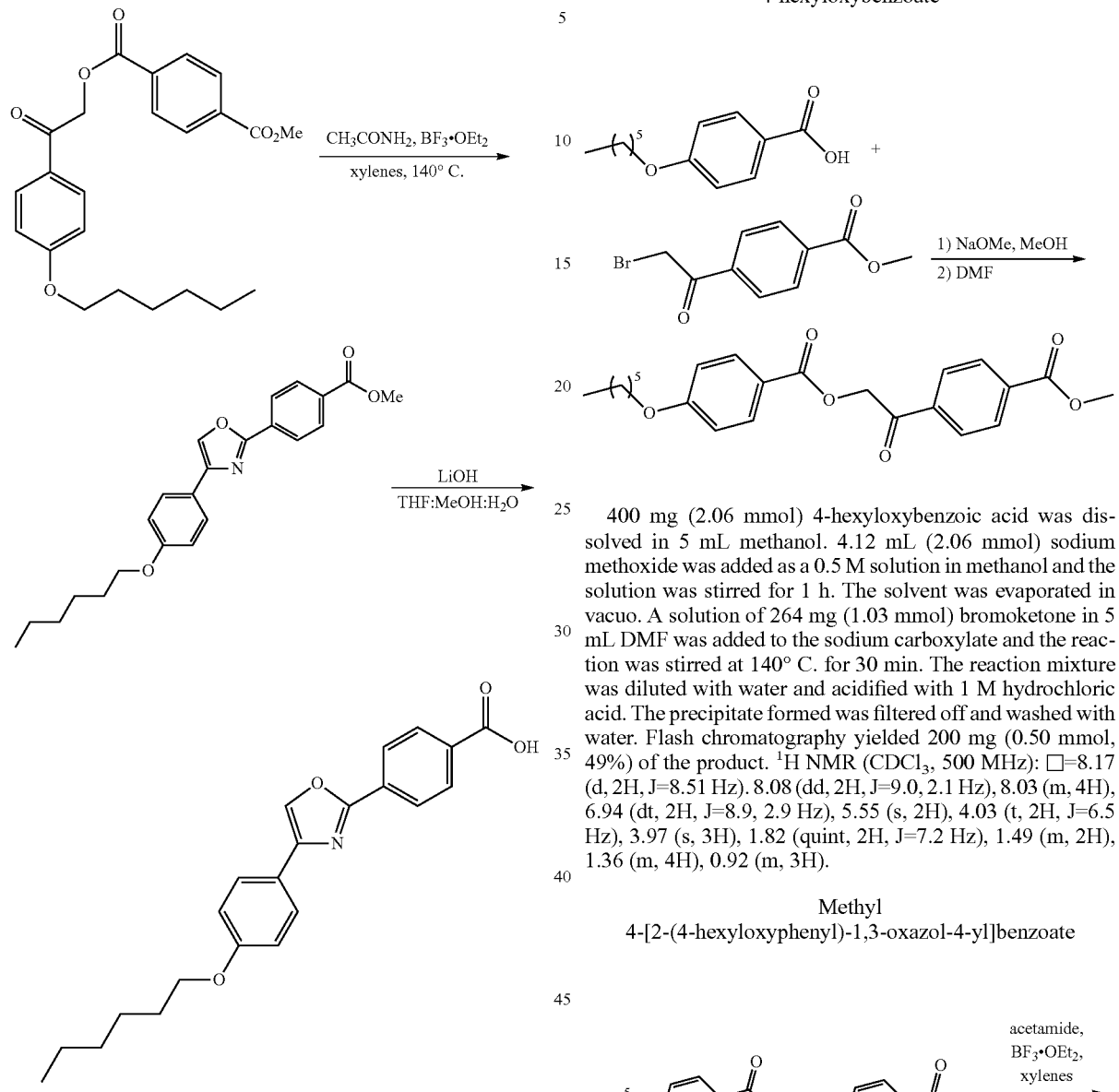

400 mg (2.06 mmol) 4-hexyloxybenzoic acid was dissolved in 5 mL methanol. 4.12 mL (2.06 mmol) sodium methoxide was added as a 0.5 M solution in methanol and the solution was stirred for 1 h. The solvent was evaporated in vacuo. A solution of 264 mg (1.03 mmol) bromoketone in 5 mL DMF was added to the sodium carboxylate and the reaction was stirred at 140° C. for 30 min. The reaction mixture was diluted with water and acidified with 1 M hydrochloric acid. The precipitate formed was filtered off and washed with water. Flash chromatography yielded 200 mg (0.50 mmol, 49%) of the product. $^1$H NMR (CDCl$_3$, 500 MHz): □=8.17 (d, 2H, J=8.51 Hz). 8.08 (dd, 2H, J=9.0, 2.1 Hz), 8.03 (m, 4H), 6.94 (dt, 2H, J=8.9, 2.9 Hz), 5.55 (s, 2H), 4.03 (t, 2H, J=6.5 Hz), 3.97 (s, 3H), 1.82 (quint, 2H, J=7.2 Hz), 1.49 (m, 2H), 1.36 (m, 4H), 0.92 (m, 3H).

Methyl 4-[2-(4-hexyloxyphenyl)-1,3-oxazol-4-yl]benzoate 140 mg (0.377 mmol) 2-[4-(methoxycarbonyl)phenyl]-2-oxoethyl 4-hexyloxybenzoate and 111 mg (5 eq) acetamide were dissolved in 5 mL xylenes. 10 uL (0.2 eq) boron trifluoride was added and the reaction was stirred at 140° C. for 18 h. Another 50 uL (1.0 eq) boron trifluoride was added and stirring continued for 24 h. The reaction was quenched with saturated sodium bicarbonate solution and extracted with DCM. The combined organic phases were dried and evaporated. Purification of the residue by flash chromatography (100% hexanes to 10% EA/hexanes) yielded 26 mg (0.068 mmol, 18%) of the product. MS: m/z=380.21 [M+1]$^+$.

4-[2-(4-Hexyloxyphenyl)-1,3-oxazol-4-yl]benzoic acid

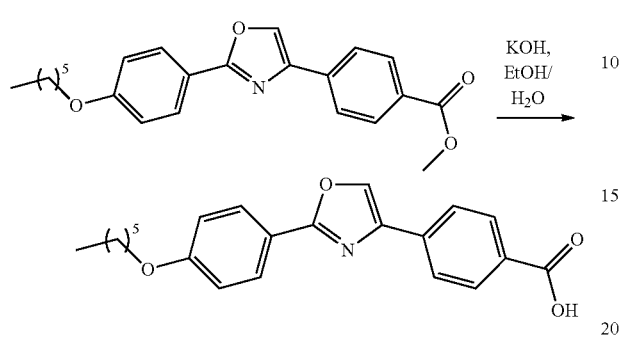

Starting from methyl 4-[2-(4-hexyloxyphenyl)-1,3-oxazol-4-yl]benzoate, 25 mg (0.07 mmol, quant.) of the title compound was isolated. HPLC: 5.127 min.

1-H-Benzotriazole methyl 4-[2-(4-hexyloxyphenyl)-1,3-oxazol-4-yl]benzoate

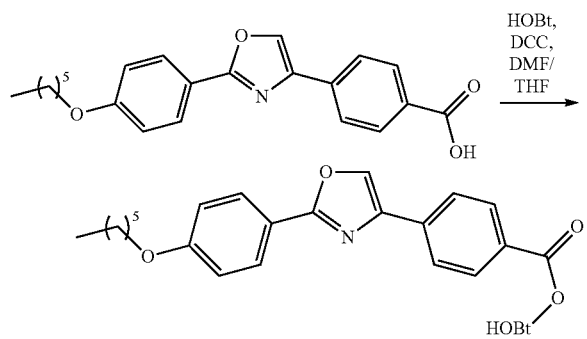

Starting from 4-[2-(4-Hexyloxyphenyl)-1,3-oxazol-4-yl]benzoic acid, 25 mg of a crude product was isolated and directly used for the next step. HPLC: 6.487 min.

(iii) With the Heterocycle being Thiazole

LP-030 Precursor 4-(5-(4-(hexyloxy)phenyl)thiazol-2-yl)benzoic acid

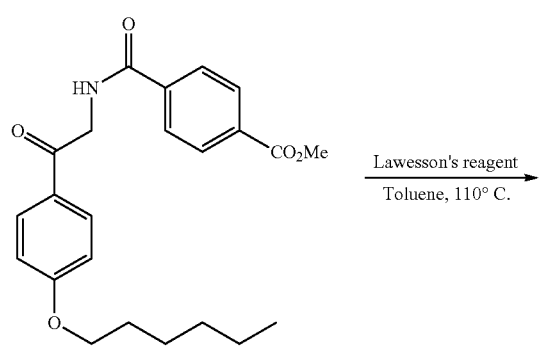

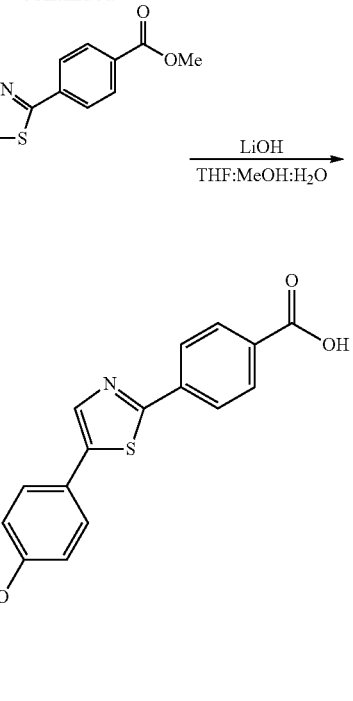

To a suspension of the 4-(5-(4-(hexyloxy)phenyl)thiazol-2-yl)benzoic acid methyl ester (synthesized from 4-hydroxyacetophenone as described above, 500 mg, 1.2 mmol) in anhydrous toluene (15 mL) was added Lawesson's reagent (1.0 g, 2.4 mmol). After heating the mixture at 110° C. for 5 h, it was cooled to room temperature and the solid formed filtered, washed with EtOAc and MeOH to afford product (450 mg, 90% yield). $^1$H NMR (500 MHz, CDCl$_3$): δ 0.94 (t, 3H, J=7.0 Hz), 1.37-1.39 (m, 4H), 1.42-1.50 (m, 2H), 1.81-1.84 (m, 2H), 3.95 (s, 3H), 4.01 (t, 2H, J=6.5 Hz), 6.96 (d, 2H, J=6.6 Hz), 7.55 (d, 2H, J=6.6 Hz), 7.98 (s, 1H), 8.05 (d, 2H, J=6.6 Hz), 8.13 (d, 2H, J=6.6 Hz). HPLC retention time: 6.495.

The thiazole obtained (400 mg) was hydrolyzed to the corresponding acid as described previously to afford 200 mg of the acid (46%). HPLC retention time: 5.267.

LP-021 Precursor

4-[5-(4-Hexyloxy-phenyl)-thiophen-2-yl]-benzoic acid

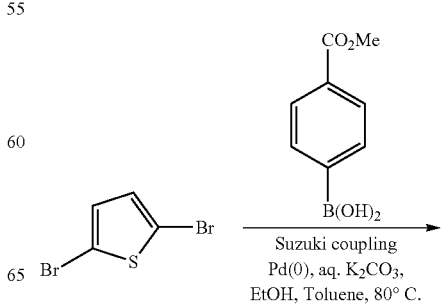

-continued

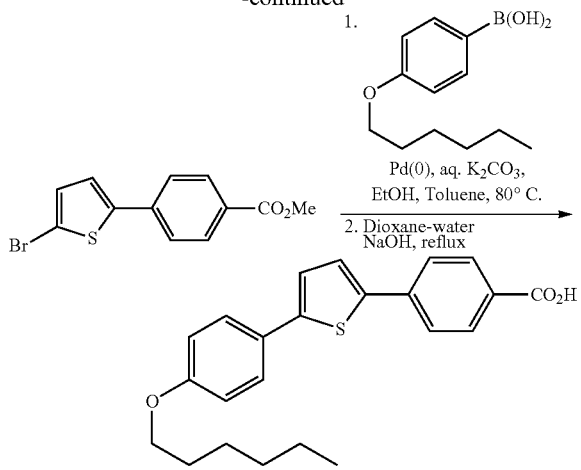

A solution of 2,5-dibromothiophene (1.0 g, 4.1 mmol), 4-methylcarboxyphenylboronic acid (370 mg, 2.05 mmol), Pd(PPh$_3$)$_4$ (30 mg) and K$_2$CO$_3$ (1.13 g, 8.2 mmol) in toluene (20 mL) containing 5 mL EtOH and 1 mL water were refluxed overnight under argon. After cooling to room temperature, the solvent was evaporated and residue partitioned between EtOAc and water. Organic layer was separated, dried, evaporated and residue purified by combiflash to afford 4-(5-Bromo-thiophen-2-yl)-benzoic acid methyl ester (200 mg) which was redissolved in toluene (10 mL), containing 4-hexyloxyphenylboronic acid (222 mg, 0.1 mmol), Pd(PPh$_3$)$_4$ (30 mg) and K$_2$CO$_3$ (189 mg, 0.13 mmol) containing 3 mL EtOH and 0.5 mL water and refluxed overnight. The resulting solution was cooled and the solid formed filtered, washed with water and methanol and dried (130 mg). It was subjected to hydrolysis using dioxane-water/NaOH overnight to afford 4-[5-(4-Hexyloxy-phenyl)-thiophen-2-yl]-benzoic acid (iv) With the Heterocycle being Pyrazole LP-028 Precursor Methyl 4-[5-(4-hexyloxyphenyl)-1H-pyrazol-3-yl]benzoate

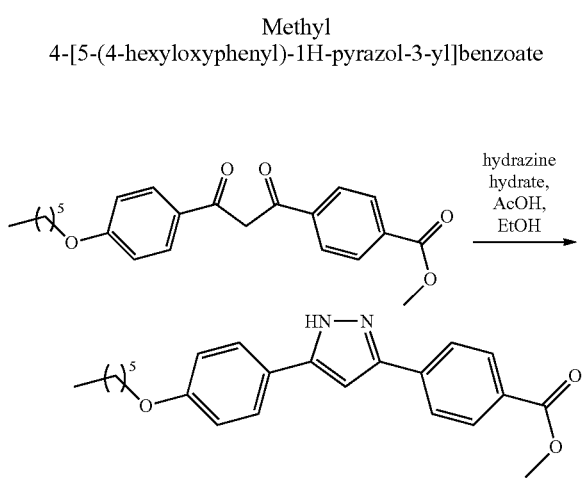

150 mg (0.39 mmol) 4-{5-[4-(pentyloxy)phenyl]isoxazol-3-yl}benzoic acid was dissolved in 10 mL ethanol. 0.2 mL hydrazine monohydrate and 1 mL acetic acid were added and the resulting solution was heated under reflux for 45 min. The volatiles were evaporated. Purification of the residue by flash chromatography (hexane/ethyl acetate 5:1) yielded 133 mg (0.35 mmol, 89%) of the title compound. $^1$H NMR (CDCl$_3$, 500 MHz): δ=8.09 (d, 2H, J=8.4 Hz), 7.82 (d, 2H, J=7.8 Hz), 7.59 (d, 2H, J=8.2 Hz), 6.91 (d, 2H, J=8.8 Hz), 6:80 (s, 1H), 3.97 (t, 2H, J=6.6 Hz), 3.94 (s, 3H), 1.80 (quint, 2H, J=6.8 Hz), 1.50 (m, 2H), 1.35 (m, 4H), 0.92 (t, 3H, J=7.0 Hz).

4-[5-(4-hexyloxyphenyl)-1H-pyrazol-3-yl]benzoic acid

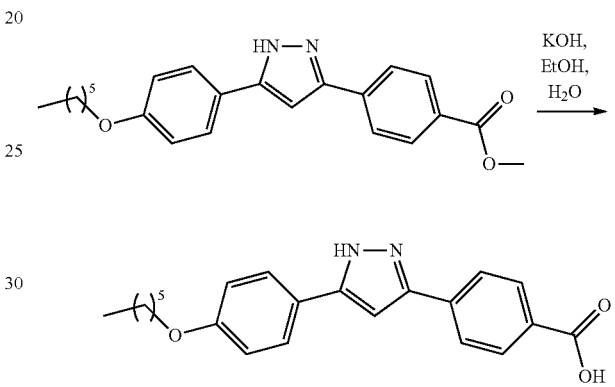

Starting from methyl 4-[5-(4-pentoxyphenyl)-1H-pyrazol-3-yl]benzoate, 126 mg (0.34 mmol, quant.) of the title compound was isolated. HPLC: 4.068 min.

1-H-benzotriazole 4-[5-(4-hexyloxyphenyl)-1H-pyrazol-3-yl]benzoate

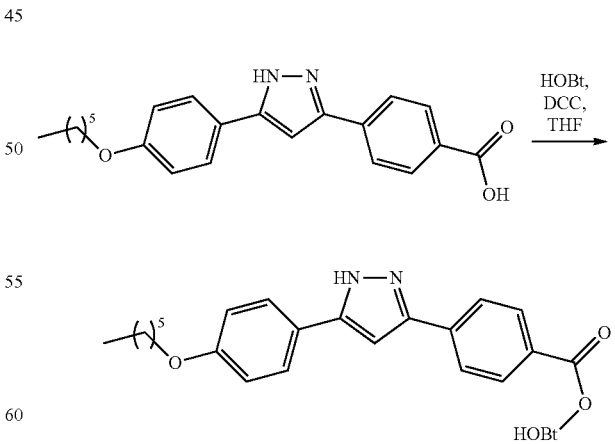

Starting from 4-[5-(4-pentoxyphenyl)-1H-pyrazol-3-yl]benzoic acid, 45 mg of a crude product was isolated that was directly used for the next step. HPLC: 5.483 min.

LP-035 Precursor

Methyl 4-[3-(4-butoxyphenyl)-1H-pyrazol-5-yl]benzoate

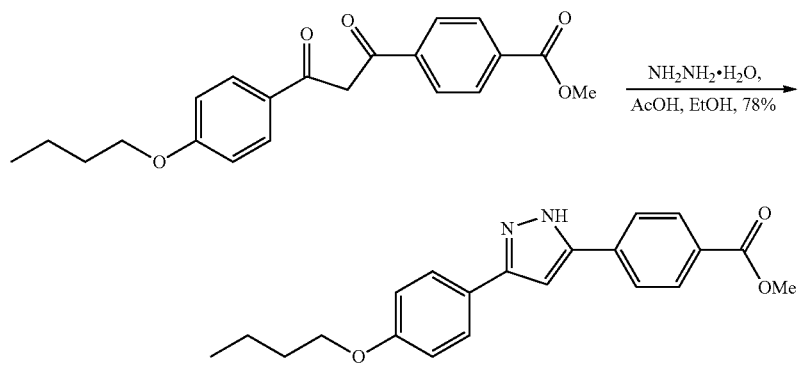

190 mg (0.54 mmol) methyl 4-[3-(4-butoxyphenyl)-3-oxopropanoyl]benzoate was dissolved in 10 mL ethanol and 0.5 mL hydrazine hydrate and 1 mL acetic acid were added. The mixture was refluxed for 1 h. Upon cooling, the product crystallized. To complete crystallisation, 5 mL water was added and the product was filtered off, washed with water and dried. A white crystalline material (150 mg, 0.42 mmol, 78%) was isolated and directly used for the next step.

4-[3-(4-Butoxyphenyl)-1H-pyrazol-5-yl]benzoic acid

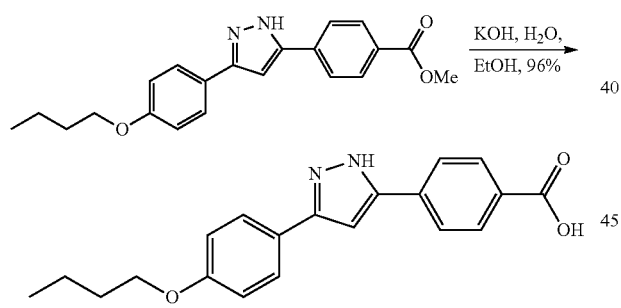

Starting from methyl 4-[3-(4-butoxyphenyl)-1H-pyrazol-5-yl]benzoate 139 mg (0.41 mmol, 96%) of the title compound was isolated. MS: m/z=337.2 [M+1]$^+$. HPLC: 3.259 min.

Pentafluorophenyl 4-[3-(4-butoxyphenyl)-1H-pyrazol-5-yl]benzoate

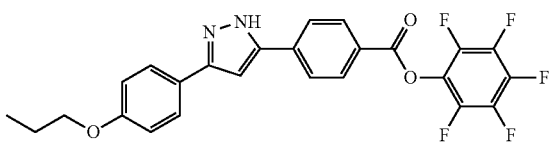

Starting from 4-[3-(4-butoxyphenyl)-1H-pyrazol-5-yl]benzoic acid, 53 mg (quant.) of a white solid was isolated and directly used for the next step. HPLC: 5.743 min.

(v) With the Heterocycle being Imidazole

LP-037 Precursor 4-(5-(4-(pentyloxy)phenyl)-1H-imidazol-2-yl)benzoic acid

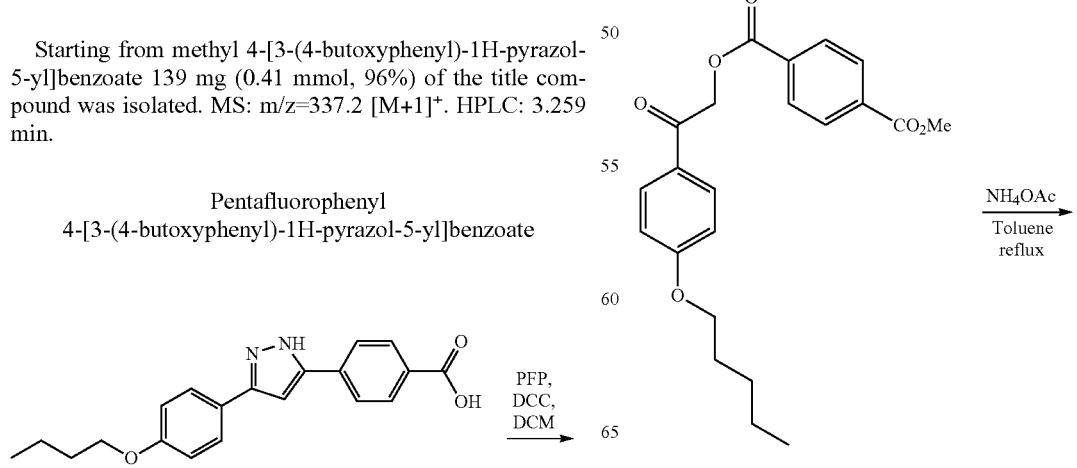

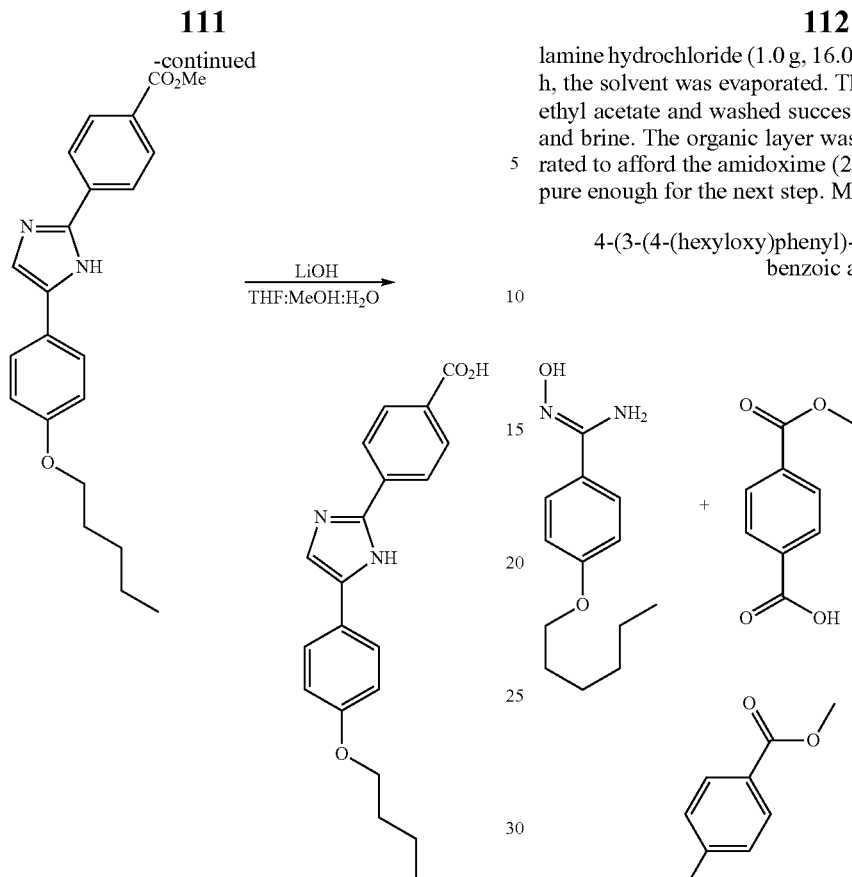

To a suspension of the β-ketoester (synthesized as described above, 0.8 g, 2.08 mmol) in toluene (10 mL) in a flask fitted with a dean-stark apparatus was added NH$_4$OAc (8.0 g, 10.8 mmol). After refluxing for 12 h, the mixture was cooled to room temperature and evaporated. The residue was diluted with water and the solid formed filtered, washed with Et$_2$O and dried to afford the product (200 mg) which underwent hydrolysis using 10 mg LiOH in 10 mL THF:MeOH:H$_2$O in the ratio 6:3:1 to afford the corresponding carboxylic acid (120 mg, 17%). Mass: m/z 351 (M+1); HPLC retention time: 1.704.

(vi) With the Heterocycle being Oxadiazole

LP-026 Precursor 4-(hexyloxy)-N'-hydroxybenzamidine

To a solution of 4-O-hexylbenzonitrile (2.5 g, 12.3 mmol, prepared by alkylation of 4-cyanophenol using 1-bromohexane following the procedure described above) in EtOH (20 mL) and pyridine (1.3 mL, 18.45 mmol) was added hydroxylamine hydrochloride (1.0 g, 16.0 mmol). After stirring for 24 h, the solvent was evaporated. The residue was dissolved in ethyl acetate and washed successively with 1 N HCl, water and brine. The organic layer was isolated, dried and evaporated to afford the amidoxime (2.5 g, 86% yield) which was pure enough for the next step. Mass: m/z 237 (M+1).

4-(3-(4-(hexyloxy)phenyl)-1,2,4-oxadiazol-5-yl)benzoic acid

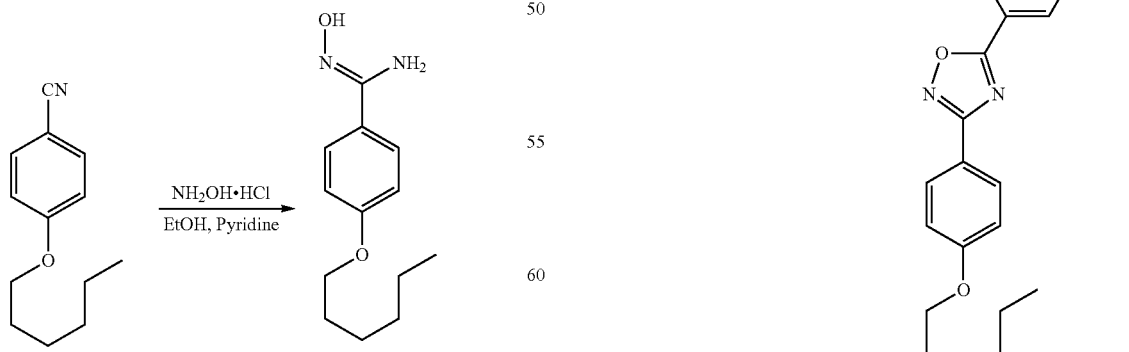

To a solution of the amidoxime (500 mg, 2.1 mmol) in DMF (10 mL) was added terephthalic acid monomethyl ester (0.6 g, 3.3 mmol), EDCl (0.6 g, 3.3 mmol), HOBt (0.49 g, 3.3 mmol) and Et₃N (0.6 mL, 4.2 mmol). After stirring overnight at room temperature, the mixture was poured into water and extracted with Ethyl acetate. The organic layer was washed with 1 N HCl, water, brine, dried over Na₂SO₄ and evaporated. The residue was dissolved in anhydrous DME (20 mL) containing Et₃N (0.6 mL, 4.2 mmol, 2.0 eq. with respect to the amidoxime). The mixture was bought to reflux and the reaction followed by TLC. After 4 h, the mixture was allowed to cool to room temperature and the solvent removed under vacuum. The residue was subjected to combiflash to afford the 1,2,4-oxadiazole (0.4 g, 50% yield). Mass: m/z: 381 (M+1). $^1$H NMR (500 MHz, CDCl₃): δ 0.93 (t, 3H, J=7.0 Hz), 1.37-1.39 (m, 4H), 1.50-1.56 (m, 2H), 1.83-1.86 (m, 2H), 3.97 (s, 3H), 4.05 (t, 2H, J=6.5 Hz), 7.03 (d, 2H, J=6.5 Hz), 8.13 (d, 2H, J=6.5 Hz), 8.23 (d, 2H, J=6.5 Hz), 8.31 (d, 2H, J=6.5 Hz).

Hydrolysis of the ester (40 mg, 0.1 mmol) as described previously using LiOH (10 mg, 0.4 mmol) gave the corresponding carboxylic acid (33 mg, 87%). Mass: m/z: 365 (M⁻¹); HPLC retention time: 5.260.

(vii) With the Heterocycle being Pyridine

LP-023 Precursor 4-(6-(4-(hexyloxy)phenyl)pyridin-3-yl)benzoic acid

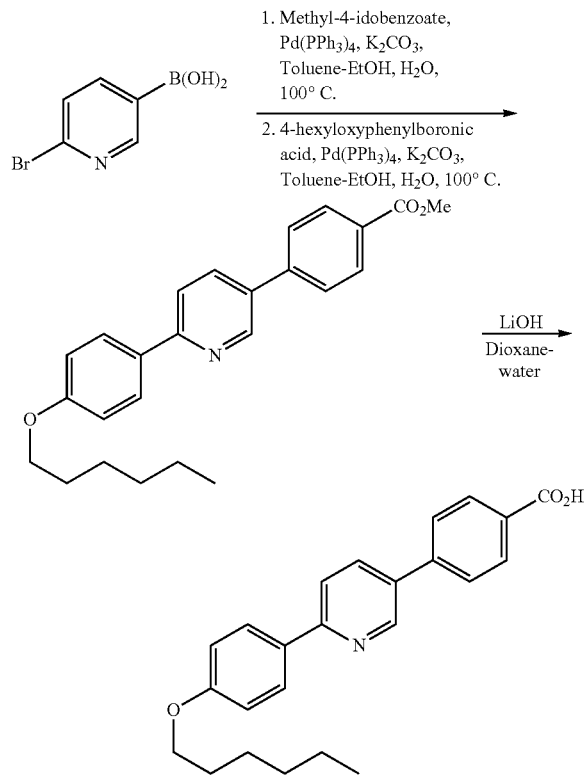

A mixture of 2-Bromopyridyl-5-boronic acid (300 mg, 1.5 mmol), methyl-4-iodobenzoate (400 mg, 1.5 mmol) and K₂CO₃ (310 mg, 2.25 mmol) in toluene (10 mL) containing EtOH (1.5 mL) and water (0.4 mL) was degassed for 5 minutes using Argon. Pd(PPh₃)₄ (40 mg, 0.03 mmol) was added and the mixture refluxed overnight under Argon. After cooling to room temperature, the solvent was removed and the residue washed extracted with EtOAc. The organic layer was washed with water, dried and evaporated. The crude product was triturated with Et₂O to afford pure product (300 mg, 70%). Mass: m/z 292 (M+1). $^1$H NMR (500 MHz, CDCl₃): δ 3.98 (s, 3H), 7.61 (d, 1H, J=8.0 Hz), 7.64 (d, 2H, J=8.0 Hz), 7.79 (dd, 1H, J=2.5, 8.0 Hz), 8.19 (d, 2H, J=8.0 Hz), 8.65 (d, 1H, J=2.2 Hz).

To the above product (300 mg, 1.0 mmol) in toluene (10 mL) containing EtOH (1.5 mL) and water (0.4 mL) was added 4-hexyloxybenzeneboronic acid (300 mg, 1.3 mmol) and K₂CO₃ (280 mg, 2.0 mmol). After degassing for 5 minutes, Pd(PPh₃)₄ (40 mg, 0.03 mmol) was added and the mixture refluxed overnight under Argon. After cooling to room temperature, the solid formed was filtered and washed with MeOH to afford product (280 mg, 75%). $^1$H NMR (500 MHz, DMSO-d₆): δ 0.90 (br s, 3H), 1.34-1.50 (m, 6H), 1.73-1.75 (m, 2H), 3.90 (s, 3H), 3.95 (m, 2H), 7.07 (d, 2H, J=8.0 Hz), 7.73-8.13 (m, 8H), 9.02 (s, 1H).

The above product was hydrolyzed by refluxing in dioxane containing 1.5 mL 1N LiOH solution overnight. The mixture was neutralized using 1N HCl. The solid formed was filtered, washed with water and dried to afford the carboxylic acid (200 mg, 71%). HPLC retention time: 5.014.

LP-020 Precursor

4-[5-(4-Hexyloxy-phenyl)-pyridin-2-yl]-benzoic acid

Using the same sequence of reactions, the regioisomer was synthesized. Thus, coupling of 2-bromopyridyl-5-boronic acid with 4-O-hexyloxy-iodobenzene followed by reacting with 4-carbomethoxyphenylboronic acid and hydrolysis gave 4-[5-(4-Hexyloxy-phenyl)-pyridin-2-yl]-benzoic acid.

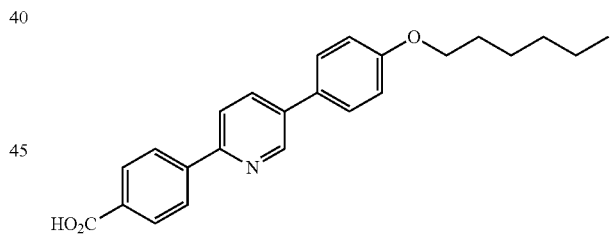

(d) Side Chains of the Form
Alkyl-Heterocycle-Phenyl-C(O)—

LP-033 Precursor

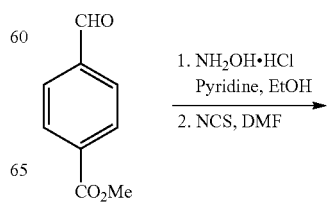

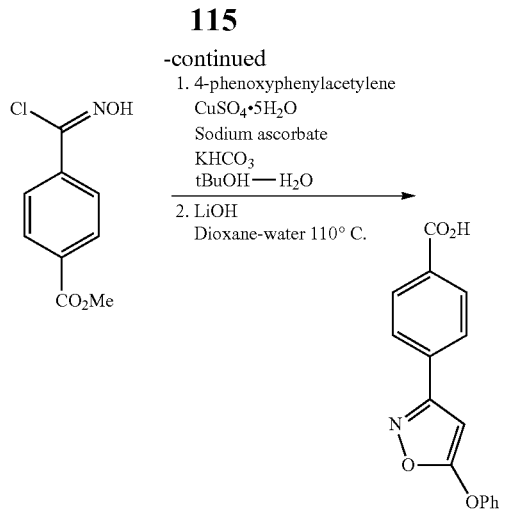

To a solution of 4-carbomethoxybenzaldehyde (2.0 g, 12.0 mmol) in EtOH (5 mL) containing pyridine (1.3 mL, 18.3 mmol) was added $NH_2OH·HCl$ (1.0 g, 14.4 mmol). After stirring at room temperature overnight, solvent was evaporated and the residue partitioned between EtOAc and 1N HCl. Organic layer was dried and evaporated to afford the oxime (2.0 g, 91%). $^1$H NMR: (500 MHz, $CDCl_3$): δ 3.97 (s, 3H), 7.96 (d, 2H, J=7.0 Hz), 8.06-8.11 (m, 3H).

The above oxime (500 mg, 2.8 mmol) was dissolved in dry DMF (3 mL) and heated to 50° C. N-Chlorosuccinimide (370 mg, 2.8 mmol) was then added and the mixture stirred at room temperature for 1 h. The mixture was diluted with water and extracted with $Et_2O$, dried and evaporated to afford the product (480 mg) which was used as such.

To a mixture of the above product (213 mg, 1.0 mmol) and 4-phenoxyphenyl acetylene (198 mg, 1.0 mmol) in t-BuOH-water (1:1 ration, 6 mL) was added sodium ascorbate (100 uL of 1 M solution, 10 mol %), $CuSO_4·5H_2O$ (2.7 mg in 100 uL water, 2 mol %) and $KHCO_3$ (433 mg, 3.5 mmol). The mixture was stirred vigorously at room temperature for 1.5 h and poured into 50 mL water. The solid formed was filtered, washed with MeOH and dried to afford product (150 mg, 51%). $^1$H NMR: (500 MHz, DMSO-$d_6$): δ 3.94 (s, 3H), 6.63 (s, 1H), 6.82-7.13 (m, 3H), 7.21-7.44 (m, 4H), 7.82 (d, 2H, J=8.5 Hz), 7.36 (d, 2H, J=8.5 Hz), 8.17 (d, 2H, J=8.5 Hz).

The product obtained above was subjected to hydrolysis as described previously using LiOH in Dioxane-water to afford the corresponding carboxylic acid (100 mg, 71%). HPLC retention time: 4.050.

(2) Side Chains Comprising Phenyl and/or Naphthyl (a) Side Chains Containing Phenyl LP-016 Precursor 4-(4-(4-(hexyloxy)phenyl)phenyl)benzoic acid

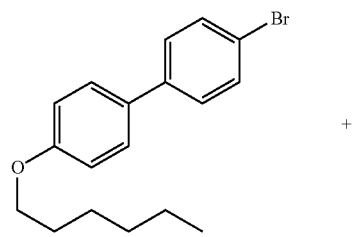

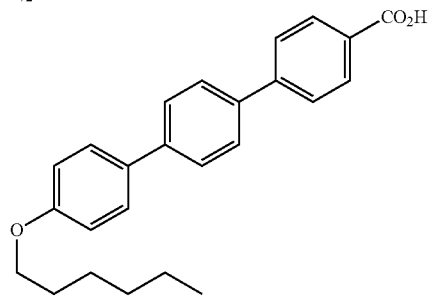

4-(4-hexyloxyphenyl)bromobenzene (200 mg, 0.6 mmol) and 4-carbomethoxyphenylboronic acid (160 mg, 0.9 mmol) were coupled as described before using $Pd(PPh_3)_4$ (40 mg, 0.03 mmol), $K_2CO_3$ (186 mg, 1.3 mmol) in toluene (10 mL) containing EtOH (1.5 mL) and water (0.4 mL) under Argon atmosphere. After refluxing for 2 h, the solid formed was filtered, washed with water and MeOH to afford product (0.2 g, 86%) which was subjected to hydrolysis as described previously by refluxing in dioxane (15 mL) containing 1N NaOH (1.0 mL) for 24 h to provide the carboxylic acid (0.13 g, 68%). $^1$H NMR (500 MHz, DMSO-$d_6$): δ 0.89 (t, 3H, J=7.0 Hz), 1.32-1.35 (m, 4H), 1.43-1.46 (m, 2H), 1.72-1.75 (m, 2H), 4.02 (t, 2H, J=6.5 Hz), 7.04 (d, 2H, J=8.2 Hz), 7.67 (d, 2H, J=8.2 Hz), 7.76 (d, 2H, J=8.2 Hz), 7.83 (d, 2H, J=8.2 Hz), 7.86 (d, 2H, J=8.2 Hz), 8.03 (d, 2H, J=8.2 Hz). Mass: m/z 376 (M+1); HPLC retention time: 5.029.

LP-017 Precursor

Using the same methodology as that described above for LP-015 precursor, but using 4-(4-heptyloxyphenyl)bromobenzene instead of the hexyl analogue, the heptyloxy terphenyl compound was synthesised.

LP-018 Precursor

Using the same methodology as that described above for LP-015 precursor, but using 4-(4-pentyloxyphenyl)bromobenzene instead of the hexyl analogue, the pentyloxy terphenyl compound was synthesised.

LP-006 Precursor 4-(4-(4-propyloxyphenyl)phenethyl)benzoic acid

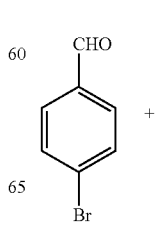

-continued

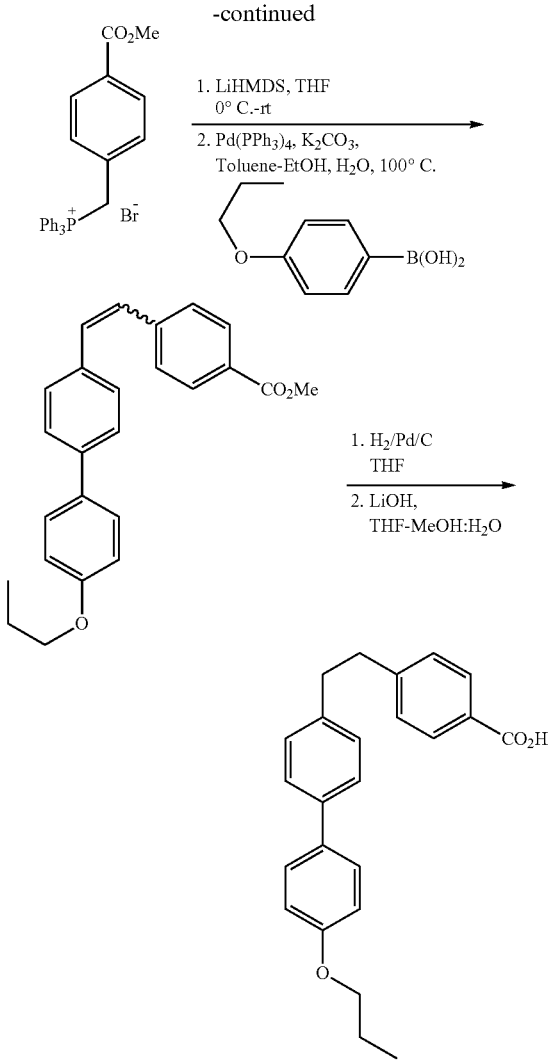

To a suspension of the wittig salt (730 mg, 1.4 mmol) in anhydrous THF (10 mL) was added LiHMDS (1 M soln in THF, 1.5 mL, 1.5 mmol) at 0° C. After 1 hr, 4-bromobenzaldehyde (250 mg, 1.3 mmo) was added as a solution in THF (2 mL) and the resulting mixture stirred at room temperature for 2 h. The reaction was quenched by adding ice and solvent evaporated. The residue was partitioned between EtOAc and water. Organic layer was dried, evaporated and residue purified by combiflash to afford the product (285 mg cis isomer and 142 mg trans isomer, 98% yield). The minor isomer (142 mg, 0.4 mmol) was dissolved in toluene (5 mL) containing EtOH (0.7 mL), water (0.2 mL), $K_2CO_3$ (124 mg, 0.9 mmol) and 4-propyloxyphenylboronic acid (120 mg, 0.6 mmol). After degassing for 5 minutes $Pd(PPh_3)_4$ (23 mg, 0.02 mmol) was added and the mixture refluxed for 3 h. The product crystalised out of the reaction mixture and was filtered, washed with water and MeOH (100 mg, 62%). $^1$H NMR: (500 MHz, DMSO-$d_6$): δ 1.01 (t, 3H, J=7.4 Hz), 1.72 (m, 2H), 3.86 (s, 3H), 3.98 (t, 3H, J=6.5 Hz), 7.01 (d, 2H, J=6.5 Hz), 7.36 (d, 1H, J=12.0 Hz), 7.45 (d, 1H, J=12.0 Hz), 7.65-7.72 (m, 6H), 7.76 (d, 2H, J=8.0 Hz), 7.96 (d, 2H, J=8.0 Hz).

The product obtained by Suzuki coupling (100 mg) was dissolved in THF and subjected to hydrogenation using Pd/C (10% wet) at 1 atm pressure overnight. Filtration of the reaction mixture through celite and evaporation of the filtrate afforded the product as white solid (100 mg). $^1$H NMR: (500 MHz, DMSO-$d_6$): δ 1.0 (t, 3H, J=7.4 Hz), 1.76 (m, 2H), 2.92-3.30 (m, 4H), 3.84 (s, 3H), 3.95 (t, 3H, J=6.5 Hz), 7.00 (d, 2H, J=6.5 Hz), 7.29 (d, 2H, J=6.5 Hz), 7.40 (d, 2H, J=6.5 Hz), 7.51 (d, 2H, J=6.5 Hz), 7.57 (d, 2H, J=6.5 Hz), 7.88 (d, 2H, J=6.5 Hz).

The product (100 mg, 0.26 mmol) was hydrolysed using LiOH (12 mg, 0.5 mmol) in dioxane (5 mL) containing water (1 mL) at 110° C. to afford the corresponding carboxylic acid (80 mg, 83%). $^1$H NMR: (500 MHz, DMSO-$d_6$): δ 1.0 (t, 3H, J=7.4 Hz), 1.73-1.77 (m, 2H), 2.90-2.98 (m, 4H), 3.98 (t, 3H, J=6.5 Hz), 6.99 (d, 2H, J=6.5 Hz), 7.29 (d, 2H, J=6.5 Hz), 7.36 (d, 2H, J=6.5 Hz), 7.53 (d, 2H, J=6.5 Hz), 7.57 (d, 2H, J=6.5 Hz), 7.85 (d, 2H, J=6.5 Hz).

LP-007 Precursor

Methyl 4-[(4-n-butylphenyl)-4-phenethenyl]-benzoate

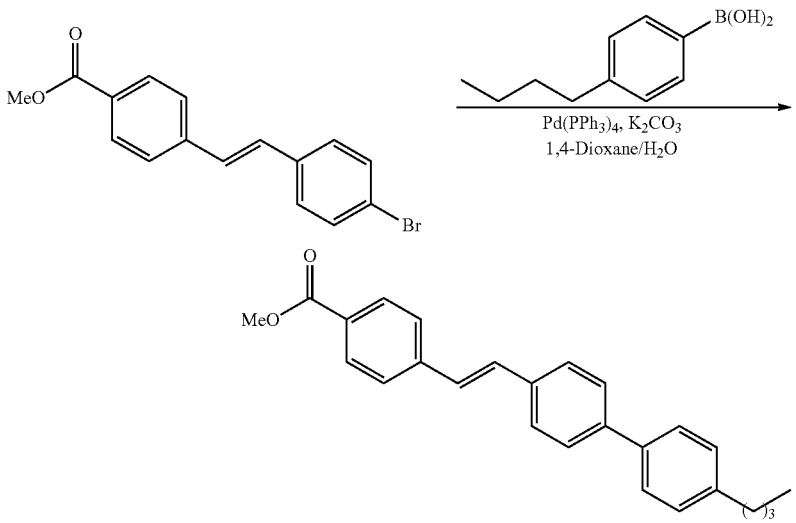

E-Methyl-4-[(4-bromophenethenyl)]-benzoate (0.11 g, 0.34 mmol) and 4-n-butylbenzene boronic acid (0.12 g, 0.68 mmol) were dissolved in 1,4-dioxane/$H_2O$ (1 mL, 4:1). The solution was purged with Argon prior to the addition of $K_2CO_3$ (0.094 g, 0.68 mmol) and Pd(PPh$_3$)$_4$ (19.3 mg, 0.017 mmol). The reaction mixture was then heated at 100° C. After 16 h, it was cooled to rt and diluted with EtOAc and water. The organic layer was separated and the aqueous layer was extracted (3×) with EtOAc. Combined organic layers was washed (2×) with brine, dried ($Na_2SO_4$), filtered and concentrated. The crude material was purified by silica gel chromatography using CombiFlash ($CH_2Cl_2$/hexanes) to give the desired product (82.9 mg, 66%). $^1$H-NMR (500 MHz, CDCl$_3$) δ 7.93 (d, 2H, J=8.0 Hz), 7.50 (d, 2H, J=7.4 Hz), 7.46 (d, 2H, J=7.4 Hz), 7.37 (d, 2H, 8.0 Hz), 7.28 (d, 2H, J=7.8 Hz), 7.25 (d, 2H, J=7.8 Hz), 6.73 (d, 1H, J=12.2 Hz), 6.63 (d, 1H, J=12.2 Hz), 3.91 (s, 3H), 2.67-2.64 (m, 2H), 1.68-1.62 (m, 2H), 1.43-1.36 (m, 2H), 0.96 (t, 3H, J=7.3 Hz).

Methyl-4-[(4-n-butylphenyl)-4-phenethyl]-benzoate

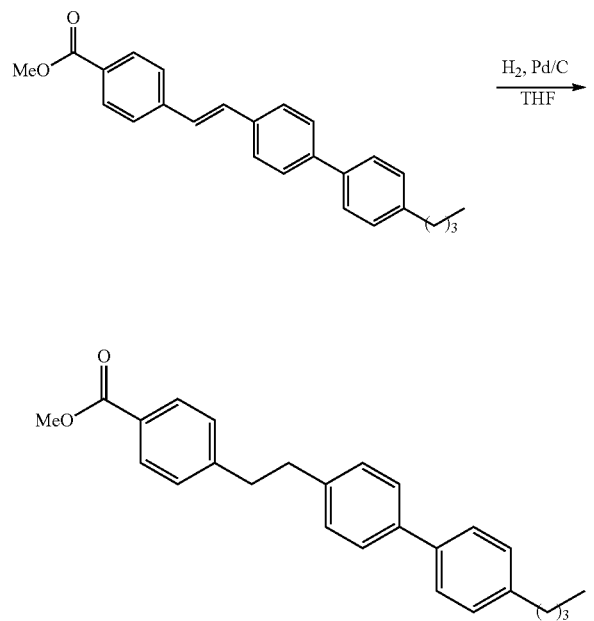

To the starting material (82.9 mg, 0.22 mmol) in THF (10 mL) was added 10% Pd/C (10 mg). The suspension was stirred at room temperature under 1 atm of $H_2$ (balloon). After 16 hr, the reaction mixture was filtered through Celite, concentrated under reduced pressure and purified by silica gel chromatography using CombiFlash ($CH_2Cl_2$/hexanes) to give the desired product (73.2 mg, 88%). $^1$H-NMR (500 MHz, CDCl$_3$) δ 7.96 (d, 2H, J=8.2 Hz), 7.51 (d, 2H, J=8.1 Hz), 7.50 (d, 2H, J=8.1 Hz), 7.26-7.24 (m, 4H), 7.21 (d, 2H, J=8.1 Hz), 3.04-2.96 (m, 4H), 2.67-2.64 (m, 2H), 1.68-1.62 (m, 2H), 1.44-1.36 (m, 2H), 0.96 (t, 3H, J=7.3 Hz).

4-[(4-n-Butylphenyl)-4-phenethyl]-benzoic acid

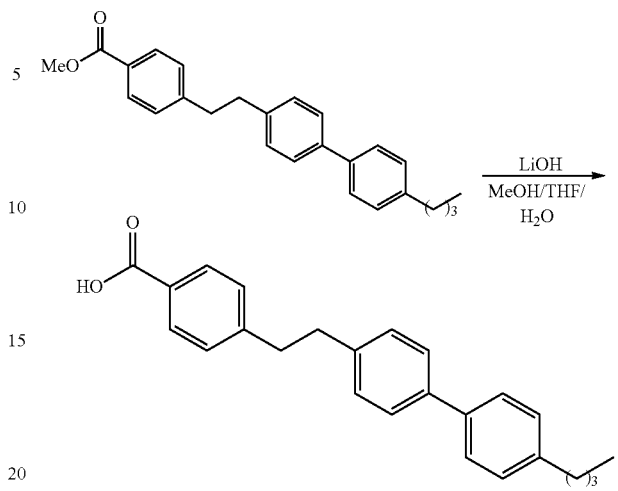

The ester (69.2 mg, 0.19 mmol) was dissolved in THF/MeOH/$H_2O$ (10 mL; 7:2:1). LiOH (8.5 mg, 0.37 mmol) was then added and the reaction mixture stirred at 50° C. After all starting material had reacted as indicated by TLC ($CH_2Cl_2$/hexanes; 1:2), solvents were removed under reduced pressure. The crude material was acidified with 1N HCl, filtered and washed with $H_2O$ and ether to give the desired acid as a white solid (58 mg, 87%). R$_t$=5.514 min; m/z 329.1546 [M–H]$^-$.

1-H-Benzotriazole-4-[4 (4-n-butylphenyl)-4-phenethyl]-benzoate

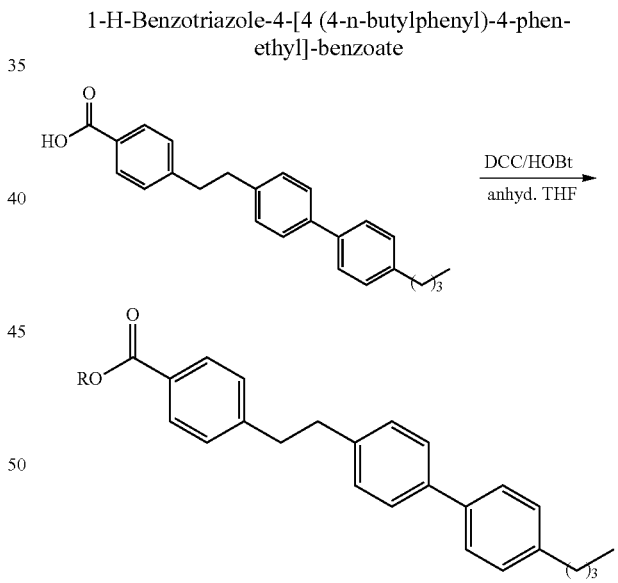

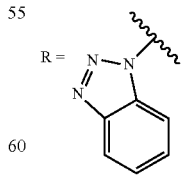

To the acid (30.5 mg, 0.085 mmol) in anhyd. THF (10 mL) under Argon atmosphere was added DCC (27.8 mg, 0.13 mmol) and HOBt (17.8 mg, 0.13 mmol). After stirring at rt for 30 min, the reaction mixture was heated at 60° C. After all starting material had reacted, the solvent was removed under reduced pressure. The crude material was taken up in warm ether and filtered to remove insoluble by-products. The filtrate was then concentrated to give the activated ester which was used as such for the next step.

LP-002 Precursor

Methyl-4-[(4-bromophenethenyl)]-benzoate

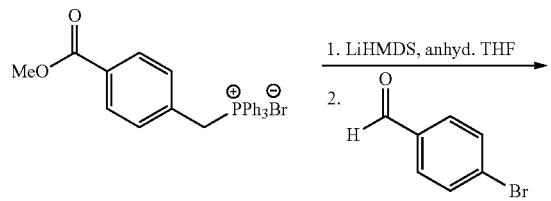

The phosphonium salt (1.46 g, 2.97 mmol) was dissolved in anhydrous THF (20 mL) and cooled to 0° C. LiHMDS (1.0M in THF) (2.97 mL, 2.97 mmol) was added drop-wise, stirred at 0° C. for 10 min then at room temperature for 1 hr. The reaction mixture was then re-cooled to 0° C. prior to the addition of 4-bromobenzaldehyde (0.50 g, 2.70 mmol). It was stirred at 0° C. for 10 min, then 1 hr at room temperature before heating at 50° C. After all starting material had reacted as indicated by TLC ($CH_2Cl_2$/hexanes, 1:2), the reaction mixture was diluted with EtOAc and quenched with sat. aq. $NH_4Cl$. The aqueous layer was extracted (3×) with EtOAc, washed with water, dried ($Na_2SO_4$), filtered and concentrated. The crude material was purified by silica gel chromatography using CombiFlash ($CH_2Cl_2$/hexanes) to give E- and Z-methyl-4-[(4-bromophenethenyl)]-benzoate (0.56 g and 0.29 g, respectively; 99% combined yield). E-isomer: $^1$H-NMR (500 MHz, $CDCl_3$) δ 7.94 (d, 2H, J=8.4 Hz), 7.76 (d, 2H, J=8.0 Hz), 7.37 (d, 2H, J=8.4 Hz), 7.50 (d, 2H, J=8.0 Hz), 6.75 (d, 1H, J=12.2 Hz), 6.63 (d, 1H, J=12.2 Hz), 3.97 (s, 3H).

Methyl-4-[(4-methoxyphenethenyl)-4-phenethenyl]-benzoate

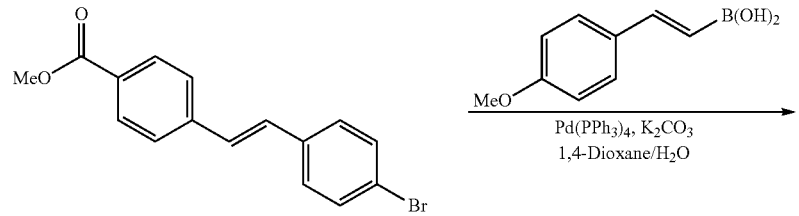

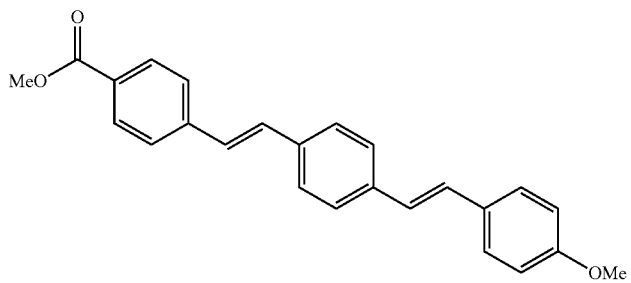

E-Methyl-4-[(4-bromophenethenyl)]-benzoate (0.23 g, 0.72 mmol) and 4-methoxyphenylvinyl boronic acid (0.26 g, 1.47 mmol) were dissolved in 1,4-dioxane/$H_2O$ (3 mL, 4:1). The solution was purged with Argon prior to the addition of $K_2CO_3$ (0.21 g, 1.50 mmol) and $Pd(PPh_3)_4$ (50 mg, 0.043 mmol). The reaction mixture was then heated at 100° C. After 16 h, it was cooled to rt and diluted with EtOAc and water. The organic layer was separated and the aqueous layer was extracted (3×) with EtOAc. Combined organic layers was washed (2×) with brine, dried ($Na_2SO_4$), filtered and concentrated. The crude material was purified by silica gel chromatography using CombiFlash ($CH_2Cl_2$/hexanes) to give the desired product (0.10 g, 52% BRSM). $^1$H-NMR (500 MHz, $CDCl_3$) δ 7.92-7.35 (m, 8H), 7.21-7.20 (m, 2H), 7.05 (d, 1H J=16.3 Hz), 6.95-6.90 (m, 3H), 6.68 (d, 1H, J=12.2 Hz), 6.61 (d, 1H, J=12.2 Hz), 3.91 (s, 3H), 3.84 (s, 3H).

Methyl-4-[(4-methoxyphenethyl)-4-phenethyl]-benzoate

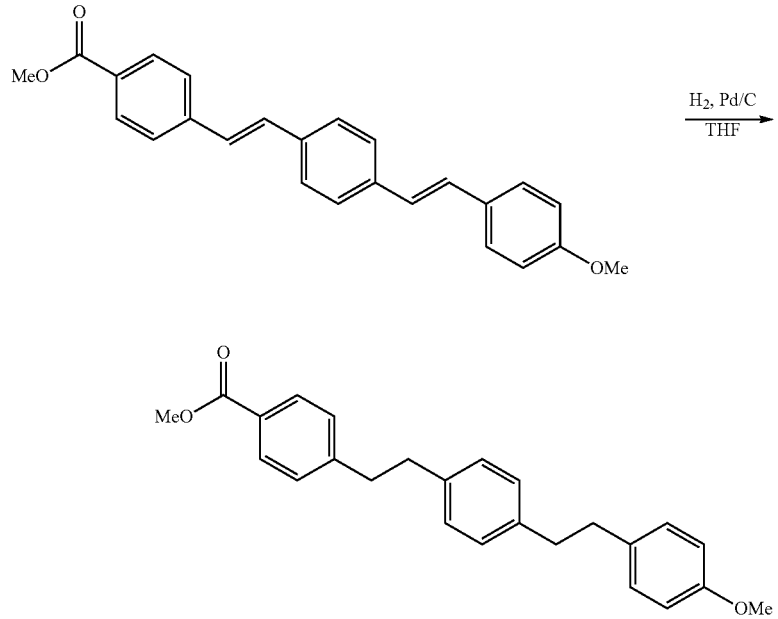 [SMILES: COC(=O)c1ccc(/C=C/c2ccc(/C=C/c3ccc(OC)cc3)cc2)cc1 ; COC(=O)c1ccc(CCc2ccc(CCc3ccc(OC)cc3)cc2)cc1 ; "THF"]

To the starting material (0.10 g, 0.28 mmol) in THF (10 mL) was added 10% Pd/C (12.1 mg). The suspension was stirred at room temperature under 1 atm of $H_2$ (balloon). After 16 hr, the reaction mixture was filtered through Celite, concentrated under reduced pressure and purified by silica gel chromatography using CombiFlash ($CH_2Cl_2$/hexanes) to give the desired product (96.0 mg, 90%). $^1$H-NMR (500 MHz, $CDCl_3$) δ 7.95 (d, 2H, J=8.2 Hz), 7.22 (d, 2H, J=8.1 Hz), 7.10-7.07 (m, 6H), 6.83 (d, 2H, J=8.5 Hz), 3.91 (s, 3H), 3.80 (s, 3H), 2.95-2.86 (m, 8H).

4-[(4-methoxyphenethyl)-4-phenethyl]-benzoic acid

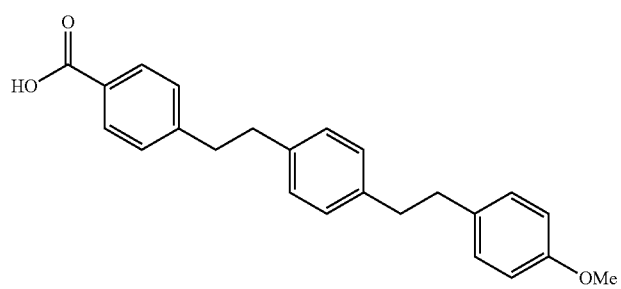

The ester (72 mg, 0.19 mmol) was dissolved in THF/MeOH/H$_2$O (10 mL; 7:2:1). LiOH (8.8 mg, 0.38 mmol) was then added and the reaction mixture stirred at 50° C. After all starting material had reacted as indicated by TLC (CH$_2$Cl$_2$/hexanes; 1:2), solvents were removed under reduced pressure. The crude material was acidified with 1N HCl, filtered and washed with H$_2$O and ether to give the desired acid as a white solid (49 mg, 71%). R$_t$=4.327 min; m/z 359.1599 [M−H]$^-$ 1-H-Benzotriazole-4-[(4-methoxyphenethyl)-4-phenethyl]-benzoate

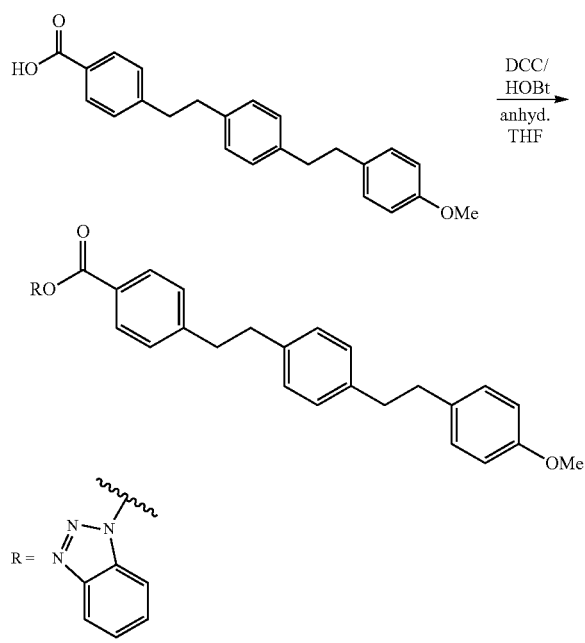

To the acid (32.1 mg, 0.089 mmol) in anhyd. THF (4 mL) under Argon atmosphere was added DCC (28.8 mg, 0.139 mmol) and HOBt (18.1 mg, 0.139 mmol). After stirring at it for 16 h, DCC (28.3 mg, 0.137 mmol) and HOBt (18.3 mg, 0.139 mmol) were again added. Reaction mixture was then stirred at 60° C. After all starting material had reacted, the solvent was removed under reduced pressure. The crude material was taken up in warm ether and filtered to remove insoluble by-products. The filtrate was then concentrated to give the activated ester which was used as such for the next step.

LP-001 Precursor

Methyl-4-[4-fluorophenethenyl)-4-phenethenyl]-benzoate

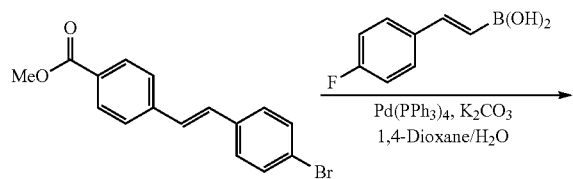

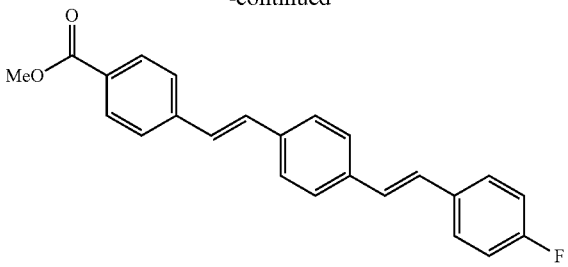

E-Methyl-4-[(4-bromophenethenyl)]-benzoate (0.25 g, 0.791 mmol) and 4-fluoro-phenylvinyl boronic acid (0.21 g, 1.28 mmol) were dissolved in 1,4-dioxane/H$_2$O (3 mL, 4:1). The solution was purged with Argon prior to the addition of K$_2$CO$_3$ (0.22 g, 1.60 mmol) and Pd(PPh$_3$)$_4$ (47.4 mg, 0.041 mmol). The reaction mixture was then heated at 80° C. After all starting material had reacted as indicated by TLC (CH$_2$Cl$_2$/hexanes, 1:2), solvents were removed under reduced pressure. The crude material was re-dissolved in CH$_2$Cl$_2$, washed with water, dried (Na$_2$SO$_4$), filtered and concentrated. The crude product was purified by silica gel chromatography using CombiFlash (EtOAc/hexanes) to give the desired compound (0.15 g, 52%). $^1$H-NMR (500 MHz, CDCl$_3$) δ 7.92 (d, 2H, J=8.2 Hz), 7.48-7.46 (m, 2H), 7.37-7.35 (m, 4H), 7.22 (d, 2H, J=8.2 Hz), 7.07-7.04 (m, 3H), 6.97 (d, 1H, J=16.3 Hz), 6.69 (d, 1H, J=12.2 Hz), 6.62 (d, 1H, J=12.2 Hz), 3.91 (s, 3H).

Methyl-4-[(4-fluorophenethyl)-4-phenethyl]-benzoate

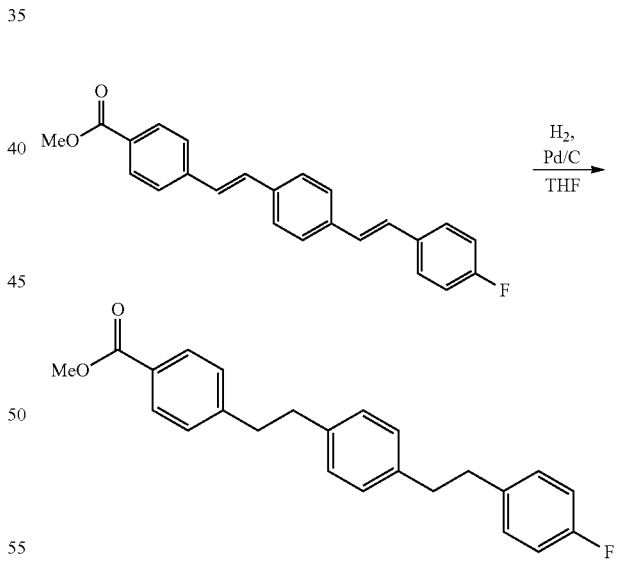

To the starting material (0.15 g, 0.414 mmol) in THF (10 mL) was added 10% Pd/C (17.2 mg). The suspension was stirred at room temperature under 1 atm of H$_2$ (balloon). After 16 hr, the reaction mixture was filtered through Celite, concentrated under reduced pressure and purified by silica gel chromatography using CombiFlash (CH$_2$Cl$_2$/hexanes) to give the desired product (0.11 g, 72%). $^1$H-NMR (500 MHz, CDCl$_3$) δ 7.95 (d, 2H, J=8.0 Hz), 7.22 (d, 2H, J=8.0 Hz), 7.12-7.06 (m, 6H), 6.96 (d, 1H, J=8.7 Hz), 6.95 (d, 1H, J=8.7 Hz), 3.92 (s, 3H), 2.99-2.85 (m, 8H).

4-[(4-fluorophenethyl)-4-phenethyl]-benzoic acid

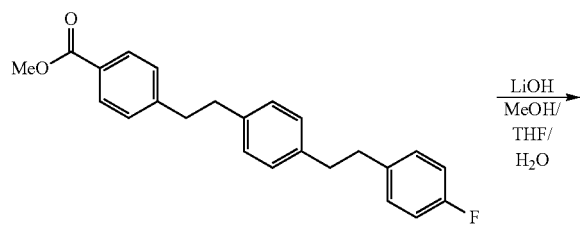

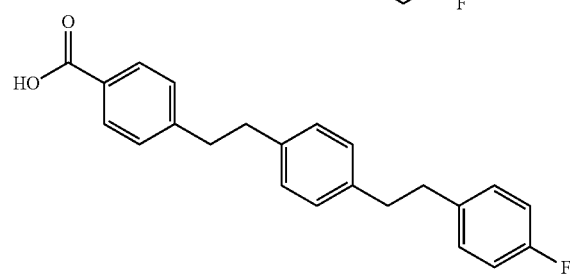

The ester (0.11 g, 0.300 mmol) was dissolved in THF/MeOH/H$_2$O (9 mL; 6:2:1). LiOH (15.7 mg, 0.654 mmol) was then added and the reaction mixture stirred at 60° C. After all starting material had reacted as indicated by TLC (CH$_2$Cl$_2$/hexanes; 1:2), solvents were removed under reduced pressure. The crude material was acidified with 1N HCl, filtered and washed with H$_2$O and ether to give the acid as a white solid (83.1 mg, 79%). R$_t$=4.469 min; m/z 347.1367 [M−H]$^-$.

1-H-Benzotriazole-4-[(4-fluorophenethyl)-4-phenethyl]-benzoate

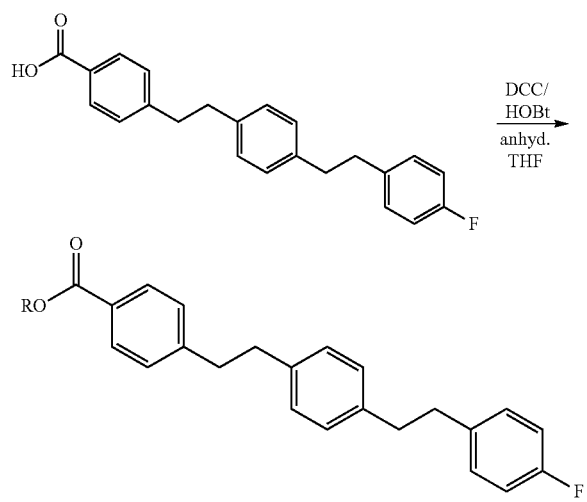

R = 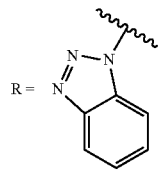

To the acid (30.3 mg, 0.087 mmol) in anhyd. THF (5 mL) under Argon atmosphere was added DCC (28.7 mg, 0.14 mmol) and HOBt (18.4 mg, 0.14 mmol). The reaction mixture was then stirred at 60° C. After 4 hr, DCC (16.8 mg, 0.081 mmol) and HOBt (10.6 mg, 0.078 mmol) were further added and the reaction mixture stirred at 40° C. overnight. After all starting material had reacted, the solvent was removed under reduced pressure. The crude material was taken up in ether and filtered to remove insoluble by-products. The filtrate was then concentrated to give the activated ester which was used as such for the next step.

LP-003 Precursor

Methyl-4-[(4-methylphenethenyl)-4-phenethenyl]-benzoate

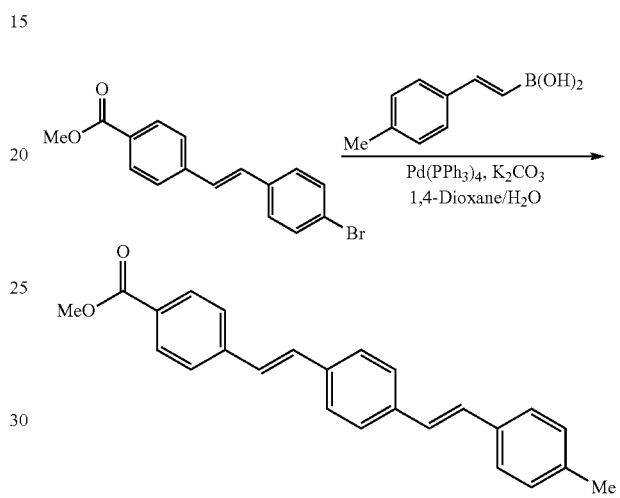

E-Methyl-4-[(4-bromophenethenyl)]-benzoate (0.262 g, 0.829 mmol) and 4-methyl-phenylvinyl boronic acid (0.23 g, 1.42 mmol) were dissolved in 1,4-dioxane/H$_2$O (3 mL, 4:1). The solution was purged with Argon prior to the addition of K$_2$CO$_3$ (0.25 g, 1.81 mmol) and Pd(PPh$_3$)$_4$ (52.5 mg, 0.045 mmol). The reaction mixture was then heated at 80° C. After all starting material had reacted as indicated by TLC (CH$_2$Cl$_2$/hexanes, 1:2), solvents were removed under reduced pressure. The crude material was re-dissolved in CH$_2$Cl$_2$, washed with water, dried (Na$_2$SO$_4$), filtered and concentrated. The crude product was purified by silica gel chromatography using CombiFlash (EtOAc/hexanes) to give the desired compound (0.10 g, 33%). $^1$H-NMR (500 MHz, CDCl$_3$) δ 7.92 (d, 2H, J=8.0 Hz), 7.41 (d, 2H, d=7.8 Hz), 7.38-7.35 (m, 4H), 7.21 (d, 2H, J=8.0 Hz), 7.17 (d, 2H, J=7.8 Hz), 7.07 (d, 1H, J=16.2 Hz), 7.01 (d, 1H, J=16.2 Hz), 6.70 (d, 1H, J=12.2 Hz), 6.61 (d, 1H, J=12.2 Hz), 3.92 (s, 3H), 2.37 (s, 3H).

Methyl-4-[(4-methylphenethyl)-4-phenethyl]-benzoate

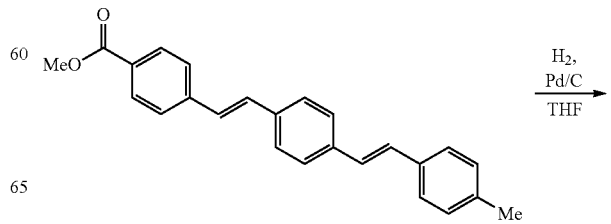

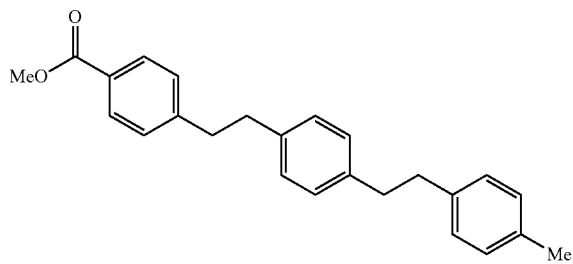

To the starting material (0.10 g, 0.28 mmol) in THF (10 mL) was added 10% Pd/C (12.5 mg). The suspension was stirred at room temperature under 1 atm of $H_2$ (balloon). After 16 hr, the reaction mixture was filtered through Celite, concentrated under reduced pressure and purified by silica gel chromatography using CombiFlash ($CH_2Cl_2$/hexanes) to give the desired product (80.0 mg, 80%). $^1$H-NMR (500 MHz, $CD_3OD$) δ 7.96 (d, 2H, J=8.0 Hz), 7.23 (d, 2H, J=8.0 Hz), 7.12-7.06 (m, 8H), 3.92 (s, 3H), 3.00-2.88 (m, 8H), 2.34 (s, 3H).

4-[(4-Methylphenethyl)-4-phenethyl]-benzoic acid

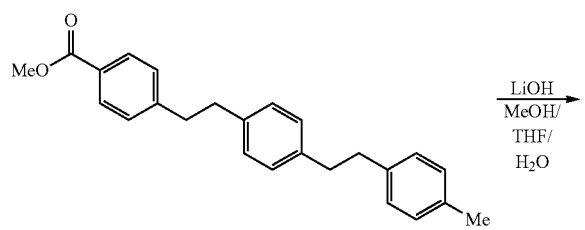

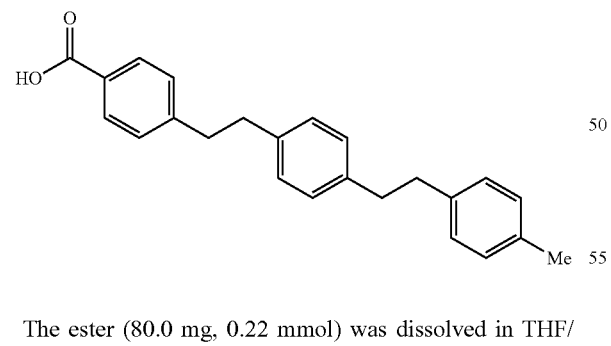

The ester (80.0 mg, 0.22 mmol) was dissolved in THF/MeOH/$H_2O$ (9 mL; 6:2:1). LiOH (10.9 mg, 0.37 mmol) was then added and the reaction mixture stirred at 50° C. After all starting material had reacted as indicated by TLC ($CH_2Cl_2$/hexanes; 1:2), solvents were removed under reduced pressure. The crude material was acidified with 1N HCl, filtered and washed with $H_2O$ and ether to give the acid as a white solid (53.4 mg, 69%). $^1$H-NMR (500 MHz, $d_6$-DMSO) δ 7.71 (d, 2H, J=7.9 Hz), 7.17-6.91 (m, 10H), 2.25 (s, 3H).

1-H-Benzotriazole-4-[(4-methylphenethyl)-4-phenethyl]-benzoate

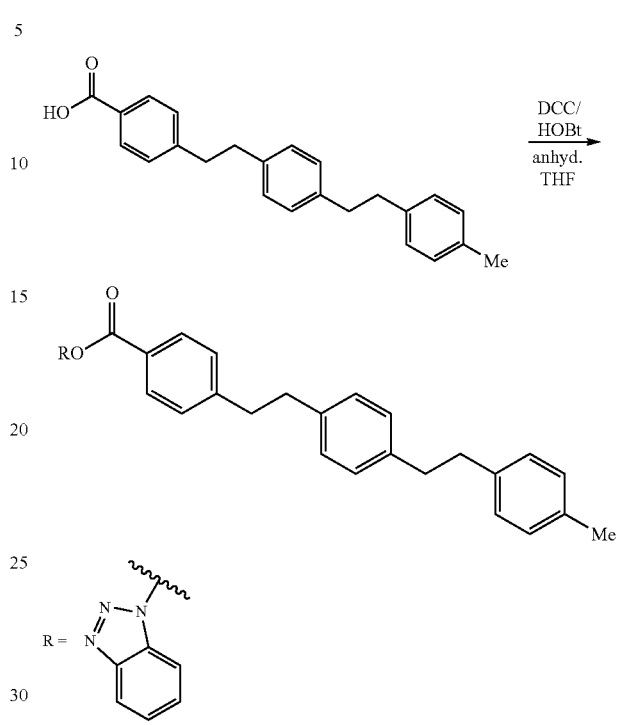

To the acid (33.3 mg, 0.097 mmol) in anhyd. THF (10 mL) under Argon atmosphere was added DCC (33.3 mg, 0.16 mmol) and HOBt (21.3 mg, 0.16 mmol). The reaction mixture was then stirred at 60° C. After 4 hr, DCC (17.4 mg, 0.084 mmol) and HOBt (11.5 mg, 0.085 mmol) were further added and the reaction mixture stirred at 40° C. overnight. After all starting material had reacted, the solvent was removed under reduced pressure. The crude material was taken up in ether and filtered to remove insoluble by-products. The filtrate was then concentrated to give the activated ester which was used as such for the next step.

(b) Side Chains Containing Naphthylene

LP-009 Precursor

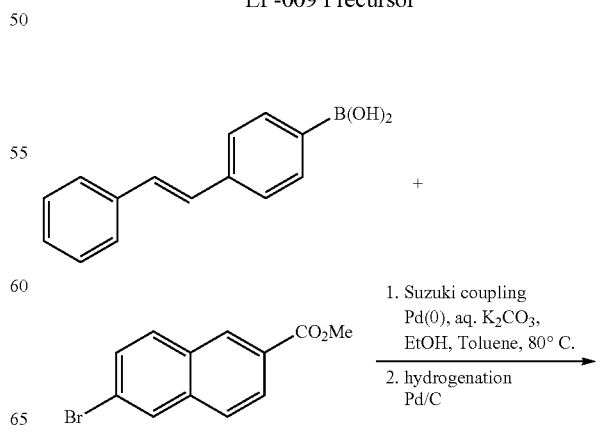

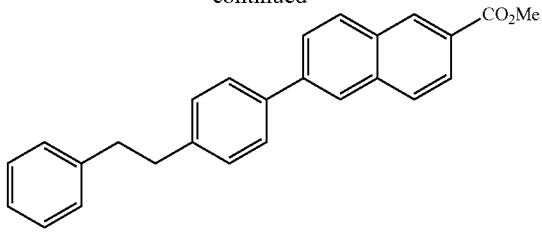

6-Bromo-naphthalene-2-carboxylic acid methyl ester (0.2 g, 0.75 mmol) and 4-styrylphenylboronic acid (0.25 g, 1.1 mmol) were dissolved in toluene/EtOH/$H_2O$ (15 mL, 10:4:1). The solution was purged with Argon prior to the addition of $K_2CO_3$ (0.31 g, 2.2 mmol) and $Pd(PPh_3)_4$ (25.0 mg). The reaction mixture was then heated at reflux overnight. After all starting material had reacted as indicated by TLC ($CH_2Cl_2$/hexanes, 1:9), solvents were removed under reduced pressure. The crude material was re-dissolved in EtOAc, washed with water, dried ($Na_2SO_4$), filtered and concentrated. The crude product was purified by silica gel chromatography using CombiFlash (EtOAc/hexanes) to give the desired compound (120 mg) which upon hydrogenation over Pd/C in THF under hydrogen atmosphere gave 6-(4-Phenethyl-phenyl)-naphthalene-2-carboxylic acid methyl ester (100 mg). This compound was subjected to hydrolysis in refluxing dioxane-water in presence of NaOH overnight to afford 6-(4-Phenethyl-phenyl)-naphthalene-2-carboxylic acid.

LP-011 Precursor

6-Bromo-2-napthaldehyde

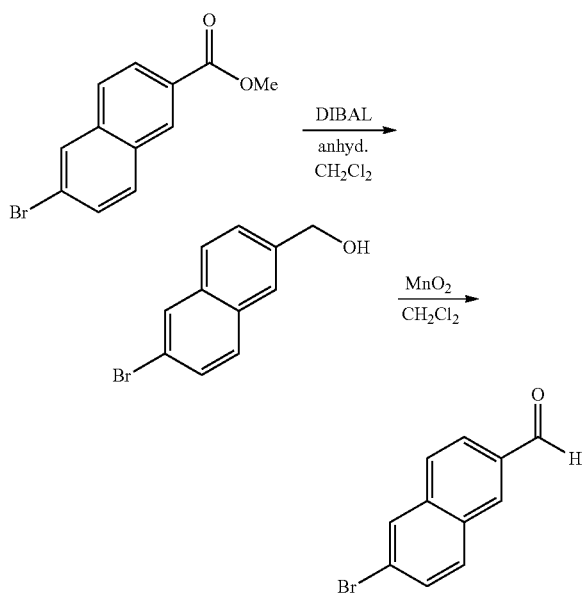

To a cooled (0° C.) solution of methyl-6-bromo-2-napthoate (1.20 g, 5.20 mmol) in anhyd. $CH_2Cl_2$ (30 mL), was added DIBAL (1.0M in toluene; 18 mL, 18 mmol) drop-wise under Argon atmosphere. The reaction mixture was stirred overnight at room temperature. After all starting material had reacted as indicated by TLC (EtOAc/hexanes, 1:4), the reaction mixture was cooled to 0° C., then MeOH carefully added. It was then diluted with ether and 20% sodium tartrate solution added. After vigorous stirring for 1 hr, the organic layer was separated and the aqueous layer extracted (2×) with ether. The combined organic extracts was washed with brine, dried ($Na_2SO_4$), filtered and concentrated. The crude product was used for the next step without further purification or characterization.

The crude product obtained above was dissolved in $CH_2Cl_2$ (50 mL) and $MnO_2$ (7.8 g, 89.7 mmol) added. The reaction mixture was stirred overnight at room temperature. After all starting material had reacted as indicated by TLC (EtOAc/hexanes, 1:4), the reaction mixture was filtered through Celite and concentrated under reduced pressure. The crude material was passed through a short silica column to give the desired aldehyde (0.66 g, 61%). $^1$H-NMR (500 MHz, $CDCl_3$) δ 10.2 (s, 1H), 8.32 (s, 1H), 8.10 (s, 1H), 8.00 (dd, 1H, J=1.5, 8.5 Hz), 7.89-7.86 (m, 2H), 7.67 (dd, 1H, J=1.9, 8.7 Hz).

Methyl-4-[2-(6-bromonaphthalen-2-yl)vinyl]-benzoate

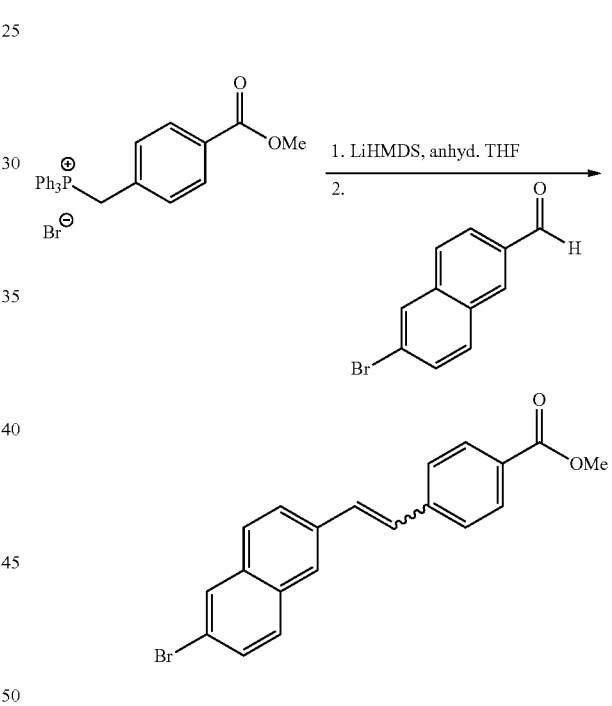

The Wittig salt (0.42 g, 0.857 mmol) was dissolved in anhyd. THF (8 mL) then cooled to 0° C. After 15 min, LiHMDS (1.0M in THF; 1.3 mL, 1.3 mmol) was added drop-wise. Ice-bath was removed and the reaction mixture was stirred at room temperature for 1 hr, then re-cooled to 0° C. prior to the drop-wise addition of the aldehyde (70.7 mg, 0.302 mol). The reaction mixture was then stirred at room temperature. After all starting material had reacted, the reaction mixture was cooled to 0° C. and diluted with EtOAc. Sat. aq. $NH_4Cl$ was carefully added to the vigorously stirred mixture. Aqueous layer was then separated and extracted with EtOAc. Combined organic extracts was washed with brine, dried ($Na_2SO_4$), filtered and concentrated. The crude material was purified by silica gel chromatography using CombiFlash ($CH_2Cl_2$/hexanes) to give the desired product (75.4 mg, 68%). $^1$H-NMR (500 MHz, $CDCl_3$) δ 7.94 (s, 1H), 7.90 (d, 2H, J=8.1 Hz), 7.68 (s, 1H), 7.58-7.50 (m, 3H), 7.33-7.27 (m, 3H), 6.83 (d, 1H, J=12.2 Hz), 6.72 (d, 1H, J=12.2 Hz), 3.91 (s, 3H).

Methyl-4-[2-(6-phenylnaphthalen-2-yl)vinyl]-benzoate

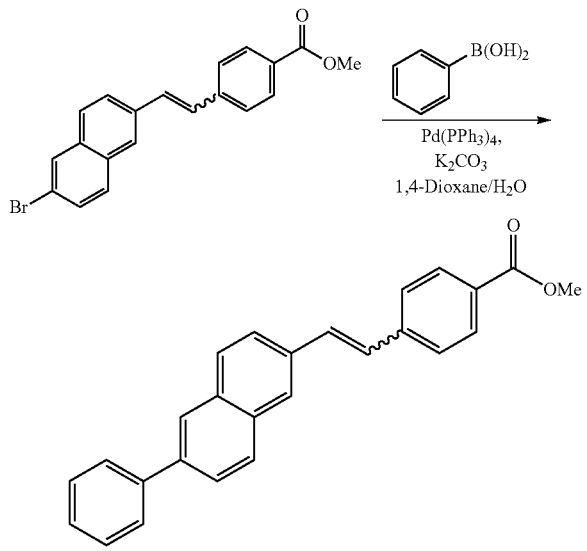

The bromo-ester (75.4 mg, 0.205 mmol) and phenylboronic acid (37.5 mg, 0.310 mmol) were dissolved in 1,4-dioxane/H$_2$O (6 mL, 4:1). The solution was purged with Argon prior to the addition of K$_2$CO$_3$ (57.1 mg, 0.413 mmol) and Pd(PPh$_3$)$_4$ (12.3 mg, 0.0106 mmol). The reaction mixture was then heated at 80° C. After all starting material had reacted as indicated by TLC (CH$_2$Cl$_2$/hexanes, 1:9), solvents were removed under reduced pressure. The crude material was re-dissolved in EtOAc, washed with water, dried (Na$_2$SO$_4$), filtered and concentrated. The crude product was purified by silica gel chromatography using CombiFlash (EtOAc/hexanes) to give the desired compound (45.0 mg, 60%). $^1$H-NMR (500 MHz, CDCl$_3$) δ 7.98 (s, 1H), 7.91 (d, 2H, J=8.4 Hz), 7.79 (d, 1H, J=8.5 Hz), 7.75-7.71 (m, 5H), 7.51-7.48 (m, 2H), 7.41-7.33 (m, 4H), 6.88 (d, 1H, J=12.2 Hz), 6.72 (d, 1H, J=12.2 Hz), 3.92 (s, 3H).

Methyl-4-[2-(6-phenylnaphthalen-2-yl)ethyl]-benzoate

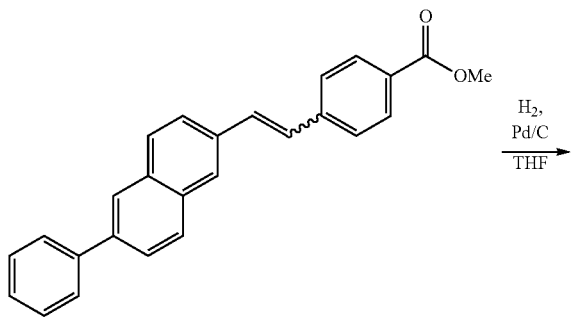

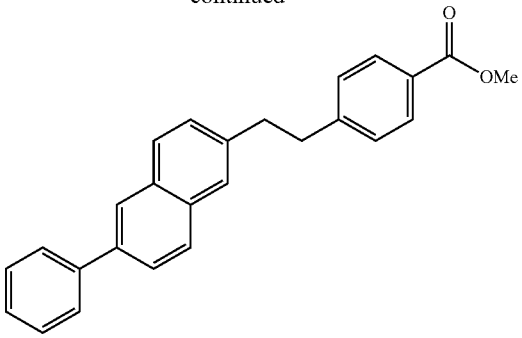

To the starting material (0.117 g, 0.320 mmol) in THF (15 mL) was added 10% Pd/C (17.2 mg). The suspension was stirred at room temperature under 1 atm of H$_2$ (balloon). After 16 hr, the reaction mixture was filtered through Celite, concentrated under reduced pressure and purified by silica gel chromatography using CombiFlash (CH$_2$Cl$_2$/hexanes) to give the desired product (0.109 g, 93%). $^1$H-NMR (500 MHz, CDCl$_3$) δ 8.02 (s, 1H), 7.97 (d, 2H, J=7.9 Hz), 7.84 (d, 2H, J=8.3 Hz), 7.75-7.72 (m, 3H), 7.61 (s, 1H), 7.51-7.48 (m, 2H), 7.40-7.27 (m, 4H), 3.92 (s, 3H), 3.13-3.10 (m, 4H).

4-[2-(6-Phenylnaphthalen-2-yl)ethyl]-benzoic acid

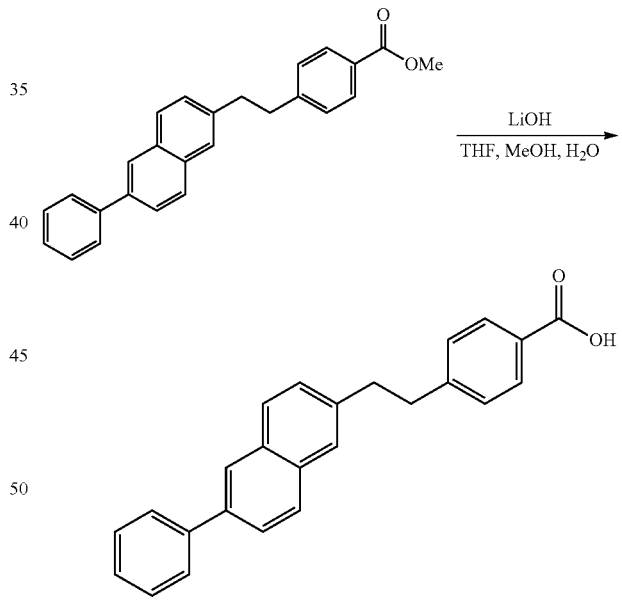

The ester (0.109 g, 0.297 mmol) was dissolved in THF/MeOH/H$_2$O (13 mL; 10:2:1). LiOH (16.7 mg, 0.696 mmol) was then added and the reaction mixture stirred at 60° C. After all starting material had reacted as indicated by TLC (CH$_2$Cl$_2$/hexanes; 1:2), solvents were removed under reduced pressure. The crude material was acidified with 1N HCl, filtered and washed with H$_2$O and ether to give the acid as a white solid (71.3 mg, 68%). $^1$H-NMR (500 MHz, d$_6$-DMSO) δ 8.15 (s, 1H), 7.90 (d, 1H, J=8.3 Hz), 7.89 (d, 1H, J=8.4 Hz), 7.84 (d, 2H, J=8.2 Hz), 7.80-7.78 (m, 3H), 7.72 (s, 1H), 7.51-7.36 (m, 6H), 3.07 (m, 4H).

1-H-Benzotriazole-4-[2-(6-phenylnaphthalen-2-yl)ethyl]-benzoate

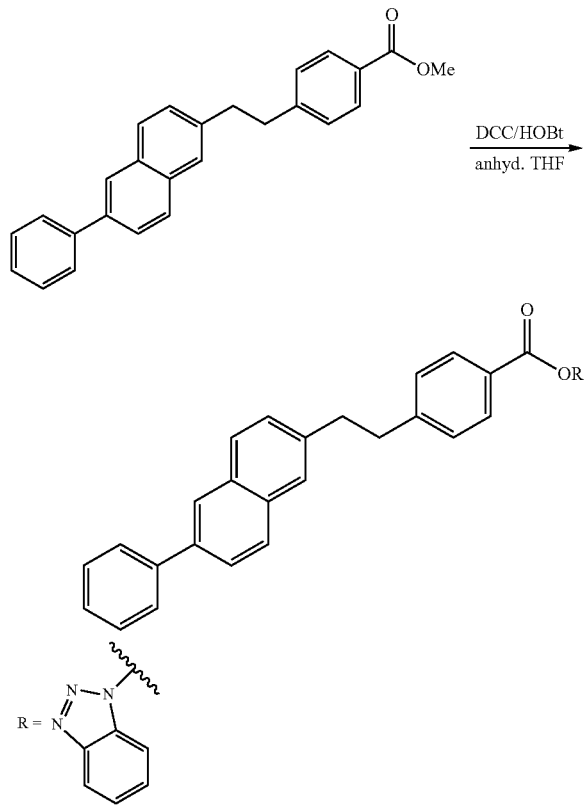

To the acid (27.4 mg, 0.078 mmol) in anhyd. THF (5 mL) under Argon atmosphere was added DCC (27.3 mg, 0.132 mmol) and HOBt (16.3 mg, 0.121 mmol). The reaction mixture was then stirred at room temperature. After 2 hr, DCC (13.3 mg, 0.064 mmol) and HOBt (16.2 mg, 0.120 mmol) were further added and the reaction mixture stirred at room temperature overnight. After all starting material had reacted, the solvent was removed under reduced pressure. The crude material was taken up in ether and filtered to remove insoluble by-products. The filtrate was then concentrated to give the activated ester which was used as such for the next step.

LP-010 Precursor

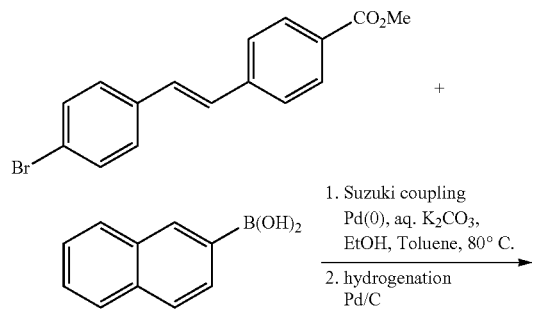

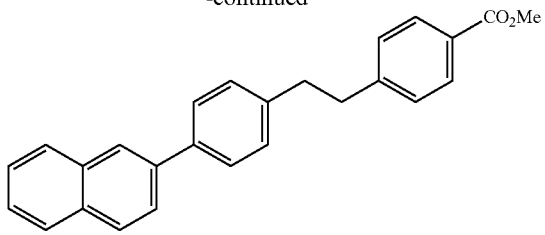

4-[2-(4-Bromo-phenyl)-vinyl]-benzoic acid methyl ester (0.2 g, 0.6 mmol) and naphthyl-2-boronic acid (0.16 g, 0.9 mmol) were dissolved in toluene/EtOH/H$_2$O (15 mL, 10:4:1). The solution was purged with Argon prior to the addition of K$_2$CO$_3$ (0.256 g, 1.8 mmol) and Pd(PPh$_3$)$_4$ (20.0 mg). The reaction mixture was then heated at reflux overnight. After all starting material had reacted as indicated by TLC (CH$_2$Cl$_2$/hexanes, 1:9), solvents were removed under reduced pressure. The crude material was re-dissolved in EtOAc, washed with water, dried (Na$_2$SO$_4$), filtered and concentrated. The crude product was purified by silica gel chromatography using CombiFlash (EtOAc/hexanes) to give the desired compound (130 mg) which upon hydrogenation over Pd/C in THF under hydrogen atmosphere gave 4-[2-(4-Naphthalen-2-yl-phenyl)-ethyl]-benzoic acid methyl ester (110 mg). This compound was subjected to hydrolysis in refluxing dioxane-water in presence of NaOH overnight to afford 4-[2-(4-Naphthalen-2-yl-phenyl)-ethyl]-benzoic acid. HPLC Rt: 4.68 min

LP-008 Precursor

2-Bromo-6-styrylnaphthalene

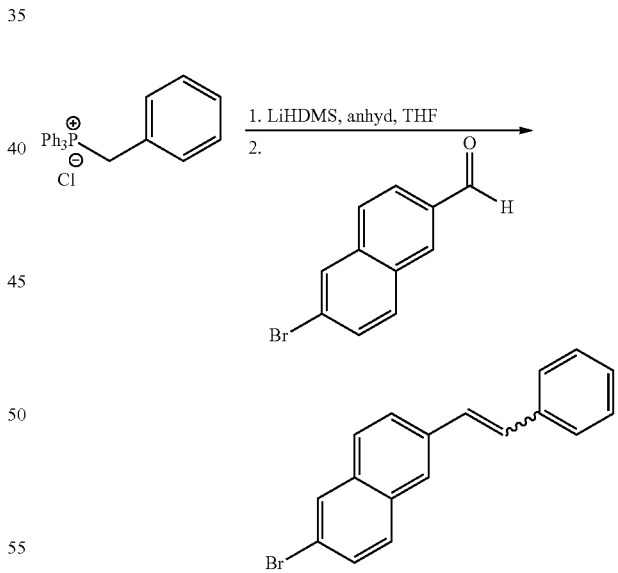

Benzyltriphenylphosphonium chloride (0.735 g, 1.89 mmol) was dissolved in anhyd. THF (15 mL) then cooled to 0° C. After 15 min, LiHMDS (1.0M in THF; 3.8 mL, 3.80 mol) was added drop-wise. Ice-bath was removed and the reaction mixture was stirred at room temperature overnight prior to the addition of the aldehyde (0.213 g, 0.906 mol). The reaction mixture was then stirred at room temperature for 16 h then worked-up by cooling to 0° C. and diluted with EtOAc. Sat. aq. NH$_4$Cl was carefully added to the vigorously stirred mixture. Aqueous layer was then separated and extracted with EtOAc. Combined organic extracts was washed with brine, dried (Na$_2$SO$_4$), filtered and concentrated. The crude material was purified by silica gel chromatography using CombiFlash (EtOAc/hexanes) to give the desired product (0.11 g, 20%). $^1$H-NMR (500 MHz, CDCl$_3$) δ 7.95 (s, 1H), 7.71 (s, 1H), 7.60-7.57 (m, 2H), 7.52 (d, 1H, J=8.5 Hz), 7.38 (d, 1H, J=8.5 Hz), 7.29-7.25 (m, 5H).

Methyl-4-[6-styrylnaphthalen-2-yl]-benzoate

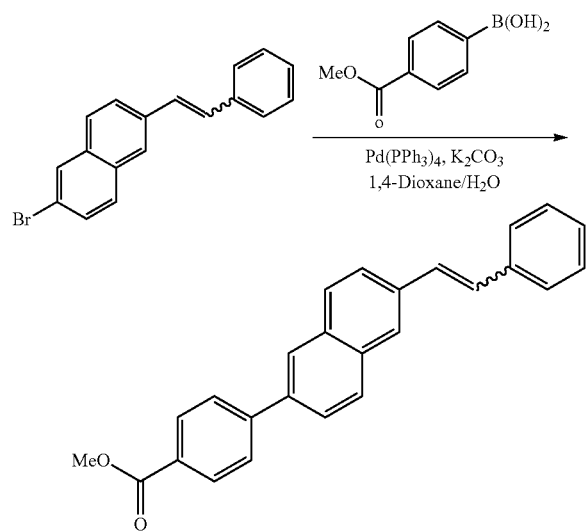

The bromo-alkene (0.115 g, 0.372 mmol) and 4-methylcarboxyphenylboronic acid (0.10 g, 0.556 mmol) were dissolved in 1,4-dioxane/H$_2$O (9 mL, 8:1). The solution was purged with Argon prior to the addition of K$_2$CO$_3$ (0.10 g, 0.723 mmol) and Pd(PPh$_3$)$_4$ (21.0 mg, 0.0182 mmol). The reaction mixture was then heated at 60° C. overnight. After all starting material had reacted as indicated by TLC (CH$_2$Cl$_2$/hexanes, 1:9), solvents were removed under reduced pressure. The crude material was re-dissolved in EtOAc, washed with water, dried (Na$_2$SO$_4$), filtered and concentrated. The crude product was purified by silica gel chromatography using CombiFlash (EtOAc/hexanes) to give the desired compound (22.1 mg, 16%). $^1$H-NMR (500 MHz, CDCl$_3$) δ 7.97 (s, 1H), 7.91 (d, 2H, J=8.4 z), 7.76 (d, 1H, J=8.6 Hz), 7.69 (s, 1H), 7.61-7.58 (m, 2H), 7.52 (d, 1H, J=8.5 Hz), 7.41 (d, 1H, J=8.5 Hz), 7.32-7.27 (m, 6H), 6.71 (d, 1H, J=12.2 Hz), 6.62 (d, 1H, J=12.2 Hz), 3.97 (s, 3H).

Methyl-4-[6-phenethylnaphthalen-2-yl]benzoate

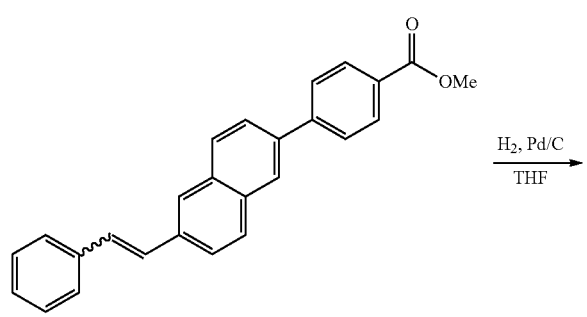

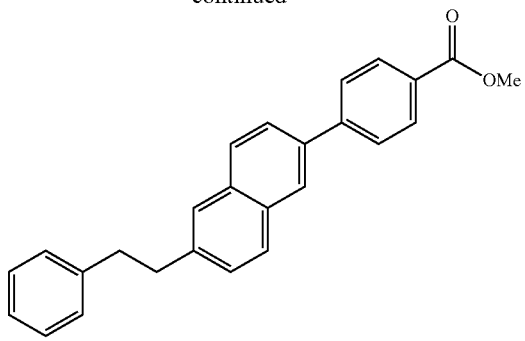

To the starting material (22.1 mg, 0.0605 mmol) in THF (10 mL) was added 10% Pd/C (5.2 mg). The suspension was stirred at room temperature under 1 atm of H$_2$ (balloon). After 16 hr, the reaction mixture was filtered through Celite, concentrated under reduced pressure and purified by silica gel chromatography using CombiFlash (CH$_2$Cl$_2$/hexanes) to give the desired product (21.4 mg, 96%). $^1$H-NMR (500 MHz, CDCl$_3$) δ 8.15 (d, 2H, J=8.0 Hz), 8.06 (s, 1H), 7.87-7.86 (m, 2H), 7.80 (d, 1H, J=8.0 Hz), 7.74 (d, 1H, J=8.6 Hz), 7.64 (s, 1H), 7.38 (d, 1H, J=8.3 Hz), 7.31-7.20 (m, 5H), 3.97 (s, 3H), 3.14-3.03 (m, 4H).

4-[6-Phenethylnaphthalen-2-yl]benzoic acid

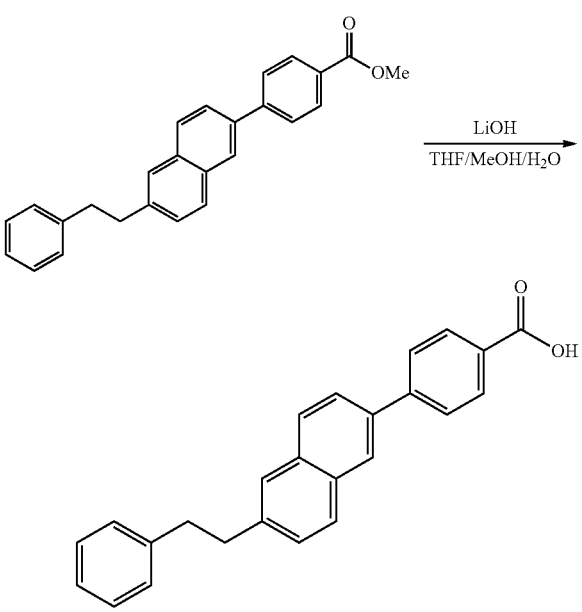

The ester (21.4 mg, 0.0583 mmol) was dissolved in THF/MeOH/H$_2$O (11 mL; 8:2:1). LiOH (3.5 mg, 0.146 mmol) was then added and the reaction mixture stirred at 60° C. After all starting material had reacted as indicated by TLC (EtOAc/hexanes; 1:9), solvents were removed under reduced pressure. The crude material was acidified with 1N HCl, filtered and washed with H$_2$O and ether to give the acid as a white solid (15.2 mg, 74%). R$_t$=4.773 min; m/z 351.1343 [M−H]$^-$.

1-H-Benzotriazole-4-[6-phenethylnaphthalen-2-yl]-benzoate

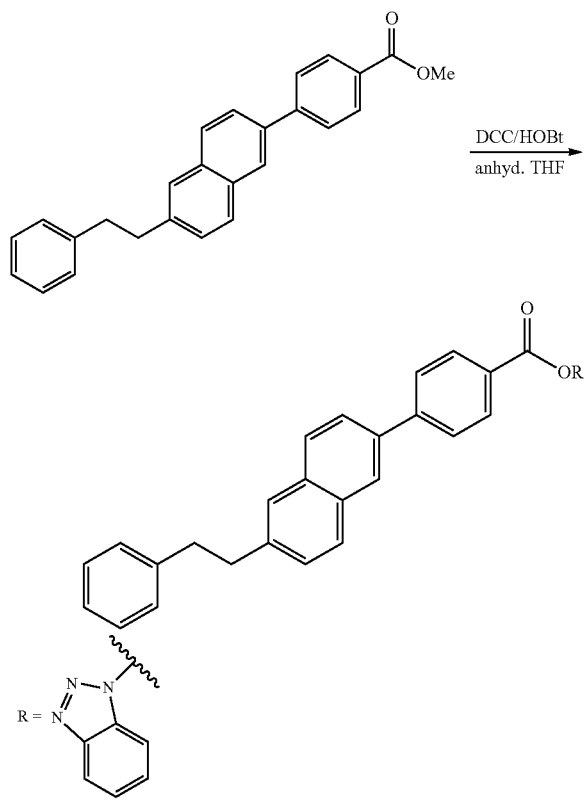

To the acid (15.2 mg, 0.043 mmol) in anhyd. THF (2 mL) under Argon atmosphere was added DCC (23.8 mg, 0.115 mmol) and HOBt (15.7 mg, 0.116 mmol). The reaction mixture was then stirred at room temperature overnight, then at 40° C. After all starting material had reacted, the solvent was removed under reduced pressure. The crude material was taken up in ether and filtered to remove insoluble by-products. The filtrate was then concentrated to give the activated ester which was used as such for the next step.

LP-013 Precursor

This precursor was synthesised by alkylation of the Naphthalene carboxylic ester with the appropriate alkylating agent, i.e. alkyl bromide followed by ester hydrolysis and preparation of activated ester.

LP-014 Precursor

This precursor was synthesised by alkylation of the Naphthalene carboxylic ester with the appropriate alkylating agent, i.e. alkyl bromide followed by ester hydrolysis and preparation of activated ester.

LP-015 Precursor

This precursor was synthesised by alkylation of the Naphthalene carboxylic ester with the appropriate alkylating agent, i.e. alkyl bromide followed by ester hydrolysis and preparation of activated ester.

(C) Coupling of Side Chains to Lipopeptide
(1) Synthesis of Activated Esters
Synthesis of Pentafluorophenyl Esters of Carboxylic Acids:
To a solution of the carboxylic acid (0.3 mmol) in anhydrous THF (2 mL) under Ar was added DCC (0.32 mmol) and pentafluorophenol (0.35 mmol) and stirred at room temperature overnight. After cooling the reaction mixture to 0° C., DCU was filtered off and the filtrate evaporated under vacuum. The residue was recrystalised from $Et_2O$-Hexane (4:1) to afford the pentafluorophenol ester.

Synthesis of HOBt Ester of Carboxylic Acids:
To a solution of the carboxylic acid (0.3 mmol) in anhydrous THF (2 mL) under Argon was added DCC (0.45 mmol) and HOBt (0.45 mmol) and stirred at room temperature overnight. After cooling the reaction mixture to 0° C., DCU was filtered off and the filtrate evaporated under vacuum to afford the HOBt ester which was used as such for coupling.

(2) Coupling with GM539
Method A. Coupling Done in the Absence of $CaCl_2$:
GM539 (20 mg, 0.015 mmol) and the pentafluorophenol ester (22 mg, 0.045 mmol) were dissolved in anhydrous DMF (0.4 mL) under Argon. DIPEA (8.3 μL, 0.045 mmol) was added and the reaction was stirred at room temperature for 2.5 h at the end of which HPLC indicated consumption of starting material. 20% piperidine in DMF (100 μL) was added to the reaction mixture and stirred for 20 min at room temperature which was sufficient to deprotect the Fmoc- group. 20% piperidine in DMF (100 μL) was added and the reaction monitored by HPLC. After completion of the reaction, the mixture was purified by preparative HPLC (gradient elution, ACN-$H_2O$ with 0.1% $HCO_2H$) and collecting fractions in tubes containing phosphate buffer to afford two separated peaks having the same molecular mass. These fractions were reanalyzed by analytical HPLC and evaporated separately. The residue was loaded on a pre-washed (with 100 mL MeOH and 100 mL water) C-18 plug and washed with 100 mL water. The compound was eluted using MeOH (50 mL) and the fractions containing product evaporated.

Method B. Coupling Done in Presence of $CaCl_2$ Using Pentafluorophenol Activated Ester:
GM539 (20 mg, 0.015 mmol) and $CaCl_2$ (3.3 mg, 0.030 mmol) were taken in anhydrous DMF (0.2 mL) under Argon. After cooling to 0° C., $Et_3N$ (10.4 uL, 0.075 mmol) was added and stirring continued for another 5 minutes at the same temperature to ensure dissolution of $CaCl_2$. Pentafluorophenylester (0.045 mmol) was then introduced at 0° C. and stirred for 2 h at the same temperature. After stirring overnight at room temperature, 20% piperidine in DMF (100 μL) was added and the reaction monitored by HPLC. After completion of the reaction, the product was purified by preparative HPLC and isolated as described in method A.

Method C: Coupling in Absence of $CaCl_2$ Using HOBt Ester
GM539 (20 mg, 0.015 mmol) and the HOBt ester (0.045 mmol) were dissolved in anhydrous DMF (0.5 mL) under Argon. DIPEA (8.3 μL, 0.045 mmol) was added and the reaction was stirred at room temperature for 2.5 h at the end of which HPLC indicated consumption of starting material. 20% piperidine in DMF (100 μL) was added and the reaction monitored by HPLC. After completion of the reaction, the product was purified by preparative HPLC and isolated as described in method A.

Method D: Coupling in Presence of $CaCl_2$ Using HOBt Ester:
GM539 (10 mg, 0.007 mmol) and $CaCl_2$ (1.7 mg, 0.015 mmol) were taken in anhydrous DMF (0.5 mL) under Argon. After cooling to 0° C., $Et_3N$ (5.4 uL, 0.038 mmol) was added and stirring continued for another 5 minutes at the same temperature to ensure dissolution of $CaCl_2$. HOBt ester (0.021 mmol) was added and the mixture stirred at 0° C. for 1 hour and then at room temperature till the reaction was complete. Piperidine (100 uL of 20% stock solution in DMF) was added and the reaction monitored by HPLC. After completion of the reaction, the product was purified by preparative HPLC and isolated as described in method A.

Method E: Coupling in Presence of $CaCl_2$ Pentafluorophenol Activated Ester:

GM539 (0.015 mmol) and $CaCl_2$ (0.03 mmol, 2 eq) was added with 1.0 ml DMF. To this suspension was added triethylamine ($Et_3N$, 0.075 mmol, 5 eq), then stirred for 10-15 min at 0° C. The activated acid was added and the mixture stirred at 0° C. for another hour. The mixture was warmed to room temperature and stirred overnight. The reaction was purified by preparative RP-HPLC (X-Terra® PrepRP$_{18}$ 19×50 mm column, acetonitrile-water as solvent).

The fractions containing the product were dried under reduced pressure, dissolved in 1 mL DMF, added with TBAF hydrate (15 eq) then stirred for 1 hr. After 3 hrs of incomplete reaction, 10 uL of 20% piperidine in DMF was added and the mixture stirred for an additional 1 hr. The mixture was purified by preparative RP-HPLC (X-Terra® PrepRP$_{18}$ 19×50 mm column, acetonitrile-water with 0.1% formic acid as solvent) using collection tubes containing 2.5 mL of 15 mM sodium phosphate buffer (pH 7.2) with 50 mm sodium chloride. Product-containing fractions were desalted using a Sep-Pak® C18 cartridge Vac 6 cc (1 g).

Method F. Coupling in the Presence of $CaCl_2$ and Pentafluorophenol Activated Ester:

To a mixture of GM539 (0.0164 mmol) and $CaCl_2$ (0.033 mmol, 2 eq) in 0.5 ml DMF was added the activated acid (3 eq in 0.5 mL DMF with 0.4 mL and THF washing). After 10-15 min stirring at room temperature, triethylamine ($Et_3N$, 0.082 mmol, 5 eq) was added at 0° C. and kept stirring for another two hours. The mixture was warmed to room temperature and stirred until all the starting material has been used up as monitored by analytical hplc. To the above coupling mixture was added piperidine (20% in DMF) and stirred at room temperature until deprotection was complete. The mixture was purified by preparative RP-HPLC (X-Terra® PrepRP18 19×50 mm column, acetonitrile-water with 0.1% formic acid as solvent) using collection tubes containing 2.5 mL of 15 mM sodium phosphate buffer (pH 7.2) with 50 mm sodium chloride. Product-containing fractions were desalted using a Sep-Pak® C18 cartridge Vac 6 cc (1 g).

(3) Examples of Coupling

To illustrate the coupling procedure, the following examples are provided:

LP-007

Coupling of GM539 with activated ester side chain followed by Fmoc deprotection to form LP-007:

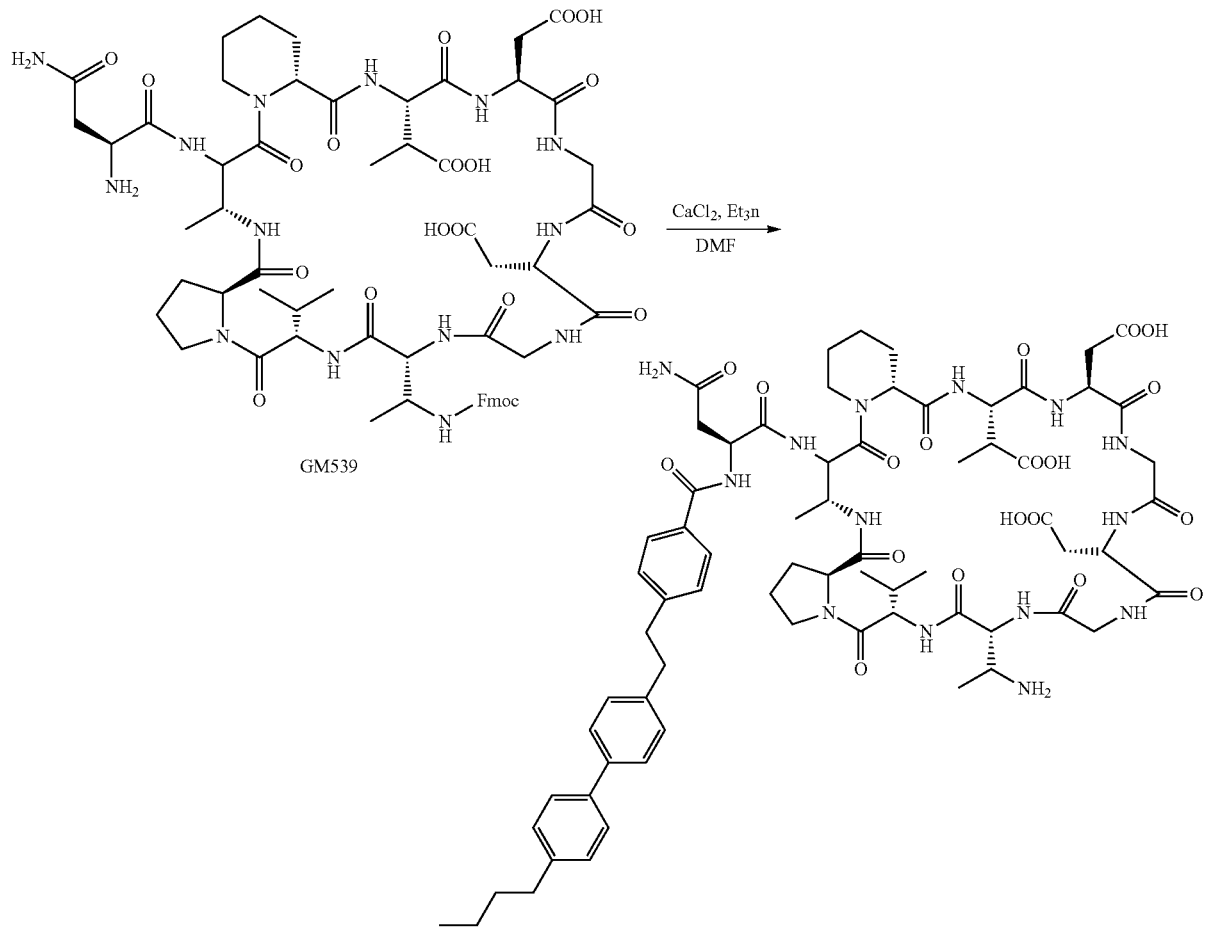

GM539 (20 mg, 0.015 mmol) and CaCl$_2$ (3.2 mg, 0.029 mmol) were dissolved in anhyd. DMF (0.5 mL) at rt. The solution was then cooled to 0° C. prior to the addition of anhyd. Et$_3$N (11 µL, 0.109 mmol). After 10 min, the crude ester was added drop-wise. The reaction mixture was stirred at 0° C. for 1 hr, then at rt. After all starting material had reacted, 20% piperidine (50 µL) was added and stirred overnight at rt. After deprotection was complete, the mixture was purified by preparative RP-HPLC (X-Terra® PrepRP$_{18}$ 19×50 mm column, acetonitrile-water as solvent) using collection tubes containing 2.5 mL of 15 mM sodium phosphate buffer (pH 7.2) with 50 mm sodium chloride. Product-containing fractions were desalted using a SepPak® C18 cartridge Vac 6 cc (1 g) and finally lypholized to give LP-007 (1.8 mg, 8%). R$_f$=3.198 min; m/z 718.3447 ½ [M+2H]$^{2+}$, 1435.6902 [M+H]$^+$.

LP-002

Coupling of GM539 with activated ester side chain followed by Fmoc deprotection to form LP-002:

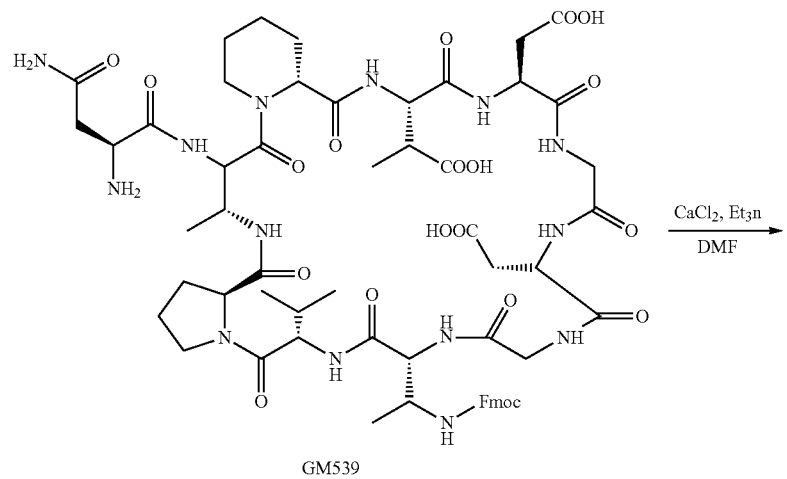

GM539

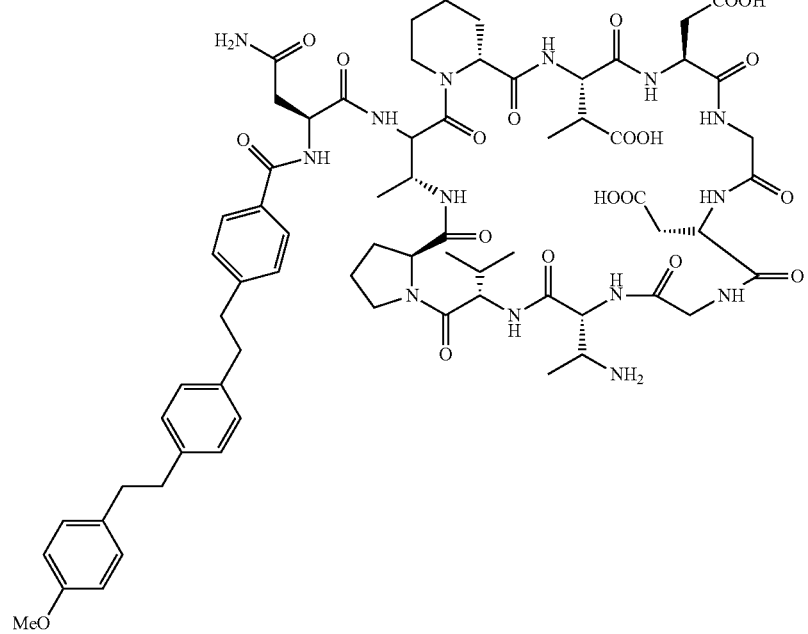

GM1250

GM539 (20 mg, 0.015 mmol) and CaCl$_2$ (3.5 mg, 0.031 mmol) were dissolved in anhyd. DMF (0.5 mL) at rt. The solution was then cooled to 0° C. prior to the addition of anhyd. Et$_3$N (11 μL, 0.109 mmol). After 10 min, the crude ester was added drop-wise. The reaction mixture was stirred at 0° C. for 1 hr, then at rt. After all starting material had reacted, 20% piperidine (50 μL) was added and stirred overnight at rt. After deprotection was complete, the mixture was purified by preparative RP-HPLC (X-Terra® PrepRP$_{18}$ 19×50 mm column, acetonitrile-water as solvent) using collection tubes containing 2.5 mL of 15 mM sodium phosphate buffer (pH 7.2) with 50 mm sodium chloride. Product-containing fractions were desalted using a Sep-Pals® C18 cartridge Vac 6 cc (1 g) and finally lypholized to give LP-002 (1.3 mg, 6%). R$_t$ 2.564 min; m/z 719.3394 ½ [M+2H]$^{2+}$, 1437.6548 [M+H]$^+$.

LP-001

Coupling of GM539 with activated ester side chain followed by Fmoc deprotection to form LP-001:

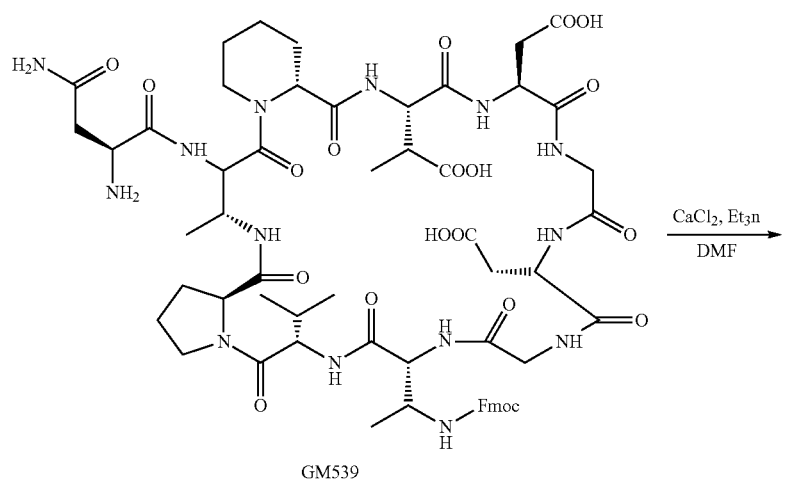

GM539

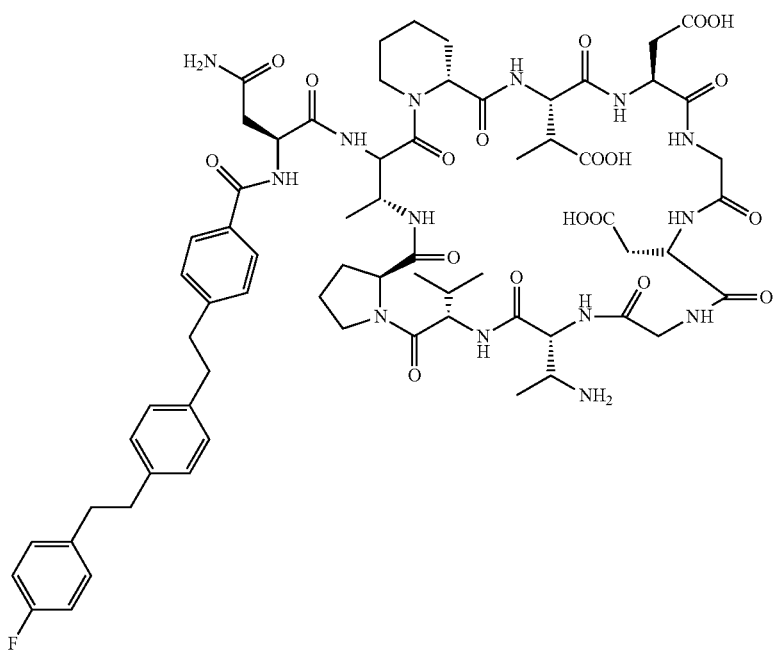

GM1273

GM539 (19.0 mg, 0.014 mmol) and CaCl$_2$ (3.3 mg, 0.030 mmol) were dissolved in anhyd. DMF (0.5 mL) at rt. The solution was then cooled to 0° C. prior to the addition of anhyd. Et$_3$N (11 μL, 0.109 mmol). After 10 min, the crude ester was added drop-wise. The reaction mixture was stirred at 0° C. for 1 hr, then at rt. After all starting material had reacted, 20% piperidine (50 μL) was added and stirred overnight at rt. After deprotection was complete, the mixture was purified by preparative RP-HPLC (X-Terra® PrepRP$_{18}$ 19×50 mm column, acetonitrile-water as solvent) using collection tubes containing 2.5 mL of 15 mM sodium phosphate buffer (pH 7.2) with 50 mm sodium chloride. Product-containing fractions were desalted using a Sep-Pals® C18 cartridge Vac 6 cc (1 g) and finally lypholized to give LP-001 (1.0 mg, 4.9%). R$_t$ 2.607 min; m/z 713.3244 ½ [M+2H]$^{2+}$, 1425.6480 [M+H]$^+$.

LP-003

Coupling of GM539 with activated ester side chain followed by Fmoc deprotection to form LP-003:

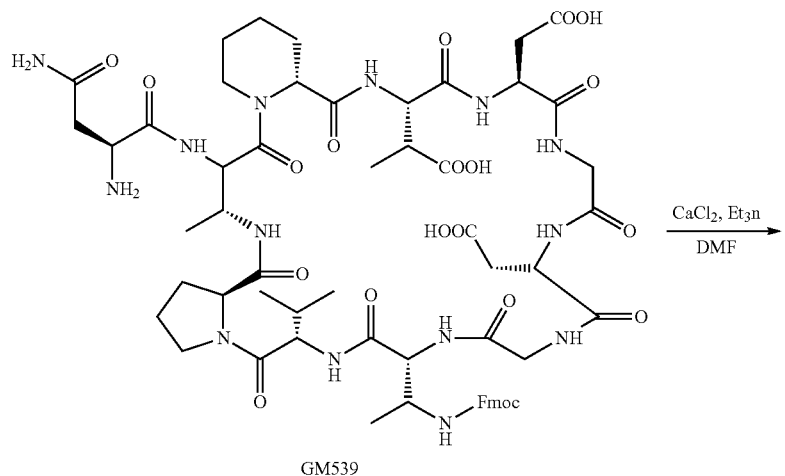

GM539

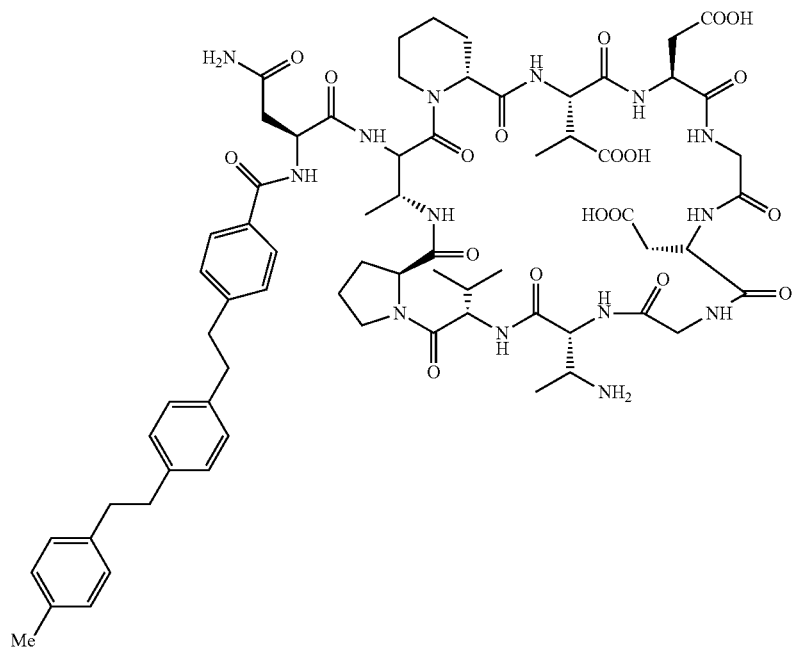

GM1289

GM539 (20.5 mg, 0.016 mmol) and $CaCl_2$ (3.7 mg, 0.033 mmol) were dissolved in anhyd. DMF (0.5 mL) at rt. The solution was then cooled to 0° C. prior to the addition of anhyd. $Et_3N$ (12 µL, 0.119 mmol). After 10 min, the crude ester was added drop-wise. The reaction mixture was stirred at 0° C. for 1 hr, then at rt. After all starting material had reacted, 20% piperidine (50 µL) was added and stirred overnight at rt. After deprotection was complete, the mixture was purified by preparative RP-HPLC (X-Terra® PrepRP$_{18}$ 19×50 mm column, acetonitrile-water as solvent) using collection tubes containing 2.5 mL of 15 mM sodium phosphate buffer (pH 7.2) with 50 mm sodium chloride. Product-containing fractions were desalted using a Sep-Pale® C18 cartridge Vac 6 cc (1 g) and finally lypholized to give LP-003 (1.2 mg, 5.4%). $R_t$=2.840 min; m/z 711.3365 ½ $[M+2H]^{2+}$, 1421.6655 $[M+H]^+$.

LP-011

Coupling of GM539 with activated ester side chain followed by Fmoc deprotection to form LP-011:

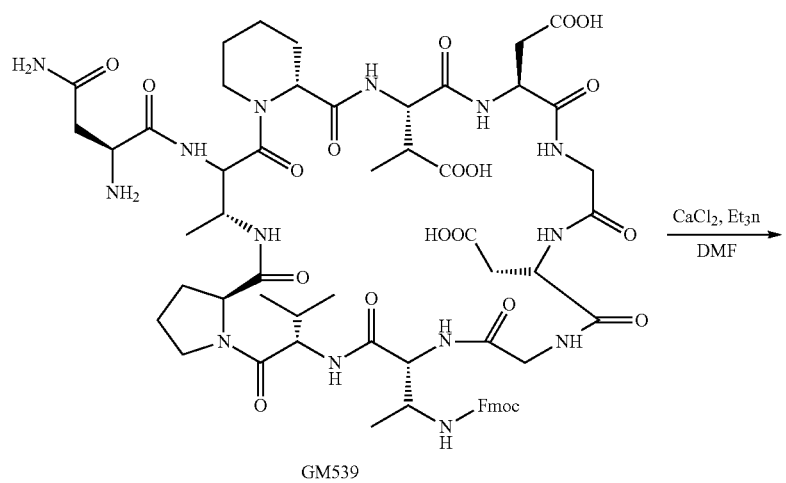

GM539

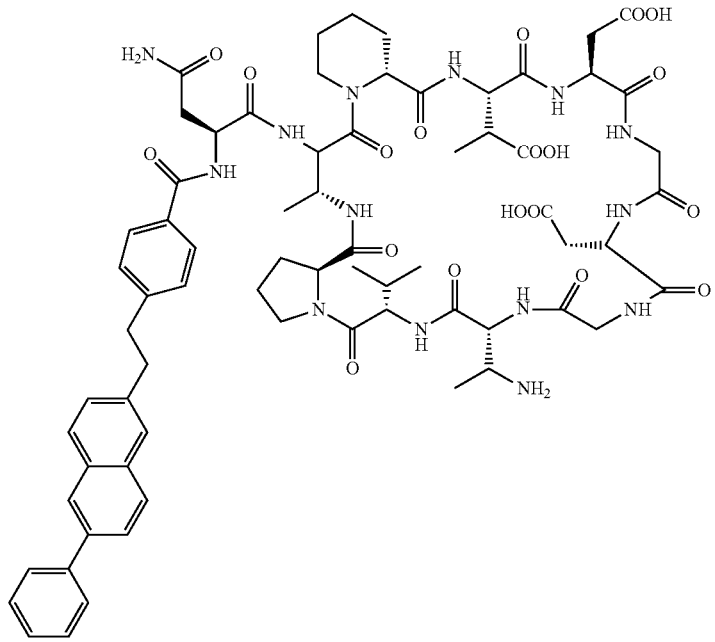

GM1294

151

GM539 (20.0 mg, 0.015 mmol) and CaCl$_2$ (3.7 mg, 0.033 mmol) were dissolved in anhyd. DMF (0.5 mL) at rt. The solution was then cooled to 0° C. prior to the addition of anhyd. Et$_3$N (12 µL, 0.119 mmol)). After 15 min, the crude ester was added drop-wise. The reaction mixture was stirred at 0° C. for 1 hr, then at rt. After all starting material had reacted, 20% piperidine (50 µL) was added and stirred overnight at rt. After deprotection was complete, the mixture was purified by preparative RP-HPLC (X-Terra® PrepRP$_{18}$ 19×50 mm column, acetonitrile-water as solvent) using collection tubes containing 2.5 mL of 15 mM sodium phosphate buffer (pH 7.2) with 50 mm sodium chloride. Product-containing fractions were desalted using a Sep-Pak® C18 cartridge Vac 6 cc (1 g) and finally lypholized to give LP-011 (1.3 mg, 6%). R$_t$=2.683 min; m/z 715.3283 ½ [M+2H]$^{2+}$, 1429.6415 [M+H]$^+$.

LP-008

Coupling of GM539 with activated ester side chain followed by Fmoc deprotection to form LP-008:

152

GM539 (19.8 mg, 0.015 mmol) and CaCl$_2$ (3.4 mg, 0.0306 mmol) were dissolved in anhyd. DMF (0.5 mL) at rt. The solution was then cooled to 0° C. prior to the addition of anhyd. Et$_3$N (12 µL, 0.119 mmol)). After 15 min, the crude ester was added drop-wise. The reaction mixture was stirred at 0° C. for 1 hr, then at rt. After all starting material had reacted, 20% piperidine (50 µL) was added and stirred overnight at rt. After deprotection was complete, the mixture was purified by preparative RP-HPLC (X-Terra® PrepRP$_{18}$ 19×50 mm column, acetonitrile-water as solvent) using collection tubes containing 2.5 mL of 15 mM sodium phosphate buffer (pH 7.2) with 50 mm sodium chloride. Product-containing fractions were desalted using a Sep-Pak® C18 cartridge Vac 6 cc (1 g) and finally lypholized to give LP-008 (3.5 mg, 16%). R$_t$=2.668 min; m/z 1429.6346 [M+H]$^+$.

LP-026

Coupling of GM539 with activated ester side chain followed by Fmoc deprotection to form LP-026:

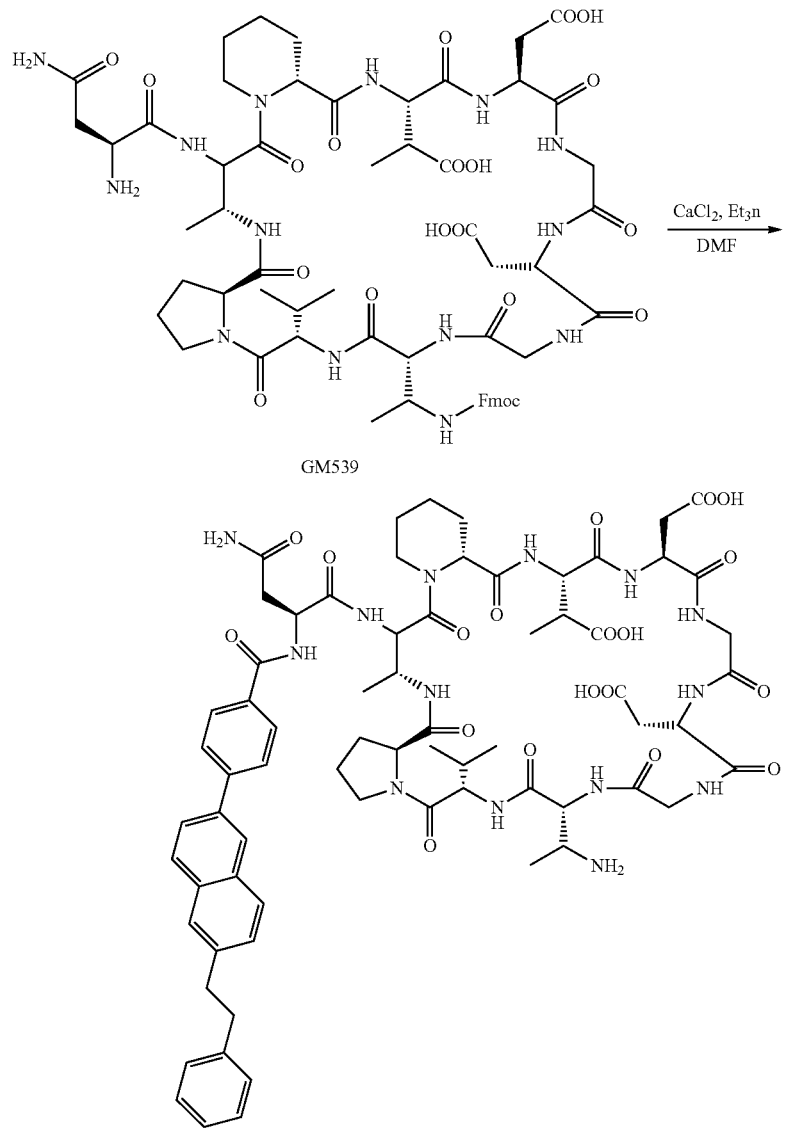

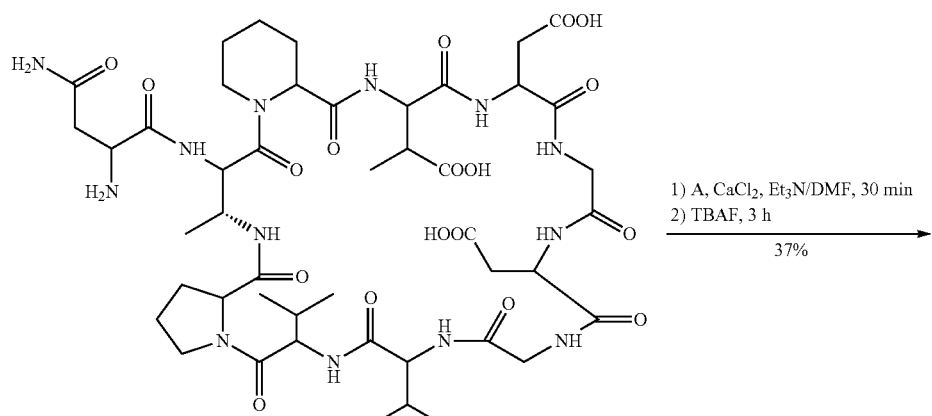

GM539

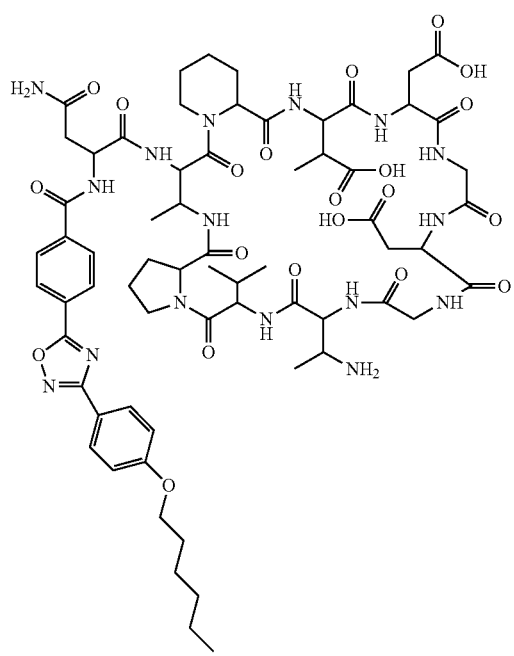

GM1221

A = 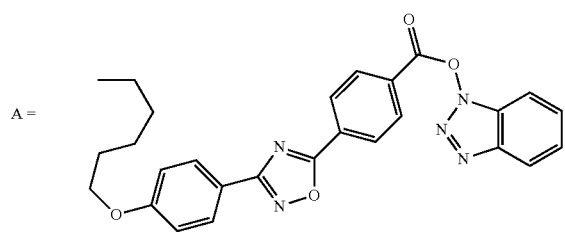

GM539 i.e. deacylated Fmoc Friulimicin B (10 mg, 0.007 mmol) and CaCl₂ (1.7 mg, 0.015 mmol) were taken in anhydrous DMF (0.2 mL) under Argon. After cooling to 0° C., Et₃N (5.2 μL, 0.007 mmol) was added and stirring continued for another five minutes at the same temperature to ensure dissolution of CaCl₂. HOBt ester (11 mg, 0.021 mmol) was added and the mixture stirred at 0° C. for 30 minutes by which time HPLC showed completion of the reaction. TBAF (40 mg, 0.15 mmol) was added and the mixture warmed to room temperature. After 3 hours, the deprotection of Fmoc was complete. The reaction mixture was centrifuged and purified by preparative HPLC (reverse phase, X-Terra® PrepRP18 19×50 mm column, acetonitrile-water with 0.1% formic acid as mobile phase) collecting in tubes containing 2.5 mL of 15 mM sodium phosphate buffer (pH 7.2) with 50 mm sodium chloride. Product-containing fractions were desalted using a Sep-Pak® C18 cartridge Vac 6 cc (1 g) to afford LP-026.

HPLC retention time: 2.934
Mass: m/z 722 (MH)+/2
Product: 4.0 mg, Yield: 37%;
Purity: >98%.

The coupling method using CaCl₂ as described herein has been found to provide higher yields and easier product isolation.

The following compounds shown in Table 1 were isolated, wherein the lipopeptide to which the side chain is attached is:
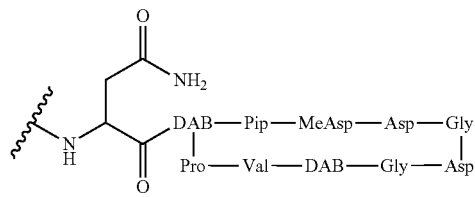
| Compound | Side chain | Method of coupling | Yield (%) | Mass m/z | Purity (%) | HPLC retention time (min)* |
|---|---|---|---|---|---|---|
| LP-001 | | D | 4.9 | 1425.648 (MH)+ | | 2.607 |
| LP-002 | | D | 6 | 1437.65 (MH)+ | | 2.564 |
| LP-003 | | D | 5.4 | 1421.666 (MH)+ | | 2.840 |
| LP-006 | | D | 46 | 1437.7 (MH)+ | >95 | 2.670 |
| LP-007 | | D | 8 | 1435.69 (MH+) | | 3.198 |
| LP-008 | | D | 16 | 1429.635 (MH)+ | | 2.668 |
| LP-009 | | D | 17 | 1429.706 (MH)+ | >93 | 2.689 |

-continued

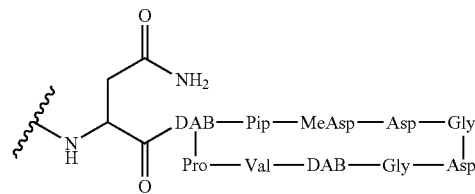

| Compound | Side chain | Method of coupling | Yield (%) | Mass m/z | Purity (%) | HPLC retention time (min)* |
|---|---|---|---|---|---|---|
| LP-010 | naphthyl-phenyl-CH2CH2-phenyl-C(O)- | D | 12 | 1429.6 (MH)+ | >95 | 2.605 |
| LP-011 | phenyl-naphthyl-CH2CH2-phenyl-C(O)- | D | 6 | 1429.64 (MH)+ | | 2.683 |
| LP-012 | biphenyl-CH2-O-naphthyl-C(O)- | D | 6 | 716.3 [(M + 2)/2]+ 727.3 [(M + 1 + 23)/2]+ | 94 | 2.455 |
| LP-013 | heptyl-O-naphthyl-C(O)- | D | 12 | 682.3 [(M + 2)/2]+ 693.3 [(M + 1 + 23)/2]+ | 97 | 2.570 |
| LP-014 | octyl-O-naphthyl-C(O)- | D | 23 | 689.3 [(M + 2)/2]+ 700.3 [(M + 1 + 23)/2]+ | 98 | 2.856 |
| LP-015 | hexyl-O-naphthyl-C(O)- | D | 29 | 675.3 [(M + 2)/2]+ 686.3 [(M + 1 + 23)/2]+ | 97 | 2.355 |
| LP-016 | pentyl-O-phenyl-phenyl-phenyl-C(O)- | D | 10 | 1451.78 (MH+). | >95 | 3.206 |
| LP-017 | heptyl-O-phenyl-phenyl-phenyl-C(O)- | D | 3 | 744.3 [(M + 1 + 23)/2]+ | 91 | 3.534 |
| LP-018 | butyl-O-phenyl-phenyl-phenyl-C(O)- | D | 7 | 730.3 [(M + 1 + 23)/2]+ | 95 | 3.026 |
| LP-020 | pentyl-O-phenyl-pyridyl-phenyl-C(O)- | D | 26 | 1452.6 (MH+) | >95 | 2.749 |

-continued

| Compound | Side chain | Method of coupling | Yield (%) | Mass m/z | Purity (%) | HPLC retention time (min)* |
|---|---|---|---|---|---|---|
| LP-021 | | D | 13 | 748.31 [(M + 2)/2] | >90 | 3.166 |
| LP-022 | | B | 11 | 722.2 [(M + 2)/2]+ | >95 | 2.970 |
| LP-023 | | D | 25 | 1452.6 (MH+) | >95 | 2.527 |
| LP-024 | | B | 20.5 | 1442.7 (MH+) | >95 | 2.849 |
| LP-025 | | F | 19.8 | 729.3 [(M + 2)/2]+ | 98 | 3.173 |
| LP-026 | | B & D | 31 (B) & 37 (D) | 1444 (MH+) | >95 | 2.786 |
| LP-027 | | D | 22 | 722.2 [(M + 2)/2] | 94 | 2.798 |
| LP-028 | | D | 1.6 | 721.3 [(M + 2)/2] | >95 | 2.564 |
| LP-029 | Error! Objects cannot be created from editing field codes. | D | 9 | 1442 (MH+) | >95 | 2.743 |

-continued

| Compound | Side chain | Method of coupling | Yield (%) | Mass m/z | Purity (%) | HPLC retention time (min)* |
|---|---|---|---|---|---|---|
| LP-030 | | D | 18 | 730.0 (MH+/2) | >95 | 2.835 |
| LP-031 | | B | 26 | 715.3 (MH+/2) | 93 | 2.475 |
| LP-032 | | D | 20 | 721.82 [(M + 2)/2]+ | 90 | 2.755 |
| LP-033 | | D | 38.5 | 717.797 [(M + 2)/2]+ | >95 | 2.366 |
| LP-034 | | C | 5 | 715.1 [(M + 2)/2] | 80 | 2.700 |
| LP-035 | | E | 2 | 707.2 [(M + 2)/2] | >99 | 1.994 |
| LP-036 | | C | 1 | 708.1 [(M + 2)/2] | 95 | 2.351 |
| LP-037 | | B | 9.5 | 1427 (MH+) | 93 | 1.567 |

-continued
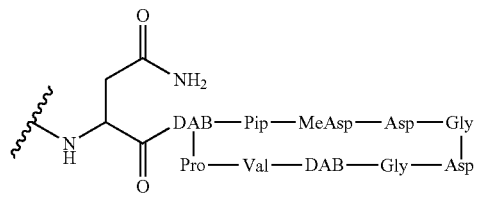
| Compound | Side chain | Method of coupling | Yield (%) | Mass m/z | Purity (%) | HPLC retention time (min)* |
|---|---|---|---|---|---|---|
| LP-038 | | C | 11 | 715.2 [(M + 2)/2] | >95 | 2.606 |
| LP-039 | | C & F | 12 | 722.2 [(M + 2)/2]$^+$ | 95 | 2.853 |
| LP-040 | | D | 4 | 731.85 [(M + 1 + 23)/2]$^+$ | >98% | 3.350 |
| LP-041 | | F | 37 | 700.2 [(M + 2)/2]$^+$ | 98 | 2.554 |
| LP-042 | | D | 34 | 714.2 [(M + 2)/2] | >95 | 3.105 |
| LP-043 | | D | 14 | 1412.6, (MH)$^{+,}$ 706.8 [(M + 2)/2]$^+$ | >95 | 2.803 |
| LP-044 | | D | 38.5 | 1384.6, (MH)$^{+,}$ 692.8 [(M + 2)/2]$^+$ | >95 | 2.297 |
| LP-045 | | D | 48 | 1398.8, (MH)$^{+,}$ 700.1 [(M + 2)/2]$^+$ | >95 | 2.515 |

-continued

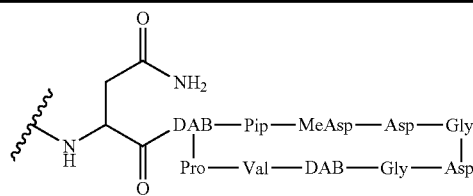

| Compound | Side chain | Method of coupling | Yield (%) | Mass m/z | Purity (%) | HPLC retention time (min)* |
|---|---|---|---|---|---|---|
| LP-046 | | D | 3.2 | 727.8 [(M + 2)/2]+ | >95 | 3.576 |
| LP-047 | | D | 8.3 | 1424.67 (MH)+ | 38 | 2.898 |
| LP-048 | | D | 18 | 1446.6 (MH+) | >95 | 2.605 |

*gradient elution using 25-100% acetonitrile-water with 0.1% formic acid in 7.5 min, 1.5 mL/min, Xterra ® column MSC18, 2.5 micron, 4.6 × 20 mm using Agilent 1100 analytical hplc system

BIOLOGICAL METHODS

Assays

Minimum inhibitory concentrations (MICs) were determined for the following assays.

The following panel of strains was used to assess antibacterial activity:
Staphylococcus aureus ATCC 29213
Staphylococcus aureus ATCC 29213 FRI-68 (strain with reduced susceptibility to friulimicin)
Staphylococcus aureus ATCC 33591 (MRSA)
Staphylococcus epidermidis ATCC 12228
Enterococcus faecalis ATCC 29212
Streptococcus pneumoniae ATCC 33400
Streptococcus pneumoniae ATCC 46919
Streptococcus pyogenes ATCC 12344

Staphylococci and enterococci were grown on cation-adjusted Mueller-Hinton agar (CAMHA) at 35° C. and streptococci were grown on CAMHB+3% lysed horse blood at 35° C. under 5% $CO_2$. Inocula for MIC determinations were grown from a single colony under the conditions described above for 24 h. Colonies were then suspended in saline (0.9% NaCl) to an OD600 nm equivalent to a 0.5 McFarland standard and then diluted to 5.55×105 CFU/ml in cation-adjusted Mueller-Hinton broth supplemented with calcium to 50 µg/ml and polysorbate (tween) 80 to 0.002% (and 3.33% lysed horse blood for streptococci). 2-fold dilution series of test compounds were prepared and diluted in CAMHB supplemented with calcium to 50 µg/ml and polysorbate (tween) 80 to 0.002% and added to wells of 96-well flat bottom microtitre plate (Griener) in 10 µl volumes. 90 µl of inocula are then added to test compound and the plates incubated for 20-24 h at 35° C.

The MIC was recorded as the lowest concentration of test compound that inhibited visible growth.

In addition, % hemolysis was measured using the following assay.

In Vitro Haemolysis Assay

The in vitro haemolysis assay usually used was an adaptation of the protocol provided by Aventis (Isert, 1995) and is described below. The main variations in comparison to the original protocol were a reduction of the assay volumes by 80% and the conducting of the assay in Eppendorf tubes. Stock solution of the antibiotics and other additives were prepared in 0.9% NaCl solution. If not specified otherwise additives and antibiotics were mixed and preincubated for 2 hours at 20° C.

Subsequently 40 µl of these mixtures were transferred into an Eppendorf tube with 40 µl fresh venous blood, mixed and incubated for 180 min at 37° C. on a horizontal shaker at 200 rounds per minute. For each series of experiments a negative control and a sample for the determination of the complete hydrolysis were prepared. In the negative control 40 µl 0.9% NaCl solution were mixed with 40 µl fresh venous blood and for the complete hydrolysis 40 µl water were mixed with 40 µl fresh venous blood. Subsequently the samples were carefully mixed with 1 ml 0.9% NaCl solution or water (sample for complete hydrolysis). After centrifugation at 2500 RFC for 5 min the degree of haemolysis in the samples was determined by measurement of the absorption of the supernatant at 540 nm. The photometer was calibrated with the negative control (blood incubated with 0.9% NaCl).

The absorption of a completely hydrolysed sample (incubated with water) was used as the 100% value for the calculation of the degree of haemolysis of the samples. If not explicitly stated otherwise this procedure was used for the experiments described in this report.

Modified Haemolysis Protocol

Stock solutions of Friulimicin-sodium salt (CBS000043, CBC000209) and test compounds (also sodium salts) were prepared in 0.9% NaCl and diluted to 3200 mg/L in 0.9% NaCl solution containing two times the salts molar concentration of $Ca^{2+}$. These test solution was then diluted in 0.9% NaCl to a second concentration of 200 mg/L. Equivalent calcium free test solutions were also prepared. All test solutions were then preincubated for 2 hours at 20° C. Subsequently 40 µl of these mixtures were transferred into triplicate Eppendorf tubes with 40 µl fresh venous blood to produce assay concentrations of test compounds of 1600 and 100 mg/L. Tubes were then mixed and incubated for 180 min at 37° C. on a horizontal shaker at 200 rounds per minute.

For each series of experiments a negative control and a sample for the determination of the complete hydrolysis were prepared. In the negative control 40 µl 0.9% NaCl solution was mixed with 40 µl fresh venous blood and for the complete haemolysis 40 µl water was mixed with 40 µl fresh venous blood. Subsequently the samples were carefully mixed with 1 ml 0.9% NaCl solution or water (sample for complete haemolysis). After centrifugation at 2500 RFC for 5 min the degree of haemolysis in the samples was determined by measurement of the absorption of the supernatant at 540 nm. The photometer was calibrated with the negative control (blood incubated with 0.9% NaCl).

The absorption of a completely haemolysed sample (incubated with water) was used as the 100% value for the calculation of the degree of haemolysis of the samples. If not explicitly stated otherwise this procedure was used for the experiments described in this report.

Additional $Ca^{2+}$ is added in the higher concentration hemolysis assay because the presence of $Ca^{2+}$ affects hemolysis; indeed Ca salt is more hemolytic than the Na salt, particularly at high drug concentrations. There is Ca in blood and hence the dosed Na salt converts in vivo to the Ca salt. Additional $Ca^{2+}$ (in addition to what is present in blood) is used because it is estimated that at the higher dose of 1600 mg/L, the intrinsic blood levels of $Ca^{2+}$ will be insufficient to convert all the drug to the Ca salt.

Biological Data

Biological data were obtained using the antibacterial assays described above.

The S. aureus ATCC 29213 assay was carried out on the following compounds: LP-001 to LP-003 LP-006 to LP-018 and LP-020 to LP-048.

For the S. aureus ATCC 29213 assay, the following compounds tested had a minimum inhibitory concentration of less than 10 µg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-038, LP-039, LP-040, LP-041, LP-042, LP-043, LP-044, LP-045, LP-046, LP-047 and LP-048.

For the S. aureus ATCC 29213 assay, the following compounds had a minimum inhibitory concentration of less than 5 µg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-039, LP-040, LP-041, LP-042, LP-043, LP-044, LP-045, LP-046, LP-047 and LP-048.

For the S. aureus ATCC 29213 assay, the following compounds had a minimum inhibitory concentration of ≤2 µg/ml: LP-001, LP-002, LP-003, LP-006, LP-007, LP-008, LP-009, LP-010, LP-011, LP-012, LP-013, LP-014, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-041, LP-042, LP-043, LP-044, LP-045, LP-047 and LP-048.

One compound, compound LP-031, had a minimum inhibitory concentration of 1 µg/ml.

The S. aureus 29213 FRI-68 assay was carried out on the following compounds: LP-001 to LP-003 LP-006 to LP-018 and LP-020 to LP-048.

For the S. aureus 29213 FRI-68 assay, the following compounds had a minimum inhibitory concentration of less than 20 µg/ml: LP-001, LP-002, LP-003, LP-006, LP-008, LP-009, LP-010, LP-011, LP-012, LP-013, LP-014, LP-015, LP-018, LP-020, LP-022, LP-023, LP-024, LP-025, LP-026, LP-027, LP-028, LP-029, LP-030, LP-031, LP-032, LP-033, LP-034, LP-035, LP-036, LP-039, LP-041, LP-042, LP-043, LP-044, LP-045, LP-047 and LP-048.

For the S. aureus 29213 FRI-68 assay, the following compounds had a minimum inhibitory concentration of less than 10 µg/ml: LP-006, LP-009, LP-010, LP-011, LP-012, LP-013, LP-014, LP-022, LP-024, LP-031, LP-033, LP-034, LP-041, LP-042, LP-043, LP-044, LP-045, LP-047 and LP-048.

For the S. aureus 29213 FRI-68 assay, the following compounds had a minimum inhibitory concentration of less than 5 µg/ml: LP-012, LP-013, LP-014, LP-022, LP-024, LP-041 and LP-048.

One compound, compound LP-031, had a minimum inhibitory concentration of 8 µg/ml.

The S. aureus 33591 (MRSA) assay was carried out on the following compounds: LP-001 to LP-003 LP-006 to LP-018 and LP-020 to LP-048.

For the S. aureus 33591 (MRSA) assay, the following compounds had a minimum inhibitory concentration of less than 10 µg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-038, LP-039, LP-040, LP-041, LP-042, LP-043, LP-044, LP-045, LP-046, LP-047 and LP-048.

For the S. aureus 33591 (MRSA) assay, the following compounds had a minimum inhibitory concentration of less than 5 µg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-040, LP-041, LP-042, LP-043, LP-044, LP-045, LP-046, LP-047 and LP-048.

For the S. aureus 33591 (MRSA) assay, the following compounds had a minimum inhibitory concentration of ≤2

μg/ml: LP-002, LP-003, LP-006, LP-007, LP-008, LP-009, LP-010, LP-011, LP-012, LP-013, LP-014, LP-016, LP-017, LP-018, LP-020, LP-022, LP-023, LP-024, LP-025, LP-026, LP-027, LP-028, LP-029, LP-030, LP-031, LP-032, LP-033, LP-034, LP-041, LP-042, LP-043, LP-044, LP-045, LP-046, LP-047 and LP-048.

One compound, compound LP-031, had a minimum inhibitory concentration of 1 μg/ml.

The *S. epidermidis* 12228 assay was carried out on the following compounds: LP-001 to LP-003 LP-006 to LP-018 and LP-020 to LP-048.

For the *S. epidermidis* 12228 assay, the following compounds had a minimum inhibitory concentration of less than 10 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-038, LP-039, LP-040, LP-041, LP-042, LP-043, LP-044, LP-045, LP-046, LP-047 and LP-048.

For the *S. epidermidis* 12228 assay, the following compounds had a minimum inhibitory concentration of less than 5 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-041, LP-042, LP-043, LP-044, LP-045, LP-047 and LP-048.

For the *S. epidermidis* 12228 assay, the following compounds had a minimum inhibitory concentration of less than ≤2 μg/ml: LP-001, LP-002, LP-003, LP-006, LP-008, LP-009, LP-010, LP-011, LP-012, LP-013, LP-014, LP-015, LP-016, LP-018, LP-020, LP-022, LP-023, LP-024, LP-025, LP-026, LP-027, LP-028, LP-029, LP-030, LP-031, LP-032, LP-033, LP-034, LP-036, LP-041, LP-042, LP-043, LP-044, LP-045, LP-047 and LP-048.

One compound, compound LP-031, had a minimum inhibitory concentration of 1 μg/ml.

The *E. faecalis* 29212 assay was carried out on the following compounds: LP-001 to LP-003, LP-006 to LP-018, LP-020 to LP-025, and LP-027 to LP-048.

For the *E. faecalis* 29212 assay, the following compounds had a minimum inhibitory concentration of less than 20 μg/ml: LP-001, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-027, LP-028, LP-029, LP-030, LP-031, LP-032, LP-033, LP-034, LP-037, LP-040, LP-041, LP-042, LP-043, LP-045, LP-046, LP-047 and LP-048.

For the *E. faecalis* 29212 assay, the following compounds had a minimum inhibitory concentration of less than 10 μg/ml: LP-003, LP-007, LP-009, LP-010, LP-011, LP-012, LP-013, LP-014, LP-016, LP-017, LP-018, LP-022, LP-023, LP-024, LP-025, LP-027, LP-028, LP-029, LP-030, LP-032, LP-033, LP-034, LP-041, LP-042, LP-043, LP-045, LP-046, LP-047 and LP-048.

For the *E. faecalis* 29212 assay, the following compounds had a minimum inhibitory concentration of less than 5 μg/ml: LP-003, LP-009, LP-011, LP-012, LP-013, LP-014, LP-016, LP-017, LP-018, LP-022, LP-024, LP-025, LP-027, LP-029, LP-030, LP-034, LP-041, LP-042, LP-043 and LP-048.

One compound, compound LP-031, had a minimum inhibitory concentration of 12 μg/ml.

The *S. pneumoniae* 33400 assay was carried out on the following compounds: LP-001 to LP-003 LP-006 to LP-018 and LP-020 to LP-048.

For the *S. pneumoniae* 33400 assay, the following compounds had a minimum inhibitory concentration of less than 20 μg/ml: LP-001, LP-002, LP-003, LP-006, LP-009, LP-010, LP-011, LP-012, LP-013, LP-014, LP-015, LP-016, LP-018, LP-020, LP-022, LP-023, LP-024, LP-025, LP-026, LP-027, LP-028, LP-029, LP-030, LP-031, LP-032, LP-033, LP-034, LP-035, LP-036, LP-037, LP-039, LP-041, LP-042, LP-043, LP-044, LP-045, LP-047 and LP-048.

For the *S. pneumoniae* 33400 assay, the following compounds had a minimum inhibitory concentration of less than 10 μg/ml: LP-002, LP-006, LP-010, LP-011, LP-012, LP-013, LP-020, LP-022, LP-023, LP-024, LP-026, LP-027, LP-031, LP-033, LP-034, LP-035, LP-041, LP-042, LP-043, LP-044, LP-045, LP-047 and LP-048.

For the *S. pneumoniae* 33400 assay, the following compounds had a minimum inhibitory concentration of less than 5 μg/ml: LP-006, LP-041, LP-045 and LP-048.

One compound, compound LP-031, had a minimum inhibitory concentration of 8 μg/ml.

The *S. pneumoniae* 49619 assay was carried out on the following compounds: LP-001 to LP-003 LP-006 to LP-018 and LP-020 to LP-048.

For the *S. pneumoniae* 49619 assay, the following compounds had a minimum inhibitory concentration of less than 20 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-038, LP-039, LP-040, LP-041, LP-042, LP-043, LP-044, LP-045, LP-046, LP-047 and LP-048.

For the *S. pneumoniae* 49619 assay, the following compounds had a minimum inhibitory concentration of less than 10 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-039, LP-040, LP-041, LP-042, LP-043, LP-044, LP-045, LP-046, LP-047 and LP-048.

For the *S. pneumoniae* 49619 assay, the following compounds had a minimum inhibitory concentration of less than 5 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-022, LP-023, LP-024, LP-025, LP-026, LP-027, LP-028, LP-029, LP-030, LP-031, LP-032, LP-033, LP-034, LP-035, LP-036, LP-037, LP-039, LP-041, LP-042, LP-043, LP-044, LP-045, LP-047 and LP-048.

One compound, compound LP-031, had a minimum inhibitory concentration of 1 μg/ml.

The *S. pyogenes* 12344 assay was carried out on the following compounds: LP-001 to LP-003 LP-006 to LP-018 and LP-020 to LP-048.

For the *S. pyogenes* 12344 assay, the following compounds had a minimum inhibitory concentration of less than 20 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-039, LP-040, LP-041, LP-042, LP-043, LP-044, LP-045, LP-046, LP-047 and LP-048.

For the *S. pyogenes* 12344 assay, the following compounds had a minimum inhibitory concentration of less than 10 μg/ml: LP-001, LP-002, LP-003, LP-006, LP-007, LP-008, LP-009, LP-010, LP-011, LP-012, LP-013, LP-014, LP-015, LP-016, LP-017, LP-018, LP-020, LP-021, LP-022, LP-023, LP-024, LP-025, LP-026, LP-027, LP-028, LP-029, LP-030, LP-031, LP-032, LP-033, LP-034, LP-035, LP-036, LP-037, LP-041, LP-042, LP-043, LP-044, LP-045, LP-047 and LP-048.

For the S. pyogenes 12344 assay, the following compounds had a minimum inhibitory concentration of less than 5 µg/ml: LP-001, LP-002, LP-003, LP-006, LP-007, LP-009, LP-010, LP-011, LP-012, LP-013, LP-014, LP-015, LP-016, LP-020, LP-022, LP-023, LP-024, LP-025, LP-026, LP-027, LP-028, LP-029, LP-030, LP-031, LP-033, LP-034, LP-035, LP-036, LP-037, LP-041, LP-042, LP-043, LP-044, LP-045, LP-047 and LP-048.

One compound, compound LP-031, had a minimum inhibitory concentration of 4 µg/ml.

The hemolysis assays were carried out on the following compounds: LP-001, LP-006 to LP-016, LP-018, LP-020 to LP-031, LP-033, LP-034, LP-036 to LP-045, LP-047 and LP-048.

For the % hemolysis at 100 mg/L assay with additional calcium, all of the compounds tested had a % hemolysis of less than 3%.

For the % hemolysis at 100 mg/L assay with additional calcium, the following compounds had a % hemolysis of ≤1%: LP-001, LP-006, LP-007, LP-008, LP-011, LP-012, LP-013, LP-014, LP-015, LP-016, LP-018, LP-020, LP-021, LP-022, LP-023, LP-024, LP-025, LP-026, LP-027, LP-029, LP-030, LP-031, LP-033, LP-034, LP-036, LP-037, LP-039, LP-038, LP-040, LP-041, LP-042, LP-043, LP-044, LP-045 and LP-047.

One compound, compound LP-031, had a % hemolysis of 0.3%.

For the % hemolysis at 100 mg/L assay without additional calcium, all of the compounds tested had a % hemolysis of less than 3%.

For the % hemolysis at 100 mg/L assay without additional calcium, the following compounds had a % hemolysis of %: LP-001, LP-007, LP-009, LP-011, LP-012, LP-013, LP-014, LP-015, LP-016, LP-018, LP-020, LP-021, LP-022, LP-023, LP-024, LP-025, LP-026, LP-027, LP-028, LP-029, LP-030, LP-031, LP-033, LP-034, LP-036, LP-037, LP-039, LP-038, LP-040, LP-041, LP-042, LP-043, LP-044, LP-045 and LP-047.

One compound, compound LP-031, had a % hemolysis of −0.2%.

For the % hemolysis at 1600 mg/L assay with additional calcium, the following compounds had a % hemolysis of less than 50%: LP-001, LP-006, LP-007, LP-008, LP-009, LP-013, LP-014, LP-015, LP-016, LP-018, LP-020, LP-021, LP-022, LP-023, LP-024, LP-025, LP-026, LP-027, LP-028, LP-029, LP-031, LP-033, LP-034, LP-036, LP-037, LP-039, LP-038, LP-040, LP-041, LP-042, LP-043, LP-044, LP-045, LP-047 and LP-048.

For the % hemolysis at 1600 mg/L assay with additional calcium, the following compounds had a % hemolysis of less than 25%: LP-001, LP-007, LP-008, LP-013, LP-014, LP-015, LP-016, LP-018, LP-020, LP-021, LP-022, LP-023, LP-024, LP-025, LP-026, LP-027, LP-028, LP-029, LP-031, LP-033, LP-034, LP-036, LP-037, LP-039, LP-038, LP-040, LP-041, LP-042, LP-043, LP-044, LP-045, LP-047 and LP-048.

One compound, compound LP-031, had a % hemolysis of 0.8%.

For the % hemolysis at 1600 mg/L assay without additional calcium, all of the compounds tested had a % hemolysis of less than 50%.

For the % hemolysis at 1600 mg/L assay without additional calcium, the following compounds had a % hemolysis of less than 25%: LP-001, LP-006, LP-007, LP-008, LP-009, LP-013, LP-014, LP-015, LP-016, LP-018, LP-020, LP-021, LP-022, LP-023, LP-024, LP-025, LP-026, LP-027, LP-028, LP-029, LP-031, LP-033, LP-034, LP-036, LP-037, LP-039, LP-038, LP-040, LP-041, LP-042, LP-043, LP-044, LP-045, LP-047 and LP-048.

One compound, compound LP-031, had a % hemolysis of 0.6%.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.
EP0629636A
FEMS Microbiol. Lett. 98 (1992) 5 109 to 116
Neu H. C., Science 257, 1992, pages 1064-1073

The invention claimed is:

1. A compound selected from compounds of the following formula, and pharmaceutically acceptable salts thereof:

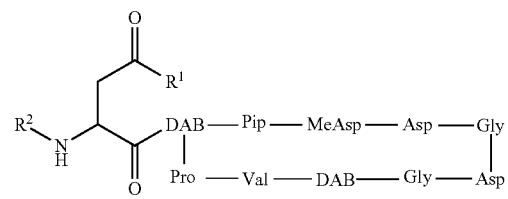

(I)

wherein:
—$R^1$ is independently —OH or —$NH_2$
and wherein:
—$R^2$ is —$R^B$
  wherein:
  —$R^B$ is independently $R^{B4}$—$R^{B3}$-$L^{B2}$-$R^{B2}$-$L^{B1}$-$R^{B1}$—C(O)—
    wherein:
    —$R^{B1}$— is independently —$R^{BP}$— or —$R^{BN}$—,
    and wherein:
    each of —$R^{B2}$—, and —$R^{B3}$— is independently —$R^{BS}$—, —$R^{BP}$—, —$R^{BN}$— or —$R^{BH}$—,
    and wherein:
    at least one of —$R^{B2}$— and —$R^{B3}$— is independently —$R^{BH}$—
      wherein:
      each —$R^{BP}$—, if present, is independently phenylene, and is optionally substituted and wherein:
each —$R^{BN}$—, if present, is independently naphthylene, and is optionally substituted
and wherein:
each —$R^{BH}$— is independently aromatic or saturated or unsaturated non-aromatic $C_{4-14}$heterocyclylene, and is optionally substituted
and wherein:
each —$R^{BS}$—, if present, is independently a single bond
and wherein:
each of -$L^{B1}$- and -$L^{B2}$- is independently -$L^S$-, -$L^{BB}$- or -$L^{BO}$-
wherein:
each -$L^S$-, if present, is independently a single bond
and wherein:
each -$L^{BB}$-, if present, is independently saturated aliphatic $C_{1-4}$alkylene, and is optionally substituted
and wherein:
each -$L^{BO}$-, if present, is independently saturated aliphatic $C_{1-4}$alkoxylene, and is optionally substituted
and wherein:
—$R^{B4}$ is independently —H, —$R^{B4A}$, —$R^{B4AA}$ or $R^{B4O}$
wherein:
—$R^{B4A}$, if present, is independently saturated or unsaturated aliphatic or alicyclic $C_{1-10}$alkyl, and is optionally substituted
and wherein:
—$R^{B4AA}$, if present, is independently $C_{6-10}$aryl-$C_{1-6}$alkyl, and is optionally substituted
and wherein:
—$R^{B4O}$, if present, is independently —$R^{B4O1}$ or $R^{B4O2}$
wherein:
—$R^{B4O1}$, if present, is independently saturated or unsaturated aliphatic or alicyclic $C_{1-10}$alkoxy, and is optionally substituted
and wherein:
—$R^{B4O2}$, if present, is independently $C_{6-10}$aryloxy, and is optionally substituted.

2. A compound according to claim 1, wherein —$R^1$ is independently —$NH_2$.

3. A compound according to claim 2, wherein, —$R^{B1}$— is independently —$R^{BP}$—, —$R^{B2}$— is independently —$R^{BH}$—, and —$R^{B3}$— is independently —$R^{BP}$—.

4. A compound according to claim 3, wherein each —$R^{BP}$— is independently

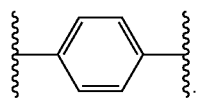

5. A compound according to claim 3, wherein —$R^{BH}$— is independently aromatic or unsaturated non-aromatic $C_{5-6}$heterocyclylene containing at least one N as a ring atom, and is optionally substituted.

6. A compound according to claim 5, wherein —$R^{BH}$ is independently

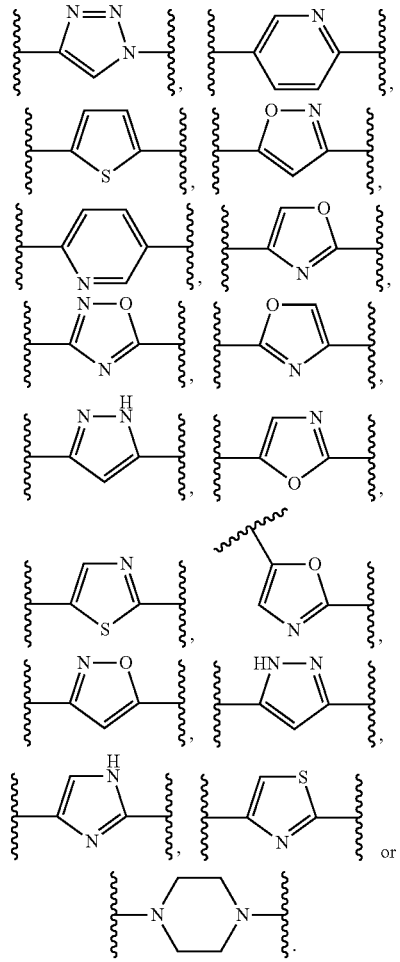

7. A compound according to claim 3, wherein each of -$L^{B1}$- and -$L^{B2}$- is independently -$L^S$-.

8. A compound according to claim 3, wherein —$R^{B4}$ is independently saturated or unsaturated aliphatic or alicyclic $C_{3-8}$alkyl, $C_6$aryl-$C_{1-2}$alkyl, or saturated or unsaturated aliphatic $C_{3-8}$alkoxy, and is optionally substituted.

9. A compound according to claim 1, wherein each of -$L^{BB}$-, if present, and -$L^{BO}$-, if present, is independently optionally substituted with one or more substituents, —$R^{S1}$, wherein each $R^{S1}$, if present, is independently selected from:
—F, —Cl, —Br, —I, or
—OH, -$L^{SS1}$-OH,
—$OR^{SS1}$,
—$NH_2$; and
-$L^{SS1}$-$NH_2$
each of —$R^{B4A}$, if present, —$R^{B4O1}$, if present, —$R^{B4O2}$, if present, and —$R^{B4AA}$, if present, is independently optionally substituted with one or more substituents, —$R^{S2}$, wherein each $R^{S2}$, if present, is independently selected from:
—$R^{SS1}$
—F, —Cl, —Br,
—$CF_3$, —$OCF_3$, —$SCF_3$,
—OH, -$L^{SS1}$-OH, —O-$L^{SS1}$-OH, —NH-$L^{SS1}$-OH, —$NR^{SS1}$-$L^{SS1}$-OH,
—$NH_2$, —$NHR^{SS1}$, —$NR^{SS1}_2$,
-$L^{SS1}$-$NH_2$, -$L^{SS1}$-$NHR^{SS1}$, -$L^{SS1}$-$NR^{SS1}_2$; and
=O, each of —R$^{BP}$—, if present, and —R$^{BN}$—, if present, is independently optionally substituted with one or more substituents, -R$^{S3}$, wherein each R$^{S3}$, if present, is independently selected from:
 —R$^{SS1}$,
 —F, —Cl, —Br, —I; and
 —OH,
and —R$^{BH}$ is independently is optionally substituted with one or more substituents, —R$^{S4}$, wherein each R$^{S4}$, if present, is independently selected from:
 —R$^{SS1}$,
 —F, —Cl, —Br, —I; and
 —OH,
wherein:
 each —R$^{SS1}$, if present, is independently saturated aliphatic C$_{1-6}$alkyl;
 each -L$^{SS1}$-, if present, is independently —(CH$_2$)$_n$—, wherein n is independently 1 to 4;
 each -L$^{JA}$-, if present, is independently saturated aliphatic C$_{1-5}$alkylene;
 each —NR$^{JA2}$R$^{JA3}$, if present, is independently C$_{4-7}$heterocyclyl, and is optionally substituted, for example, with one or more groups selected from —R$^{J44}$, —CF$_3$, —F, —OH, —OR$^{J44}$, —NH$_2$, —NHR$^{J44}$, —NR$^{J44}$$_2$, and =O; wherein each —R$^{J44}$ is independently saturated aliphatic
 each —R$^{JA1}$ is independently:
  —R$^{JB1}$, —R$^{JB2}$, —R$^{JB3}$, —R$^{JB4}$, —R$^{JB5}$, —R$^{JB6}$, —R$^{JB7}$, —R$^{JB8}$,
  -L$^{JB}$-R$^{JB4}$, -L$^{JB}$-R$^{JB5}$, -L$^{JB}$-R$^{JB6}$, -L$^{JB}$-R$^{JB7}$, or -L$^{JB}$-R$^{JB8}$;
 each —R$^{JB1}$ is independently saturated aliphatic C$_{1-6}$alkyl;
 each —R$^{JB2}$ is independently aliphatic C$_{2-6}$alkenyl;
 each —R$^{JB3}$ is independently aliphatic C$_{2-6}$alkynyl;
 each —R$^{JB4}$ is independently saturated C$_{3-6}$cycloalkyl;
 each —R$^{JB5}$ is independently C$_{3-6}$cycloalkenyl;
 each —R$^{JB6}$ is independently non-aromatic C$_{4-7}$heterocyclyl;
 each —R$^{JB7}$ is independently C$_{6-10}$carboaryl;
 each —R$^{JB8}$ is independently C$_{5-10}$heteroaryl;
 each -L$^{JB}$- is independently saturated aliphatic C$_{1-3}$alkylene;
wherein:
 each —R$^{JB4}$, —R$^{JB5}$, —R$^{JB6}$, —R$^{JB7}$, and —R$^{JB8}$ is optionally substituted, for example, with one or more substituents —R$^{JC1}$ and/or one or more substituents —R$^{JC2}$,
 each —R$^{JB1}$, —R$^{JB2}$, —R$^{JB3}$, and -L$^{JB}$- is optionally substituted, for example, with one or more substituents —R$^{JC2}$, and
wherein:
 each —R$^{JC1}$ is independently saturated aliphatic C$_{1-4}$alkyl, phenyl, or benzyl;
 each —R$^{JC2}$ is independently:
  —F, —Cl, —Br, —I,
  —CF$_3$, —OCF$_3$,
  —OH,
  —CN,
  —NO$_2$,
  —NH$_2$,
  —C(=O)OH,
  —C(=O)NH$_2$.

10. A compound according to claim 1, wherein —R$^2$ is independently selected from:

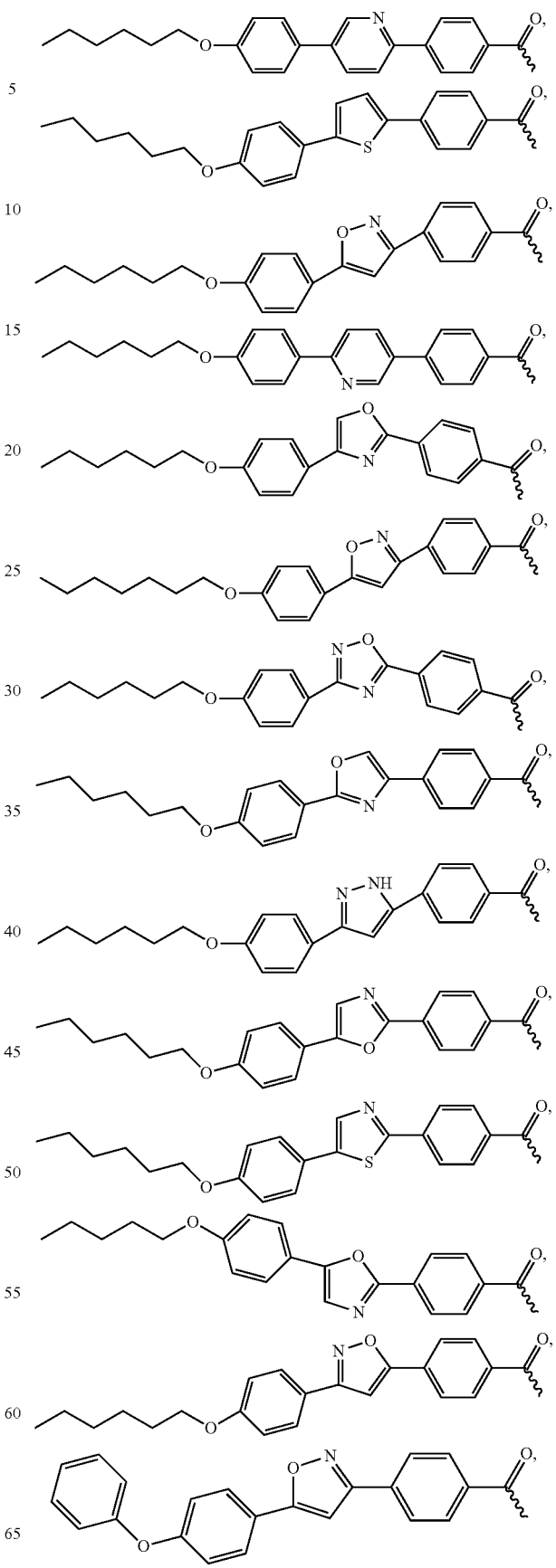

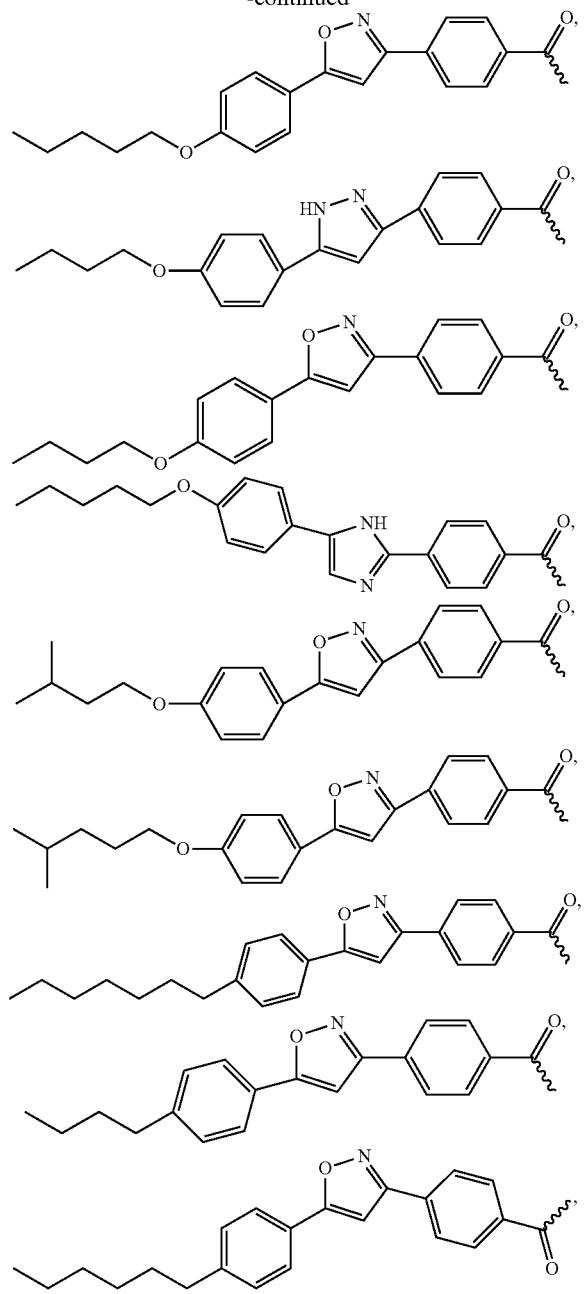
11. A pharmaceutical composition comprising a compound according to claim 1, and a pharmaceutically acceptable carrier, diluent, or excipient.
12. A method for treating a bacterial infection or bacterial disease comprising administering to a patient in need thereof a compound according to claim 1.
* * * * *